United States Patent
Osten et al.

(10) Patent No.: US 11,597,726 B2
(45) Date of Patent: Mar. 7, 2023

(54) RING DEUTERATED GABOXADOL AND ITS USE FOR THE TREATMENT OF PSYCHIATRIC DISORDERS

(71) Applicant: Certego Therapeutics Inc., Boston, MA (US)

(72) Inventors: Pavel Osten, Brooklyn, NY (US); Kristin K. Baldwin, New York, NY (US); Robert DeVita, Westfield, NJ (US); Samuel Desjardins, Blainville (CA); Jeffrey Albert, Boulevard Montreal (CA)

(73) Assignee: Certego Therapeutics Inc., Boston, MA (US)

( * ) Notice: Subject to any disclaimer, the term of this patent is extended or adjusted under 35 U.S.C. 154(b) by 35 days.

(21) Appl. No.: 17/326,270

(22) Filed: May 20, 2021

(65) Prior Publication Data
US 2022/0127261 A1    Apr. 28, 2022

Related U.S. Application Data

(60) Provisional application No. 63/027,923, filed on May 20, 2020, provisional application No. 63/028,457, filed on May 21, 2020, provisional application No. 63/027,953, filed on May 20, 2020, provisional application No. 63/028,472, filed on May 21, 2020.

(51) Int. Cl.
| C07D 471/04 | (2006.01) |
| A61K 31/437 | (2006.01) |
| A61K 45/06 | (2006.01) |
| A61P 25/24 | (2006.01) |

(52) U.S. Cl.
CPC .......... *C07D 471/04* (2013.01); *A61K 31/437* (2013.01); *A61K 45/06* (2013.01); *A61P 25/24* (2018.01)

(58) Field of Classification Search
CPC ..... C07D 471/04; A61K 31/437; A61K 45/06
USPC ........................................................ 514/302
See application file for complete search history.

(56) References Cited

U.S. PATENT DOCUMENTS

| 4,278,676 A | 7/1981 | Krogsgaard-Larsen |
| 4,353,910 A * | 10/1982 | Perregaard ........... C07D 498/04 546/116 |
| 4,362,731 A | 12/1982 | Hill |
| 8,097,625 B2 | 1/2012 | Lalji et al. |
| 8,193,216 B2 | 6/2012 | Kumke et al. |
| 9,351,968 B1 | 5/2016 | During |
| 9,682,069 B2 | 6/2017 | During |
| 9,744,159 B2 | 8/2017 | During |
| 10,111,865 B2 | 10/2018 | During et al. |
| 10,195,165 B2 | 2/2019 | During |
| 11,123,332 B2 | 9/2021 | Osten et al. |
| 2002/0165217 A1 | 11/2002 | Howard, Jr. |
| 2004/0024038 A1 | 2/2004 | Ebert et al. |
| 2005/0137222 A1 | 6/2005 | Ebert et al. |
| 2005/0234093 A1 | 10/2005 | Sanchez et al. |
| 2005/0282911 A1 | 12/2005 | Hakkarainen et al. |
| 2007/0287753 A1 | 12/2007 | Charney et al. |
| 2007/0299048 A1 | 12/2007 | McKerman |
| 2008/0159958 A1 | 7/2008 | Radek et al. |
| 2008/0262029 A1 | 10/2008 | Crocker et al. |
| 2009/0048288 A1 | 2/2009 | Ebert et al. |
| 2009/0203731 A1 | 8/2009 | Sanchez et al. |
| 2009/0274775 A1 | 11/2009 | Satow |
| 2010/0093787 A1 | 4/2010 | Lundahl et al. |
| 2011/0082171 A1 | 4/2011 | Ferguson et al. |
| 2011/0301190 A1 | 12/2011 | Kumke et al. |
| 2015/0313903 A1 | 11/2015 | During |
| 2016/0228418 A1 | 8/2016 | During |
| 2017/0020892 A1 | 1/2017 | Thompson et al. |
| 2017/0119704 A1 | 5/2017 | During |
| 2017/0246152 A1 | 8/2017 | During |
| 2017/0296519 A1 | 10/2017 | During et al. |
| 2017/0304358 A1 | 10/2017 | Ghaemi |
| 2017/0319556 A1 | 11/2017 | During |
| 2017/0348232 A1 | 12/2017 | During |
| 2017/0348255 A1 | 12/2017 | During |
| 2018/0065984 A1 | 3/2018 | DeFaveri et al. |
| 2018/0098974 A1 | 4/2018 | During |
| 2018/0148380 A1 | 5/2018 | Eckel et al. |
| 2018/0235942 A1 | 8/2018 | During |
| 2018/0235950 A1 | 8/2018 | Sonesson |

(Continued)

FOREIGN PATENT DOCUMENTS

| AR | 105378 A1 | 9/2017 |
| AR | 105670 A1 | 10/2017 |

(Continued)

OTHER PUBLICATIONS

Lee et al., 2015, "Use of ketamine in acute cases of suicidality", Innovations in Clinical Neuroscience; 12(1-2):29-31.
Geier, Michelle, 2012, "Lithium as augmentation for major depressive disorder," Mental Health Clinician, 2(1):15-17.
University of Oxford, 2010, "Combination therapy better than leading drug for bipolar disorder, study suggests," ScienceDaily. ScienceDaily [retrieved on Apr. 11, 2022]. Retrieved from the Internet: <URL: www.sciencedaily.com/releases/2009/12/091231165336.htm>.
"Ketamine for Depression and Suicide Risk (Ketamine)," Clinical Trial (ClinicalTrials.gov Identifier: NCT02094898) [online], Aug. 11, 2017, [retrieved on Jan. 18, 2022]. Retrieved from the Internet: <URL:https://clinicaltrials.gov/ct2/show/NCT02094898>.
Chu et al., 2009, "Metabolism and Renal Elimination of Gaboxadol in Humans: Role of UDP-Glucuronosyltransferases and Transporters," 26:459-468.

(Continued)

*Primary Examiner* — Niloofar Rahmani
(74) *Attorney, Agent, or Firm* — Jones Day

(57) ABSTRACT

Ring deuterated gaboxadol is provided. The ring deuterated gaboxadol is useful in the treatment of psychiatric disorders and is more effective than non-deuterated gaboxadol in such treatments. Deuterated gaboxadol is useful in combinations with other compounds to provide additive and synergistic effects for patient therapies. In a specific embodiment, the deuterated gaboxadol is d6-gaboxadol.

54 Claims, 48 Drawing Sheets

(56) References Cited

U.S. PATENT DOCUMENTS

| | | |
|---|---|---|
| 2018/0303805 A1 | 10/2018 | During |
| 2018/0338959 A1 | 11/2018 | During |
| 2018/0344709 A1 | 12/2018 | During |
| 2018/0344745 A1 | 12/2018 | During |
| 2019/0060400 A1 | 2/2019 | During |
| 2019/0076415 A1 | 3/2019 | During |
| 2019/0085358 A1 | 3/2019 | During |
| 2019/0091209 A1 | 3/2019 | During |
| 2019/0105308 A1 | 4/2019 | During |
| 2019/0111033 A1 | 4/2019 | During |
| 2019/0117632 A1 | 4/2019 | During |
| 2019/0117633 A1 | 4/2019 | During |
| 2019/0321341 A1 | 10/2019 | During |
| 2019/0321342 A1 | 10/2019 | During |
| 2022/0008388 A1 | 1/2022 | Osten et al. |
| 2022/0008398 A1 | 1/2022 | Osten et al. |

FOREIGN PATENT DOCUMENTS

| | | |
|---|---|---|
| BR | 112018004680 A2 | 9/2018 |
| CA | 2692334 A1 | 12/2004 |
| CA | 2994952 A1 | 2/2017 |
| CA | 3071939 A1 | 2/2019 |
| CA | 3064266 A1 | 11/2019 |
| CA | 3064299 A1 | 11/2019 |
| CN | 102137667 A | 7/2011 |
| CN | 107595850 A | 1/2018 |
| DE | 102005020882 A1 | 11/2006 |
| EA | 007287 B1 | 8/2006 |
| EA | 200300594 A1 | 8/2006 |
| EP | 0000338 B1 | 11/1981 |
| EP | 0840601 B1 | 10/2001 |
| EP | 1337247 A1 | 8/2003 |
| EP | 2145620 A2 | 1/2010 |
| EP | 1641456 B1 | 3/2010 |
| EP | 2145620 A3 | 3/2010 |
| ME | 00030 B | 6/2010 |
| MX | 2018001720 A | 9/2018 |
| MX | 2019001669 A | 9/2019 |
| MX | 2019009190 A | 9/2019 |
| NZ | 565880 A | 7/2011 |
| NZ | 623341 A | 4/2016 |
| PT | 1641456 E | 6/2010 |
| TW | 200501951 A | 1/2005 |
| TW | 200924757 A | 6/2009 |
| UA | 90656 C2 | 5/2010 |
| UA | 91496 C2 | 8/2010 |
| WO | WO 2002/040009 A1 | 11/2001 |
| WO | WO 2004/112786 A2 | 12/2004 |
| WO | WO 2005/023820 A1 | 3/2005 |
| WO | WO 2005/073237 A2 | 10/2005 |
| WO | WO 2005/073237 A3 | 10/2005 |
| WO | WO 2005/094820 A1 | 10/2005 |
| WO | WO 2007/111880 A2 | 10/2007 |
| WO | WO 2009/056146 A1 | 10/2008 |
| WO | WO 2009/021521 A2 | 2/2009 |
| WO | WO 2015/153658 A2 | 10/2015 |
| WO | WO 2016/073653 A1 | 11/2015 |
| WO | WO 2017/015049 A1 | 1/2017 |
| WO | WO 2017/027249 A1 | 2/2017 |
| WO | WO 2017/044578 A1 | 3/2017 |
| WO | WO 2018/031748 A1 | 2/2018 |
| WO | WO 2018/144827 A1 | 8/2018 |
| WO | WO 2018/217718 A1 | 11/2018 |
| WO | WO 2019/006161 A1 | 1/2019 |
| WO | WO 2019/028234 A1 | 2/2019 |
| WO | WO 2019/055369 A1 | 3/2019 |
| WO | WO 2019/195813 A1 | 10/2019 |
| WO | WO 2020/106927 A1 | 5/2020 |
| WO | WO 2020/106976 A1 | 5/2020 |
| WO | WO 2021/236876 A2 | 5/2021 |

OTHER PUBLICATIONS

Dyck et al., 1986, "Effects of Deuterium Substitution on the Catabolism of β-Phenylethylamine: An In Vivo Study," Journal of Neurochemistry, 46(2):399-404.

Eilers, R., 1995, "Therapeutic Drug Monitoring for the Treatment of Psychiatric Disorders," Clin. Pharmacokinet., 29(6):442-450.

Kambayashi et al., 2020, "How the Deuteration of Dronedarone Can Modify Its Cardiovascular Profile: In Vivo Characterization of Electropharmacological Effects of Poyendarone, a Deuterated Analogue of Dronedarone," 20(4):339-350.

Lankford, et al., 2008, "Effect of Gaboxadol on Sleep in Adult and Elderly Patients with Primary Insomnia: Results From Two Randomized, Placebo-Controlled, 30-Night Polysomnography Studies," 31(10):1359-1370.

Timmins, G.S., 2014, "Deuterated drugs; where are we now?" Expert Opinion in Therapeutic Patents, 24(10):1067-1075.

Timmins, G.S., 2017, "Deuterated drugs; updates and obviousness analysis," Expert Opinion in Therapeutics Patents, 27(12):1353-1361.

"An Open-Label Study to Evaluate the Long-Term Safety, Tolerability, and Efficacy of OV101 in Individuals With Angelman Syndrome," Clinical Trial (ClinialTrials.gov Identifier: NCT03882918 [online], Jan. 21, 2019,[retrieved on Oct. 24, 2022]. Retrieved from the Internet: <https://clinicaltrials.gov/ct2/show/NCT03882918>.

"A Phase 1 Single Dose PK Study in Adolescent Subjects With Fragile X Syndrome or Angelman Syndrome," Clinical Trial (ClinialTrials.gov Identifier: NCT03109756 [online], Apr. 3, 2017,[retrieved on Oct. 24, 2022]. Retrieved from the Internet: <https://clinicaltrials.gov/ct2/show/NCT03109756>.

"A Study in Adults and Adolescents with Angelman Syndrome," Clinical Trial (ClinicalTrials.gov Identifier: NCT02996305) [online], Dec. 19, 2016, [retrieved on Jan. 6, 2022]. Retrieved from the Internet: <URL: https://clinicaltrials.gov/ct2/show/NCT02996305>.

"A Study of Gaboxadol in Primary Insomnia," Clinical Trial (ClinicalTrials.gov Identifier: NCT00209963) [online], Sep. 21, 2005, [retrieved on Jan. 6, 2022]. Retrieved from the Internet: <https://clinicaltrials.gov/ct2/show/NCT00209963>.

"Short-term Study of Combination Treatment of Escitalopram and Gaboxadol in Major Depressive Disorder," Clinical Trial, Dec. 11, 2006, NCT00807248.

Abou-Saleh et al., 2017, "Lithium in the episode and suicide prophylaxis and in augmenting strategies in patients with unipolar depression," Int J Bipolar Disord., 5(1):11 (9 pages).

American Psychiatric Association, 2002, "Practice Guideline for the Treatment of Patients with Bipolar Disorder," Am J Psychiatry, 159(4 Suppl):1-50.

American Psychiatric Association, DSM-5 Task Force, 2013, "Diagnostic and statistical manual of mental disorders:DSM-5($5^{th}$ Ed.)". American Psychiatric Publishing, Inc. (992 pages).

Andersen et al., 1989, "The Brief Psychiatric Rating Scale," Psychopathology, 22:168-176.

Ando et al., 2017, "Lithium Levels in Tap Water and the Mental Health Problems of Adolescents: An Individual-Level Cross-Sectional Survey," The Journal of Clinical Psychiatry, 78:e252-e256.

Artigas, 2015, "Developments in the field of antidepressants", where do we go now?, European Neuropsychopharmacology, 25:657-670.

Autry et al., 2011, "NMDA receptor blockade at rest triggers rapid behavioural antidepressant responses," Nature, 475:91-95.

Azevedo et al., 2020a, "Brain-wide mapping of c-fos expression in the single prolonged stress model and the effects of pretreatment with ACH-000029 or prazosin," Neurobiology of Stress, 13:100226-100236.

Azevedo et al., 2020b, "The serotonergic and alpha-I adrenergic receptor modulator ACH-000029 ameliorates anxiety-like behavior in a post-traumatic stress disorder model," Neuropharmacology, 164:107912-107922.

Bahr, 2019, "Balanced Parenting: The Effects of Family Functioning on Suicide and Non-Suicidal Self-Injury in Adolescents," Intuition: The BYU Undergraduate Journal of Psychology, 14(2), Article 2 (12 pages).

(56) References Cited

OTHER PUBLICATIONS

Baldessarini et al., 2003, "Lithium treatment and suicide risk in major affective disorders: update and new findings," J Clin Psychiatry, 64 Suppl 5:44-52.
Baldessarini et al., 2006, "Decreased risk of suicides and attempts during long-term lithium treatment: a meta-analytic review," Bipolar Disord., 8(5 Pt 2):625-639.
Beck et al., 1961, "An inventory for measuring depression," Arch Gen Psychiatry, 4:561-571.
Beck et al., 1979, "Assessment of suicidal intention: the Scale for Suicide Ideation," J Consult Clin Psychol., 47:343-352.
Berggren et al., 1978, "The Effect of Lithium on Amphetamine-Induced Locomotor Stimulation," Psychopharmacology, 59:41-45.
Bersani et al., 2016, "Potential Neuroprotective Effect of Lithium in Bipolar Patients Evaluated by Neuropsychological Assessment: Preliminary Results," Human Psychopharmacology: Clinical and Experimental, 31:19-28.
Boateng et al., 2010, "Characterisation of freeze-dried wafers and solvent evaporated films as potential drug delivery systems to mucosal surfaces," Int J Pharm., 389 (1-2):24-31.
Bremner et al., 1998, "Measurement of dissociative states with the clinician administered dissociative states scale (CADSS)," Journal of Traumatic Stress: Official Publication of the International Society for Traumatic Stress Studies, 11:125-136.
Brown et al., 2000, "Risk factors for suicide in psychiatric outpatients: a 20-year prospective study," Journal of Consulting and Clinical Psychology, 68:371-377.
Browne et al., 2013, "Antidepressant effects of ketamine: mechanisms underlying fast-acting novel antidepressants," Frontiers in Pharmacology, 4:161 (18 pages).
Cade, 1949, "Lithium salts in the treatment of psychotic excitement," Med J Aust., 2(10):349-352.
Cao et al., 2019, "Identifying Ketamine Responses in Treatment-Resistant Depression Using a Wearable Forehead EEG," IEEE transactions on Bio-medical Engineering, 66(6):1668-1679.
Cappeliez et al., 1990, "Effects of Lithium on an Amphetamine Animal Model of Bipolar Disorder," Progress in Neuro-Psychopharmacology and Biological Psychiatry, 14:347-358.
Carter et al., 2013, "An updated review of the optimal lithium dosage regimen for renal protection," Canadian Journal of Psychiatry, 58(10):595-600.
Chaturvedi et al., 2011, "Fast Dissolving Films: A Review," Curr Drug Deliv., 8(4):373-380.
Ciper and Bodmier, 2005, "Preparation and characterization of novel fast disintegrating capsules (Fastcaps) for administration in the oral cavity," Int J Pharm., 303 (1-2):62-71.
Cipriani et al., 2005, "Lithium in the prevention of suicidal behavior and all-cause mortality in patients with mood disorders: a systematic review of randomized trials," The American Journal of Psychiatry, 162(10):1805-1819.
Cipriani et al., 2013, "Lithium in the prevention of suicide in mood disorders: updated systematic review and meta-analysis," BMJ (Clinical Research Edition), 346:f3646.
Clayton-Smith et al., 2001, "Angelman syndrome: evolution of the phenotype in adolescents and adults," Developmental Medicine & Child Neurology, 43:476-480.
Cogram et al., 2019, "Gaboxadol Normalizes Behavioral Abnormalities in a Mouse Model of Fragile X Syndrome," Front Behav Neurosci., 13:141.
Cryan et al., 2004, "In search of a depressed mouse: utility of models for studying depression-related behavior in genetically modified mice," Mol Psychiatry, 9(4):326-357.
Cryan et al., 2005, "Assessing substrates underlying the behavioral effects of antidepressants using the modified rat forced swimming test," Neurosci Biobehav Rev., 29(4-5):547-569.g.
Dadiomov et al., 2019, "The effects of ketamine on suicidality across various formulations and study settings," The Mental Health Clinician, 9(1):48-60.

Davis et al., 2018, "Lithium and nephrotoxicity: a literature review of approaches to clinical management and risk stratification," BMC Nephrology, 19(1):305 (7 pages).
Davis et al., 2018, "Lithium and nephrotoxicity: unravelling the complex pathophysiological threads of the lightest metal," Nephrology (Carlton, Vic.), 23(10):897-903.
Deacon et al., 2007, "Effects of Short-term Treatment With Gaboxadol on Sleep Maintenance and Initiation in Patients with Primary Insomnia," Sleep, 30(3):282-287.
Deligiannidis et al., 2014, "Pharmacotherapy for mood disorders in pregnancy: a review of pharmacokinetic changes and clinical recommendations for therapeutic drug monitoring," Journal of Clinical Psychopharmacology, 34(2):244-255.
Dijk et al., 2010, "Sex differences and the effect of gaboxadol and zolpidem on EEG power spectra in NREM and REM sleep," Journal of Psychopharmacology (Oxford, England), 24(11):1613-1618.
Domany et al., 2020, "Ketamine for acute suicidal ideation. An emergency department intervention: A randomized, doubleblind, placebo-controlled, proof-of-concept trial," Depression and Anxiety, 37:224-233.
Domschke et al., 2015, "Magnetoencephalographic Correlates of Emotional Processing in Major Depression Before and After Pharmacological Treatment," The International Journal of Neuropsychopharmacology, 19(2):pyv093.
Dunn et al., 2005, "Does Lithium Therapy Protect Against the Onset of Dementia?" Alzheimer Disease & Associated Disorders, 19:20-22.
Emrich et al., 1983, "Therapeutic effects of GABA-ergic drugs in affective disorders. A preliminary report," Pharmacology, Biochemistry, and Behavior, 19(2):369-372.
Engber et al., 1998, "Differential Patterns of Regional C-Fos Induction in the Rat Brain by Amphetamine and the Novel Wakefulness-promoting Agent Modafinil," Neuroscience Letters, 241(2-3):95-98.
First et al., 1995a, "The structured clinical interview for DSM-III-R personality disorders (SCID-II). Part I: Description," Journal of Personality Disorders, 9:83-91.
Foster et al., 1983, "THIP Treatment of Huntington's Disease," Neurology, 33(5):637-639.
Friemel, 2007, "Postnatal development and kinetics of [3H] gaboxadol binding in rat brain: in vitro homogenate binding and quantitative autoradiography," Brain Research, 1170:39-47.
Gálvez et al., 2018, "Repeated intranasal ketamine for treatment-resistant depression—the way to go? Results from a pilot randomised controlled trial," Journal of Psychopharmacology, 32:397-407.
Gelenberg et al., 1989, "Comparison of Standard and Low Serum Levels of Lithium for Maintenance Treatment of Bipolar Disorder," New England Journal of Medicine, 321:1489-1493.
Grandjean et al., 2009, "Lithium: Updated Human Knowledge Using an Evidence-Based Approach: Part III: Clinical Safety," CNS Drugs, 23:397-418.
Greden, 2002, "Unmet need: what justifies the search for a new antidepressant?" Journal of Clinical Psychiatry 63:3-7.
Grunebaum et al., 2012, "Pilot randomized clinical trial of an SSRI vs bupropion: effects on suicidal behavior, ideation, and mood in major depression," Neuropsychopharmacology, 37:697-706.
Grunebaum et al., 2017, "Ketamine versus midazolam in bipolar depression with suicidal thoughts: A pilot midazolam controlled randomized clinical trial," Bipolar Disorders, 19:176-183.
Grunebaum et al., 2018, "Ketamine for Rapid Reduction of Suicidal Thoughts in Major Depression: A Midazolam-Controlled Randomized Clinical Trial," The American Journal of Psychiatry, 175(4):327-335.
Hamilton, 1960, "A rating scale for depression," Journal of Neurology, neurosurgery, and Psychiatry, 23:56-62.
Hammad et al., 2006, "Suicidality in pediatric patients treated with antidepressant drugs," Archives of general psychiatry, 63(3):332-339.
Harbeson et al., 2014, "Deuterium Medicinal Chemistry: A New Approach to Drug Discovery and Development," Medchem News, 2:8-22.

(56) References Cited

OTHER PUBLICATIONS

Harmer et al., 2009, "Effect of Acute Antidepressant Administration on Negative Affective Bias in Depressed Patients," The American Journal of Psychiatry, 166(10):1178-1184.

Herrera et al., 1996, "Activation of C-Fos in the Brain," Progress in Neurobiology, 50(2-3):83-107.

Hoehn-Saric, 1983, "Effects of THIP on Chronic Anxiety," Psychopharmacology, 80:338-341.

Holi et al., 2005, "Psychometric properties and clinical utility of the Scale for Suicidal Ideation (SSI) in adolescents," BMC Psychiatry, 5:1-8.

Horton et al., 2012, "Maximum Recommended Dosage of Lithium for Pregnant Women Based on a PBPK Model for Lithium Absorption," Advances in Bioinformatics, 2012:352729 (9 pages).

Hunt et al., 1987, "Induction of C-Fos-like Protean in Spinal Cord Neurons Following Sensory Stimulation," Nature, 328(6131):632-634.

International Preliminary Report on Patentability, dated May 25, 2021, for corresponding PCT Application No. PCT/US19/62554, filed Nov. 21, 2019 (1 page.).

International Preliminary Report on Patentability, dated May 25, 2021, for corresponding PCT Application No. PCT/US19/62644, filed Nov. 21, 2019 (1 page.).

International Search Report & Written Opinion of the International Searching Authority, dated Dec. 6, 2021, for corresponding PCT Application No. PCT/US2021/33315, filed May 20, 2021 (17 pages).

International Search Report and Written Opinion of the International Searching Authority, dated Feb. 4, 2020, for corresponding PCT Application No. PCT/US19/62554, filed Nov. 21, 2019 (8 pages).

International Search Report and Written Opinion of the International Searching Authority, dated Jan. 27, 2020, for corresponding PCT Application No. PCT/US19/62644, filed Nov. 21, 2019 (13 pages).

Ionescu et al., 2016, "Current Trends in Identifying Rapidly Acting Treatments in Depression," Curr. Behav. Neurosci. Rep., 3(2):185-191.

Ivkovic et al., 2014, "Lithium-induced Neurotoxicity: Clinical Presentations, Pathophysiology, and Treatment," Psychosomatics, 55:296-302.

Jain et al., 2010, "From Single Genes to Gene Networks: High-throughput-high-content Screening for Neurological Disease," Neuron, 68:207-217.

Judenhofer et al., 2008. "Simultaneous PET-MRI: a New Approach for Functional and Morphological Imaging," Nature Medicine, 14:459-465.

Kall et al., 2007, "Development and validation of a selective and sensitive bioanalytical procedure for the quantitative determination of gaboxadol in human plasma employing mixed mode solid phase extraction and hydrophilic interaction liquid chromatography with tandem mass spectroscopic detection," Journal of Chromatography B, 858:168-176.

Kasper et al., 2012, "Combining Escitalopram With Gaboxadol Provides No Additional Benefit in the Treatment of Patients With Severe Major Depressive Disorder," Int J Neuropsychopharmacol, 15(6):715-725.

Kato et al., 2007, "Animal Models of Bipolar Disorder," Neuroscience & Behavioral Reviews, 31:832-842.

Kessing et al., 2010, "Does Lithium Protect Against Dementia?" Bipolar Disorders, 12:87-94.

Kessing et al., 2018, "Effectiveness of Maintenance Therapy of Lithium vs Other Mood Stabilizers in Monotherapy and in Combinations: a Systematic Review of Evidence from Observational Studies," Bipolar Disorders, 20:419-431.

Kiss, 2018, "C-Fos Expression in the Hypothalamic Paraventricular Nucleus After a Single Treatment with a Typical Haloperidol and Nine Atypical Antipsychotics: A Pilot Study," Endocrine Regulations, 52(2):93-100.

Kjaer et al., 1983, "The analgesic effect of the GABA-agonist TRIP in patients with chronic pain of malignant origin. A phase-1-2 study," British Journal of Clinical Pharmacology, 16:477-485.

Korsgaard et al., 982, "The Effect of Tetrahydroisoxazolopyridinol (THIP) in Tardive Dyskinesia: A new Gamma-Aminobutyric Acid Agonist," Arch. Gen. Psychiatry, 39:1017-1021.

Krishnan and Nestler, 2011, "Animal Models of Depression: Molecular Perspectives," Current Topics Behavioral Neurosciences, 7:121-147.

Krogsgaard-Larsen et al., 1982, "Deuterium Labelling of the GABA Agonists THIP, Piperidine-4-sulphonic Acid and the GABA Uptake Inhibitor THPO," Journal of Labelled Compounds and Radiopharmaceuticals, XIX(5):689-702.

Krystal et al., 2019, "Rigorous Trial Design Is Essential to Understand the Role of Opioid Receptors in Ketamine's Antidepressant Effect—Reply," JAMA Psychiatry, 76(6):658-659.

Lamey et al., 1990, "Buccal and Sublingual Delivery of Drugs," Routes of Drug Administration. Ed. Florence and Salole (Butterworth-Heinemann), Chapter 2, pp. 30-47.

Lapidus et al., 2014, "A randomized controlled trial of intranasal ketamine in major depressive disorder," Biological Psychiatry, 76:70-76.

Larsen et al., 2010, "5-Hydroxy-l-tryptophan alters gaboxadol pharmacokinetics in rats: Involvement of PAT1 and rOat1 in gaboxadol absorption and elimination," Eur J Pharm Sci.; 39(1-3):68-75.

Levine et al., 1986, "SAFTEE: a technique for the systematic assessment of side effects in clinical trials," Psychopharmacology Bulletin, 22:343-381.

Ljubicic et al., 2008, "Lithium Treatments: Single and Multiple Daily Dosing," the Canadian Journal of Psychiatry, 53:323-334.

Lowe et al., 2020, "Ketamine treatment in depression: a systematic review of clinical characteristics predicting symptom improvement," Current topics in Medicinal Chemistry, 20:1398-1414.

Lucki et al., 2001, "Sensitivity to the effects of pharmacologically selective antidepressants in different strains of mice," Psychopharmacology (Berl), 155(3):315-322.

Lundahl et al., 2012, "EEG Spectral Power Density Profiles During NREM Sleep for Gaboxadol and Zolpidem in Patients with Primary Insomnia," Journal of Psychopharmacology, 26(8):1081-1087.

Madhusudham, 2014, "Nonconvulsive Status Epilepticus and Creutzfeldt-Jakob-like EEG Changes in a Case of Lithium Toxicity," Epilepsy & Behavior Case Reports, 2:203-205.

Mann, 2003, "Neurobiology of suicidal behavior," Natural Reviews Neuroscience 4(10):819-828.

Marcatoni et al., 2020, "A systematic review and meta-analysis of the efficacy of intravenous ketamine infusion for treatment resistant depression: Jan. 2009-Jan. 2019," Journal of Affective Disorders., 77:831-841.

Markou et al., 2009, "Removing Obstacles in Neuroscience Drug Discovery: the Future Path for Animal Models," Neuropsychopharmacology, 34:74-89.

McIntyre et al., 2021, "Synthesizing the evidence for ketamine and esketamine in treatment-resistant depression: an international expert opinion on the available evidence and implementation," American Journal of Psychiatry, 178(5):383-399.

Shahid et al. (eds.), 2012, "Manual for the Profile of Mood States (POMS)," Stop, That and One Hundred Other Sleep Scales, Chapter 68: 285-286.

Megarbane et al., 2014, "Lithium-related Neurotoxicity Despite Serum Concentrations in the Therapeutic Range: Risk Factors and Diagnosis," Shanghai Archives of Psychiatry, 26:243-244.

Meltzer et al., 2003, "Clozapine treatment for suicidality in schizophrenia: international suicide prevention trial (InterSePT)," Archives of General Psychiatry, 60(1):82-89.

Meuiner et al., 2004, "Mechanism of Oxidation Reactions Catalyzed by Cytochrome P450 Enzymes," Chem. Rev. 104(9):3947-3980.

Mohr et al., 1986, "GABA-agonist Therapy for Alzheimer's disease," Clinical Neuropharmacology, 9(3):257-263.

Mondrup et al., 1983, "The acute Effect of the GABA-Agonist, THIP, on Proprioceptive and Flexor Reflexes in Spastic Patients," Acta. Neurol. Scand., 67(1):48-54.

(56) References Cited

OTHER PUBLICATIONS

Muraki et al., 2001, "Effect of subchronic lithium treatment on citalopram-induced increases in extracellular concentrations of serotonin in the medial prefrontal cortex," J. Neurochem., 76(2):490-497.

Murrough et al., 2015, "Ketamine for Rapid Reduction of Suicidal Ideation: A Randomized Controlled Trial," Psychological Medicine, 45:571-580.

Muthukumaraswamy, 2014, "The use of magnetoencephalography in the study of psychopharmacology (pharmaco-MEG)," J Psychopharmacol., 28(9):815-829.

Muthukumaraswamy, 2015, "Differences between magnetoencephalographic (MEG) spectral profiles of drugs acting on GABA at synaptic and extrasynaptic sites: a study in healthy volunteers," Neuropharmacology, 88:155-163.

Nagar et al., 2011, "Orally disintegrating tablets: formulation, preparation techniques and evaluation," Journal of Applied Pharmaceutical Science, 1(4):35-45.

Naiman et al., 1981, "Practicality of a lithium dosing guide," Am. J. Psychiatry, 138(10):1369-1371.

Nunes et al., 2013, "Microdose Lithium Treatment Stabilized Cognitive Impairment in Patients with Alzheimer's Disease," Current Alzheimer Research, 10:104-107.

Nutt et al., 2015, "Differences Between Magnetoencephalographic (MEG) Spectral Profiles of Drugs Acting on GABA at Synaptic and Extrasynaptic Sites: A Study in Healthy Volunteers," Neuropharmacology, 88:155-163.

Öhlund et al., 2018, "Reasons for Lithium Discontinuation in Men and Women with Bipolar Disorder: A retrospective Cohort Study," BMC Psychiatry, 18:37 (10 pages).

Oquendo et al., 2008, "Issues for DSM-V: suicidal behavior as a separate diagnosis on a separate axis," Am J Psychiatry, 65(11):1383-1384.

Overall and Gorham, 1962, "The brief psychiatric rating scale," Psychological Reports, 10:799-812.

Pammolli et al., 2011, "The productivity Crisis in Pharmaceutical R&D," Nat. Rev. Drug Discovery, 10:428-438.

Perrin at al., 2007, "Secondary Deuterium Isotope Effects on the Acidity of Carboxylic Acids and Phenols," J. Am. Chem. Soc., 129(14):4490-4497.

Perrin et al., 2005, "Stereochemistry of β-Deuterium Isotope Effects on Amine Basicity," J. Am. Chem. Soc., 127(26):9641-9647.

Perry et al., 1981, "Lithium kinetics in single daily dosing," Acta. Psychiatr. Scand., 64(4):281-294.

Pochwat et al., 2019, "An updated on NMDA antagonists in depression," Expert Review of Neurotherapeutics, 19(11):1055-1067.

Porsolt et al., 1977, "Depression: a new animal model sensitive to antidepressant treatments," Nature, 266:730-732.

Post, 2018, "The New News About Lithium: An Underutilized Treatment in the United States," Neuropsychopharmacology, 43:1174-1179.

Price et al., 2009, "Effects of intravenous ketamine on explicit and implicit measures of suicidality in treatment-resistant depression," Biological Psychiatry, 66:522-526.

Price et al., 2014, "Effects of ketamine on explicit and implicit suicidal cognition: A randomized controlled trial in treatment-resistant depression," Depression and Anxiety, 31:335-343.

Quartini ct al., 2016, "Lithium: From Mood Stabilizer to Putative Cognitive Enhancer," Neural Regeneration Research, 11:1234-1235.

Rej et al., 2014, "Lithium Dosing and Serum Concentrations Across the Age Spectrum: From Early Adulthood to the Tenth Decade of Life," Drugs & Aging, 31:911-916.

Renier et al., 2016, "Mapping of Brain Activity by Automated Volume Analysis of Immediate Early Genes," Cell, 165(7):1789-1802.

Roberts et al., 2017, "The Evidence for Lithium in Suicide Prevention," The British Journal of Psychiatry, 211:1-396.

Roose et al., 1983, "Depression, delusions, and suicide," Am. J. Psychiatry, 140(9):1159-1162.

Roth et al., 2010, "Effect of Gaboxadol on Patient-Reported Measures of Sleep and Waking Function in Patients with Primary Insomnia: Results From two Randomized, Controlled, 3-Month Studies," Journal of Clinical Sleep Medicine, 6(1):30-39.

Rybakowski et al., 2010, "Excellent Lithium responders Have Normal Cognitive Functions and Plasma BDNF Levels," International Journal of Neuropsychopharmacology, 13:617-622.

Salminen et al., 1996, "Expression of Fos Protein in Various Rat Brain Areas Following Acute Nicotine and Diazepam," Pharmacology Biochemistry and Behavior, 54(1):241-248.

Sani et al., 2017, "Treatment of Bipolar Disorder in a Lifetime Perspective: Is Lithium Still the Best Choice?" Clinical Drug Investigation, 37:713-727.

Schou et al., 1968, "Lithium Poisoning," American Journal of Psychiatry, 125:520-527.

Schramm et al., 2007, "Binding isotope effects: boon and bane," Current Opinion in Chemical Biology, 11(5):529-536.

Schultz et al., 1981, "Preliminary Studies on the Absorption, Distribution, Metabolism, and Excretion of THIP in Animal and Man using 14C-labelled Compound," Acta Pharmacological ct Toxicologica, 49(2):116-124.

Schwartz et al., 2009, "Enzymatic transition states and dynamic motion in barrier crossing," 5:511-558.

Scott ct al., 2017, "Cross-validation of Clinical Characteristics and Treatment Patterns Associated with Phenotypes for Lithium Response Defined by the Alda Scale," Journal of Affective Disorders, 208:62-67.

Sechzer et al., 1986, "Aberrant parenting and delayed offspring development in rats exposed to lithium," Biological Psychiatry, 21:1258-1266.

Semba et al., 1996, "Differential expression of c-fos mRNA in rat prefrontal cortex, striatum, N. accumbens and lateral septum after typical and atypical antipsychotics: an in situ hybridization study," Neurochem. Int., 29(4):435-442.

Severus et al., 2014, "Lithium for Prevention of Mood Episodes in Bipolar Disorders: Systematic Review and Meta-Analysis," International Journal of Bipolar Disorders, 2:15-31.

Shepard et al., 2016, "Suicide and Suicidal Attempts in the United States: Costs and Policy Implications," Suicide Life Threat Behav., 46(3):352-362.

Sienaert et al., 2013, "How to initiate lithium therapy: a systematic review of dose estimation and level prediction methods," J. Affect Disord., 146(1):15-33.

Singh et al. 2011, "Improving tolerability of lithium with a once-daily dosing schedule," Am. J. Ther., 18(4):288-291.

Slattery et al., 2005, "Comparison of Alterations in C-fos and Egr-1 (zif268) Expression Throughout the Rat Brain Following Acute Administration of Different Classes of Antidepressant Compounds," Neuropsychopharmacology, 30(7):1278-1287.

Sleigh et al., 2014, "Ketamine—More Mechanisms of Action than Just NMDA Blockade," Trends in Anaesthesia and Critical Care, 4:76-81.

Sumner et al., 2004, "Testing the validity of c-fos expression profiling to aid the therapeutic classification of psychoactive drugs," Psychopharmacology (Berl), 171(3):306-321.

Tiihonen et al., 2016, "Real-World Effectiveness of Pharmacological Treatments in Severe Unipolar Depression in a Nationwide Cohort of 123,712 Patients," American College of Neuropsychopharmacology. Poster.

Toffol et al., 2015, "Lithium is associated with decrease in all-cause and suicide mortality in high-risk bipolar patients: A nationwide registry-based prospective cohort study," J. Affect Disord., 183:159-165.

Turowski et al., 2003, "Deuterium Isotope Effects on Hydrophobic Interactions: The Importance of Dispersion Interactions in the Hydrophobic Phase," J. Am. Chem. Soc., 125(45):13836-13849.

Uher et al., 2010, "Trajectories of change in depression severity during treatment with antidepressants," Psychological Medicine, 40(8):1367-1377.

Vita et al., 2015, "Lithium in drinking water and suicide prevention: a review of the evidence," Int. Clin. Psychopharmacol., 30(1):1-5.

(56) References Cited

OTHER PUBLICATIONS

Wang et al., 2017, "The recent progress in animal models of depression," Progress in Neuro-Psychopharmacology and Biological Psychiatry, 77:99-109.

Wesseloo et al., 2017, "Lithium Dosing Strategies During Pregnancy and the Postpartum Period," The British Journal of Psychiatry, 211:31-36.

Wheatley and Key, 2007, "Use of Deuterium Labeling Studies to Determine the Stereochemical Outcome of Palladium Migrations during an Asymmetric Intermolecular Heck Reaction," Journal of Organic Chemistry, 72(19):7253-7259.

Witte et al., 2006, "Factors of suicide ideation and their relation to clinical and other indicators in older adults," Journal of Affective Disorders, 94:165-172.

Won et al., 2017, "An Oldie but Goodie: Lithium in the Treatment of Bipolar Disorder Through Neuroprotective and Neurotrophic Mechanisms," International Journal of Molecular Sciences, 18:2679-2695.

Zhou et al., 2020, "Predictors of response to repeated ketamine infusions in depression with suicidal ideation: an ROC curve analysis," Journal of Affective Disorders, 264:263-271.

\* cited by examiner

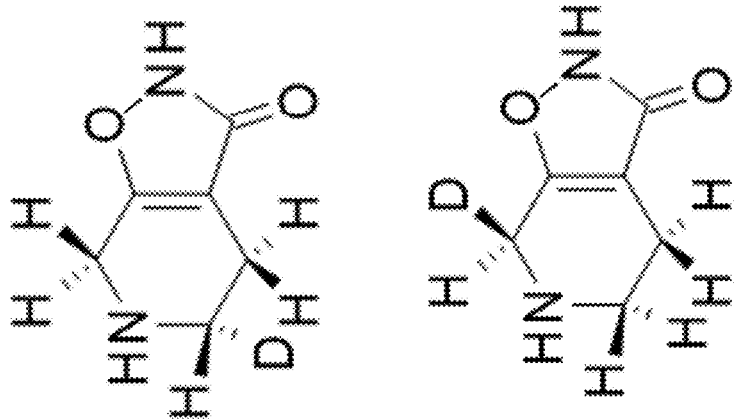
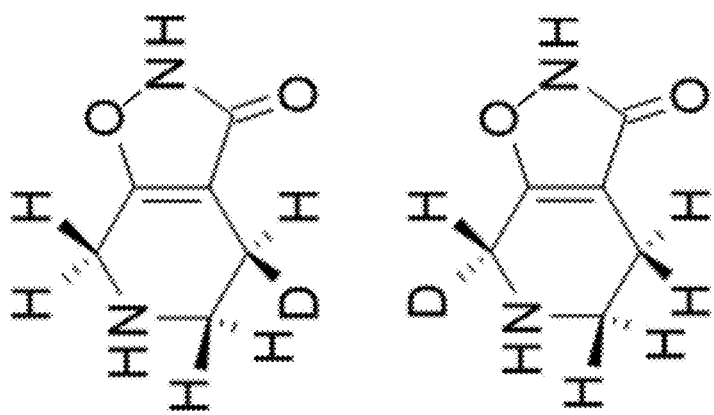
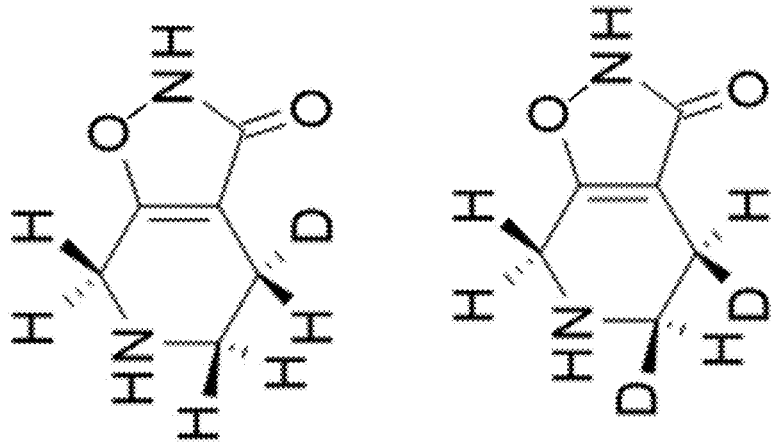
FIG. 1A

FIG. 1B
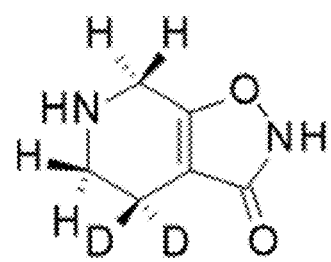 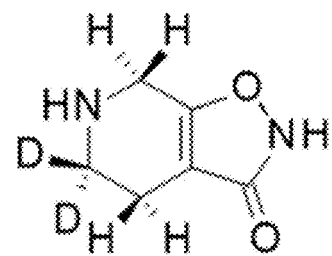 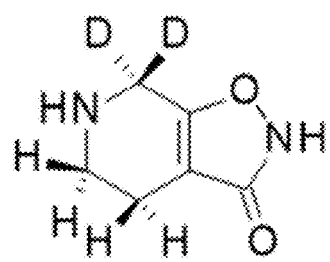
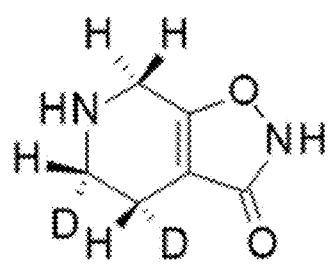 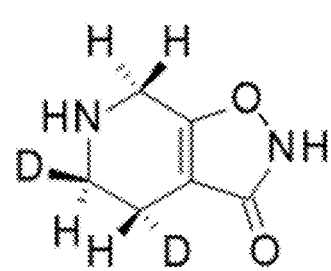 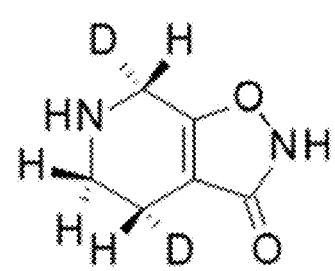
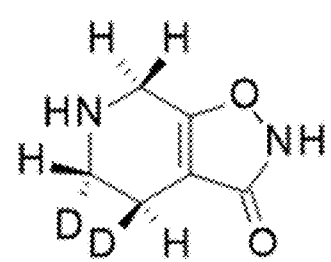 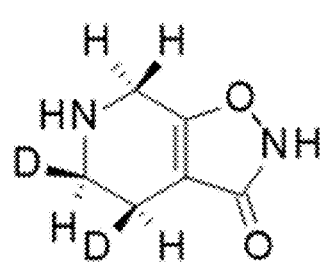 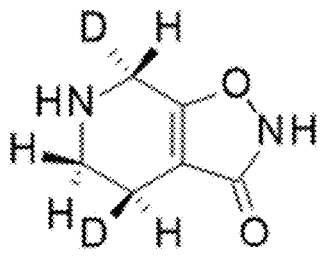
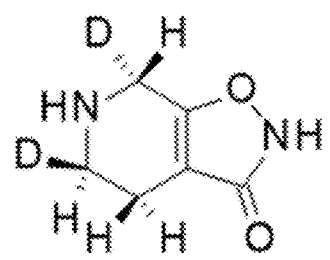 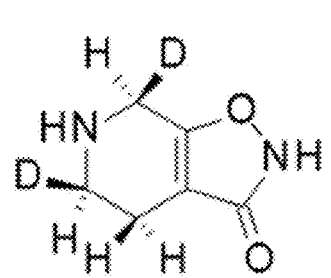 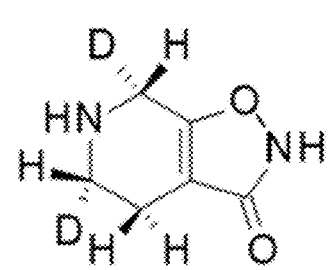

FIG. 2
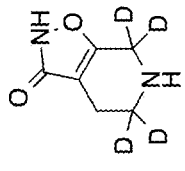 4,5,6,7-tetrahydroisoxazolo[5,4-c]pyridin-3(2H)-one-5,5,7,7-$d_4$
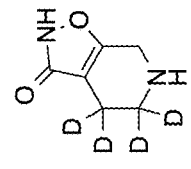 4,5,6,7-tetrahydroisoxazolo[5,4-c]pyridin-3(2H)-one-4,4,5,5-$d_4$
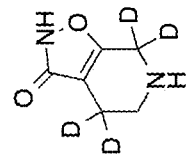 4,5,6,7-tetrahydroisoxazolo[5,4-c]pyridin-3(2H)-one-4,4,7,7-$d_4$
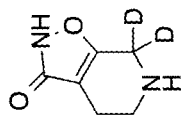 4,5,6,7-tetrahydroisoxazolo[5,4-c]pyridin-3(2H)-one-7,7-$d_2$
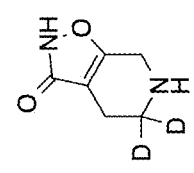 4,5,6,7-tetrahydroisoxazolo[5,4-c]pyridin-3(2H)-one-5,5-$d_2$
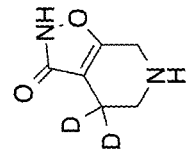 4,5,6,7-tetrahydroisoxazolo[5,4-c]pyridin-3(2H)-one-4,4-$d_2$
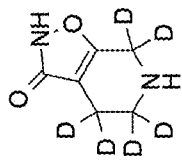 4,5,6,7-tetrahydroisoxazolo[5,4-c]pyridin-3(2H)-one-4,4,5,5,7,7-$d_6$
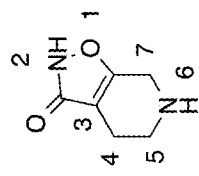

Synthesis of Gaboxadol-d2

Synthesis of Gaboxadol-d4

Synthesis of Gaboxadol-d6

FIG. 18
A    ILA
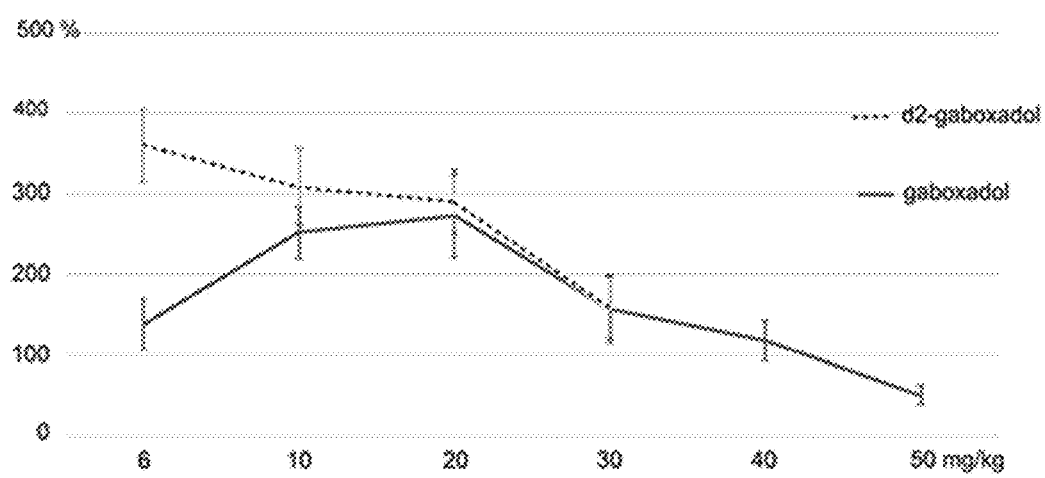
ILA
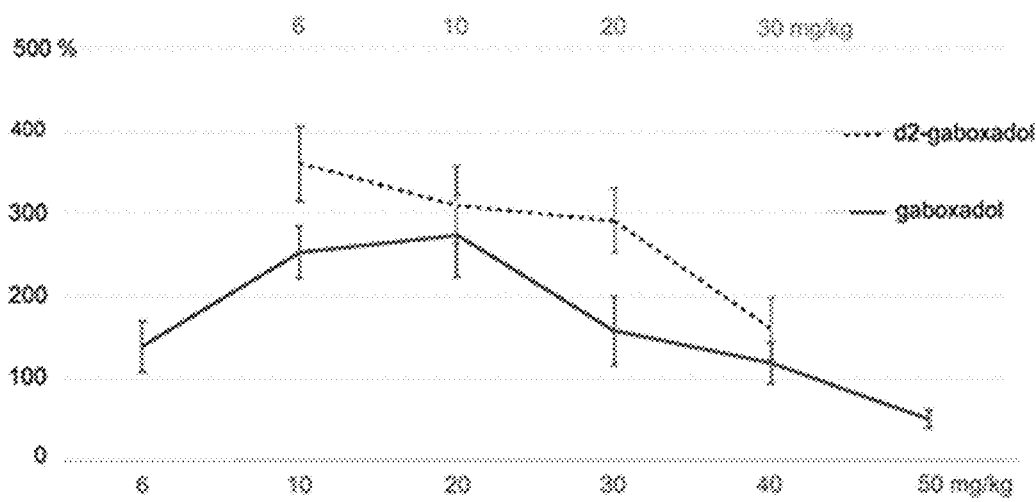

FIG. 18 (continued)
B
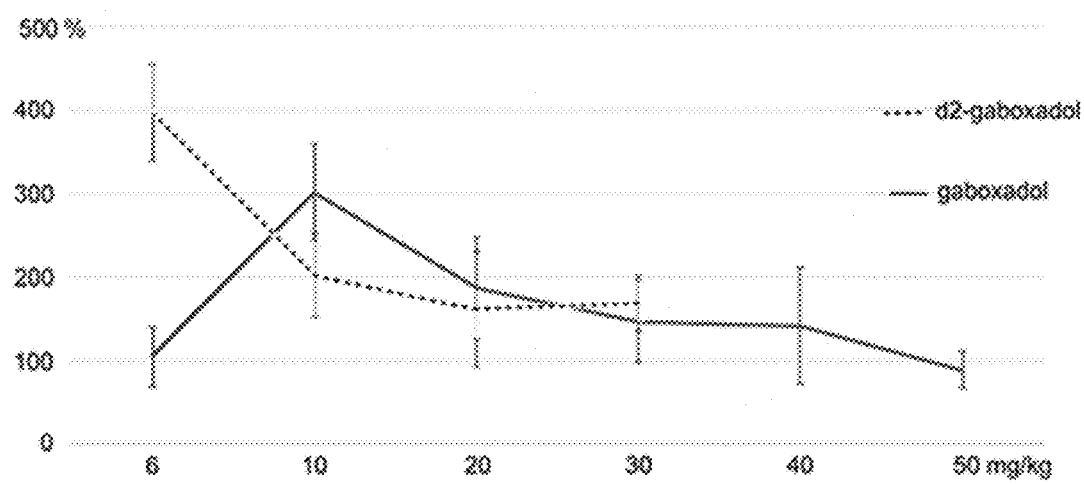
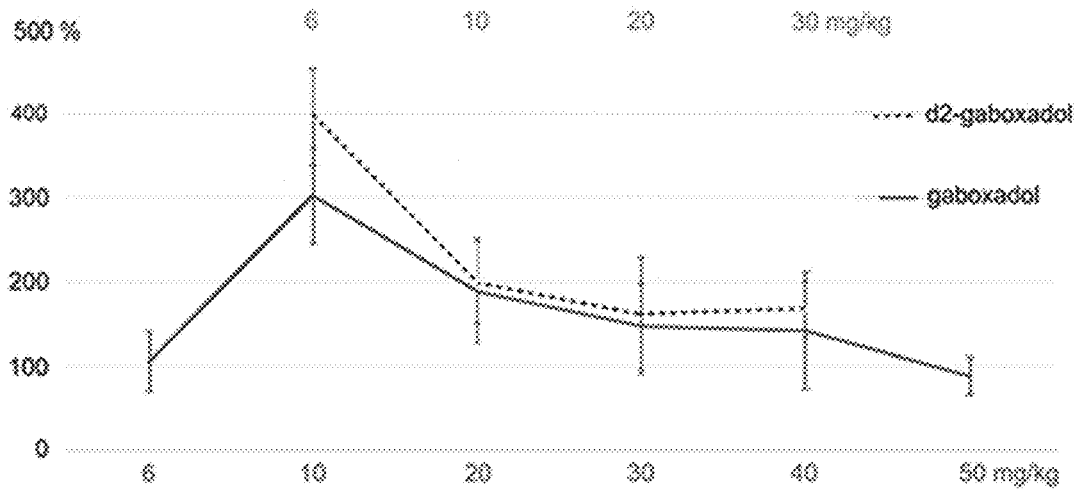

FIG. 19
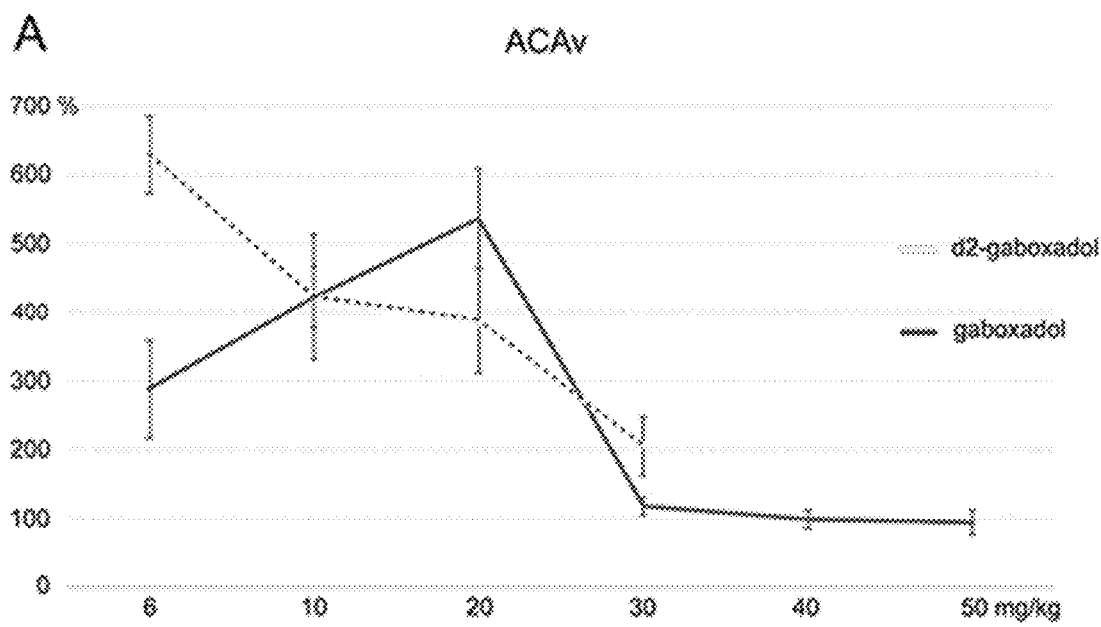
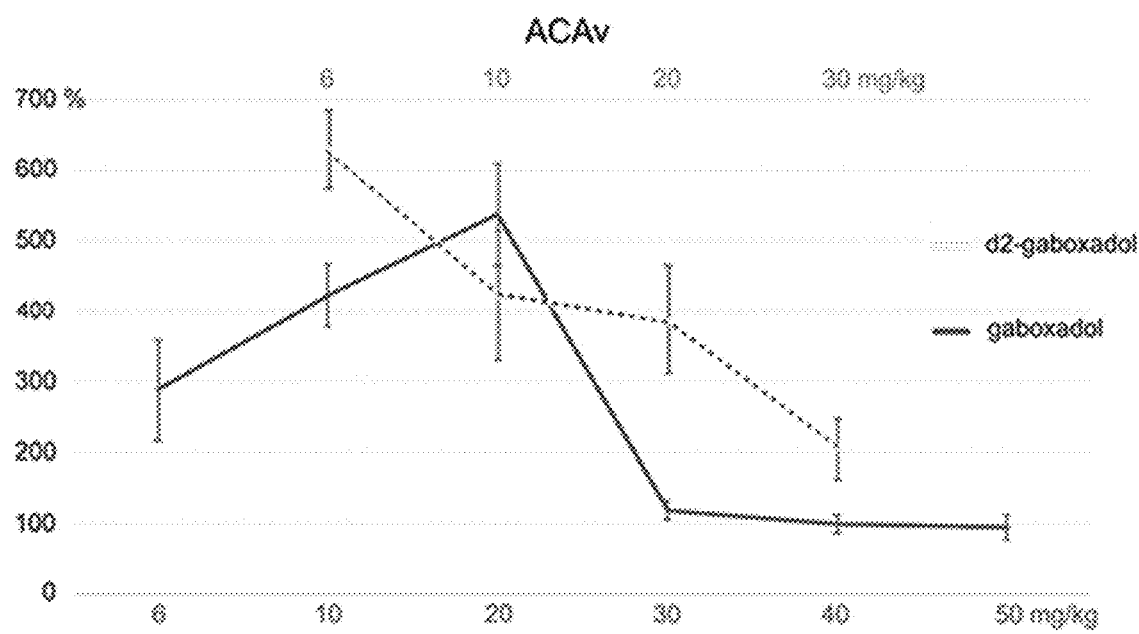

FIG. 19 (continued)
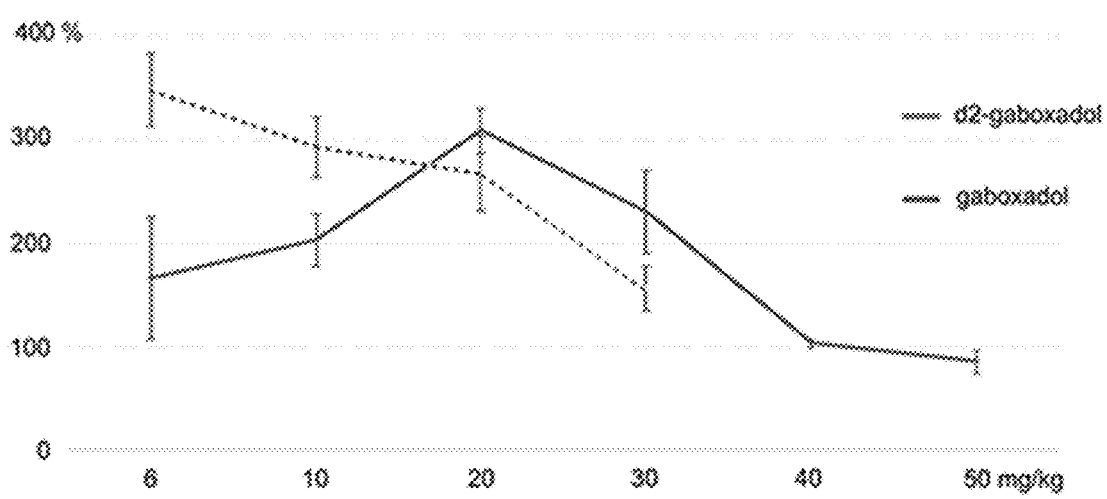
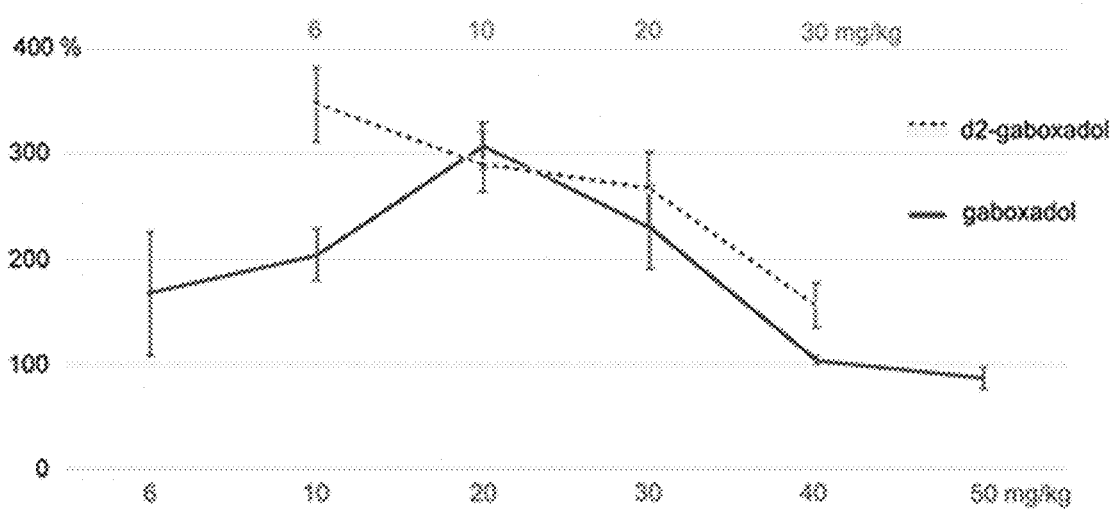

Figure 25: Ketamine dose-curve pharmacomaps.
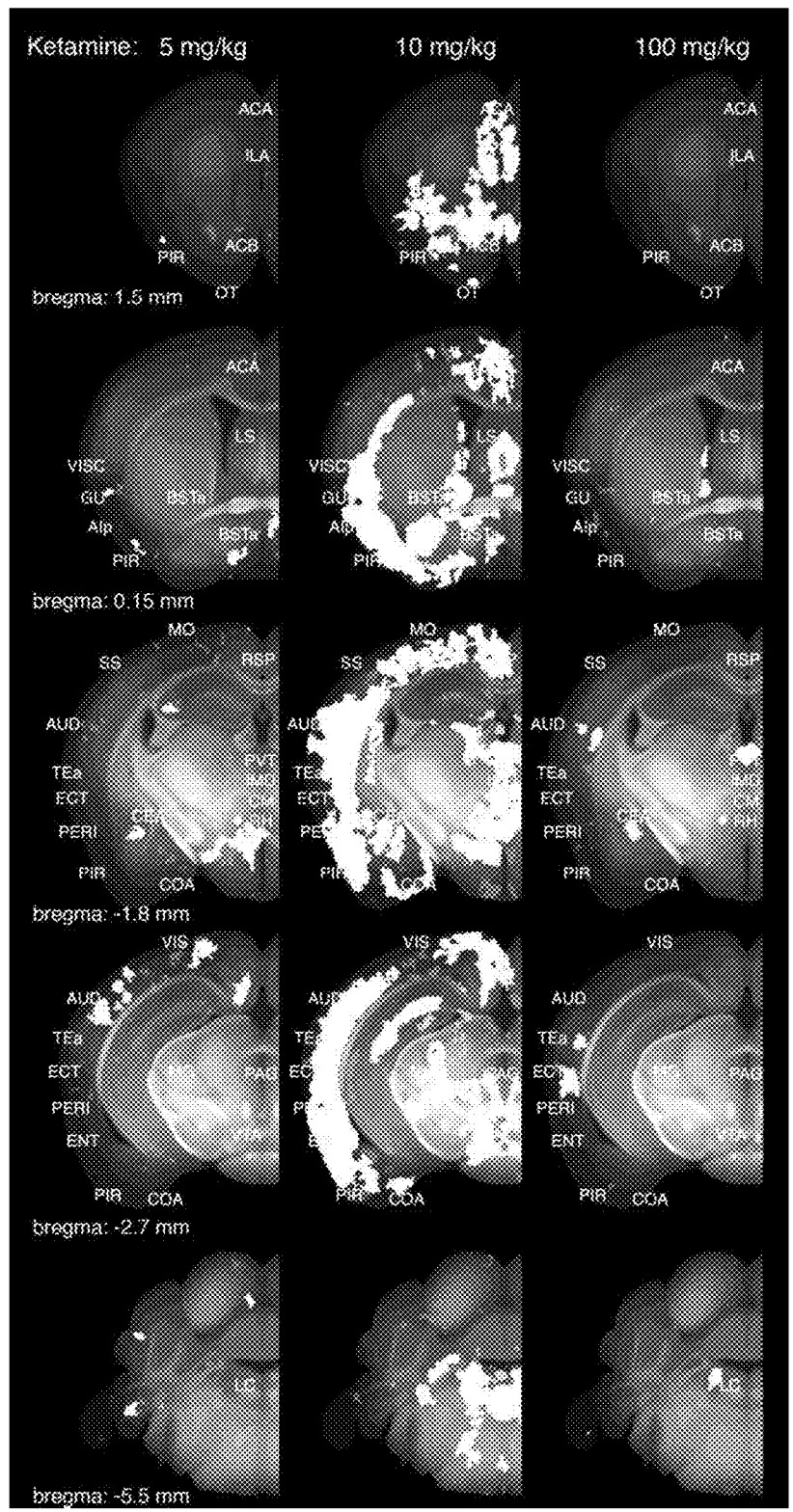

Figure 26: Gaboxadol and Ketamine side-by-side pharmacomap comparison
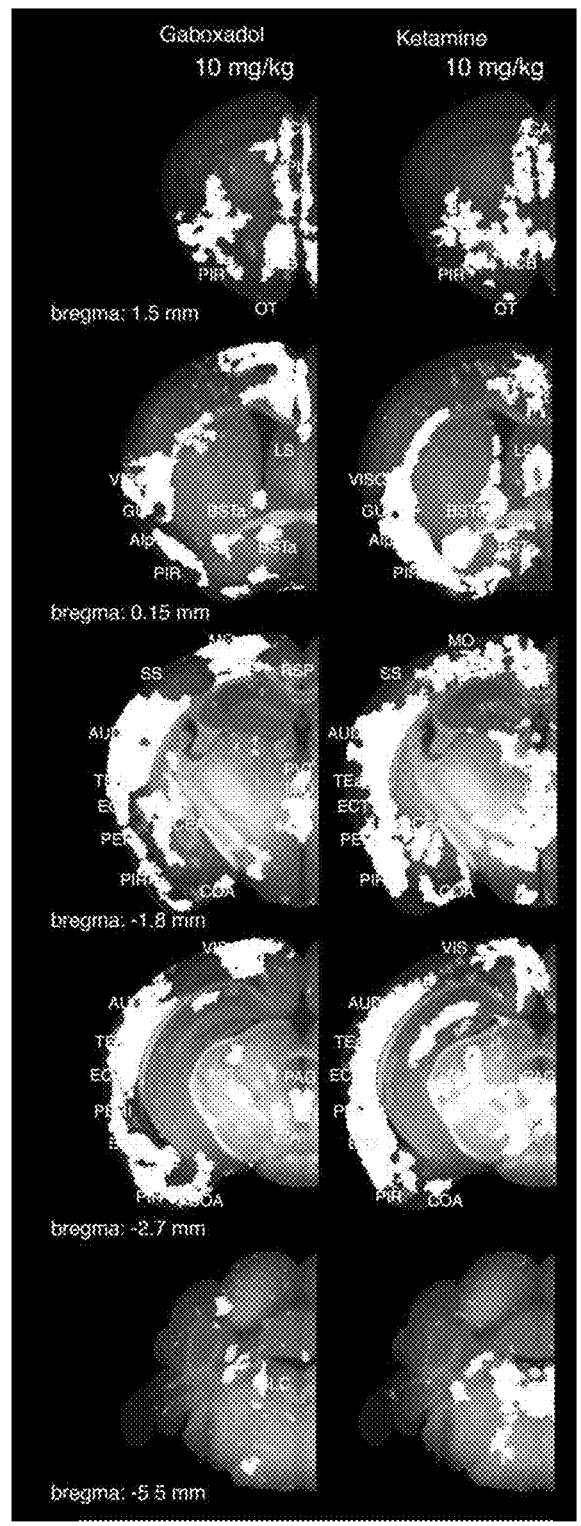

Figure 27A: Synergistic effect of co-application of gaboxadol and ketamine at sub-threshold doses
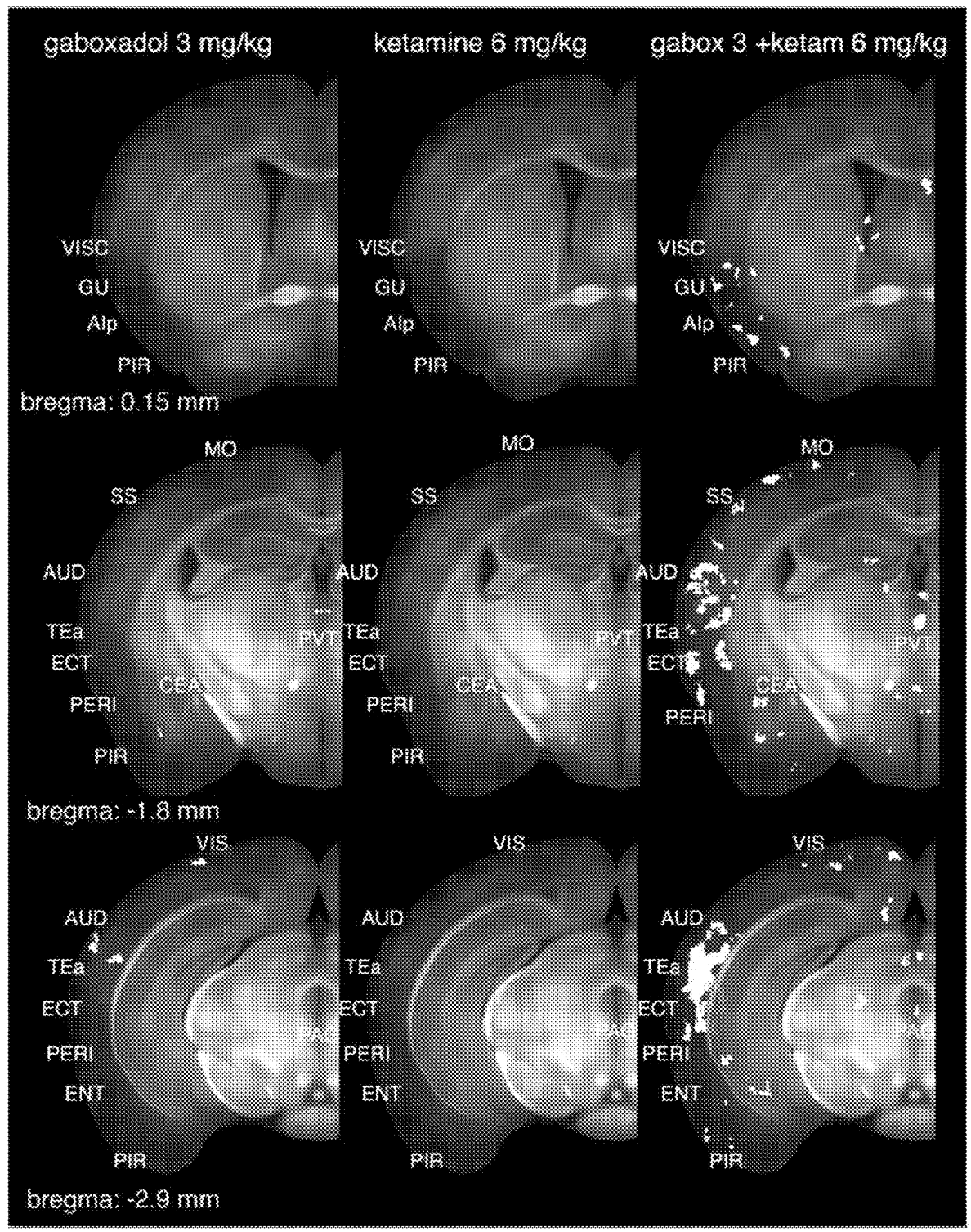

Figure 27B: Synergistic effect of co-application of gaboxadol and ketamine at sub-threshold doses
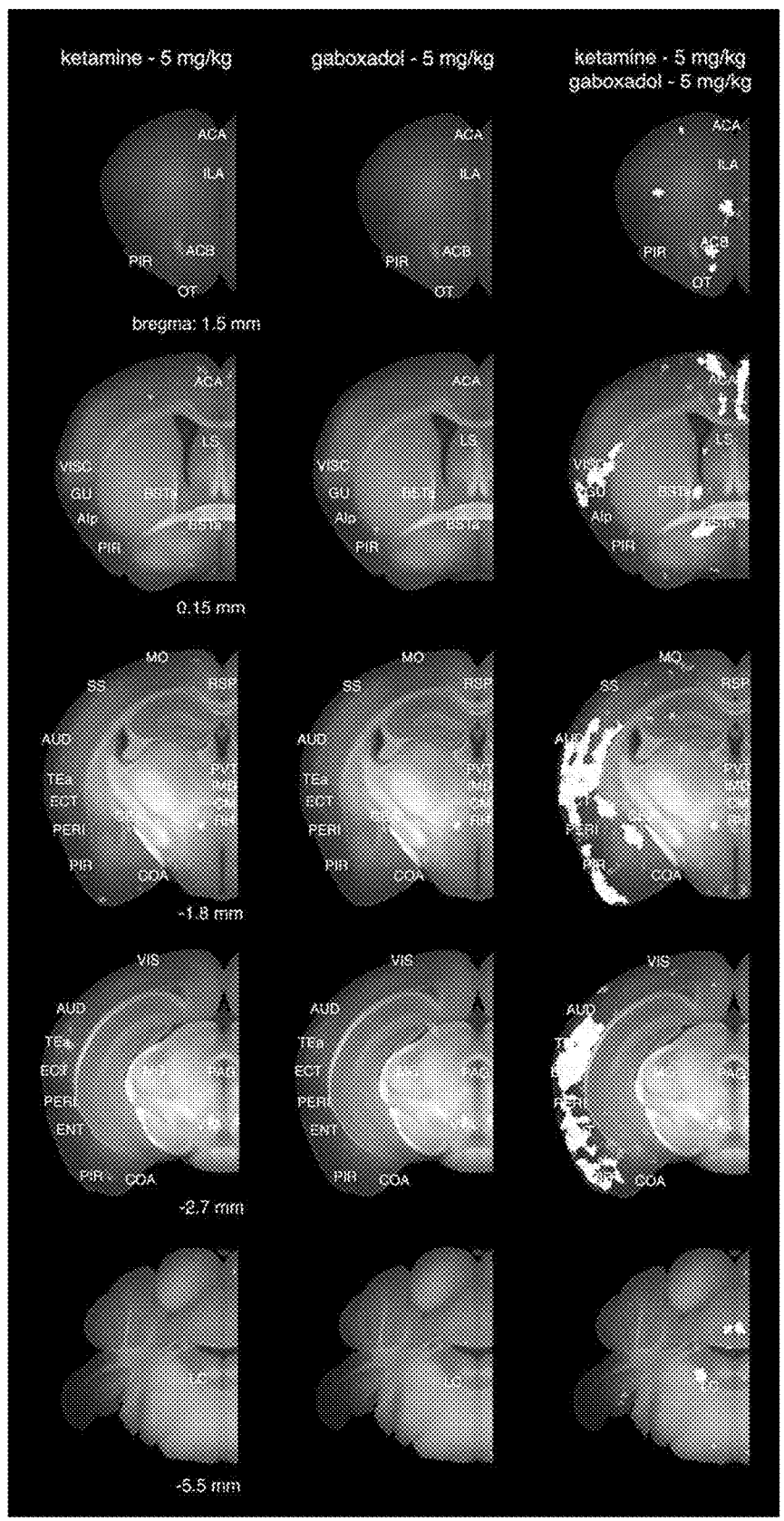

Figure 28: Forced Swim Test
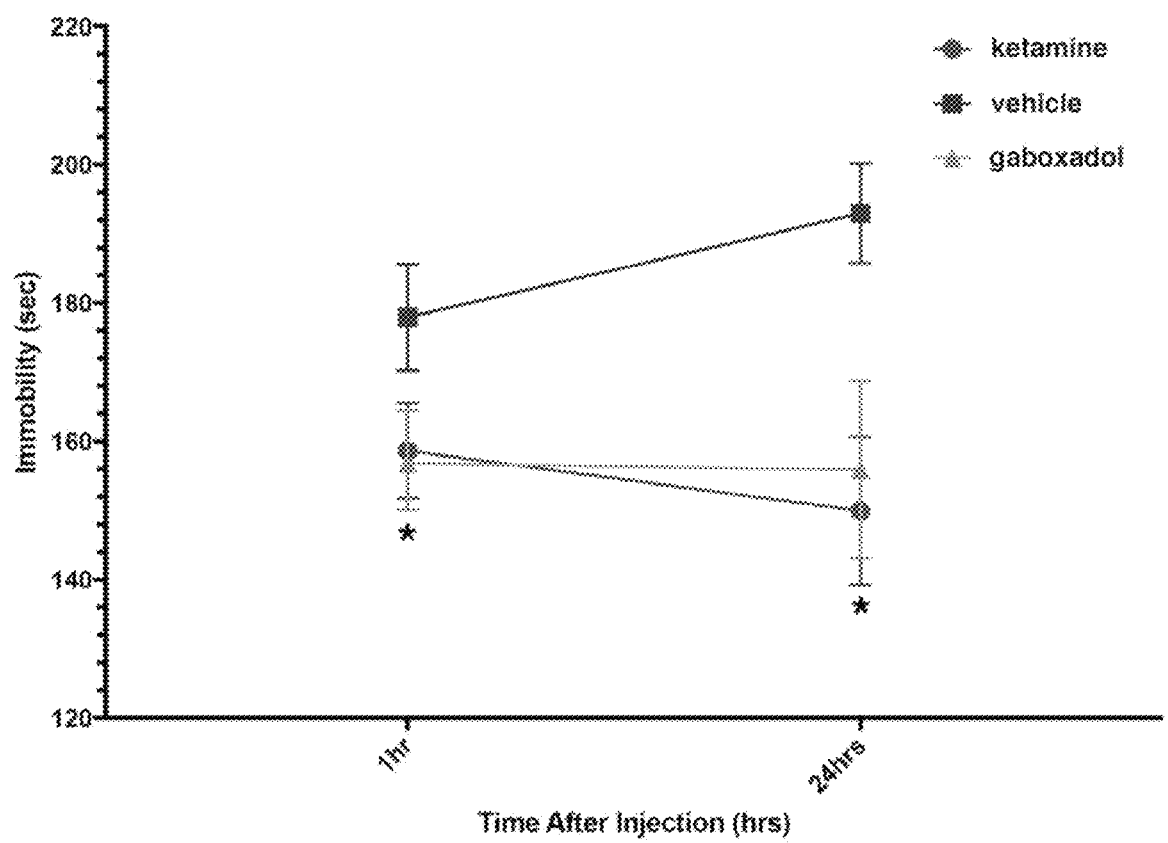

RING DEUTERATED GABOXADOL AND ITS USE FOR THE TREATMENT OF PSYCHIATRIC DISORDERS

CROSS-REFERENCES TO RELATED APPLICATIONS

This application claims the benefit of U.S. Provisional Patent Application No. 63/027,923 filed May 20, 2020, U.S. Provisional Patent Application No. 63/027,953 filed May 20, 2020, U.S. Provisional Patent Application No. 63/028,457 filed May 21, 2020, U.S. Provisional Patent Application No. 63/028,472 filed May 21, 2020, each of which is incorporated herein by reference in its entirety.

FIELD OF THE INVENTION

This invention relates to methods and compositions for treating psychiatric disorders using an effective dose of deuterated gaboxadol, or a pharmaceutically acceptable salt thereof, alone or in combination with other drugs, such as ketamine and/or lithium, for subjects in need thereof, and relates to deuterated gaboxadol, the synthesis of deuterated gaboxadol and compositions comprising deuterated gaboxadol for making medicaments useful in therapy.

BACKGROUND OF THE INVENTION

According to the World Health Organization, depression is the leading cause of disability and ill health in the world affecting more than 300 million people worldwide and costing the global economy an estimated $1 trillion in lost productivity each year. The Centers for Disease Control (CDC) estimate that in the U.S. alone, 20-25% of all adults aged 18 and older and 10.9% of young adults aged 18-25 experience at least one episode of major depression each year. Left untreated, mental diseases, like major depression, are a major contributor to suicide in the U.S which takes the lives of more than 47,000 Americans every year or one death by suicide every 11 minutes (Shepard et al., Suicide Life Threat Behav. (2016) 46(3):352-62.). There is one suicide for every estimated 25 suicide attempts which means each year there are an estimated quarter million people who become suicide survivors. Hence, there is a critical unmet need for medications for the treatment of psychiatric disorders such as suicidal ideation and treatment-resistant depression (TRD).

Psychiatric disorders are common in across the world and in the United States, with nearly one in five U.S. adults estimated to experience a mental illness (over 50 million in 2019), with the highest prevalence of mental illness seen among females and young adults aged 18-25 years, including (alphabetically) Agoraphobia, Anorexia Nervosa, Any Anxiety Disorder, Attention-Deficit/Hyperactivity Disorder (ADHD), Autism Spectrum Disorder (ASD), Binge Eating Disorder, Bipolar Disorder, Borderline Personality Disorder, Bulimia Nervosa, Dementia, Eating Disorders, Generalized Anxiety Disorder, Major Depression, Obsessive-Compulsive Disorder (OCD), Panic Disorder, Persistent Depressive Disorder (Dysthymic Disorder), Personality Disorders, Post-Traumatic Stress Disorder (PTSD), Postpartum Depression, Schizophrenia, Social Anxiety Disorder, Social and other Specific Phobias and Treatment-resistant Depression (TRD). It is widely observed that psychopharmacological agents used to treat psychiatric disorders have only modest efficacy and considerable side-effects. Hence, there is a critical unmet need for medications for the treatment of psychiatric disorders.

Gaboxadol, also called gaboxadolum, or THIP (4,5,6,7-tetrahydroisoxazolo (5,4-c) pyridin-3-ol; $C_6H_8N_2O_2$; Cas Number: 64603-91-4; PubChem CID: 3448) is a selective $GABA_A$ receptor agonist with a preference for δ-subunit containing $GABA_A$ receptors. In the early 1980s gaboxadol was the subject of a series of pilot studies that tested its efficacy as an analgesic and anxiolytic, as well as a treatment for tardive dyskinesia, Huntington's disease, Alzheimer's disease (Mohr, Bruno et al. Clin Neuropharmacol. 1986; 9(3):257-63) and spasticity. In the 1990s gaboxadol moved into late stage development for the treatment of insomnia. The development was discontinued after the compound failed to show significant effects in sleep onset and sleep maintenance in a three-month efficacy study (ClinicalTrials.gov Identifier: NCT00209963). Methods of treating depression with gaboxadol are disclosed in WO2004112786, which is incorporated by reference herein in its entirety.

A clinical trial has been undertaken to investigate the efficacy of gaboxadol in the treatment of symptoms of Angelman Syndrome (a developmental disorder) (ClinicalTrials.gov Identifier: NCT02996305) (Cogram, Deacon et al. 2019). Patent applications on related subject matter include U.S. Pat. No. 9,744,159, published US Patent Application No. 2017/348232 and WIPO International Patent Application WO2017015049, the contents of which are incorporated herein by reference in their entireties.

A clinical trial by Lundbeck reported at ClinicalTrials.gov Identifier: NCT00807248 treated 490 patients with daily oral doses of escitalopram (20 mg) and gaboxadol (5 mg or 10 mg). The trial found that oral gaboxadol at this amount provided no additional benefit relative to escitalopram alone in the treatment of patients with severe major depressive disorder. A report on this trial is found at Kasper et al (2012) Int J Neuropsychopharmacol. 2012 July; 15(6):715-25. The trial did not test the effect of gaboxadol alone.

Gaboxadol (4,5,6,7-tetrahydroisoxazolo[5,4-c]pyridine-3-ol) (THIP)) is also described in EP Patent No. 0000338 EP 0840601, EP1641456, U.S. Pat. Nos. 4,278,676, 4,362,731, 4,353,910, and WO 2005/094820, the contents of which are hereby incorporated by reference herein in their entireties.

Effects of deuteration are described in (Harbeson and Tung, 2014; Perrin and Dong, 2007; Perrin et al., 2005; Turowski et al., 2003). Binding isotope effects can contribute positively or negatively to a measured deuterium kinetic isotope effect (DIE) (Schramm, 2007; Schwartz and Schramm, 2009). These DIE changes are primarily due to the increase in energy required for the cleavage of the carbon-deuterium (C-D) covalent bond than the energy required to cleave the carbon-hydrogen (C—H) bond. The primary DIE can be expressed as kH/kD, the ratio of the rate of C—H vs. C-D bond-cleavage (Harbeson and Tung, 2014). Such DIE effect can be expected for example in drug metabolism by cytochrome P450s (CYPs) (Meunier et al., 2004). Gaboxadol is not metabolized by CYPs and the majority (84-93%) of the drug is excreted in the form of unchanged, unmetabolized drug and a glucuronic acid conjugate in urine (Schultz et al., 1981).

Citation of a reference, including publications, patents, and patent applications, herein shall not be construed as an admission that such reference is prior art to the present invention.

SUMMARY OF THE INVENTION

Treatment of psychiatric disorders by administering compounds to patients in need of therapy requires compounds that are useful in eliciting favorable responses from patients. The use of deuterated gaboxadol addresses this need by providing a compound that elicits a higher response in the brain of patients compared to non-deuterated gaboxadol. Deuterated gaboxadol can be administered to patients along with additional compounds to provide additive or synergistic responses in patients.

The present invention provides gaboxadol that has deuterium present at ring carbon positions of the tetrahydropyridine ring of the molecule. Ring carbon deuterated d2-gaboxadol 7,7 and d6-gaboxadol are herein shown to elicit higher levels of brain activation in particular brain areas of interest than equivalent doses of non-deuterated gaboxadol as measured by whole brain activation studies in mice, thereby indicating for the first time that ring carbon deuterated gaboxadol may be a superior agent for treating psychiatric disorders.

The present disclosure, as shown in the Examples, describes that the administration of deuterated gaboxadol is a more pharmacologically effective treatment than an equivalent dose of gaboxadol and evokes a broad brain activation pattern which is very similar to ketamine, at lower doses than gaboxadol, with some key differences that are presumed to be related to a better safety profile of gaboxadol.

In addition, as shown in the Examples below, brain imaging in mice also shows additive and synergistic effects between gaboxadol and ketamine, suggesting that even though the drugs act at very different molecular targets, their downstream effect leads to a shared brain circuit-based mechanism For the purposes of the description herein, the terms "ring carbon deuterated gaboxadol" and "deuterated gaboxadol" and "deuterated gaboxadol compound" are used interchangeably to refer to forms of gaboxadol enriched with deuterium above the naturally occurring abundance of deuterium (i.e., deuterium occurs in place of hydrogen in all molecules in nature at approximately 0.0156%, the natural abundance of deuterium) and having deuterium atoms at one or more of the ring carbon positions of the tetrahydropyridine ring of gaboxadol (i.e., positions 4, 5 and 7). Individual forms of deuterated gaboxadol including forms having 1 to 6 deuterium atoms are described below. In a specific embodiment, the ring carbon deuterated gaboxadols of the present invention are synthesized to incorporate deuterium, at one or more of the 6 hydrogen positions associated with the ring carbons of the tetrahydro-pyridine ring of gaboxadol, for example, by any of the methods provided herein or using processes known in the art.

In one aspect, the invention provides methods of treating a psychiatric disorder by administering to a patient in need thereof a pharmaceutical composition comprising a therapeutically effective amount of deuterated gaboxadol or a pharmaceutically acceptable salt thereof, in a specific embodiment administering about 1 mg to about 300 mg of deuterated gaboxadol or a pharmaceutically acceptable salt thereof.

Embodiments of the therapeutic aspects of this invention include a method of treatment comprising administering deuterated gaboxadol. As used herein, treatment and therapy can be interchangeable. A course of therapy can include a first administration of deuterated gaboxadol and an additional administration or multiple additional administrations of deuterated gaboxadol. In this type of course of therapy, as used herein, the initial administration can be referred to as a prior administration and the additional administration(s) can be referred to as a subsequent administration(s). As used herein, a "first administration" or "initial administration" or "prior administration" can be used interchangeably, and also can be referred to as a "prior administration" when a subsequent administration is contemplated. Herein, "additional administration" or "subsequent administration" can be used interchangeably.

A specific embodiment of the invention provides methods of treating a psychiatric disorder (in a particular embodiment, reducing risk of suicide and/or treating depression, e.g., achieving rapid relief of depression or one or more depression symptoms) comprising administering to a patient in need thereof an effective amount of deuterated gaboxadol, or a pharmaceutically acceptable salt thereof, sufficient to treat the psychiatric disorder, to reduce the risk of suicide and/or to treat the depression (e.g., by achieving relief of one or more depression symptoms). The deuterated gaboxadol of the present invention can be administered alone or in combination with other drugs.

A specific embodiment of the invention is a method of treating a psychiatric disorder (in a particular embodiment, reducing risk of suicide and/or treating depression, e.g., achieving rapid relief of depression or one or more symptoms of depression) comprising administering to a patient in need thereof a single dose treatment of about 1 mg to about 300 mg, and preferably 1 mg to about 200 mg, and more preferably 50 mg to 100 mg deuterated gaboxadol, or a pharmaceutically acceptable salt thereof, wherein the treatment provides improvement in the patient within 1 day.

In a specific embodiment, the method of treating is to achieve rapid relief or rapid onset of treatment effect of the psychiatric disorder, e.g. of one or more symptoms of the psychiatric disorder, where rapid relief, rapidly alleviate or rapid onset of treatment effect is relief or onset of treatment effect within 24 hours or 12 hours or 6 hours or 2 hours after administering the deuterated gaboxodal to the patient.

In a particular embodiment, the method of treatment comprises performing an initial administration of deuterated gaboxadol or a pharmaceutically acceptable salt thereof and optionally, additional administration(s) of deuterated gaboxadol, where an additional, subsequent administration is done within about 12 hours immediately following the prior, initial administration, preferably within about 6 hours, and most preferably within about 180 minutes of the initial administration. The optional second administration, sometimes referred to as a subsequent administration, may be administered if a clinical test of the patient demonstrates insufficient response in the 160 minutes immediately after the first administration. In one embodiment, the insufficient response is an EEG power density increase of less than 30% at the time point about 160 minutes after the first administration. The EEG power density is preferably calculated in the 4.75-8.0 Hz range. Alternatively, the insufficient response may be a whole head MEG planar gradiometer increase of less +3 in the combined delta, theta and alpha activity at the time point about 160 minutes after the first administration. The additional administration comprises deuterated gaboxadol up to the remainder of the maximum total first dose of 200-300 mg. Insufficient response may also mean failure to achieve a specified blood level of gaboxadol.

In certain embodiments, the method of treatment comprises performing an initial administration of deuterated gaboxadol or a pharmaceutically acceptable salt thereof and optionally performing additional administration(s) of non-deuterated gaboxadol, or a pharmaceutically acceptable salt thereof, within about 12 hours immediately following the initial administration of deuterated gaboxadol, preferably within about 6 hours, and most preferably within about 180 minutes of the initial administration, if an insufficient response is noted.

In certain embodiments, the method of treatment comprises performing an initial administration of gaboxadol or a pharmaceutically acceptable salt thereof and optionally performing an additional administration(s) of deuterated gaboxadol, or a pharmaceutically acceptable salt thereof, within about 12 hours immediately following the initial administration of gaboxadol, if an insufficient response is noted.

In a specific embodiment, provided is a method for reducing an imminent risk of suicide in a patient suffering from acute suicidality comprising administering a single dose of 10 to 200 mg deuterated gaboxadol, or a pharmaceutically acceptable salt thereof, to the patient, optionally wherein the dose reduces the incidence of suicidal ideation within about 24 hours of the administration.

In a specific embodiment, provided is a method of treating a psychiatric disorder, e.g, reducing risk of suicide or achieving a rapid relief from depression, comprising administering to a patient in need thereof a first pharmaceutical composition comprising deuterated gaboxadol or a pharmaceutically acceptable salt thereof and a second pharmaceutical composition comprising ketamine, SAGE-217, tiagabine, clozapine, and/or gaboxadol and pharmaceutically acceptable salts thereof. The second pharmaceutical composition can be administered concurrently, contemporaneously or sequentially.

In certain embodiments, deuterated gaboxadol and ketamine are each provided at a synergistic dose and may be administered contemporaneously, concurrently, or sequentially, and in the same or separate pharmaceutical compositions.

A specific embodiment of the invention is a therapy for reducing a risk of suicide and/or treating depression, e.g., achieving a rapid relief of depression or one or more symptoms of depression, comprising performing a first administration of deuterated gaboxadol, or a pharmaceutically acceptable salt thereof, to a patient in need thereof in an amount sufficient to reduce the risk of suicide and/or to treat depression, e.g., to rapidly alleviate depressive symptoms, and optionally, performing an additional administration(s) of deuterated gaboxadol, or a pharmaceutically acceptable salt thereof, within less than about 6 hours immediately following the first administration, and if the patient experiences a recurrence of the risk of suicide and/or depressive symptoms, performing additional administration (s).

In certain embodiments, the first administration comprises administration of gaboxadol, or a pharmaceutically acceptable salt thereof, and the additional administration(s) comprises the administration of deuterated gaboxadol, or a pharmaceutically acceptable salt thereof.

In certain embodiments, the first administration comprises administration of deuterated gaboxadol, or a pharmaceutically acceptable salt thereof, and the additional administration(s) comprises the administration of gaboxadol, or a pharmaceutically acceptable salt thereof.

In certain embodiments, one or more additional administrations are provided at 1, 2, 3, 4, 5, 6 or 7 days after the first administration.

In certain embodiments, the optional second or additional administration is performed if a neurological test of the patient demonstrates an insufficient response within about 180 minutes immediately after the first administration.

In certain embodiments, the insufficient response is an electroencephalogram (EEG) power density increase of less than 30% over baseline within about 180 minutes after the first administration or a whole head magnetoencephalography (MEG) planar gradiometer increase of less than +3 in a combined delta, theta and alpha activity within about 180 minutes after the first administration.

In certain embodiments, the electroencephalogram (EEG) power density is calculated in a 0.25-8.0 Hz range or in a 4.75-8.0 Hz range.

In certain embodiments, the electroencephalogram (EEG) power density is calculated in a Sigma (11.5-15.0 Hz), Beta-1 (15.5-20.0 Hz), Beta-2 (20.5-25.0 Hz) or Beta-3 (25.5-32.0 Hz) range.

In certain embodiments, the optional second or additional administration(s) of deuterated gaboxadol, gaboxadol, or a pharmaceutically acceptable salt thereof, is performed if a neurological test of the patient demonstrates an insufficient response within about 30, about 60, about 90 or about 120 minutes immediately after the first administration.

In certain embodiments, the insufficient response is an electroencephalogram (EEG) power density increase of less than 30% over baseline within about 180 minutes after the first administration or a whole head magnetoencephalography (MEG) planar gradiometer increase of less than +3 in a combined delta, theta and alpha activity within about 30, about 60, about 90 or about 120 minutes after the first administration.

In certain embodiments, the method provides improvement in at least one symptom of risk of suicide, wherein the symptom can be, but is not limited to suicidal ideation, acute suicidality, recurrent thoughts of death, action(s) towards suicide, suicide attempt(s), risk of self-harm and/or treatment-resistant depression.

In certain embodiments, the patient has not been previously treated with, or is not currently being treated with, or is not responding to, an anti-depressive treatment.

In certain embodiments, the first and/or an additional administration comprises about 1 mg to about 300 mg, preferably about 1 mg to about 200 mg, deuterated gaboxadol or a pharmaceutically acceptable salt thereof.

In certain embodiments, the first and/or an additional administration comprises about 1 mg to about 300 mg deuterated gaboxadol or a pharmaceutically acceptable salt thereof.

In certain embodiments, the first and/or an additional administration comprises about 1 mg to about 20 mg deuterated gaboxadol or a pharmaceutically acceptable salt thereof.

In certain embodiments, the first and/or an additional administration comprises about 5 mg to about 10 mg deuterated gaboxadol or a pharmaceutically acceptable salt thereof.

In certain embodiments, the first and/or an additional administration comprises about 50 mg, 75 mg or 100 mg deuterated gaboxadol or a pharmaceutically acceptable salt thereof.

In certain embodiments, the first and/or an additional administration is of an oral dosage form. In certain embodiments, the oral dosage form is an orally disintegrating form.

In certain embodiments, the first and/or an additional administration is performed intranasally.

In certain embodiments, a plasma $T_{max}$ of deuterated gaboxadol is achieved within 45 minutes after the first administration.

In certain embodiments, the method further comprises additionally administering to the patient, before, after or concurrently with the first administration, any one of: lithium, ketamine, AXS-05 (fixed combination of dextromethorphan and bupropion), SAGE-217, allopregnanolone, ganaxolone, alfadolone, alfaxolone, hydroxydione, minaxolone, pregnanolone, renanolone, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, clozapine, and [2-amino-4-(2,4,6-trimethylbenzylamino)-phenyl]-carbamic acid ethyl ester (AA29504), and a pharmaceutically acceptable salt of any of the foregoing.

In certain embodiments, the therapy comprises administering in combination a dose of deuterated gaboxadol, or a pharmaceutically acceptable salt thereof, together with a dose of a second pharmaceutical agent, wherein the dose of deuterated gaboxadol, or a pharmaceutically acceptable salt thereof, is about 20 mg or less, and the effect of the combination is additive or synergistic with respect to administration of the agents separately and not in combination.

In certain embodiments, the therapy comprises concurrently administering a synergistic dose of deuterated gaboxadol, or a pharmaceutically acceptable salt thereof, together with a synergistic dose of ketamine wherein the synergistic dose of deuterated gaboxadol, or a pharmaceutically acceptable salt thereof, is about 20 mg or less and the synergistic dose of ketamine is about 10 mg or less.

In certain embodiments, the synergistic dose of deuterated gaboxadol, or a pharmaceutically acceptable salt thereof, is about 20 mg, about 19 mg, about 18 mg, about 17 mg, about 16 mg, about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, about 1 mg or less.

In certain embodiments, a synergistic dose of ketamine is about 10 mg, about 9 mg, about 8 mg, about 7 mg, about 6 mg, about 5 mg, about 4 mg, about 3 mg, about 2 mg, about 1 mg or less than about 1 mg.

In certain embodiments, provided herewin is a use of deuterated gaboxadol alone for the manufacture of a medicament for the treatment of a psychiatric disorder including but not limited to reducing risk of suicide in a patient at risk of suicide, treatment resistant depression and/or rapidly alleviate depressive symptoms.

An aspect of this invention includes methods and compositions wherein deuterated gaboxadol can act synergistically with lithium to enhance lithium's action on brain signaling activity. In particular, the combination of a sub-standard dose range of lithium (e.g. <600 mg per day) with deuterated gaboxadol is believed to reduce the amount of lithium needed to treat psychiatric disorders, such as bipolar disorder (both in acute mania and long-term maintenance), depression, treatment resistant depression and suicidality potentially without the aforementioned side effects, especially chronic side-effects, such as nephrotoxicity and chronic kidney disease. Thus, co-administration of deuterated gaboxadol and a sub-standard dose of lithium lowers the risks of side-effects and is expected to facilitate the management of bipolar disorder and other psychiatric disorders responsive to lithium treatment. In addition, a standard dose range of lithium (e.g. 600 mg to 1800 mg, with a daily maximum dose of 2400 mg) also is believed to synergize or, in certain embodiments, to act additively, with deuterated gaboxadol, indicating that adding deuterated gaboxadol to a standard dose of lithium may prove useful for the augmentation of the response to lithium in treatment-resistant patients who do not initially respond to conventional lithium monotherapy.

In an aspect of this invention, a synergistic combination comprises deuterated gaboxadol and lithium, or a pharmaceutically acceptable salt of either or both compounds thereof.

In certain embodiments, provided herein is a synergistic combination in a pharmaceutical composition comprising deuterated gaboxadol another compound, such as lithium, or a pharmaceutically acceptable salt of either or both compounds thereof and a pharmaceutically acceptable carrier.

In certain embodiments, provided herein is a synergistic combination that is a pharmaceutical composition comprising deuterated gaboxadol, or a pharmaceutically acceptable salt thereof and a second pharmaceutical composition comprising lithium, or a pharmaceutically acceptable salt thereof and a pharmaceutically acceptable carrier.

In certain embodiments, wherein deuterated gaboxadol and lithium are given in combination, the lithium is given in a sub-standard dose that when administered daily to a subject in need thereof is ineffective at treating bipolar disorder, depression, treatment-resistant depression or suicidality.

In certain embodiments, wherein deuterated gaboxadol and lithium are given in combination, the lithium is given in a sub-standard dose that when administered daily to a subject in need thereof, is below the medically recommended dose for treating bipolar disorder, depression, treatment-resistant depression, or suicidality.

In certain embodiments, wherein deuterated gaboxadol and lithium are given in combination, the lithium is given in a dose that is an animal equivalent of a sub-standard dose of lithium that is ineffective at activating c-fos signaling in an animal model's brain as measured by Pharmacomapping.

In preclinical testing, the sub-standard lithium human dose range can be established and differentiated from the standard dose range, for example, by mapping lithium-induced brain activation, represented by the visualization of the induction of the immediate early gene (IEG) c-fos, in an animal such a mouse or rat, or by recording lithium-induced changes in an animal's electroencephalogram (EEG).

In certain embodiments of this aspect, the sub-standard dose of lithium is in the range from about 50 to about 600 mg lithium carbonate per day.

In certain embodiments of this aspect, deuterated gaboxadol is given at a human dose that, when given to an animal such as a mouse or rat at an animal equivalent dose (AED), fails to evoke or evokes only a low or moderate induction of c-fos activity in the brain as measured by Pharmacomapping. In a specific embodiment, low induction of c-fos activity in the brain is indicated by activation of one to two cortical areas, such as anterior cingulate (ACA) and retrosplenial (RSP) cortex and/or one to three subcortical areas, such as bed nuclei stria terminalis (BST), central amygdala (CEA), and locus coeruleus (LC). In a specific embodiment, moderate induction of c-fos activity in the brain is indicated by activation of three to six cortical areas, such as ACA, RSP, gustatory (GU), visceral (VISC), auditory (AUD) and visual (VIS) cortex and/or four to six subcortical areas, such as BST, CEA, LC, nucleus of reunions (RE), romboid nucleus (RH) and central medial nucleus (CM) of the thalamus.

In certain embodiments of this aspect, the dose of deuterated gaboxadol administered is in the range from about 1 to about 15 mg, about 15 to about 30 mg, or about 30 to about 300 mg deuterated gaboxadol per day for an adult human.

In certain embodiments of this aspect, the lithium is given at a standard dose of lithium.

In certain embodiments of this aspect, the standard dose range of lithium is in the range from about 600 to about 1800 mg, with a daily maximum dose of 2400 mg, of lithium carbonate per day for an adult human.

In certain embodiments of this aspect, the deuterated gaboxadol is given as a dose which, when given to an animal such as a mouse or rat at an animal equivalent dose (AED), evokes a strong induction of c-fos activity in the brain. In a specific embodiment, strong induction of c-fos activity in the brain is indicated by activation of more than 6 cortical areas, such as ACA, RSP, GU, VISC, AUD, VIS, motor (MO), agranular insular (AI), somatosensory (SS), prelimbic (PL) and infralimbic (ILA), parietal (PTL), temporal associational (TEa), ectorhinal (ECT), entorhinal (ENT), perirhinal (PERI), and piriform (PIR) cortex and claustrum (CLA) and/or more than 6 subcortical areas, such as BST, CEA, LC, RE, RH, CM, hippocampal CA1 region, cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), paraventricular hypothalamic nucleus (PVH), dorsomedial nucleus of the hypothalamus (DMH), tuberomammillary nucleus (TM), parasubthalamic nucleus (PSTN) and subthalamic nucleus (STN), parabrachial nucleus, and nucleus of the solitary tract (NTS).

In certain embodiments of this aspect, the amounts of lithium and deuterated gaboxadol administered daily to a subject in need thereof, are synergistically effective at inducing IEG c-fos signaling in at least one region of a subject's cortical brain selected from the group consisting of motor (MO), gustatory (GU), visceral (VISC), agranular insular (AI), somatosensory (SS), auditory, visual (VIS), auditory (AUD), prelimbic (PL) and infralimbic (ILA), retrosplenial (RSP), parietal (PTL), temporal associational (TEa), ectorhinal (ECT), entorhinal (ENT), perirhinal (PERI), piriform (PIR), and anterior cingulate (ACA) cortex, and claustrum (CLA).

In certain embodiments of this aspect, the amounts of lithium and deuterated gaboxadol administered daily to a subject in need thereof, are synergistically effective at inducing IEG c-fos signaling in at least two regions of a subject's cortical brain selected from the group consisting of motor (MO), gustatory (GU), visceral (VISC), agranular insular (AI), somatosensory (SS), auditory, visual (VIS), auditory (AUD), prelimbic (PL) and infralimbic (ILA), retrosplenial (RSP), parietal (PTL), temporal associational (TEa), ectorhinal (ECT), entorhinal (ENT), perirhinal (PERI), piriform (PIR), and anterior cingulate (ACA) cortex, and claustrum (CLA).

In certain embodiments of this aspect, the amounts of lithium and deuterated gaboxadol administered daily to a subject in need thereof, are synergistically effective at inducing IEG c-fos signaling in at least three regions of a subject's cortical brain selected from the group consisting of motor (MO), gustatory (GU), visceral (VISC), agranular insular (AI), somatosensory (SS), auditory, visual (VIS), auditory (AUD), prelimbic (PL) and infralimbic (ILA), retrosplenial (RSP), parietal (PTL), temporal associational (TEa), ectorhinal (ECT), entorhinal (ENT), perirhinal (PERI), piriform (PIR), and anterior cingulate (ACA) cortex, and claustrum (CLA).

In certain embodiments of this aspect, the amounts of lithium and deuterated gaboxadol administered daily to a subject in need thereof, are synergistically effective at inducing IEG c-fos signaling in at least one region of a subject's subcortical brain selected from the group consisting of hippocampal CA1 region, the bed nuclei stria terminalis (BST), central amygdala (CEA), cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), nucleus of reunions (RE), rhomboid nucleus (RH), and central medial nucleus (CM) of the thalamus, paraventricular hypothalamic nucleus (PVH), dorsomedial nucleus of the hypothalamus (DMH), tuberomammillary nucleus (TM), parasubthalamic nucleus (PSTN) and subthalamic nucleus (STN), parabrachial nucleus, locus coeruleus (LC), and nucleus of the solitary tract (NTS).

In certain embodiments of this aspect, the amounts of lithium and deuterated gaboxadol administered daily to a subject in need thereof, are synergistically effective at inducing IEG c-fos signaling in at least two regions of a subject's subcortical brain selected from the group consisting of hippocampal CA1 region, the bed nuclei stria terminalis (BST), central amygdala (CEA), cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), nucleus of reunions (RE), rhomboid nucleus (RH), and central medial nucleus (CM) of the thalamus, paraventricular hypothalamic nucleus (PVH), dorsomedial nucleus of the hypothalamus (DMH), tuberomammillary nucleus (TM), parasubthalamic nucleus (PSTN) and subthalamic nucleus (STN), parabrachial nucleus, locus coeruleus (LC), and nucleus of the solitary tract (NTS).

In certain embodiments of this aspect, the amounts of lithium and deuterated gaboxadol administered daily to a subject in need thereof, are synergistically effective at inducing IEG c-fos signaling in at least three regions of a subject's subcortical brain selected from the group consisting of hippocampal CA1 region, the bed nuclei stria terminalis (BST), central amygdala (CEA), cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), nucleus of reunions (RE), rhomboid nucleus (RH), and central medial nucleus (CM) of the thalamus, paraventricular hypothalamic nucleus (PVH), dorsomedial nucleus of the hypothalamus (DMH), tuberomammillary nucleus (TM), parasubthalamic nucleus (PSTN) and subthalamic nucleus (STN), parabrachial nucleus, locus coeruleus (LC), and nucleus of the solitary tract (NTS).

In certain embodiments of this aspect, the amount of deuterated gaboxadol another compound, such as lithium, when administered daily to a subject in need thereof, are synergistically effective at treating the subject's psychiatric disorder selected from the group consisting of bipolar disorder, depression, treatment resistant depression and suicidality.

In certain embodiments of this aspect, the treatment of the subject's psychiatric disorder is effective at improving a score of at least one psychiatric rating scale specific for bipolar disorder, depression, treatment resistant depression or suicidality.

In certain embodiments of this aspect, the deuterated gaboxadol another compound, such as lithium, when administered to a subject diagnosed with depression, are synergistically effective at increasing the subject's Montgomery-Asberg Depression Rating Scale (MADRS) score.

In certain embodiments of this aspect, the deuterated gaboxadol another compound, such as lithium, when administered to a subject in need thereof, are synergistically effective at increasing a score of at least one psychiatric rating scale specific for bipolar disorder, depression, treatment resistant depression or suicidality.

In certain embodiments of this aspect, the deuterated gaboxadol another compound, such as lithium, when administered to a subject in need thereof, are synergistically effective at increasing a score of at least two psychiatric rating scales specific for bipolar disorder, depression, treatment resistant depression or suicidality.

In certain embodiments of this aspect, the deuterated gaboxadol another compound, such as lithium, when administered to a subject in need thereof, are synergistically effective at increasing a score of at least three psychiatric rating scales specific for bipolar disorder, depression, treatment resistant depression or suicidality.

In certain embodiments of this aspect, the lithium, when administered daily to a subject in need thereof, is in an amount sufficient to maintain the serum level of lithium in the range of about 0.2 to about 1.2 mmol/L.

In certain embodiments of this aspect, the lithium, when administered daily to a subject in need thereof, is in an amount sufficient to maintain the subject's serum level of lithium in the range of about 0.4 to about 0.8 mmol/L.

In another aspect of this invention, a pharmaceutical composition is disclosed that comprises any one of the preceding embodiments of the synergistic combination of lithium and deuterated gaboxadol.

In certain embodiments of this aspect, the pharmaceutical composition is in the form of a single tablet for oral consumption.

In certain embodiments of this aspect, the pharmaceutical composition is in a form of a controlled release formulation.

In certain embodiments of this aspect, the pharmaceutical composition is in a form of an oral dose formulation.

In certain embodiments of this aspect, the pharmaceutical composition further comprises one or more inert pharmaceutically acceptable excipients.

In certain embodiments of this aspect, the pharmaceutical composition is in the form of a single dosage unit having separate compartments for the lithium and deuterated gaboxadol or a pharmaceutically acceptable salt of either or both compounds thereof.

In another aspect, a kit is disclosed that comprises any one of the preceding pharmaceutical compositions.

In another aspect, a method is disclosed for treating a subject in need thereof comprising administering any one of the previous embodiments of the synergistic combination of lithium and deuterated gaboxadol.

In certain embodiments of this aspect, the subject is diagnosed with a psychiatric disorder.

In certain embodiments of this aspect, the psychiatric disorder is chosen from bipolar disorder, depression, treatment-resistant depression or suicidality.

In certain embodiments of this aspect, the combination reduces at least one adverse side effect selected from the group consisting of nephrotoxicity, nephrogenic diabetes insipidus, chronic kidney disease, diarrhea, hand tremor, increased thirst, increased urination, vomiting, weight gain, impaired memory, poor concentration, drowsiness, muscle weakness, hair loss, acne and decreased thyroid function.

In certain embodiments of this aspect, the combination reduces at least two adverse side effects selected from the group consisting of nephrotoxicity, nephrogenic diabetes insipidus, chronic kidney disease, diarrhea, hand tremor, increased thirst, increased urination, vomiting, weight gain, impaired memory, poor concentration, drowsiness, muscle weakness, hair loss, acne and decreased thyroid function In certain embodiments of this aspect, the combination reduces at least three adverse side effects selected from the group consisting of nephrotoxicity, nephrogenic diabetes insipidus, chronic kidney disease, diarrhea, hand tremor, increased thirst, increased urination, vomiting, weight gain, impaired memory, poor concentration, drowsiness, muscle weakness, hair loss, acne and decreased thyroid function In another aspect, a method for treating a human diagnosed with bipolar disorder, depression, treatment-resistant depression or acute suicidality is disclosed that comprises administering a synergistic combination of deuterated gaboxadol at a dose ranging from about 1 to about 300 mg/day, contemporaneously with lithium at a dose from about 50 mg to about 1800 mg lithium carbonate, with a maximum daily dose of 2400 mg [for a 60 kg human]; or from about 0.8 mg/kg to about 30 mg/kg, with a maximum dose of 40 mg/kg, of lithium carbonate; or in an amount sufficient to achieve a lithium serum concentration of about 0.2 to 1.2 mmol/L; wherein the combination is administered at least once per day.

In another aspect, a method for treating a human diagnosed with an acute form of bipolar disorder, depression, treatment-resistant depression or suicidality comprising administering a synergistic combination of deuterated gaboxadol at a dose in the range of from about 1 mg to about 150 mg/day, contemporaneously with lithium at a dose of from about 300 mg to about 1800 mg lithium carbonate/day [for a 60 kg human]; or in an amount sufficient to achieve a lithium serum concentration of 0.4 to 1.2 mmol/L, wherein the combination is administered at least once per day.

In another aspect, a method for treating a patient diagnosed with an acute form of bipolar disorder, depression, treatment-resistant depression or suicidality comprising administering a synergistic combination of deuterated gaboxadol at a dose in the range of from about 1 mg to about 150 mg/day, contemporaneously with lithium at a dose of from about 50 mg to about 900 mg lithium carbonate [e.g., for a 60 kg human]; or in an amount sufficient to achieve a lithium serum concentration of about 0.2 to 1.0 mmol/L; wherein the combination dose is administered at least once per day.

In another aspect, a method for treating a patient diagnosed with an acute form of bipolar disorder, depression, treatment-resistant depression or suicidality comprising administering an additive combination of deuterated gaboxadol at a dose in the range of from about 1 mg to about 150 mg/day, contemporaneously with lithium at a dose from about 50 mg to about 900 mg lithium carbonate [e.g., for a 60 kg human]; or in an amount sufficient to achieve a lithium serum concentration of about 0.2 to 1.0 mmol/L, wherein the combination dose is administered at least once per day.

In another aspect, a use of deuterated gaboxadol and lithium in the preparation of a fixed dose combination medicament is disclosed, wherein the lithium is present in a range from about 10 mg to about 300 mg [optionally in the form of lithium carbonate 50 mg to about 1800 mg]; and wherein the deuterated gaboxadol is present in a range from about 1 mg to about 150 mg for treatment of a human patient diagnosed with bipolar disorder, depression or acute suicidality.

In another aspect, a use of a fixed dose combination comprising lithium and deuterated gaboxadol in unit dosage form is disclosed wherein the lithium is present in a range from about 10 mg to about 360 mg [optionally in the form of lithium carbonate 50 mg to about 1800 mg] and wherein the deuterated gaboxadol is present in a range from about 1 mg to about 150 mg for the treatment of a human patient diagnosed with bipolar disorder, depression or acute suicidality.

In another aspect, a use of a fixed dose combination comprising lithium and deuterated gaboxadol in unit dosage form for once daily administration is disclosed, wherein the deuterated gaboxadol is present from about 1 mg to about 150 mg, and the lithium for the first week is present in the range of from about 40 mg to about 360 mg [optionally in the form of lithium carbonate 200 mg to about 1800 mg], and after the first week the lithium is present in the range of from about 10 mg to about 180 mg [optionally in the form of lithium carbonate 50 mg to about 900 mg], for the treatment of a human patient diagnosed with bipolar disorder, depression or acute suicidality.

In another aspect, a use of a synergistic combination of deuterated gaboxadol and lithium, or a pharmaceutically acceptable salt of either or both compounds thereof, is disclosed for reducing one or symptoms of bipolar disorder, depression, or suicidality.

In another aspect, a use of a synergistic combination of deuterated gaboxadol and lithium, or a pharmaceutically acceptable salt of either or both compounds thereof, is disclosed in the manufacture of a medicament for reducing one or symptoms of bipolar disorder, depression, or suicidality.

An aspect of this invention is deuterated gaboxadol having at least one deuterium present at a ring carbon of the tetrahydro-pyridine ring of gaboxadol.

An aspect of this invention is ring carbon deuterated gaboxadol with deuterium at all 6 ring carbon hydrogen positions of the tetrahydro-pyridine ring of gaboxadol.

An aspect of this invention is deuterated gaboxadol with deuterium at 5 of the 6 ring carbon hydrogen positions of the tetrahydro-pyridine ring of gaboxadol.

An aspect of this invention is deuterated gaboxadol with deuterium at 3 of the 6 ring carbon hydrogen positions of the tetrahydro-pyridine ring of gaboxadol.

An aspect of this invention is deuterated gaboxadol with deuterium at ring carbon hydrogen positions 5,5,7,7 of the tetrahydro-pyridine ring of gaboxadol.

An aspect of this invention is deuterated gaboxadol made by one of the synthetic schemes disclosed herein.

An aspect of this invention is the use of deuterated gaboxadol for the manufacture of a medicament for the treatment of psychiatric disorders including but not limited to reducing risk of suicide in a patient at risk of suicide, treatment resistant depression and/or achieving fast-acting relief of depressive symptoms.

BRIEF DESCRIPTION OF THE DRAWINGS

FIG. 1A shows the d1-gaboxadol form has 6 potential species.

FIG. 1B shows the d2-gaboxadol form has 15 potential species.

FIG. 2 shows forms of deuterated gaboxadol and the ring numbering system

FIG. 25 shows an exemplary ketamine dose-curve Pharmacomaps. White color indicates the spatial areas of significant drug-evoked activation. The very broad activation pattern evoked by ketamine at 10 mg/kg included the following anatomical structures: Cortex: anterior cingulate (ACA), prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (Tea), perirhinal (PERI) and entorhinal (ENT), and ectorhinal (ECT) cortical areas; Basal ganglia: the nucleus accumbens (ACB), lateral septum (LS), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG) and the periaqueductal gray (PAG); Brainstem: locus coeruleus (LC).

FIG. 26 shows an exemplary side-by-side comparison between a gaboxadol and a ketamine Pharmacomap. White color indicates the spatial areas of significant drug-evoked activation (green is for inhibition which in this case is only very sparse without clear anatomical significance). Gaboxadol at 10 mg/kg (left panels) evokes a broad brain activation that is highly similar to that of ketamine at 10 mg/kg (right panels). This includes: Cortex: anterior cingulate (ACA), prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (TEa), perirhinal (PERI) and entorhinal (ENT), and ectorhinal (ECT) cortical areas; Basal ganglia: the nucleus accumbens (ACB), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG) and the periaqueductal gray (PAG); Brainstem: locus coeruleus (LC).

FIG. 27A-27B shows an example of the synergistic effect obtained by the co-administration of gaboxadol and ketamine. White color indicates the spatial areas of significant drug-evoked activation (green is for inhibition which in this case is only very sparse without clear anatomical significance). Gaboxadol at 3 mg/kg (left panel); Ketamine at 6 mg/kg (middle panel); Gaboxadol at 3 mg/kg and Ketamine at 6 mg/kg (right panel). This includes: Cortex: anterior cingulate (ACA), prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (TEa), perirhinal (PERI) and entorhinal (ENT), and ectorhinal (ECT) cortical areas; Basal ganglia: the nucleus accumbens (ACB), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG) and the periaqueductal gray (PAG); Brainstem: locus coeruleus (LC).

FIG. 28 shows exemplary results of a forced swim test. Both ketamine (round symbols) and gaboxadol (triangle symbols) significantly reduced the time spent in floating (immobility) during a 6 min forced swim compared to a control vehicle-treated group.

DETAILED DESCRIPTION OF THE INVENTION

Figure 1C:
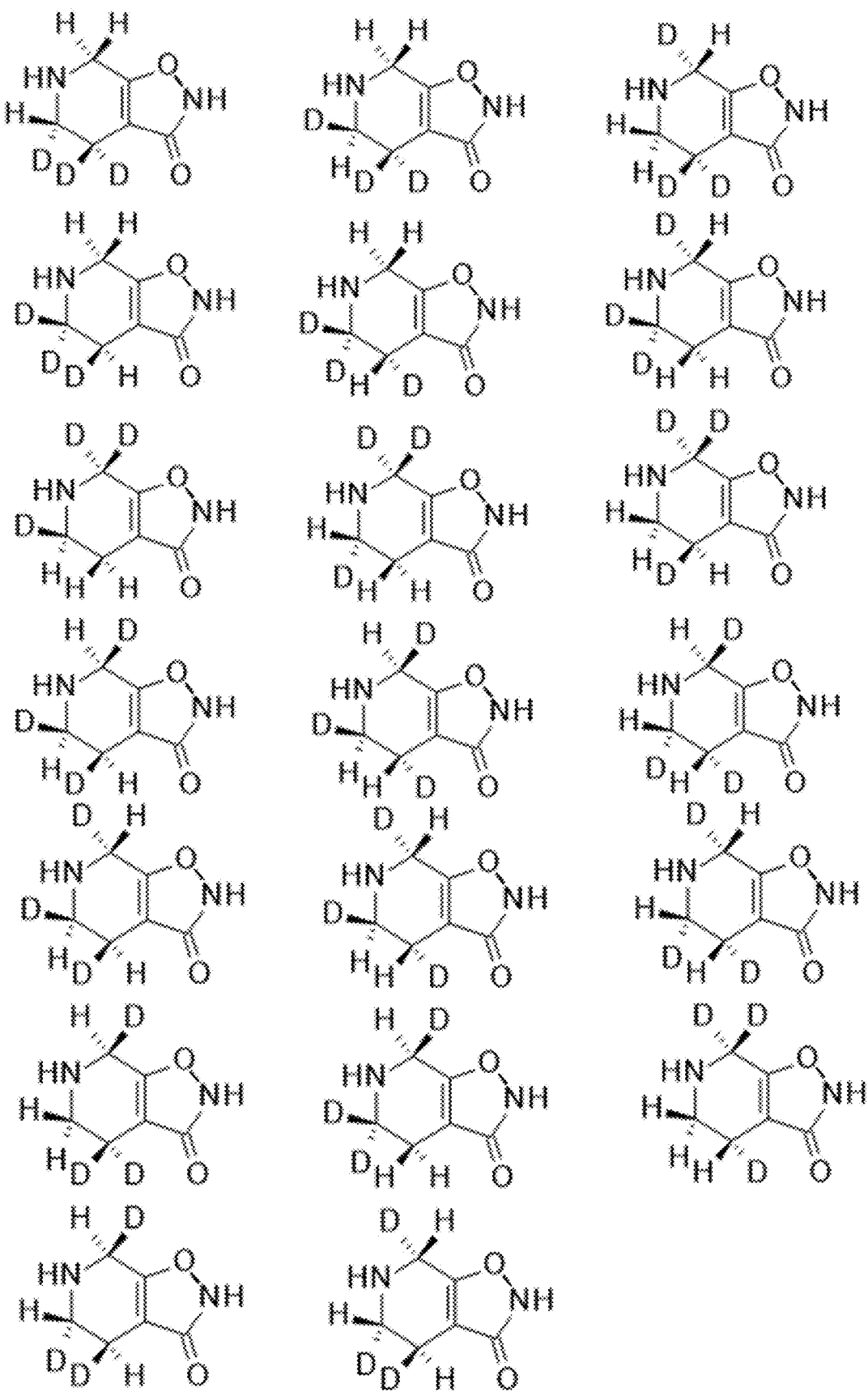
FIG. 1C shows the d3-gaboxadol form has 20 potential species.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Definitions and certain specific embodiments Unless defined otherwise, all technical and scientific terms used herein have the same meanings as commonly understood by one of skill in the art to which the disclosure herein belongs.

As used herein, the singular forms "a," "an," and "the," are intended to include the plural forms as well, unless the context clearly indicates otherwise.

In certain embodiments, the term "about" or "approximately" as used herein means within an acceptable error range for the particular value as determined by one of ordinary skill in the art, which will depend in part on how the value is measured or determined, i.e., the limitations of the measurement system.

In specific embodiments, when the term "about" or "approximately" when used to modify a numeric value-means plus or minus 20%, 10%, 5%, 1%, or 0.1% of the value. In certain embodiments, the term "about" means plus or minus 10% of the stated value. In certain embodiments, the term "about" means plus or minus 5% of the stated value. In certain embodiments, the term "about" means plus or minus 1% of the stated value. In certain embodiments, the term "about" means plus or minus 0.1% of the stated value.

In a specific embodiment of a method of treating a psychiatric disorder as provided herein, when deuterated gaboxadol is administered in combination with a second therapeutic agent (different from deuterated gaboxadol) to treat the psychiatric disorder, the deuterated gaboxadol and the second therapeutic agent can be administered concurrently, sequentially or contemporaneously, and can be in the same or separate compositions. In certain embodiments, the administrations of deuterated gaboxadol and another compound, such as lithium, is "contemporaneous."

In certain embodiments, an administration of deuterated gaboxadol and the other compound is "contemporaneous" if deuterated gaboxadol is administered to a patient in need thereof within about 5 minutes, about 30 minutes, about 1 hour, about 2 hours, about 3 hours, about 4 hours, about 5 hours, about 6 hours, about 7 hours, about 8 hours, about 9 hours, about 10 hours, about 11 hours or about 12 hours of the administration of the other compound. In certain embodiments, deuterated gaboxadol is administered to a patient in need thereof within about 2 hours of the administration of the other compound.

In certain embodiments, an administration of deuterated gaboxadol and the other compound is "concurrently." The term "concurrently" is used in its normal meaning of at the same time.

In certain embodiments, an administration of deuterated gaboxadol and the other compound is "sequential," also referred to as administered "sequentially", "sequential" administration, and like phrasing. The terms "sequential" and "sequentially" are used in their normal meaning of one after the other. A sequential course of administration can also be contemporaneous.

In certain embodiments, a contemporaneous administration of another compound and deuterated gaboxadol can comprise the other compound being administered simultaneously with deuterated gaboxadol either as separate doses of individual pharmaceutical compostions, or in a combined dose single pharmaceutical composition.

In a specific embodiment, the subject in the methods of treatment provided herein is a mammal, e.g., a human, mouse, rat, guinea pig, dog, cat, horse, cow, pig, or non-human primate, such as a monkey, chimpanzee, or baboon. The terms "subject" and "patient" are used interchangeably. In certain embodiments, a subject is a human suffering from a psychiatric disorder such as depression or bipolar disorder. In certain embodiments, the subject is a human. In certain embodiments, the human is a pediatric human. In certain embodiments, the subject is an adult human.

For the purposes of the description herein, the terms "ring carbon deuterated gaboxadol" and "deuterated gaboxadol" and "deuterated gaboxadol compound" are used interchangeably to refer to forms of gaboxadol enriched with deuterium above the naturally occurring abundance of deuterium (i.e., deuterium occurs in place of hydrogen in all molecules in nature at approximately 0.0156%, the natural abundance of deuterium) and having deuterium atoms at one or more of the ring carbon positions of the tetrahydro-pyridine ring of gaboxadol (i.e., positions 4, 5 and 7). As such, deuterated gaboxadol may have 1 to 6 deuteriums, and preferably 2, 4 or 6 deuteriums conjugated to said ring carbons, and including 1, 3 or 5 deuteriums conjugated to said ring carbons. The term "d1-gaboxadol" refers to deuterated gaboxadol with one deuterium atom bound to tetrahydro-pyridine ring carbon atoms. The term "d2-gaboxadol" refers to deuterated gaboxadol with two deuterium atoms bound to tetrahydro-pyridine ring carbon atoms. The term "d3-gaboxadol" refers to deuterated gaboxadol with three deuterium atoms bound to tetrahydro-pyridine ring carbon atoms. The term "d4-gaboxadol" refers to deuterated gaboxadol with 4 deuterium atoms bound to tetrahydro-pyridine ring carbon atoms. The term "d5-gaboxadol" refers to deuterated gaboxadol with five deuterium atoms bound to tetrahydro-pyridine ring carbon atoms. The term "d6-gaboxadol" refers to deuterated gaboxadol with 6 deuterium atoms bound to tetrahydro-pyridine ring carbon atoms. As used herein, ring carbon deuterated gaboxadol and deuterated gaboxadol may be considered generic terms (also a "genus") encompassing these various deuterated forms of gaboxadol.

As used herein, "forms" of deuterated gaboxadol may be distinguished from "species" of deuterated gaboxadol as follows: "forms" refers to the number of ring carbon conjugated deuteriums in a gaboxadol molecule, i.e. from one to six deuterium atoms. Thus d1-gaboxadol is a form of gaboxadol. This form of gaboxadol may comprise up to 6 different deuterated species, as shown in FIG. 1A. For the purpose of this invention and the descriptions herein, each of the enantiomers of ring carbon deuterated gaboxadol is counted as an individual species. Mass spectrometry can typically distinguish forms d1-, d2-, etc. by mass. However, it is understood that a form of deuterated gaboxadol may comprise a variety of species which are not distinguished by mass.

The term "gaboxadol" alone without any qualification indicates that the gaboxadol is non-deuterated gaboxadol.

A composition of deuterated gaboxadol can be described by the percentage of a particular deuterated form of gaboxadol in the composition. For example, a composition that is 50% d6-gaboxadol indicates that half of the gaboxadol molecules in the composition are d6-gaboxadol and half of the molecules are another form of deuterated gaboxadol or non-deuterated gaboxadol. In another example, a composition of deuterated gaboxadol can be about 80% d6-gaboxadol, about 18% d5-gaboxadol and about 2% other forms of deuterated gaboxadol or non-deuterated gaboxadol.

In specific embodiments, a method of treatment provided herein is to achieve, and a therapeutically effective amount is sufficient to achieve, a therapeutic result, e.g., to relieve to some extent one or more symptoms of the disease or condition being treated. In certain instances, the result is a reduction and/or alleviation of the signs, symptoms, or causes of a disease, or any other desired alteration of a biological system. In some embodiments, the effective amount is a dose that is generally effective in alleviating, reducing, noticeably reducing, or eliminating, symptoms associated with bipolar disorder or mania. In certain instances, an "effective amount" for therapeutic uses is the amount of the composition comprising an agent as set forth herein required to provide a clinically significant decrease in a disease. In a specific embodiment, an "effective" amount in any individual case is determined using any suitable technique, such as a dose escalation study.

In certain embodiments, an "effective amount" or "therapeutically effective amount" of deuterated gaboxadol is the amount of a single dose of the deuterated gaboxadol sufficient to treat a psychiatric disorder.

In certain embodiments, an "effective amount" or "therapeutically effective amount" of gaboxadol or deuterated gaboxadol is the amount of two doses of gaboxadol, deuterated gaboxadol, or a combination of doses of the two, sufficient to treat a psychiatric disorder In a specific embodiment, a method of treatment is to achieve an improvement that is a reduction of one or more of the symptoms or underlying pathology of a psychiatric disorder.

In a specific embodiment, a method of treatment is to achieve an improvement that is an improvement in next day functioning, e.g., an improvement wherein the beneficial effect on at least one symptom lasts over at least a period of time, e.g., at least about 6 hours, at least about 12 hours, at least about 24 hours etc., to rapidly alleviate the symptoms of the patient.

In specific embodiments of a method of treatment provided herein, the administering is orally or intranasally.

In specific embodiments, a patient in need thereof" or a "subject in need thereof" is a patient or subject that has been diagnosed with a psychiatric disorder or is at risk of a psychiatric disorder or has symptoms of a psychiatric disorder.

As used herein, unless stated otherwise, the term "treatment-resistant" is used as that term is understood by one skilled in the art. In a specific embodiment, treatment resistant depression is depression displaying a lack of therapeutic response after at least one treatment period during which an antidepressant is administered for about six weeks.

In specific embodiments, the methods of treatment comprise administering that is oral, intraduodenal, parenteral injection (comprising intravenous, subcutaneous, intraperitoneal, intramuscular, intravascular or infusion), topical, rectal, or any other suitable route of administration. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In some embodiments, the agents and compositions described herein are administered orally.

In a specific embodiment, a pharmaceutically acceptable carrier is a molecular entity that is approved by a regulatory agency of a federal or a State government, e.g., the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

In specific embodiments, "treat," "treatment" or "treating" according to the invention can be to reverse, alleviate, ameliorate, inhibit, slow down or stop the progression or severity of a psychiatric disorder. In specific embodiments, "treat," "treatment" or "treating" a psychiatric disorder comprises reducing or alleviating at least one symptom of the psychiatric disorder, decreasing one or more symptoms or clinical markers of the psychiatric disorder, reducing or halting the progression of the psychiatric disorder, improving one or more symptoms or markers of the psychiatric disorder, achieving a cessation of or at least slowing of progress or of worsening of symptoms compared to what would be expected in the absence of treatment, alleviation of one or more symptom(s), diminishment of extent of disease, achieving stabilized (i.e., not worsening) state of disease, delay or slowing of disease progression, amelioration or palliation of the disease state, remission (whether partial or total), decreased mortality, palliative treatment alleviating the clinical symptoms of the psychiatric disorder in a subject that is afflicted with the psychiatric disorder, arresting or reducing development of the psychiatric disorder or at least one clinical or subclinical symptom thereof, and/or a statistically significant and/or mathematically significant reduction in a symptom of the psychiatric disorder. Permanently curative treatment may occur, but is not required to achieve "treatment" herein. Treatment can be performed by administration of a drug to a patient or subject in need thereof. Treatment can comprise a single administration of a drug, multiple administrations of a drug over time, administration of multiple drugs concurrently or sequentially over time, administration of various doses of a drug, or an appropriate combination of the above.

In a specific embodiment, provided is a method of preventing a psychiatric disorder in a patient in need thereof comprising administering an effective amount of deuterated gaboxadol to the patient. In a specific embodiment, the patient is at risk of developing the psychiatric disorder, for example, as indicated by a test diagnostic for such risk. In specific embodiments, "manage," "managing" and "management" of a psychiatric disorder comprises preventing the recurrence of the psychiatric disorder in a patient who has already suffered from the disorder, and/or lengthening the time that a patient who has suffered from theor disorder remains in remission, or modulating the threshold, development and/or duration of the disorder or changing the way that a patient responds to the disorder.

"Unit dosage form" or "UDF" means a physically fixed unit dose of a formulation which is conveniently administered in unit form (e.g. requires no measuring or adjusting of dosage before consumption). A patient may consume one or more UDFs at a time.

"Rapid antidepressant", "rapid-acting antidepressant" "rapidly alleviate," "rapid alleviation" or "fast-acting antidepressant" in specific embodiments refers to a medication capable of providing effective treatment of depression (e.g., delivering therapeutic relief) (as may be objectively or subjectively observed) within 24 hrs from first treatment with the medication, preferably within about 6 hours, and most preferably with about 180 minutes of first treatment, also referred to herein in specific embodiments as "rapid relief" or "rapid alleviation" of depressive symptoms. The provision of an effective treatment providing the relief described above can also be referred to as proving improvement of next day function.

"Rapid anti-suicidal agent", "rapid-acting anti-suicidal agent" or "fast-acting anti-suicidal agent" in specific embodiments refers to a medication capable of providing effective treatment of suicidal ideation (e.g., delivering therapeutic relief) (as may be objectively or subjectively observed) within 24 hrs from first treatment with the medication, preferably within about 6 hours, and most preferably with about 180 minutes of first treatment, also referred to herein in specific embodiments as "rapid relief" or "rapid alleviation of suicidality. The provision of an effective treatment providing the relief described above can also be referred to as providing improvement of next day function.

As used herein, unless stated otherwise, the term "synergy" or "synergism" or "synergistically" or "synergistic" with reference to the therapeutic effect of a combination of deuterated gaboxadol and another agent, consistent with its art-accepted meaning, refers to the therapeutic effect when treated with a combination of deuterated gaboxadol and another compound where the therapeutic effect of the compounds administered in combination is greater than the sum of their individual therapeutic effects when administered not in combination. For example, in certain embodiments, a combination of lithium and deuterated gaboxadol may exhibit a synergistic effect in treating, preventing and/or managing a psychiatric disorder. Several types of synergy are recognized by those skilled in the art. By way of example, some synergies may be recognized by the format 1+1=3, wherein the resulting effect of the combination is more than additive of the compounds administered individually. By way of another example, another synergy is of the type 0+0=1, wherein the resulting effect of the combination is more than additive of the compounds administered individually and wherein the two compounds which individually demonstrate no effect (at a given test dose) demonstrate efficacy when administered together. The latter synergy is considered particularly remarkable when the test compounds are not known to act through similar or related pathways.

In certain embodiments, an additive combination of a compound and deuterated gaboxadol is effective at treating, preventing and/or managing a psychiatric disorder.

As used herein, "c-fos signaling," "c-fos activity," "c-fos expression," "c-fos activation," "c-fos gene expression," are used interchangeably and refer to the activation in the brain of the expression of an immediate early gene (IEG) that is c-fos, as measured, for example, by immunohistochemistry, in situ hybridization of c-fos-specific probes, GFP expression in c-fos-GFP mice or by pharmacomapping as disclosed herein (see Examples 6-19).

As used herein, and unless otherwise indicated, the term "sub-standard dose" for lithium refers to human doses in the range of about 50 to about 600 mg for an adult human that would be expected to lack therapeutic efficacy in lithium monotherapy of bipolar disorder, depression, treatment-resistant depression and suicidality.

As used herein, and unless otherwise indicated, the term "standard dose" for lithium refers to human doses in the range of 600 to 1800 mg, with a maximum daily dose of 2400 mg (for an adult human), lithium carbonate that would be expected to be therapeutically effective as a lithium monotherapy of bipolar disorder, depression, treatment-resistant depression and suicidality.

In a specific embodiment, a psychiatric disorder is a medical problem involving significant changes in thinking, emotion, and/or behavior, and distress and/or problems functioning in social, work, or family activities. Psychiatric disorders comprise but are not limited to bipolar disorder, schizophrenia, borderline personality disorder, depression, major depressive disorder, treatment resistant depression, generalized anxiety disorder, addictive disorders, including drug abuse, alcohol abuse, behavioral addictions, suicidal ideation, acute suicidality, risk of self-harm, agoraphobia, anorexia nervosa, an anxiety disorder, attention-deficit/hyperactivity disorder (ADHD), autism spectrum disorder (ASD), binge eating disorder, bipolar disorder, bulimia nervosa, dementia, eating disorders, obsessive-compulsive disorder (OCD), panic disorder, persistent depressive disorder (dysthymic disorder), personality disorders, post-traumatic stress disorder (PTSD), postpartum depression, schizophrenia, social anxiety disorder, social or other specific phobia or condition associated with or displaying one or more symptoms including but not limited to extreme sadness, excessive worry, severe changes in mood, difficulty discerning reality from delusion, isolation and avoidance of friends or social activities; sudden changes in sleeping habits, eating habits, or sex drive; alcohol or drug abuse; and suicidal thoughts.

"Suicidal ideation", also described as "suicidalness", "suicidal thoughts", "suicidal impulse", "suicidal compulsions", "suicidalism", and "suicidality", is a recognized condition. In specific embodiments of this condition, the patient has one or more of the following: a subjective wish to die, passive and active suicide attempt thoughts, significant duration and frequency of ideation, lack of control, lack of deterrents, preparatory behavior for a suicide attempt, and other symptoms. The condition may be assessed by score on the Scale for Suicidal Ideation (Beck et al. J Consult Clin Psychol 1979; 47:343-352). In a specific embodiment, suicidal ideation includes thinking about or having an unusual preoccupation with suicide. The range of severity of suicidal ideation varies greatly from fleeting thoughts, to extensive thoughts, to detailed planning, role playing (e.g., standing on a chair with a noose), and incomplete attempts. Suicidal ideation is distinct from, and possibly overlapping in the patient with conditions which are diagnosed (under DSM-V) as major depressive disorder, treatment resistant depression, disruptive mood dysregulation disorder, major depressive disorder (including major depressive episode), persistent depressive disorder (dysthymia), premenstrual dysphoric disorder, substance/medication-induced depressive disorder, depressive disorder due to another medical condition, other specified depressive disorders, and unspecified depressive disorder.

In a specific embodiment, a patient "at risk of suicide" is a human subject having a clinically or subjectively assessed short- or medium-term risk of taking active steps towards self-harm with a risk of death. In a specific embodiment, a patients at risk of suicide is a patient diagnosed under DSM-V or other criteria as experiencing suicidal ideation, acute suicidality, recurrent thoughts of death and/or suicidal attempts. The term "at risk of suicide" does not necessarily follow from a diagnosis of depression, major depressive disorder, treatment resistant depression, bi-polar disorder, mania and other disturbed psycho-social conditions but distinct sub-sets of such patients may be separately identified as being at risk of suicide.

In certain embodiments, a person at risk of suicide has not been diagnosed with any psychiatric illness including major depression.

In certain embodiments, a person at risk of suicide does not have major depression.

In certain embodiments, a person at risk of suicide does not have Huntington's disease, Parkinson's disease, Amyotrophic Lateral Sclerosis, Alzheimer's disease, Fragile X syndrome, or Angelman syndrome.

In certain embodiments, a person at risk of suicide is being treated with antidepressants.

Deuterated Gaboxadol

It has now been found that ring carbon deuterated gaboxadol (gaboxadolum or THIP (4,5,6,7-tetrahydroisoxazolo (5,4-c) pyridin-3-ol; $C_6H_8N_2O_2$; Cas Number: 64603-91-4; PubChem CID: 3448)) has advantageous properties, comprising enhanced neurological activity as exhibited by evocation of brain activation in particular areas, believed to be useful for treating psychiatric disorders, compared to non-deuterated gaboxadol (see Examples 7 and 8 herein below).

In one aspect, this invention relates to ring carbon deuterated gaboxadol, pharmaceutically acceptable salts thereof, pharmaceutical compositions thereof, methods of making such compounds, and methods of use thereof.

In one aspect, the invention provides a compound of Formula I

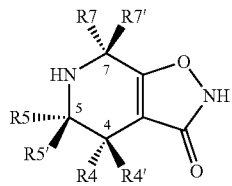

or a pharmaceutically acceptable salt thereof, wherein R4, R4', R5, R5', R7 and R7' are independently H or D, and wherein at least one of R4, R4', R5, R5', R7 and R7' is D.

Figure 1D:
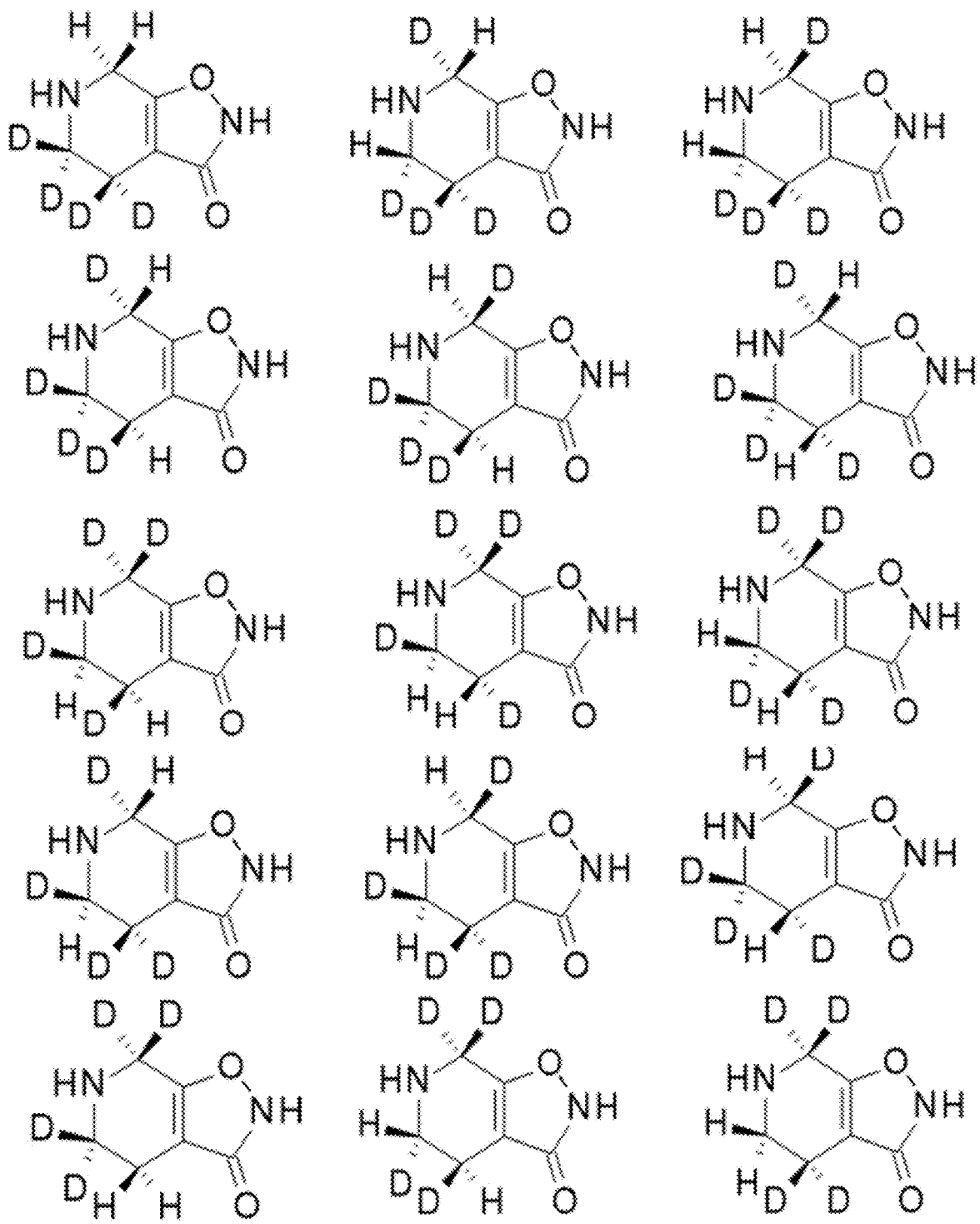
FIG. 1D shows the d4-gaboxadol form has 15 potential species.
Figure 1E:
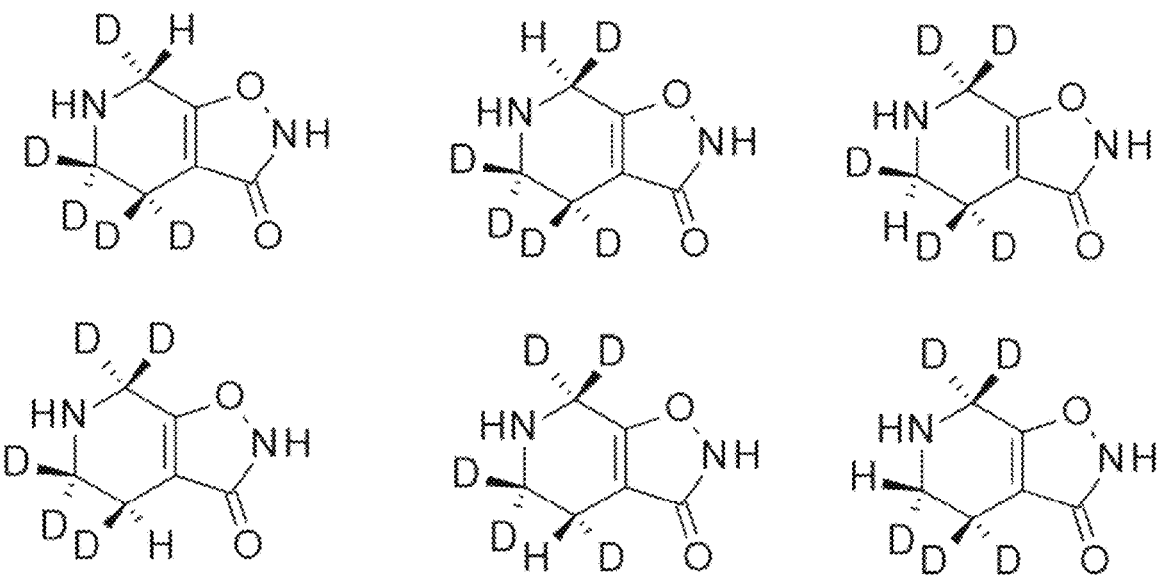
FIG. 1E shows the d5-gaboxadol form has 6 potential species.
Figure 1F:
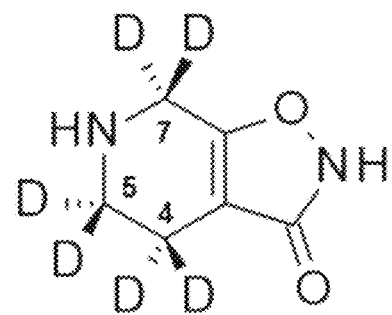
FIG. 1F shows that d6-gaboxadol has only one species.

Deuterated gaboxadol is sometimes referred to herein as dn-gaboxadol, where n indicates the number of D at the sites selected from among R4, R4', R5, R5', R7 and R7' in the compound. If not further specified by context or implication, D may be at any of the sites selected from among R4, R4', R5, R5', R7 and R7'. A specific form of deuterated gaboxadol may be referred to herein as dn-gaboxadol followed by the ring carbon positions of the tetrahydro-pyridine ring of gaboxadol at which the deuterium atom is incorporated. For example, when the deuterium is incorporated at R7 and R7', the deuterated gaboxadol may be referred to herein as d2-gaboxadol 7, 7.

d1-gaboxadol has 6 species as shown in FIG. 1A.
d2-gaboxadol has 15 species as shown in FIG. 1B.
d3-gaboxadol has 20 species as shown in FIG. 1C.
d4-gaboxadol has 15 species as shown in FIG. 1D.
d5-gaboxadol has 6 species as shown in FIG. 1E.
d6-gaboxadol has only one species, as shown in FIG. 1F.

In certain embodiments, if none of R4, R4', R5, and R5' are H, then R7 and R7' are not both D.

In certain embodiments, if all of R4, R4', R5, and R5' are D, then at least one of R7 and R7' are D.

In certain embodiments, all of R4, R4', R5, R5', R7 and R7' are D, and thus the deuterated gaboxadol is d6-gaboxadol. In a preferred embodiment, the deuterated gaboxadol is d6-gaboxadol.

It will be recognized that some variation of natural isotopic abundance occurs in a synthesized compound typically depending upon the origin of chemical materials used in the synthesis. Thus, a preparation of Formula I will inherently contain small amounts of isotopologues at each atom of the molecule. In particular, the compounds of the invention may contain isotopes at the sites marked H, N, O and at the carbons. Normally such isotopes will be present at their natural isotopic abundance in a preparation. It is technically possible to enrich or deplete such isotopes relative to natural amounts. The invention comprises such isotopic variation, enrichment or depletion at these other atoms so long as the deuteration at one or more of R4, R4', R5, R5', R7 and R7' of Formula I are as described herein.

It will be recognized that a single deuteration of at any one of the positions 4, 5, or 7 will generate a chiral center at that position. The diversity of stereochemical alternatives increases the diverse species of deuterated gaboxadol disclosed herein.

In another aspect, the invention provides a composition comprising one or more compounds of Formula I, or a pharmaceutically acceptable salt thereof.

The compositions of the invention may comprise exclusively one form of deuterated gaboxadol, or it may contain two or more forms of deuterated gaboxadol, each of which is selected from among the compounds set out in FIGS. 1A-1F. The relative proportions of the forms of deuterated gaboxadol will depend on the synthetic methods employed and efforts to separate and purify the forms. Exemplary embodiments of such compositions are set out elsewhere in this disclosure.

In another aspect, the invention provides a pharmaceutical composition comprising a composition comprising one or more compounds of Formula I, or a pharmaceutically acceptable salt thereof, in a pharmaceutically acceptable carrier.

Deuterated gaboxadol or deuterium enriched gaboxadol or a composition comprising the foregoing may be described by the percentage of incorporation of deuterium in the place of hydrogen at positions R4, R4', R5, R5', R7 and R7' of the compound of Formula I. The percentage incorporation of deuterium in ring carbon deuterated gaboxadol does not include deuterium that is bound to heteroatoms in the molecule. The percentage incorporation of deuterium generally refers to, in a given sample of gaboxadol compound, the percentage of gaboxadol molecules that have deuterium incorporated at one or more of the positions R4, R4', R5, R5', R7 and R7' out of the total amount of the molecules including deuterated and nondeuterated. For example, a deuterium percentage incorporation of 1% means that 1% of compounds of Formula 1 in a given sample contain deuterium at one or more of positions R4, R4', R5, R5', R7 and R7'. Non-deuterated gaboxadol is distinguishable from deuterium enriched gaboxadol and the percentage of deuterated gaboxadol may be determined. Deuterated gaboxadol or deuterium enriched gaboxadol means that the compound gaboxadol is enriched with deuterium above the naturally occurring abundance of deuterium (i.e., deuterium occurs in place of hydrogen in all molecules in nature at approximately 0.0156%, the natural abundance of deuterium). In certain embodiments the percentage incorporation of deuterium is at least 1%, 5%, 10%, 15%, 20%, 25%, 30%, 35%, 40%, 45%, 50%, 55%, 60%, 65%, 70%, 75%, 80%, 85%, 90%, 95%, or 98%, or the deuterated gaboxadol comprises at least 1%, 5%, 10%, 15%, 20%, 25%, 30%, 35%, 40%, 45%, 50%, 55%, 60%, 65%, 70%, 75%, 80%, 85%, 90%, 95%, or 98% of the total gaboxadol molecules (comprising deuterated and non-deuterated forms) in the composition.

Further, a preparation of deuterated gaboxadol can be described by the percentage of a particular deuterated form of gaboxadol in the preparation. For example, a preparation that is 50% d6-gaboxadol indicates that half of the gaboxadol molecules in the preparation are d6-gaboxadol and half of the molecules are another form of deuterated gaboxadol or non-deuterated gaboxadol.

In some embodiments, it may be further specified what is the percentage of a specific form of deuterated gaboxadol, such as d6-, d5- or d4-gaboxadol. For example, a preparation of deuterated gaboxadol can be about 80% d6-gaboxadol, about 18% d5-gaboxadol and about 2% other forms of deuterated gaboxadol or gaboxadol (see, e.g., Table IV). In certain embodiments, a preparation of deuterated gaboxadol comprises at least about 50%, 55%, 60%, 65%, 70%, 75%, 80%, 85%, 90%, 95%, or 98% d6-gaboxadol. In certain embodiments, a preparation of deuterated gaboxadol comprises in the range of about 0-60%, 60-70%, 70-80%, 80-90%, or 90-100% d6-gaboxadol. In certain embodiments, a preparation of deuterated gaboxadol comprises about 50%, 55%, 60%, 65%, 70%, 75%, 80%, 85%, 90%, 95%, 98%, or 100% d6-gaboxadol. It is observed that species of deuterated gaboxadol within a form of deuterated gaboxadol are not easily distinguished by MS or NMR analysis. As shown in FIG. 1E, d5-gaboxadol has 6 species. These have identical weights that are not easily distinguishable by MS. For the present specification, in a specific embodiment, the percentage does not necessarily specify which species of d5-gaboxadol are present in a composition, only the total amount of all species which are represented as the form of d5-gaboxadol represented by the peak.

In further embodiments, the synthesis may generate a known specific species of gaboxadol, such as the d2-gaboxadol 4,5,6,7-tetrahydroisoxazolo(5,4-c)pyridin-3(2H)-one-7,7 in Example 1B. In this case, it may be possible to know the specific species of d2-gaboxadol in the formulation, and thereby the percentage of that specific species, as well as the form.

As used in this specification, a composition where at least 10% of the compounds have D at one or more of R4, R4', R5, R5', R7 and R7' means the deuterium may be at one or more of any of indicated positions, so long as at least 10% of the gaboxadol compounds (deuterated and nondeuterated gaboxadol compounds) of the composition have at least one deuterium. A composition where at least 10% of the compounds have D at three or more of R4, R4', R5, R5', R7 and R7' means that at least 10% of the compounds (deuterated and nondeuterated gaboxadol compounds) are d3-gaboxadol or higher. Such composition may also contain d2-, d1- and non-deuterated gaboxadol, but this does not count towards the total percentage indicated.

For clarity, as used in this specification, the percentage of deuterated gaboxadol in a composition (or preparation) does not mean the total amount of deuterium relative to the total amount of gaboxadol. By such measure one might confuse a 10% d6-gaboxadol composition with a 60% d1-gaboxadol composition as the total deuterium per unit gaboxadol is the same. Herein, percentage may be used in reference to a composition to state the percentage of the particular form of gaboxadol within the total gaboxadol (deuterated plus nondeuterated) in the composition. As used herein, the former would be a composition of 10% d6-gaboxadol, while the latter would be a composition of 60% d1-gaboxadol.

For therapeutic use, the deuterated gaboxadol preferably is stable under the conditions it will be exposed to upon administration to the patient, e.g., in the aqueous physiological environment including acidic or basic environments in the body of a patient. For this reason, any proposed use of deuteration via an exchangeable proton, such as the amine N—H, via proton-deuterium equilibrium exchange is unlikely to be therapeutically different from non-deuterated gaboxadol, and would not be expected to behave in vivo as ring carbon deuterated gaboxadol of the invention Unlike the hydrogens of amine and hydroxyl moieties that can participate in exchange reactions, carbon backbone hydrogens are stable against exchange even in non-protic environments and under physiological conditions. Therefore, the present invention contemplates the use of gaboxadols that are deuterated at the ring carbons. The deuteration of the ring carbons yields gaboxadols with 2, 4 or 6 deuteriums per molecule. Partial deuteration at each ring carbon yields gaboxadols with 1, 3 or 5 deuteriums per molecule. Various forms of deuterated gaboxadol having from one to six ring carbon bound deuterium atoms per molecule are shown in FIGS. 1-2. As discussed herein above, these are examples of "ring carbon deuterated gaboxadol" or simply "deuterated gaboxadol."

Herein, we describe the various exemplary forms of deuterated gaboxadol by reference to the ring numbering convention shown in FIG. 2. These forms are 4,5,6,7-tetrahydroisoxazolo(5,4-c)pyridin-3(2H)-one-4,4-d2; 4,5,6,7-tetrahydroisoxazolo(5,4-c)pyridin-3(2H)-one-5,5-$d_2$; 4,5,6,7-tetrahydroisoxazolo(5,4-c)pyridin-3(2H)-one-7,7-$d_2$; 4,5,6,7-tetrahydroisoxazolo(5,4-c)pyridin-3(2H)-one-4,4,7,7-d4; 4,5,6,7-tetrahydroisoxazolo(5,4-c)pyridin-3(2H)-one-4,4,5,5-d4; 4,5,6,7-tetrahydroisoxazolo(5,4-c)pyridin-3(2H)-one-5,5,7,7-$d_4$; and 4,5,6,7-tetrahydroisoxazolo(5,4-c)pyridin-3(2H)-one-4,4,5,5,7,7-$d_6$.

Other forms of deuterated gaboxadol can have an unpaired deuterium on a ring carbon such that the ring carbon has one hydrogen and one deuterium. These include d1, d3 and d5 gaboxadols, for example, 4,5,6,7-tetrahydroisoxazolo(5,4-c)pyridin-3(2H)-one-4-$d_1$, 4,5,6,7-tetrahydroisoxazolo(5,4-c)pyridin-3(2H)-one-5-$d_1$; 4,5,6,7-tetrahydroisoxazolo(5,4-c)pyridin-3(2H)-one-7-$d_1$; other d1-gabixadols; 4,5,6,7-tetrahydroisoxazolo(5,4-c)pyridin-3(2H)-one-4,4,5-$d_3$; 4,5,6,7-tetrahydroisoxazolo(5,4-c)pyridin-3(2H)-one-4,4,7-$d_3$; 4,5,6,7-tetrahydroisoxazolo(5,4-c)pyridin-3(2H)-one-5,5,7-$d_3$; other d3-gaboxadols; 4,5,6,7-tetrahydroisoxazolo(5,4-c)pyridin-3(2H)-one-4,4,5,5,7-$d_5$; 4,5,6,7-tetrahydroisoxazolo(5,4-c)pyridin-3(2H)-one-4,5,5,7,7-d5; and 4,5,6,7-tetrahydroisoxazolo(5,4-c)pyridin-3(2H)-one-4,4,5,7,7-d5. Each of the named compounds above can describe two molecules depending on which side of the tetrahydro-pyridine ring the unpaired deuterium resides on the molecule.

Herein we also refer to ring carbon deuterated forms of gaboxadol in an abbreviated manner as gaboxadol d2, gaboxadol d3, gaboxadol d4, gaboxadol d5 and gaboxadol d6. In some instances, the d can be capitalized as D. In some instances, a dash may or may not be used. In each case, we refer to deuterated gaboxadol and the integer 1 through 6 refers to the number of deuterium atoms in a molecule of gaboxadol. In some instances, the integer may be a subscript or a superscript.

Ring carbon deuterated gaboxadols are preferably prepared by synthesis from deuterated precursors. Exemplary synthetic pathways are schematically represented in, for example, FIGS. 3 and 5-11, and synthesis is described elsewhere herein.

Synthesized forms of deuterated gaboxadol can comprise deuteration of at least 25% of the synthetically targeted insertion sites and more preferably, at least 30%, 35%, 40%, 45%, 50%, 55%, 60%, 65%, 70%, 75%, 80%, or 85%, and most preferably at least 90%, 95% or 100% deuteration at the intended sites.

As demonstrated elsewhere in this specification, mass spectrometry (MS) may be employed to identify the relative amounts of the various forms of ring carbon deuterated gaboxadol (d1-d6), and any non-deuterated gaboxadol, in a composition of deuterated gaboxadol synthesized as described herein or by other syntheses. Certain types of MS, such as high resolution MS (FIRMS) will provide greater precision. Others such as electrospray ionization MS (ESI- MS) are also suitable. Those skilled in the art will understand how to prepare a sample for MS analysis. An analytical chemist will want to consider certain additional steps for characterizing a sample due to the nature of a composition of deuterated gaboxadol. For example, if there is a potential that the sample contains exchange reaction deuterated gaboxadol, the sample may be pre-treated to remove any deuterium that is bound to heteroatoms in the molecule. Such pre-treatment will reduce ambiguity in the results allowing for more precise assessment of the forms of ring carbon deuterated gaboxadol in a sample.

The analytical chemist will also understand that the peaks identified by MS do not distinguish between the species of d1 to d5, only the total amount of each form of ring carbon deuterated gaboxadol. In a specific embodiment, the species of each form need not be distinguished in order to calculate the relative ratio of the forms to each other, or to calculate the percentage of each form in the composition. In another example, the skilled analytical chemist will recognize that d6-gaboxadol and non-deuterated gaboxadol have only one form each. By MS, these forms will generally show one predominant mass peak, but will also show a small amount of a one neutron heavier form due to incorporation of carbon-13 isotope (1.1% of naturally occurring carbon) or nitrogen-15 isotope (0.4% of naturally occurring nitrogen). In a specific embodiment, the analytical chemist uses the minor peak one neutron heavier than d6-gaboxadol to estimate the approximate ratio of carbon-13 or nitrogen-15 isotopes in the source material for the composition of deuterated gaboxadol under investigation.

Ring carbon deuterated gaboxadol may be provided as a pharmaceutically acceptable salt, such as, but not limited to, an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, lithium, sulfuric, sulfamic, phosphoric or nitric acid addition salts may be used. In certain embodiments, deuterated gaboxadol is provided as deuterated gaboxadol monohydrate.

In certain embodiments, a base salt form of ring carbon deuterated gaboxadol is prepared wherein the base is an inorganic base or an organic base selected from: aluminum, ammonium, calcium, copper, ferric, ferrous, magnesium, manganic salts, manganous, potassium, sodium, zinc bases, and primary, secondary, and tertiary amines, substituted amines including naturally occurring substituted amines, cyclic amines, and basic ion exchange resins, such as arginine, betaine, caffeine, choline, N,N-dibenzyl(ethylene) diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine.

It will be understood that reference in this disclosure to "deuterated gaboxadol" will also apply to pharmaceutically acceptable salts, e.g. pharmaceutically acceptable acid addition salts, hydrates or solvates of the base or salt, as well as anhydrates, and also amorphous, or crystalline forms, unless the context indicates otherwise.

In certain embodiments, deuterated gaboxadol or a pharmaceutically acceptable salt thereof is crystalline, such as the crystalline hydrochloric acid salt, the crystalline hydrobromic acid salt, or the crystalline zwitter ion monohydrate. In certain embodiments, deuterated gaboxadol is provided as a crystalline monohydrate.

Uses of Deuterated Gaboxadol

Deuterated gaboxadol is useful in the treatment of psychiatric disorders. The invention provides a method of treating a psychiatric disorder comprising administering to a human patient in need thereof a therapeutically effective amount of a deuterated gaboxadol compound (which can be, for example, d6-gaboxadol). In a specific embodiment, a pharmaceutical composition is administered, wherein the pharmaceutical composition comprises a therapeutically effective amount of the deuterated gaboxadol compound and a pharmaceutically acceptable carrier. In a specific embodiment, the psychiatric disorder is Agoraphobia, Anorexia Nervosa, Any Anxiety Disorder, Attention-Deficit/Hyperactivity Disorder (ADHD), Autism Spectrum Disorder (ASD), Binge Eating Disorder, Bipolar Disorder, Borderline Personality Disorder, Bulimia Nervosa, Dementia, Eating Disorders, Generalized Anxiety Disorder, Major Depression, Obsessive-Compulsive Disorder (OCD), Panic Disorder, Persistent Depressive Disorder (Dysthymic Disorder), Personality Disorders, Post-Traumatic Stress Disorder (PTSD), Postpartum Depression, Schizophrenia, Social Anxiety Disorder, or a Social or other Specific Phobia, or Treatment-resistant Depression (TRD). Deuterated gaboxadol can be administered to patients alone or in combination with additional compounds to provide additive or synergistic responses in patients.

As shown in Example 7 herein below, deuterated gaboxadol 4,5,6,7-tetrahydroisoxazolo[5,4-c]pyridin-3(2H)-one-7,7-d2 (d2-gaboxadol 7,7) at 6 mg/kg surprisingly evoked considerably higher brain activation than non-deuterated gaboxadol at the same dose in several brain areas implicated in cognitive processing and antidepressant drug activity, as measured in whole brain activation studies in mice. As shown in Example 8 herein below, d6-gaboxadol evoked considerably higher brain activation than non-deuterated gaboxadol at the same dose across a number of brain areas implicated in cognitive processing as well as antidepressant drug activity in mice, and d6-gaboxadol-induced onset of sedation in mice was faster than that of d2-gaboxadol 7,7, while both d6-gaboxadol- and d2-gaboxadol 7,7-induced onset of sedation was faster than that of nondeuterated gaboxadol.

Preferably, the ring carbon deuterated gaboxadol compound is more active in one or more areas of the brain than non-deuterated gaboxadol, preferably, about 50%, 60%, 70%, 80%, 90%, 100%, 125%, 150%, 175%, 200%, 225%, 250%, 275%, 300%, 325%, 350%, 375%, 400%, 425%, 450%, 475% and 500% or higher, more active in one or more areas of the brain than non-deuterated gaboxadol administered at equivalent doses by weight. Stated alternatively, the effective dose of ring carbon deuterated gaboxadol is significantly lower than the dose of non-deuterated gaboxadol required to achieve the same effect. This is sometimes referred to as a left shift dose response, as described in the Examples below. As is well known in the art, use of a lower dose of a therapeutic agent is highly preferred when possible, and sometimes medically necessary.

Various forms of the deuterated gaboxadol of the invention can be used in combinations as determined to be appropriate by a physician, psychiatrist or other professional attending to a patient in need of treatment. For example, an individual administration can be any of d2-gaboxadol, d4-gaboxadol or d6-gaboxadol. Further, combinations of d2-gaboxadol, d4-gaboxadol and d6-gaboxadol can be provided in an individual administration or separately in multiple administrations. Finally, individual administrations can comprise mixtures of d2-gaboxadol, d4-gaboxadol and d6-gaboxadol. Each of the forgoing combinations may comprise a proportion of d1-gaboxadol, d3-gaboxadol, d5-gaboxadol and/or non-deuterated gaboxadol. The administration of the appropriate compound, combination of compounds and single or multiple administrations of the same will be determined by a skilled physician, psychiatrist or other professional attending to a patient in need of treatment by taking into account the particular needs of any individual patient.

Described herein are methods, compositions and pharmaceutical compositions for therapy of psychiatric disorders with deuterated gaboxadol or a pharmaceutically acceptable salt thereof.

The invention provides treatment of a patient in need thereof comprising administering deuterated gaboxadol. Such treatment may be one or more times daily, or periodic, such as every 2, 3, 4, 5, 6, 7, 8, 9 or 10 days, or intermittent or sporadic such as a first and optional second doses of the deuterated gaboxadol within about 1-about 12 hours of each other, followed by a washout period during which no deuterated gaboxadol is administered.

In certain embodiments, deuterated gaboxadol is administered once with no additional administration for 1, 2, 3, 4, 5, 6, 7, 8, 9 or 10 days. If the treatment is successful, a further administration of deuterated gaboxadol need not be administered at all until the patient again experiences undesired symptoms.

In a specific embodiment, this invention provides a striking contrast with previous proposed treatment modalities by using lower doses of deuterated gaboxadol than non-deuterated gaboxadol. Previous suggested uses of gaboxadol, none of which have been clinically approved, comprise as an analgesic, an anxiolytic, combined anxiolytic and anti-depressant acting as an add-on to escitalopram, for treatment of insomnia and for treatment of insomnia and for treatment of symptoms of certain genetic developmental disorders (Foster et al., 1983; Hoehn-Saric, 1983; Kasper et al., 2012; Kjaer and Nielsen, 1983; Korsgaard et al., 1982; Mohr et al., 1986; Mondrup and Pedersen, 1983). In specific embodiments, the invention provides deuterated gaboxadol for treating a psychiatric disorder, such as rapidly reducing risk of suicide in an urgent care situation and rapidly alleviating depression, for example treatment-resistant depression and/or at the onset of a treatment of major depression to bridge the delayed effect of traditional antidepressants.

In certain embodiments, the incidence of suicidal ideation within a population of patients suffering from acute suicidality is reduced by 10%, 20%, 30%, 40%, 50%, 60%, 70%, 80%, 90%, 95% or 100% within 24 hours after administration of deuterated gaboxadol.

In a specific embodiment, provided is a method of treating a psychiatric disorder comprising administering a first treatment of one dose of deuterated gaboxadol, preferably exhibiting a higher pharmacological activity than gaboxadol, wherein the one dose results in rapid relief of the psychiatric disorder (effective treatment).

Example 7 herein demonstrates in mice that approximately 6 mg/kg of ring carbon deuterated gaboxadol (7,7-d2) has an equivalent effect on brain activation in mice of approximately 10 to 20 mg/kg non-deuterated gaboxadol. Thus, deuterated gaboxadol may have a two to four fold higher potency than nondeuterated gaboxadol, and thus it is contemplated that, for any given dose of non-deuterated gaboxadol, e.g., converted from a mouse dose, the equivalent dose of deuterated gaboxadol may be less, for example, 2 to 5 times less.

In certain embodiments, the amount of deuterated gaboxadol in mg/kg to be administered daily to a human adult can be extrapolated by the foregoing information and/or by calculation from a dosage of gaboxadol administered to an experimental animal, e.g. a mouse, using the formula for dose translation based on body surface area (BSA) and by consulting, for example, Table I.

In certain embodiments, a dosage of deuterated gaboxadol refers to the amount of deuterated gaboxadol in mg administered daily to an adult human.

TABLE I

CONVERSION OF MOUSE GABOXADOL DOSE (mg/kg) TO HUMAN EQUIVALENT DOSE (HED) OF GABOXADOL (mg/kg) BASED ON BODY SURFACE AREA

| mg/kg gaboxadol× (MOUSE) | Animal Km Human Km= | mg/kg gaboxadol× (HUMAN) | DAILY DOSE (mg gaboxadol) for 60 kg HUMAN | |
|---|---|---|---|---|
| 1× | 0.08= | 0.08× | 60= | 4.8 |
| 3× | 0.08= | 0.24× | 60= | 14.4 |
| 6× | 0.08= | 0.48× | 60= | 28.8 |
| 10× | 0.08= | 0.8× | 60= | 48 |
| 15× | 0.08= | 1.2× | 60= | 72 |
| 20× | 0.08= | 1.6× | 60= | 96 |
| 25× | 0.08= | 2× | 60= | 120 |
| 30× | 0.08= | 2.4× | 60= | 144 |

In certain embodiments, the first dose of a pharmaceutical composition comprising deuterated gaboxadol leads to a rapid relief of the psychiatric disorder, with durable effect for at least 3, 4, 5, 6, or 7 days after administration, also referred to as rapid alleviation.

In certain embodiments, methods comprise administering to a patient in need thereof a first dose of a pharmaceutical composition comprising about 1 mg to about 300 mg deuterated gaboxadol or a pharmaceutically acceptable salt thereof wherein the first dose provides improvement in the patient for 3, 4, 5, 6, or 7 or more days after administration to the patient. In particular embodiments, no gaboxadol in any form is administered to the patient for 3, 4, 5, 6, or 7 or more days following the first dose.

Specific embodiments described herein provide that a patient in need thereof is administered a pharmaceutical composition comprising deuterated gaboxadol. The deuterated gaboxadol can be provided as a pharmaceutically acceptable salt thereof. Examples of pharmaceutically acceptable salts are provided elsewhere herein.

In certain embodiments, deuterated gaboxadol is provided as deuterated gaboxadol monohydrate. One skilled in the art will readily understand that the amounts of active ingredient in a pharmaceutical composition may be adjusted depending on the form of deuterated gaboxadol provided. For example, pharmaceutical compositions of comprising 5.0, 10.0, 15.0, 33.0, 50.0 or 150.0 mg deuterated gaboxadol correspond to 5.6, 11.3, 16.9, 37, 56 or 169 mg deuterated gaboxadol monohydrate, respectively.

In certain embodiments, the deuterated gaboxadol is crystalline.

Exemplary Dosages of Deuterated Gaboxadol

In a specific embodiment, provided is a method of treating a psychiatric disorder comprising administering to a patient in need thereof a first dose of a pharmaceutical composition comprising about 1 mg to about 300 mg deuterated gaboxadol or a pharmaceutically acceptable salt thereof.

In specific embodiments, deuterated gaboxadol is present in pharmaceutical compositions in an amount that is in the range of 1 mg to 150 mg, about 5 mg to about 20 mg, about 33 mg to about 75 mg, about 33 mg to about 100 mg, about 50 mg to 100 mg, or about 33 mg to about 150 mg deuterated gaboxadol or a pharmaceutically acceptable salt thereof. In specific embodiments, the pharmaceutical compositions comprise about 1, 2, 3, 4, 5, 6, 7, 8, 9, 10, 11, 12, 13, 14, 15, 16, 17, 18, 19, 20, 25, 30, 33, 35, 40, 45, 50, 55, 60, 65, 70, 75, 80, 85, 90, 95, 100, 105, 110, 115, 120, 125, 130, 135, 140, 145, 150, 175, 200, 250, or 300 mg deuterated gaboxadol or a pharmaceutically acceptable salt thereof.

In a preferred embodiment, when deuterated gaboxadol is used as a single or primary agent, the first administration is a single dose in the range of about 1 mg to about 300 mg.

In certain embodiments, when deuterated gaboxadol is used as a single or primary agent, the first administration is a single dose of about 1 mg to about 20 mg, about 5 mg to about 10 mg, about 10 mg to about 30 mg, about 25 mg to about 50 mg, about 33 mg to about 150 mg, about 40 mg to about 150 mg. 50 mg to about 150 mg, about 50 mg to about 100 mg, about 60 mg to about 300 mg, about 70 mg to about 300 mg, about 80 mg to about 300 mg, about 90 mg to about 300 mg, about 100 mg to about 300 mg, about 110 mg to about 300 mg, about 120 mg to about 300 mg, about 130 mg to about 300 mg, about 140 mg to about 300 mg, about 150 mg to about 300 mg, about 200 mg to about 300 mg, or about 250 mg to about 300 mg of deuterated gaboxadol.

In certain embodiments, the dose of deuterated gaboxadol that is administered is about 50 mg, 75 mg or 100 mg In a specific embodiment when the deuterated gaboxadol first administration is in combination with another agent such as ketamine or other second pharmaceutical agent, the deuterated gaboxadol may be used in a specific embodiment at a low dose of about 1 mg to about 10 mg, for example, 1, 2, 3, 4, 5, 6, 7, 8, 9 or 10 mg.

In a specific embodiment, when the deuterated gaboxadol first treatment is in combination with another agent such as lithium or other second pharmaceutical agent, in a specific embodiment the deuterated gaboxadol may be used at a low dose of about 1 mg to about 20 mg, for example 1, 2, 3, 4, 5, 6, 7, 8, 9, 11, 12, 13, 14, 15, 16, 17, 18, 19, or 20 mg.

In certain embodiments, a plasma Tmax of deuterated gaboxadol is achieved within 45 minutes after administration.

In certain embodiments, the dose of deuterated gaboxadol, or a pharmaceutically acceptable salt thereof, can be about 20 mg, about 19 mg, about 18 mg, about 17 mg, about 16 mg, about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, about 1 mg or less.

Doses of salts or hydrates of deuterated gaboxadol that are equivalent on a molar basis to the amount of any given dose of deuterated gaboxadol recited above are meant to be within the scope of the invention.

In certain embodiments, deuterated gaboxadol is administered daily (e.g. once per day) or optionally more than once per day, for example in a dose determined by a treating physician. In alternative embodiments it may be administered intermittently, such as regularly at some stages of treatment and irregularly at other stages, allowing for a washout period (during which no deuterated gaboxadol is administered) between doses of 48 hours, 3 4, 5, 6, 7, 8, 9 or 10 days, In certain embodiments, deuterated gaboxadol is administered once with no additional administration for 1, 2, 3, 4, 5, 6, 7, 8, 9 or 10 days.

Dose Form

In a specific embodiment, the invention contemplates administration of pharmaceutical compositions comprising deuterated gaboxadol or a pharmaceutically acceptable salt thereof, optionally designed for rapid onset of treatment effect. A wide variety of dose forms may be employed including those described previously in the literature. Preferred dose forms are suitable for oral or intranasal administration.

In a specific embodiment, pharmaceutical compositions herein may be provided with immediate release or standard release profiles. Pharmaceutical compositions may further comprise a pharmaceutically acceptable "carrier." In specific embodiments, the pharmaceutically acceptable carrier can be or comprise one or more of a diluent, binder, lubricant disintegrants, filler, and coating composition. In a specific embodiment, a unit dosage form (UDF) is provided. In a preferred embodiment, the pharmaceutical composition or UDF is a pill, tablet, capsule, film, or wafer, any of which may optionally be orally disintegrating, or a lollipop, lozenge, oil, tincture, or syrup. The formulation process can be adjusted accordingly. Pills and tablets can be prepared from solid formulations. Syrups, oils and tincture are liquid formulations. In specific embodiments, an orally disintegrating film, wafer, tablet or a lollipop or lozenge provides the UDF in an oral form wherein the active ingredients are at least partly absorbed directly in the buccal cavity. Capsules may be used, either containing solid formulations or liquid formulations (e.g. powders or particles in a hard-gel, or oil-based formulations in a soft-gel). In a specific embodiment, an oil based formulation with little or no water is used, and is typically easily encapsulated. Oil-in-water formulations may used that comprise microemulsions, liposomes, nanoemulsions, or other forms known in the art.

Tablets may be prepared by mixing the active ingredients with ordinary adjuvants and/or diluents and subsequently compressing the mixture in a convenient tableting machine. Examples of adjuvants or diluents comprise: corn starch, lactose, talcum, magnesium stearate, gelatin, lactose, gums, and the like. Any other pharmaceutically acceptable adjuvant or additive such as colorings, aroma, preservatives, etc. may also be used provided that they are compatible with the active ingredients.

A wide variety of technologies are available for a buccal or sublingual formulation such as an orally disintegrating thin film, wafer or tablet, or a lollipop, and/or lozenge. Sublingual tablets, wafers, films and strips can be designed to rapidly disintegrate (5-15 seconds) providing rapid access to buccal cavity capillaries and avoiding the hostile environment of the gastrointestinal tract. Lollipops and lozenges provide a combination of buccal and gastric administration. The technologies are widely used with therapeutic agents where rapid onset is desired. (See Lamey and Lewis "Buccal and Sublingual Delivery of Drugs" Ch 2 in "Routes of Drug Administration" Ed. Florence and Salole (Butterworth-Heinemann)). In a specific embodiment, an orally disintegrating tablet ODT is used (See Lamey and Lewis (1990))

Prior art formulations of non-deuterated gaboxadol, or pharmaceutically acceptable salts thereof, which can be used for deuterated gaboxadol, are disclosed in the following patent publications: WO2018144827, US20110082171, US20090048288, WO2006118897, WO2006102093, GB2410434, US20050137222, WO2002094225, WO2001022941, the contents of which are incorporated by reference herein in their entireties.

Deuterated gaboxadol can be administered in an oral dosage form.

Treatment and its Therapeutic Effect

In one aspect, the invention contemplates treatment of a psychiatric disorder in a patient having a psychiatric disorder comprising administering to the patient a pharmaceutical composition comprising deuterated gaboxadol or a pharmaceutically acceptable thereof, e.g., upon diagnosis of a patient as having a psychiatric disorder. In a specific embodiment, patients present at an urgent care facility or at a doctor's office where the diagnosis is made. The method of the invention comprises administration of the treatment dose with patient consent promptly after the diagnosis.

In a specific embodiment, the invention also contemplates treatment with a pharmaceutical composition comprising deuterated gaboxadol, or a pharmaceutically acceptable salt thereof, upon first diagnosis of a depression in a patient not treated previously with antidepressants and in need of rapid antidepressive relief before the time typical of delayed onset of clinically efficacy of traditional antidepressants, such as selective serotonin reuptake inhibitors (SSRIs), serotonin and noradrenaline reuptake inhibitors (SNRIs), tricyclic antidepressants (TCAs), tetracyclic antidepressants (TeCAs), monoamine oxidase inhibitors (MAOIs), or noradrenaline and specific serotoninergic antidepressants (NASSAs). Typically, patients present at an urgent care facility or at a doctor's office where the diagnosis is made.

In a specific embodiment, the invention also contemplates a treatment with a pharmaceutical composition comprising deuterated gaboxadol, or a pharmaceutically acceptable salt thereof, in a patient with treatment-resistant depression and in need of rapid relief when treatment with traditional antidepressants either has failed to induce a clinical relief or has failed to provide continuous relief after an initial period of successful treatment. Typically, patients present at an urgent care facility or at a doctor's office where the diagnosis is made. In a specific embodiment, the method of the invention contemplates administration of the first dose with patient consent promptly after the diagnosis. In certain embodiments, the patient has received, or is recommended for, electric shock therapy.

A preferred biomarker measure of rapid onset is to measure brain activity by electroencephalography (EEG). EEG is a measure of neurological activity well known to those skilled in the art. Standard techniques and instruments are widely available. Low frequency wavelength emissions are measured across a spectral range typically 0.2-35 Hz at multiple sites on the patient's head. Power spectra are assessed at each wavelength (or across a range of wavelengths) to observe and detect neurological activity. EEG may be used in the context of measuring neurological response to drugs such as gaboxadol as described in Dijk et al. (2010) J. Psychopharmacology. 24(11) 1613-1618. See also Lundahl et al. (2011) J Psychopharmacol 26: 1081.

Magnetoencephalography is an alternative neuroimaging technique with high temporal resolution and moderately good spatial resolution that allows direct measurement of the magnetic fields generated by synchronized ionic neural currents in the brain. When combined with pharmacological interventions, MEG (pharmaco-MEG) is a powerful tool for measuring the effects of experimental modulations of neurotransmission in the living human brain, in both patient and healthy control groups (Muthukumaraswamy, 2014). Compared with EEG, it can provide superior spatial resolution, and reduced contamination of the brain signals by physiological artefacts such as blinks and muscle potentials. See Nutt et al. Neuropharmacology 88 (2015) 155-163.

In a specific embodiment, the invention contemplates that the administration of a pharmaceutical composition comprising deuterated gaboxadol, or a pharmaceutically acceptable sals thereof, demonstrates rapid onset of therapeutic effect, e.g., induces rapid reduction of symptoms of the psychiatric disorder. A biomarker measure of the rapid onset may be obtained by EEG. An EE power density increase of about 30% or more across spectra in the 0.25 Hz-8.0 Hz range within about 180 minutes of an administration is indicative of rapid onset of effect. Preferably patients will record a power density increase of about 50% or more across this range. More preferably patients will record a power density increase of about 50% or more across the 4.75-8.0 Hz range. EEG power density increases have been described in Dijk (2010) and Lundahl (2011), upon administration of gaboxadol, in the context of other disease indications. In a specific embodiment, this technique is used with deuterated gaboxadol in the indications disclosed in the instant invention.

Alternatively, MEG may be employed as a biomarker to observe rapid onset of therapeutic effect of the administration of deuterated gaboxadol or gaboxadol. In the context of a different therapeutic indication, Nutt et al (2015) observed the administration of gaboxadol to lead to a whole head MEG planar gradiometer increase of +3 or higher in the combined delta, theta and alpha activity at the time point 160 minutes after the first treatment. In a specific embodiment, a method of treatment of the invention achieves an increase of +3 or greater within about 180 minutes of the first treatment.

In a specific embodiment, a method of treatment of the invention achieves a durable effect in that the administration of a pharmaceutical composition comprising deuterated gaboxadol reduces the symptoms of the psychiatric disorder for about 3, 4, 5, 6, 7, 8, 9, 10 or more days post-administration.

Without wishing to be bound by theory, it is contemplated based on the examples below, that the administration of deuterated gaboxadol induces a chemical form of brain activation through δ subunit-containing $GABA_A$ receptors which may be interpreted as a physiological effect comparable to electroconvulsive therapy (ECT). According to one aspect of the invention, the effect of the administration may optionally be enhanced by maintenance dosing of deuterated gaboxadol daily after the first administration, although one skilled in the art may select less frequent dosing, such as every 2, 3, 4, 5, 6 or 7 days after the first treatment. Thus, provided is a method of treating a psychiatric disorder comprising repeated steps of daily administering of deuterated gaboxadol to a patient in need thereof. In an alternative specific embodiment of a method of treating a psychiatric disorder in a patient, less frequent dosing than daily dosing is employed, such as repeated steps of administering deuterated gaboxadol every 2, 3, 4, 5, 6 or 7 days after the first treatment In a specific embodiment of one form of therapy, no further dosing is performed until the patient symptoms indicate a further treatment would be beneficial, which may arise 3, 4, 5, 6 or more days following said first administration, or may not arise at all for a longer period. Stated otherwise, in a specific embodiment, additional administrations with deuterated gaboxadol could optionally be avoided in the 3-day period following completion of the first administration, e.g., if such additional dosing would reduce the effectiveness of treatment. In a specific embodiment, the event that a 3-day or longer period following the first administration is selected, the period may be considered a "washout" period. In specific embodiments, the 3-day no-treatment period may be extended to 4, 5, or 6 days, or longer, if reduced symptoms of the psychiatric disorder are maintained. It is further understood that if or when symptoms of a psychiatric disorder return at a time greater than 3 days after the first administration, a follow-up treatment of deuterated gaboxadol or a pharmaceutically acceptable salt thereof may be administered. In some cases, 4-day, 5-day, 6-day or weekly dosing, each of which are examples of "intermittent dosing", will be indicated for a patient. In a specific embodiment, in each case the dosing is considered a continuation of a treatment of a disorder according to the present invention.

In a further embodiment, the treatment of a psychiatric disorder with deuterated gaboxadol, or a pharmaceutically acceptable salt thereof, comprises an initial administration of a pharmaceutical composition comprising deuterated gaboxadol, or a pharmaceutically acceptable salt thereof, and optionally, a second administration of a pharmaceutical composition comprising deuterated gaboxadol, or a pharmaceutically acceptable salt thereof, within about 12 hours immediately following the initial administration. In certain embodiments, the total amount of the first and second administration does not exceed 200 mg in total.

Deuterated gaboxadol of the present invention can be used in combination with gaboxadol (i.e., non-deuterated gaboxadol). Either form can be the first or second administration in a specific embodiment of a method of treatment of the invention when two administrations are performed.

Various forms of the deuterated gaboxadol of the invention can be used in combinations as determined to be appropriate by a physician, psychiatrist or other professional attending to a patient in need of treatment. For example, an individual administration can be any of d2-gaboxadol, d4-gaboxadol or d6-gaboxadol. Further, combinations of d2-gaboxadol, d4-gaboxadol and d6-gaboxadol or of any two of the foregoing can be provided in an individual administration or separately in multiple administrations. Further, individual administrations can comprise mixtures of d2-gaboxadol, d4-gaboxadol and d6-gaboxadol. Each of the forgoing combinations may comprise a proportion of d1-gaboxadol, d3-gaboxadol, d5-gaboxadol and/or non-deuterated gaboxadol. The administration of the appropriate compound, combination of compounds and single or multiple administrations of the same can be determined by a skilled physician, psychiatrist or other professional attending to a patient in need of treatment by taking into account the particular needs of any individual patient.

In a specific embodiment, the decision regarding the optional second administration is based on measuring indicators of the patient's response to the first administration. Any response of the patient may be used to make the decision, including a change in any behavior or any physiological or biological marker of response. In a specific embodiment, an insufficient response to the first administration precedes the performing of a second administration.

A preferred patient response for determining sufficiency of response is based on measuring the patient's neurological response according to EEG or MEG. In a specific embodiment, an "insufficient response" is an EEG power density increase of less than 50% or optionally less than 30% across the spectra 0.25-8.0 Hz at the time point 160 minutes after the first administration. In another specific embodiment, an "insufficient response" is an EEG power density increase of less than 50% or optionally less than 30% across the spectra 4.75-8.0 Hz at the time point 160 minutes after the first administration In a specific embodiment, an insufficient response to the first administration is a whole head MEG planar gradiometer increase of less than +3 in the combined delta, theta and alpha activity at the time point 160 minutes after the first administration.

In a specific embodiment, an insufficient response is a continuance of observable symptoms of the psychiatric disorder, such as suicidal ideation, acute suicidality, risk of self-harm and/or treatment resistant depression.

In a specific embodiment, a method of treating a psychiatric disorder comprising administering a pharmaceutical composition comprising deuterated gaboxadol can comprise a second administration within a maximum of about 12 hours from the first administration in order to achieve a desired therapeutic effect. Preferably the second administration will follow shortly after the confirmation of insufficient response by EEG or MEG at the 160 min time point. The second administration may be delayed for various patient care reasons but preferably is within about 12 hours of the first administration.

In a specific embodiment, a washout period between the first treatment and a subsequent treatment (in a specific embodiment, of at least 48 hours and optionally 3 days or more after the first treatment) reflects the neurological impact of the deuterated gaboxadol treatment which corresponds to the observation in ketamine clinical trials of an extended period of 7 or more days where a first treatment is sufficient to alleviate symptoms of a psychiatric disorder, such as but not limited to, suicidal ideation, recurrent thoughts of death, actions towards suicide and suicide attempts as described in U.S. Pat. No. 9,359,220, the content of which is incorporated by reference herein in its entirety. In a specific embodiment, it also corresponds to the observed period of reduction of suicidal ideation in certain patients who have undergone electroconvulsive therapy. While not being bound by theory, it is believed that if administering of therapeutic agent were to occur during the time period that instead is a washout period, for example administering of maintenance doses of therapeutic agent or further electroconvulsive therapy, this may be counter-effectual due to the re-stimulation of neurological areas which would interfere with the desirable pattern of neurological recovery from the electro- or chemical-shock of the first treatment.

Oral administration can employ any orally acceptable form including but not limited to a pill, tablet, capsule, syrup etc. Such forms can be manufactured according to techniques well known to those skilled in the art.

A particularly preferred form for rapid onset is an orally disintegrating dosage form (ODDF), which provides immediate release in the patient's buccal cavity enhancing buccal absorption of the drug. An ODDF is a solid dosage form, containing a medicinal substance or active ingredient, that disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets as is common with conditions which are psychiatric in nature.

In certain embodiments, pharmaceutical compositions herein provide immediate release of deuterated gaboxadol or a pharmaceutically acceptable salt thereof, and when administered to an oral cavity, disintegrate in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds based upon, e.g., the United States Pharmacopeia (USP) disintegration test method set forth at section 701, Revision Bulletin Official Aug. 1, 2008.

In preferred embodiments, the ODDF results in pharmacokinetic properties which include a Tmax of 20 minutes or less. In certain embodiments, pharmaceutical compositions herein provide a Tmax of 20 minutes or less, a Tmax of 19 minutes or less, a Tmax of 18 minutes or less, a Tmax of 17 minutes or less, a Tmax of 16 minutes or less, a Tmax of 15 minutes or less, a Tmax of 14 minutes or less, a Tmax of 13 minutes or less, a Tmax of 12 minutes or less, a Tmax of 11 minutes or less, a Tmax of 10 minutes or less, a Tmax of 9 minutes or less, a Tmax of 8 minutes or less, a Tmax of 7 minutes or less, a Tmax of 6 minutes or less, or a Tmax of 5 minutes or less. Such pharmaceutical compositions can be ODDFs such as orally disintegrating tablets (ODTs).

An ODT is a solid dosage form that is, for example, a tablet, film or wafer, containing a medicinal substance or active ingredient, that disintegrates rapidly, usually within a matter of seconds when placed upon the tongue. The disintegration time for ODTs generally ranges from several seconds to about a minute. ODTs are designed to disintegrate or dissolve rapidly on contact with saliva, thus eliminating the need to chew the tablet, swallow the intact tablet, or take the tablet with liquids. As with ODDFs in general, this mode of administration can be beneficial to people who require rapid onset of treatment.

In certain embodiments, the fast dissolving property of the ODTs requires quick ingress of water into the tablet matrix. This may be accomplished by maximizing the porous structure of the tablet, incorporation of suitable disintegrating agents and use of highly water-soluble excipients in the formulation. Excipients used in ODTs typically contain at least one superdisintegrant (which can have a mechanism of wicking, swelling or both), a diluent, a lubricant and optionally a swelling agent, sweeteners and flavorings. See, e.g., Nagar et al., Journal of Applied Pharmaceutical Science, 2011; 01 (04):35-45. Superdisintegrants can be classified as synthetic, natural and co-processed. In this context, synthetic superdisintegrants can be exemplified by sodium starch glycolate, croscarmellose sodium, crosslinked polyvinylpyrrolidone, low-substituted hydroxypropyl cellulose, microcrystalline cellulose, partially pregelatinized starch, cross-linked alginic acid, or modified resin. Natural superdisintegrants such as processed mucilages and gums are obtained from plants and can be exemplified by *Lepidium sativum* seed mucilage, banana powder, gellan gum, locust bean gum, xanthan gum, guar gum, gum karaya, *Cassia fistula* seed gum, *Mangifera indica* gum, carrageenan, agar from *Gelidium amansii* or other red algae, soy polysaccharide or chitosan. Diluents that can be used include, e.g., mannitol, sorbitol, xylitol, calcium carbonate, magnesium carbonate, calcium sulfate, magnesium trisilicate and the like. Lubricants that can be used include, e.g., magnesium stearate and the like. Those skilled in the art are familiar with ODT manufacturing techniques.

Other ODDFs which may be used include rapidly dissolving films which are thin oral strips that release medication such as deuterated gaboxadol or a pharmaceutically acceptable salt thereof quickly after administration to the oral cavity. The film is placed on a patient's tongue or any other mucosal surface and is instantly wet by saliva whereupon the film rapidly hydrates and dissolves to release the medication. See. e.g., Chaturvedi et al., Curr Drug Deliv. 2011 July; 8 (4):373-80. In a specific embodiment, fastcaps are used. Fastcaps are a rapidly disintegrating drug delivery system based on gelatin capsules. In contrast to conventional hard gelatin capsules, fastcaps consist of a gelation of low bloom strength and various additives to improve the mechanical and dissolution properties of the capsule shell. See, e.g., Ciper and Bodmeier, Int J Pharm. 2005 Oct. 13; 303 (1-2):62-71. In a specific embodiment, freeze dried (lyophilized) wafers are used. Freeze dried (lyophilized) wafers are rapidly disintegrating, thin matrixes that contain a medicinal agent. The wafer or film disintegrates rapidly in the oral cavity and releases drug which dissolves or disperses in the saliva. See, e.g., Boateng et al., Int J Pharm. 2010 Apr. 15; 389 (1-2):24-31. Those skilled in the art are familiar with various techniques utilized to manufacture ODDFs such as freeze drying, spray drying, phase transition processing, melt granulation, sublimation, mass extrusion, cotton candy processing, direct compression, etc. See, e.g., Nagar et al., supra.

When administered, ODDFs containing deuterated gaboxadol or a pharmaceutically acceptable salt thereof disintegrate rapidly to release the drug, which dissolves or disperses in the saliva. The drug may be absorbed in the oral cavity, e.g., sublingually, buccally, from the pharynx and esophagus or from other sections of gastrointestinal tract as the saliva travels down. In such cases, bioavailability can be significantly greater than that observed from conventional tablet dosage forms which travel to the stomach or intestines where drug can be released.

Intranasal forms enhance rapid uptake of deuterated gaboxadol via the nasal and pulmonary system. Intranasal formulations of therapeutic agents are well known and those skilled in the art may adapt deuterated gaboxadol to such a format. Design choices depend on whether the product will be a solution or suspension. Critical parameters include pH and buffer selection, osmolality, viscosity, excipient selection and choice of penetration enhancers or other components to enhance residence time in the nasal cavity. (See DPT Laboratories Ltd publications at www.dptlabs.com).

In a specific embodiment, a desirable target of the invention is to rapidly achieve a blood level which achieves GABAA receptor saturation in the brain. GABAA receptor saturation level of non-deuterated gaboxadol is a blood level over 900 ng/ml. Using deuterated gaboxadol those skilled in the art may calculate GABAA receptor saturation level in the brain, Cmax, Tmax and the AUC at different time points. For comparison, non-deuterated gaboxadol has GABAA receptor saturation level in the brain of about 900 mg/ml, and a 20 mg dose has a Cmax of 900 ng/ml, plasma Tmax is achieved within 90 minutes the first treatment and AUC0-∞ about 900 ng*hr/ml.

In a specific embodiment of a method of the invention comprising two administrations of deuterated gaboxadol (e.g., within the first about 12 hours), different routes of administration of deuterated gaboxadol may be employed. For example, if the first administration is oral, the second administration is intranasal, or vice versa. Alternatively, both administrations may be of the same route of administration.

Combination Therapy

In certain embodiments, provided herein are methods of treating a psychiatric disorder, comprising administering to a patient in need thereof a pharmaceutical composition comprising deuterated gaboxadol or a pharmaceutically acceptable salt thereof, and a second, different pharmaceutical composition comprising an active agent selected from the group consisting of lithium, ketamine, SAGE-217, allopregnanolone ganaxolone, alfadolone, alfaxolone, hydroxydione, minaxolone, pregnanolone, renanolone, a pregnane neurosteroid, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, gaboxadol, clozapine, [2-amino-4-(2,4,6-trimethylbenzylamino)-phenyl]-carbamic acid ethyl ester (AA29504), AXS-05 (fixed combination of dextromethorphan and bupropion) and a pharmaceutically acceptable salt of any of the foregoing.

In certain embodiments, provided herein are methods of treating a psychiatric disorder comprising administering to a patient in need thereof a pharmaceutical composition comprising deuterated gaboxadol or a pharmaceutically acceptable salt thereof, and wherein a second pharmaceutical composition comprising a second active agent may be also administered according to a prescribed schedule and dose, which may optionally be timed to be at the same time as deuterated gaboxadol administration.

In certain embodiments, the deuterated gaboxadol and the second active agent (of the second pharmaceutical composition) may be provided in a combined dosage form, such as a fixed dose combination, when co-administration is to be done.

The combinations of the invention may provide additive and/or synergistic effects. In certain embodiments, upon administration the first pharmaceutical composition comprising deuterated gaboxadol and the second pharmaceutical composition comprising a second active agent provide a synergistic effect to improve at least one symptom of a psychiatric disorder. In preferred embodiments, the combination therapy demonstrates a synergistic effect and employs a dose of deuterated gaboxadol and a dose of the active agent of the second pharmaceutical composition in which one or both of deuterated gaboxadol or the second active agent are provided at doses known to be individually sub-threshold for therapeutic effect. In certain embodiments, the invention contemplates a combination therapy wherein the amount of deuterated gaboxadol administered is 30 mg, 25 mg, 20 mg, 15 mg, 12 mg, 10 mg, 6 mg, 5 mg or less. In certain embodiments, the second pharmaceutical composition comprises ketamine and the amount of ketamine can be about 10, 9, 8, 7, 6, 5, 4, 3, 2, or 1 mg or less. In other embodiments, the second pharmaceutical composition comprises lithium.

Lithium

It will be understood that reference in this disclosure to "lithium" will also apply to any lithium-containing compound comprising a lithium salt, such as lithium carbonate, a cocrystal as well as a synthetic lithium pharmaceutical, such as an isotope-modified lithium compound.

Lithium Salts

The most common lithium-containing compound for treatment of mental conditions is naturally occurring lithium carbonate (Li2CO3). The lithium carbonate molecule consists of a central carbon atom bonded to the oxygen ions, with two oxygen ions each bonded to a lithium ion. The electron valence of the constituent atoms dictates both the molecular structure and the chemical and biochemical reactions of the molecule. The molecular weight of Li being 6.94 g/mol and that of $Li_2CO_3$ mass being 73.89 g/mol, the mass of lithium ion (Li+) in a dose of lithium carbonate equates to 18.79% of the mass of lithium carbonate ($Li_2CO_3$).

In certain embodiments, other salt forms that can serve as a source of lithium include, but are not limited to, for example, lithium benzoate, lithium bromide, lithium fluoride, lithium cacodylate, lithium caffeine sulfonate, lithium chloride, lithium orotate, lithium citrate, lithium dithiosalicylate, lithium formate, lithium gaboxadolyate, lithium gaboxadolate, Lithium gaboxadolinate, lithium glycerophosphate, lithium iodate, lithium lactate and lithium salicylate. Lithium citrate ($Li_3C_6H_5O_7$) is approved by the FDA for treating mania and bipolar disorder and is available to be taken orally in the form of capsules, syrup and tablets. Lithium orotate ($LiC_5H_3N_2O_4$) and some other lithium compounds can be commercially available over the counter as vitamins.

In certain embodiments, a source of lithium comprises a lithium deuterated gaboxadol salt.

In certain embodiments, a composition of a lithium salt, preferably an organic anion salt of lithium, and a complementary neutral organic compound are combined in a stoichiometric ratio. In a specific embodiment, the cocrystal thus formed has the formula LiX.aM, wherein X is, for example, salicylate or lactate, M is a neutral organic molecule, and a is from 0.5 to 4. In specific variations of the invention, the lithium salicylate or lithium lactate has a molar ratio to the organic molecule of 1:1 or 1:2. Optionally, the organic molecule is an amino acid, synthetic amino acid, xanthine, polyphenol, or sugar. In general, organic anion lithium ionic cocrystal compositions may be prepared by combining the lithium salt and the complementary organic compound (i.e., the cocrystal precursor) in a solvent and using a commonly used method to promote crystallization such as evaporating or cooling the solvent to form the cocrystals.

Examples of amino acids or synthetic amino acids that can be used are alanine, arginine, asparagine, aspartic acid, cysteine, isoleucine, glutamic acid, glutamine, glycine, histidine, leucine, lysine, methionine, phenylalanine, proline, selenocysteine, serine, taurine, threonine, tryptophan, tyrosine, nicotinic acids, and valine. By way of further example, the amino acid is an L-amino acid such as L-phenylalanine, L-leucine, or L-tyrosine. In an alternative embodiment, the amino acid is a D-amino acid such as D-phenylalanine, D-leucine, or D-tyrosine. In an alternative embodiment, the cocrystal precursor comprises a non-proteinogenic amino acid. Synthetic amino acids can include the naturally occurring side chain functional groups or synthetic side chain functional groups which modify or extend the natural amino acids with alkyl, substituted alkyl, cycloalkyl, heterocyclic, substituted heterocyclic, aryl alkyl, aryl, heteroaryl, heteroaryl alkyl, and like moieties as framework and with carboxyl, amine, hydroxyl, phenol, carbonyl, or thiol functional groups; exemplary synthetic amino acids include β-amino acids and homo or β-analogs of natural (standard) amino acids. Other exemplary amino acids include pyrrolysine, betaine, and carnitine.

Examples of xanthine are caffeine, paraxanthine, theophylline, and threobromine.

Examples of polyphenols can be classified into the following categories: (1) phenolic acids, (2) flavonoids, (3) stilbenoids; (4) tannins, (5) monophenol such as hydroxytyrosol or p-tyrosol, (6) capsacin and other capsaicinoids and (7) curcumin. Phenolic acids form a diverse group including, for example, (a) hydroxycinnamic acids, e.g., p-coumaric acid, caffeic acid, and ferulic acid; (b) hydroxybenzoid acids, e.g., p-hydroxybenzoic acid, gallic acid, and ellagic acid; and (c) rosmarinic acid.

In certain embodiments, flavonoids can be resveratrol, epigallocatechin-3-gallate (EGCG), quercetin, ferulic acid, ellagic acid, hespereten, and protocatechuic acid.

In certain embodiments where the organic molecule is a sugar, the sugar can include monosaccharides and disaccharides. For example, the sugar can be fructose, galactose, glucose, lactitol, lactose, maltitol, maltose, mannitol, melezitose, myoinositol, palatinite, raffinose, stachyose, sucrose, trehalose, or xylitol.

In certain embodiments, the composition optionally comprises one or more nutraceuticals, selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, resveratrol, epigallocatechin-3-gallate (EGCG), quercetin, ferulic acid, ellagic acid, hespereten, and protocatechuic acid. By way of further example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hespereten, and protocatechuic acid.

In certain embodiments, the lithium salt and the complementary neutral organic compound are combined in an aqueous system. In certain embodiments, the lithium salt and complementary neutral organic compound may be dissolved in polar organic solvents such as acetone, acetonitrile, DMSO and alcohols.

In certain embodiments, organic anion lithium ionic cocrystal compositions may be prepared by combining a lithium-containing compound, an organic acid, and a complementary neutral organic compound, in a solvent, such as water, and using a commonly used method to promote crystallization such as evaporating or cooling the solvent.

Compositions and methods of making and administering lithium salt and/or cocrystal compounds are known in the art and are described, for example, in U.S. Pat. No. 9,744,189, the content of which is incorporated by reference herein in its entirety.

Isotope Modified Lithium Compounds

Many atoms come in several stable isotopes, distinguished by the number of neutrons inside their atomic nucleus. Lithium has two stable isotopes, lithium-7 with 4 neutrons and lithium-6 with 3 neutrons. In nature, 92.5% of lithium atoms are lithium-7 while lithium-6 constitutes the other 7.5%. By and large, biology is insensitive to the different atomic isotopes. However, an experiment from 1986 reported that rat mothers treated with lithium-7 ignored their pups and nursed them infrequently, while in contrast lithium-6-treated mothers were more alert and groomed and nursed their pups more often than normal mothers (Sechzer et al., 1986). Therefore, synthetic lithium-6 purified compounds, comprised predominantly of lithium-6 (greater than 95% of the total lithium), may be effective at treating mental conditions with reduced alertness levels, such as chronic and major depression—disorders that are not well treated with the present lithium pharmaceuticals which all have the natural lithium-isotope abundance concentrations (i.e. 92.5% lithium-7 and only 7.3% lithium-6). Purifying lithium-6 requires synthetic means, since all naturally occurring lithium (as mined from dried lake beds, for example) contain the natural abundance of the lithium isotopes.

In naturally occurring lithium compounds, such as lithium carbonate, the concentration of lithium-7 and lithium-6 atoms matches nature's ratio-92.5% lithium-7 and 7.5% lithium-6. But, this concentration ratio can be modified by synthetic means, and synthetic isotope-modified lithium compounds may be used to treat various psychiatric disorders and conditions, including those resistant to existing medications or in combination with deuterated gaboxadol as disclosed herein.

Li-6-Purified Compounds:

A purified Li-6 compound can be any lithium containing compound with lithium-6 present in an amount of at least 95% of the total lithium (i.e. lithium-6 and lithium-7) in the compound. The 95% threshold is much higher than the 7.5% natural abundance of lithium-6 that occurs in (un-synthesized) lithium pharmaceuticals, and is close to the ideal limit of lithium compounds with 100% lithium-6.

Li-7-Purified Compounds:

A Li-7-purified compound can be any lithium containing compound with a percentage of lithium-7 in the compound being at least 99% of the total lithium content. This lithium-7 concentration is significantly higher than the 92.5% natural abundance of lithium-7. The Li-7-purified compounds can have very low lithium-6 concentrations (below 1%), much lower than the 7.5% natural lithium-6 abundance.

Li-6-Enriched Compounds:

A Li-6-enriched compound can be any lithium containing compound with the percentage of lithium-6 present in the compound greater than 10% but less than 95% of the total lithium content. The 10% lithium-6 is significantly greater than the natural lithium-6 abundance of 7.5%. While lithium-6 concentrations in Li-6-enriched compounds can, in principle, be varied arbitrarily—in practical terms, it may be possible to control the concentration in increments of 10%. In certain embodiments, a Li-6-enriched compound class may comprise lithium-6 concentrations in the approximate ranges, about 10%-25%, about 25%-35%, about 35%-45%, about 45%-55%, about 55%-65%, about 65%-75%, about 75%-85% and about 85%-95%. In certain embodiments, the average lithium-6 concentrations in a Li-6-enriched compound can be about 20%, about 30%, about 40%, about 50%, about 60%, about 70%, about 80% and about 90%.

Li-7-Enriched Compounds:

A Li-7-enriched compound can be any lithium containing compound having a percentage of lithium-7 greater than about 95% but less than about 99% of the total lithium content. The 95% lithium-7 is significantly greater than the natural lithium-7 abundance of 92.5%.

Methods of making and administering isotope-modified lithium compounds are known in the art and are described, for example, in U.S. Pat. No. 9,044,418, the content of which is incorporated by reference herein in its entirety.

Human Equivalent Doses of Lithium

In certain embodiments, the amount of lithium carbonate in mg/kg administered daily to a human adult can be extrapolated from a dosage of lithium carbonate administered to an experimental animal, e.g. a mouse, using the formula for dose translation based on body surface area (BSA) (described elsewhere herein) and by consulting, for example, Table II. In certain embodiments, a dosage of lithium carbonate is administered that is the amount of lithium carbonate in mg for administration daily to a 60 kg adult human.

TABLE II

CONVERSION OF MOUSE LITHIUM CARBONATE (mg/kg) DOSE TO HUMAN EQUIVALENT DOSE (HED) (mg/kg) OF LITHIUM BASED ON BODY SURFACE AREA

| mg/kg | | mg/kg | | Daily dose for 60 kg human | |
|---|---|---|---|---|---|
| Li2CO3× MOUSE | Animal Km Human Km= | Li2CO3× HUMAN | 60 kg= | mg Li2CO3 | mg Li+ ion |
| 10× | 0.08= | 0.8× | 60= | 48 | 9.13 |
| 14.1× | 0.08= | 1.128× | 60= | 67.68 | 12.87 |
| 20× | 0.08= | 1.6× | 60= | 96 | 18.25 |
| 50× | 0.08= | 4× | 60= | 240 | 45.63 |
| 100× | 0.08= | 8× | 60= | 480 | 91.25 |
| 150× | 0.08= | 12× | 60= | 720 | 136.88 |
| 200× | 0.08= | 16× | 60= | 960 | 182.51 |
| 250× | 0.08= | 20× | 60= | 1200 | 228.14 |
| 300× | 0.08= | 24× | 60= | 1440 | 273.76 |
| 350× | 0.08= | 28× | 60= | 1680 | 319.39 |
| 400× | 0.08= | 32× | 60= | 1920 | 365.02 |
| 450× | 0.08= | 36× | 60= | 2160 | 410.65 |
| 500× | 0.08= | 40× | 60= | 2400 | 456.27 |

Lithium Monotherapy

Lithium was first described as a mood stabilizer by the Australian psychiatrist John Cade in 1949 for the treatment of acute mania (Cade J F Med J Aust. 1949; 2(10):349-52). Approved in 1970 by the U.S. Food and Drug Administration, the mechanism of action of lithium remains a mystery, though it is has been proposed that lithium's action stems, at least in part, from the ability of the Li+ ion to inhibit glycogen synthase kinase 3 and inositol monophosphatase by displacing magnesium, a cofactor essential for enzymatic activity (see, for example, U.S. Pat. No. 9,265,764, the content of which is incorporated by reference herein in its entirety). Lithium is now widely prescribed for the treatment of bipolar disorder, unipolar depression, treatment resistant depression and suicide prevention.

Treatment of Bipolar Disorder

Bipolar disorder is a mood disorder characterized by unusually intense emotional states that occur in distinct periods called "mood episodes." An overly elated or over-excited state is called a manic episode, and an extremely sad or hopeless state is called a depressive episode. Individuals suffering from bipolar disorder experience manic episodes, also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. Patients affected by bipolar disorder have had at least one manic or hypomanic (mild mania) episode. Patients with full manias and depression are indicated as having "bipolar I disorder". Patients with hypomania and depression are described as having "bipolar II disorder." Onset of episodes tends to be acute, with symptoms developing over days to weeks.

Symptoms of mania or a manic episode include both mood changes and behavioral changes. Mood changes include the following: a long period of feeling "high," or an overly happy or outgoing mood; and extremely irritable mood, agitation, feeling "jumpy" or "wired." Behavioral changes include the following: talking very fast, jumping from one idea to another, having racing thoughts; being easily distracted; increasing goal-directed activities, such as taking on new projects; being restless; sleeping little; having an unrealistic belief in one's abilities; behaving impulsively and taking part in a lot of pleasurable; and high-risk behaviors, such as spending sprees, impulsive sex, and impulsive business investments.

Symptoms of depression or a depressive episode include both mood changes and behavioral changes. Mood changes include the following: a long period of feeling worried or empty; and loss of interest in activities once enjoyed, including sex. Behavioral Changes include the following: feeling tired or "slowed down"; having problems concentrating, remembering, and making decisions; being restless or irritable; changing eating, sleeping, or other habits; and thinking of death or suicide, or attempting suicide.

In adult bipolar patients, the dose of lithium needed to achieve treatment efficacy in acute mania typically begins with a dose between 600-900 mg lithium carbonate per day or approximately 10 to 15 mg/kg for an adult human, which is gradually increased up to 1800 mg or approximately 30 mg/kg for an adult human of lithium carbonate per day. Lithium has been traditionally given in 2-4 divided doses, but a single evening dose has also been used and was shown to have a comparable therapeutic efficacy with improved compliance and even lesser renal adverse effects (Carter et al., 2013; Ljubicic et al., 2008; Singh et al., 2011). The maximum daily dose usually should not exceed 2400 mg lithium carbonate or approximately 40 mg/kg for an adult human. The typical therapeutic concentration of lithium in the serum for acute treatment of manic episodes is in the range of 0.6 to 1.2 mmol/L and the number of patients with a positive therapeutic response increases as the serum lithium concentration increases.

For long-term control of bipolar disease (BD) in adults, the recommended dose is between 900 to 1500 mg lithium carbonate/day or approximately 15 to 25 mg/kg for an adult human adult orally per day. Lithium concentrations in the blood considered safe for BD maintenance treatment are in the range as low as 0.4 mmol/L to 1.2 mmol/L, with the higher end of the range improving the likelihood of effective prophylactic therapy. However, given the concerns about side-effects caused by the long term use of lithium, the lower target ranges of 0.4 to 0.8 mmol/L are often used. In contrast, concentrations between 1.2-2.5 mmol/L may be associated with mild toxicity, concentrations between 2.5 and 3.5 mmol/L result in severe toxicity, and concentrations greater than 3.5 mmol/L can be life-threatening.

In pediatric BD patients, dosing of lithium is typically within the range estimates for adults when accounting for body size, i.e. 20-30 mg per kg of lithium carbonate per day in an acute treatment and 10 to 25 mg of lithium carbonate per kg for chronic treatment.

Dosing in older patients should be carefully monitored to account for age-related lower renal function, typically leading to two to threefold decreases in doses needed to achieve the desired serum concentration (Rej et al., 2014).

Lithium treatment and monitoring during pregnancy is particularly challenging because increased glomerular filtration rate leads to a substantial reduction of lithium levels and risk of BD relapse. Clinical strategy in pregnancy is therefore to increase lithium dose during pregnancy and in addition achieve higher serum levels during the early postpartum period that is associated with a strongly increased risk of relapse (Deligiannidis et al., 2014). However, as the kidney functions return to normal in the postpartum period, high lithium doses can lead to acute toxicity to the mother as well as to the infant (Horton et al., 2012; Wesseloo et al., 2017).

In adults and children 12 years of age or older suffering from acute mania, the oral dose of extended-release lithium tablets can be 900 mg 2 times a day, or 600 mg 3 times a day of lithium. For the long-term treatment of mania, in adults and children 12 years of age or older the oral dose of lithium can be 600 mg 2 times a day, or 3 times a day up to 1200 mg per day. Treatment of mania in children younger than 12 years of age is not recommended.

Treatment of Unipolar Depression and Suicide Prevention

Unipolar depression or major depressive disorder (MDD) is used as that term is understood in art, and refers to a diagnosis that is guided by diagnostic criteria listed in DSM-IV or ICD-10, or in similar nomenclatures (DSM IV-TR—Desk reference to the diagnostic criteria from DSM-IV-TR, American Psychiatric Association, Washington D.C. 2000; Kaplan, H. I. et al. Kaplan and Sadock's Synopsis of Psychiatry (8th edition) 1998 Williams & Wilkins, Baltimore). Unipolar depression is a major clinical problem with lifetime prevalence in Western cultures estimated to be between 4%-12%. Although approximately 70% of patients respond to treatment with antidepressants, up to 75% have a recurrence within 10 years and a very high proportion of sufferers remain undiagnosed and untreated. The unipolar connotes a difference between major depression and bipolar depression, which refers to an oscillating state between depression and mania. Instead, unipolar depression is solely focused on the "lows" characterized by a rumination on negative emotions. DSM IV requires for the diagnosis of major depression the presence of a major depressive episode. This in turn consists of at least five of the nine symptoms present during the same 2-week period, of which depressed mood or loss of interest or pleasure has to be one of the symptoms. Changes in weight/appetite, sleep, energy, psychomotor retardation or agitation, guilt, decreased concentration, suicidality are the other symptoms. It should also be noted that depression is not the only psychiatric disorder leading to suicide. Other disorders like bipolar disorder, psychotic disorders (like schizophrenia), anxiety disorders (including panic disorders, OCD, PTSD), alcohol and drug addictions, and personality disorders may also lead to suicide.

Lithium is also used as an adjunct treatment and for reducing suicidality in unipolar depression, especially in a population of patients with treatment-resistant depression (Cipriani et al., 2013; Cipriani et al., 2005; Roberts et al., 2017). In addition, lithium has also been recommended in the prophylaxis of recurrent unipolar depressive episodes in this population, with the suggestion to start the prophylactic life-long treatment after the occurrence of 2 episodes of severe depression with suicidal risk within 5 years (Abou-Saleh et al., 2017; Baldessarini et al., 2003; Post, 2018; Tiihonen et al., 2016; Toffol et al., 2015). Remarkably, lithium appears to have an anti-suicide effect even at very low concentrations in drinking water, typically less than 150 μg/L (Ando et al., 2017; Vita et al., 2015).

Despite its well-established efficacy in the treatment of BD, lithium treatment has several disadvantages. The therapeutically effective window is very narrow which means even modest changes in serum concentration can have significant toxicity leading to, for example, nephrotoxicity accompanied with extreme thirst, nausea, vomiting, diarrhea, drowsiness, muscle weakness, tremor, lack of coordination, hallucinations, seizures (blackout or convulsions), vision problems, dizziness, fainting, slow heart rate, or fast or uneven heartbeats. In addition, long-term therapeutic maintenance amongst BD patients can be quite variable, with only approximately 30% of patients showing good long-term efficacy (Scott et al., 2017). Therefore, the development of a lithium form with good therapeutic efficacy in a broader population of BD would dramatically improve BD treatment options.

Based on clinical practice guidelines lithium is, and has been since the 1960s, the first line treatment for mood stabilization and reduction of suicidality in bipolar disorders (BD), providing acute anti-manic therapeutic relief and preventing BD relapses to countless BD patients (Baldessarini et al., 2006; Cipriani et al., 2013; Kessing et al., 2018; Roberts et al., 2017; Sani et al., 2017; Severus et al., 2014). However, despite lithium's widespread use, it is not uncommon for patients to experience serious side effects from this medication.

For example, a first concern about lithium treatment is undoubtedly its very narrow therapeutic window, requiring the caregiver to maintain a serum concentration of typically 0.6-1.0 mmol/L for maintenance of bipolar disorder and typically higher levels of 1.0-1.2 mmol/L in acute mania treatment (Association, 2002; Gelenberg et al., 1989; Grandjean and Aubry, 2009). As lower levels are considered to be ineffective and lithium serum levels above this range can result in serious side-effects and toxicity, any treatment with lithium necessarily needs constant monitoring. This is especially true in BD patients who are pregnant because the associated increase in glomerular filtration rate can substantially reduce serum lithium levels to a point where there is a significant risk of BD relapse.

Acute lithium toxicity can present as non-convulsive status epilepticus, slowing of EEG alpha rhythm, pathological 3-10 Hz delta rhythm and diffuse spike discharges, life-threatening coma, hypothonia and hyporeflexia (Ivkovic and Stern, 2014; Madhusudhan, 2014; Megarbane et al., 2014; Schou et al., 1968).

Additionally, chronic side-effects associated with long-term maintenance lithium treatment include hypothyroidism, nephrogenic diabetes insipidus and significant nephrotoxicity and chronic kidney disease especially in patients already diagnosed with kidney failure (Davis et al., 2018a; Davis et al., 2018b). In an epidemiological study that examined reasons for discontinuing lithium therapy amongst BD patients, the majority (62%) of people stopped taking lithium because of the adverse events, primarily renal disease, diarrhea and/or tremor (Ohlund et al., 2018). In 2014 alone, there were 6,850 reported cases of lithium toxicity in the United States. Lithium treatment therefore requires very careful monitoring and titration of serum lithium concentrations to achieve a long lasting therapeutic benefit.

Accordingly, there is an ongoing need for improved treatment options that mitigate the side effects associated with lithium treatment of many severe psychiatric disorders including bipolar disorder.

Ketamine

Ketamine is a drug with dissociative and glutamate NMDA receptor-blocking properties that was approved by the U.S. Food and Drug Administration in 1970 for anesthetic use. It has become a target of research for its antidepressant effects, which occur within hours at subanesthetic doses. Reports of reduction in suicidal ideation after ketamine infusion are promising, but the conclusiveness of results for major depression has been limited by measurement of suicidal ideation with a single item from a depression inventory, lack of a control group, use of a saline control, and use of samples with low levels of suicidal ideation or mixed diagnoses.

Clinical trials have established the efficacy of ketamine on reduction of suicidal ideation. An example may be found at ClinicalTrials.gov Identifier: NCT01700829, described in associated publication (Grunebaum et al., 2018). This trial is a randomized clinical trial of an adjunctive intravenous infusion of ketamine compared with the short-acting benzodiazepine anesthetic midazolam in patients with major depressive disorder who had clinically significant suicidal ideation, as assessed by score on the Scale for Suicidal Ideation (SSI). The primary outcome measure was SSI score 24 hours after infusion. Other outcome measures include global depression ratings, clinical ratings during 6-week open follow-up treatment, and safety measures. IV ketamine has been effective in treating acute cases of suicidality (Lee et al. (2015) Innov Clin Neurosci. 2015 January-February; 12(1-2): 29-31.) Janssen Pharmaceuticals has received FDA approval for the purified S-enantiomer of ketamine known as esketamine, and launched under the tradename Spravato® esketamine. Spravato® is approved for the treatment of treatment resistant depression and depressive symptoms in adults with major depressive disorder with acute suicidal ideation or behavior (see Spravato® Prescribing Information). Details on esketamine may be found at ClinicalTrials.gov Identifier: NCT01627782 and the Spravato™ esketamine product label.

Human Equivalent Doses (HED)

Dosages of a medication administered to experimental animals, e.g. rodents, can be extrapolated to a human equivalent dose (HED) using the Body Surface Area (BSA) method (see, e.g. the "Guidance for Industry: Estimating the Maximum Safe Starting Dose in Initial Clinical Trials for Therapeutics in Adult Healthy Volunteers" (July 2005) available for download on the FDA's web site at www.fda.gov/files/drugs/published/Estimating-the-Maximum-Safe-Starting-Dose-in-Initial-Clinical-Trials-for-Therapeutics-in-Adult-Healthy-Volunteers.pdf, the content of which is incorporated by reference herein in its entirety; see Table III below).

The human equivalent dose (HED) can be calculated using the following equation:

HED (mg/k)=Animal dose (mg/kg) multiplied by (Animal $K_m$/Human $K_m$)

Where $K_m$ refers to a conversion factor in kg/m$^2$ equal to the body weight in kg divided by the surface area in m$^2$. Hence, a daily human equivalent dose (mg/kg) or a daily dose (mg) administered to an adult human. human can be extrapolated from a daily dose of a medication administered to a mouse (mg/kg).

TABLE III

Conversion of Animal Doses to Human Equivalent Doses Based on Body Surface Area

| Species | Reference Body Weight | Working Weight Range[a] (kg) | Body Surface Area (m$^2$) | Dose in mg/m$^2$ Multiply by $k_m$ | To Convert Animal Dose in mg/kg to HED[b] in mg/kg, Either | |
|---|---|---|---|---|---|---|
| | | | | | Divide Animal Dose By | Multiply Animal Dose By |
| Human | 60 | — | 1.62 | 37 | — | — |
| Child[c] | 20 | — | 0.80 | 25 | — | — |
| Mouse | 0.020 | 0.011-0.034 | 0.007 | 3 | 12.3 | 0.081 |
| Hamster | 0.080 | 0.047-0.157 | 0.016 | 5 | 7.4 | 0.135 |
| Rat | 0.150 | 0.080-0.270 | 0.025 | 6 | 6.2 | 0.162 |
| Ferret | 0.300 | 0.160-0.540 | 0.043 | 7 | 5.3 | 0.189 |
| Guinea pig | 0.400 | 0.208-0.700 | 0.05 | 8 | 4.6 | 0.216 |
| Rabbit | 1.8 | 0.9-3.0 | 0.15 | 12 | 3.1 | 0.324 |
| Dog | 10 | 5-17 | 0.50 | 20 | 1.8 | 0.544 |
| Primates: | | | | | | |
| Monkeys[d] | 3 | 1.4-4.9 | 0.25 | 12 | 3.1 | 0.324 |
| Marmoset | 0.350 | 0.140-0.720 | 0.06 | 6 | 6.2 | 0.162 |
| Squirrel monkey | 0.600 | 0.200-0.970 | 0.09 | 7 | 5.3 | 0.189 |
| Baboon | 12 | 7-23 | 0.60 | 20 | 1.8 | 0.541 |
| Micro-pig | 20 | 10-33 | 0.74 | 27 | 1.4 | 0.730 |
| Mini-pig | 40 | 25-64 | 1.14 | 35 | 1.1 | 0.946 |

[a]For animal weights within the specified ranges, the HED for a 60 kg human calculated using the standard $k_m$ value will not vary more than ±20 percent from the HED calculated using a $k_m$ value based on the exact animal weight.
[b]Assumes 60 kg human. For species not listed or for weights outside the standard ranges, human equivalent dose can be calculated from the formula: HED = animal dose in mg/kg × (animal weight in kg/human weight in kg)$^{0.33}$.
[c]The $k_m$ value is provided for reference only since healthy children will rarely be volunteers for phase 1 trials.
[d]For example, cynomolgus, rhesus, and stumptail.

SAGE-217 is an investigational medication which is under development by SAGE Therapeutics for the treatment of major depressive disorder, postpartum depression, essential tremor, Parkinson's disease, insomnia, and seizures. It is a synthetic, orally active, inhibitory pregnane neurosteroid, and acts as a positive allosteric modulator of the GABA$_A$ receptor. The drug was developed as an improvement of allopregnanolone (brexanolone) with high oral bioavailability and a biological half-life suitable for once-daily administration. As of February 2018, SAGE-217 is in phase II clinical trials for major depressive disorder, postpartum depression, essential tremor, and Parkinson's disease and is in phase I clinical studies for insomnia and seizures. It is also in the preclinical stage of development for dyskinesias. The SAGE-217 chemical formula is 3α-Hydroxy-3β-methyl-21-

(4-cyano-1H-pyrazol-1'-yl)-19-nor-5β-pregnan-2β-one; 3β-Methyl-21-(4-cyano-1H-pyrazol-1'-yl)-19-norpregnanolone; 3α-Hydroxy-3β-methyl-5β-dihydro-21-(4-cyano-1H-pyrazol-1'-yl)-19-norprogesterone.

Combinations of Deuterated Gaboxadol and Lithium

A largely automated drug-screening platform called "pharmacomapping" comprises whole-brain detection of drug-evoked neuronal activation represented by drug-evoked expression of the immediate early genes (IEG), e.g., c-fos. Pharmacomapping is commercially available as a fee for service by CRO Certerra, Inc. in Farmingdale, N.Y.

Pharmacomapping of mouse or rat brain activity in response to various psychoactive medications, including antipsychotics, antidepressants, stimulants and anxiolytics (Engber et al., 1998; Salminen et al., 1996; SEMBA et al., 1996; Slattery et al., 2005; Sumner et al., 2004) confirmed that the imaging of c-fos activation in the rodent brain is a valid method of screening for psychoactive drugs (Sumner et al., 2004).

The therapeutic efficacy of deuterated gaboxadol in the methods of treatment according to the present invention is indicated by the results of using the pharmacomapping approach as set out in the Examples. Among other things, the Examples herein use pharmacomapping to show that deuterated gaboxadol has an effect on activation in the mouse brain, and that this effect corresponds to the effect of lithium, and the effect of ketamine in the brain. It is observed that the effect is enhanced when the drugs are used in combination, particularly deuterated gaboxadol and lithium. It is further observed that the combination therapy has an effect that may be described as additive or as synergistic. Based on these data, it is believed that doses comparable to standard human doses of lithium are suitable for use in combination with deuterated gaboxadol. In addition, based on these data, it is believed that doses that are below standard human doses of lithium, herein sometimes referred to as "sub-standard doses of lithium" are suitable for use in combination with deuterated gaboxadol.

Figure 29:
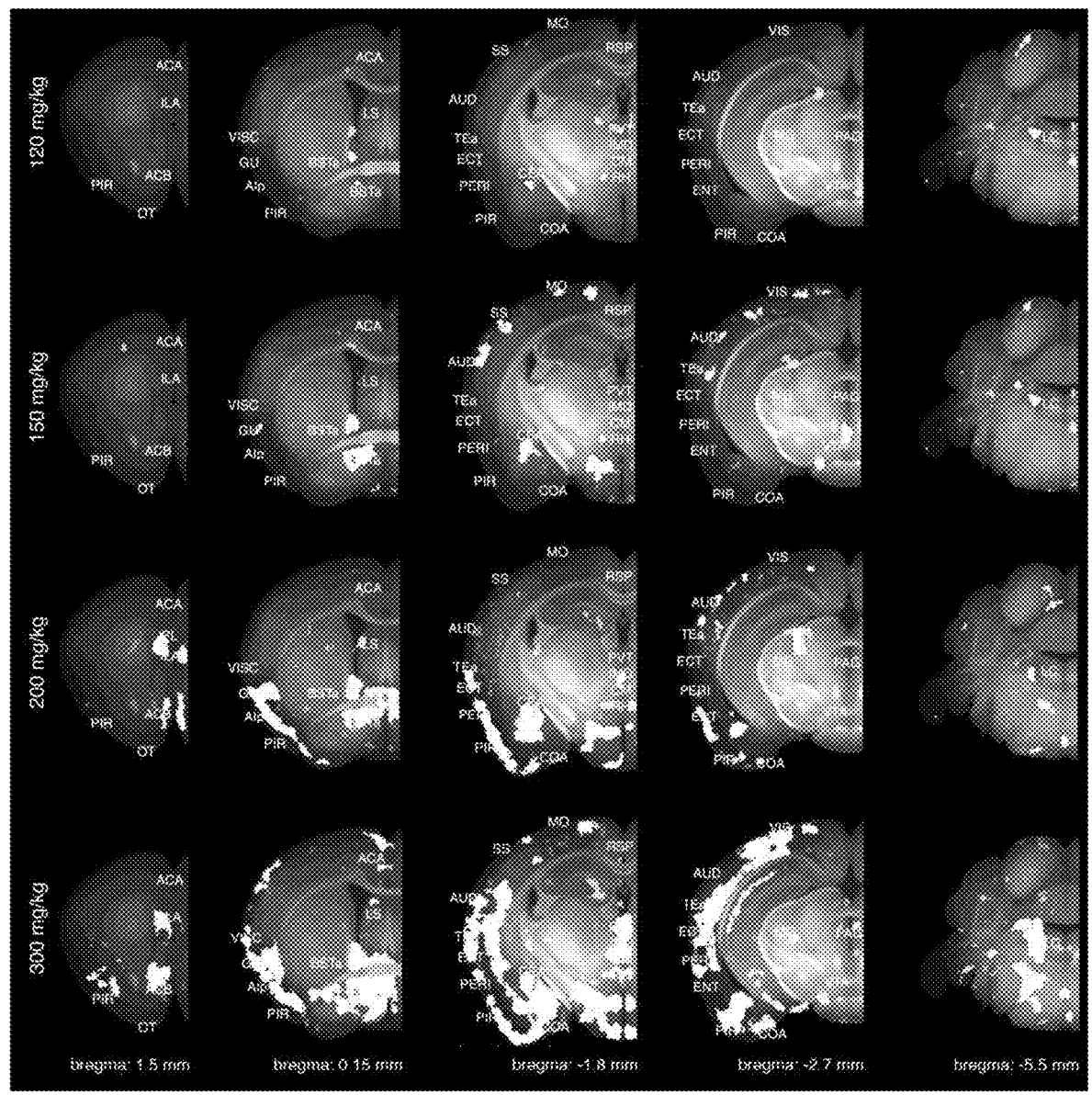
FIG. 29 shows exemplary lithium dose-curve pharmacomaps. White color indicates the spatial areas having significant lithium-evoked induction of c-fos activity in a mouse brain. The broad activation pattern induced by lithium with increasing dose was localized, for example, to the following anatomical structures: Cortex: prelimbic (PL) and infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (Tea), perirhinal (PERI) and entorhinal (ENT), and ectorhinal (ECT) cortex; Basal ganglia: the nucleus accumbens (ACB), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG); Brainstem: locus coeruleus (LC).

Using the experimental approach of pharmacomapping, deuterated gaboxadol is shown in Example 19 and FIGS. 34-38 to act in combination with a standard dose and with a sub-standard dose of lithium to activate c-fos expression in the same regions of the brain as seen with standard therapeutically effective lithium monotherapy seen in Example 15 and FIG. 29. Importantly, the brains of mice receiving either the low dose of deuterated gaboxadol alone or sub-standard dose lithium alone did not elicit any detectable or significant c-fos activity. As a consequence, combination therapy using a low dose of deuterated gaboxadol (e.g., in the range of 1-20 mg daily or less frequently than daily) and a substandard dose of lithium, or a pharmaceutically acceptable salt of either or both compounds thereof, wherein the substandard dose is lower than the dose normally used in monotherapy, is indicated to be effective, and side-effects associated with the larger amounts of lithium used in monotherapy are expected to be reduced or prevented altogether.

Additionally, a standard dose of lithium also acts in combination with (i.e. synergistically and/or additively) with deuterated gaboxadol (Example 19) (FIGS. 34-38), suggesting that gaboxadol may be able to augment conventional lithium monotherapy especially in those patients who do not respond to conventional monotherapy or who relapse.

Sub-Standard Doses of Lithium

In a specific embodiment, a "sub-standard" dose of lithium is defined as a human equivalent dose of lithium carbonate that when applied in an animal, such as a mouse, does not elicit any detectable or elicits only low induction of brain c-fos signaling.

In certain embodiments, a "sub-standard" dose of lithium is a daily dose of lithium carbonate that by itself, i.e. as lithium monotherapy, is unable to treat depression, treatment resistant depression acute suicidality or bipolar disorder. In certain embodiments, a "sub-standard" dose of lithium in a human is a daily dose of less than about 10 mg lithium carbonate/kg, which corresponds to a dose of less than about 600 mg lithium carbonate/day, for an adult human. For comparative purposes, a corresponding "sub-standard" dose of lithium in mice is a daily dose below about 120 mg/kg of lithium carbonate.

In certain embodiments, a "sub-standard" daily dose of lithium for an adult human patient refers to a daily dose in the range of about 50-600 mg lithium carbonate, about 55-600 mg lithium carbonate, about 60-600 mg lithium carbonate, about 65-600 mg lithium carbonate, about 70-600 mg lithium carbonate, about 75-600 mg lithium carbonate, about 80-600 mg lithium carbonate, about 85-600 mg lithium carbonate, about 90-600 mg lithium carbonate or about 95-600 mg lithium carbonate, about 100-600 mg lithium carbonate, about 105-600 mg lithium carbonate, about 110-600 mg lithium carbonate, about 115-100 mg lithium carbonate, about 120-100 mg lithium carbonate, about 125-600 mg lithium carbonate, about 130-600 mg lithium carbonate, about 135-600 mg lithium carbonate, about 140-600 mg lithium carbonate, about 145-600 mg lithium carbonate, about 150-600 mg lithium carbonate, about 155-600 mg lithium carbonate, about 160-600 mg lithium carbonate, about 165-600 mg lithium carbonate, about 170-600 mg lithium carbonate, about 175-600 mg lithium carbonate, about 180-600 mg lithium carbonate, about 185-600 mg lithium carbonate, about 190-600 mg lithium carbonate, about 195-600 mg lithium carbonate, about 200-600 mg lithium carbonate, about 215-600 mg lithium carbonate, about 210-600 mg lithium carbonate, about 215-100 mg lithium carbonate, about 220-100 mg lithium carbonate, about 225-600 mg lithium carbonate, about 230-600 mg lithium carbonate, about 235-600 mg lithium carbonate, about 240-600 mg lithium carbonate, about 245-600 mg lithium carbonate, about 250-600 mg lithium carbonate, about 255-600 mg lithium carbonate, about 260-600 mg lithium carbonate, about 265-600 mg lithium carbonate, about 270-600 mg lithium carbonate, about 275-600 mg lithium carbonate, about 280-600 mg lithium carbonate, about 285-600 mg lithium carbonate, about 290-600 mg lithium carbonate, about 295-600 mg lithium carbonate, about 300-600 mg lithium carbonate, about 315-600 mg lithium carbonate, about 310-600 mg lithium carbonate, about 315-600 mg lithium carbonate, about 320-600 mg lithium carbonate, about 325-600 mg lithium carbonate, about 330-600 mg lithium carbonate, about 335-600 mg lithium carbonate, about 340-600 mg lithium carbonate, about 345-600 mg lithium carbonate, about 350-600 mg lithium carbonate, about 355-600 mg lithium carbonate, about 360-600 mg lithium carbonate, about 365-600 mg lithium carbonate, about 370-600 mg lithium carbonate, about 375-600 mg lithium carbonate, about 380-600 mg lithium carbonate, about 385-600 mg lithium carbonate, about 390-600 mg lithium carbonate or about 395-600 mg lithium carbonate.

In certain embodiments, a "sub-standard" daily dose of lithium for an adult human adult patient refers to a daily dose in the range of about 50-600 mg lithium carbonate, 50-595 mg lithium carbonate, 50-590 mg lithium carbonate, 50-585 mg lithium carbonate, 50-580 mg lithium carbonate, 50-575 mg lithium carbonate, 50-570 mg lithium carbonate, 50-565 mg lithium carbonate, 50-560 mg lithium carbonate, 50-555 mg lithium carbonate, 50-550 mg lithium carbonate, 50-545 mg lithium carbonate, 50-540 mg lithium carbonate, 50-535 mg lithium carbonate, 50-530 mg lithium carbonate, 50-525 mg lithium carbonate, 50-520 mg lithium carbonate, 50-515 mg lithium carbonate, 50-510 mg lithium carbonate, 50-505 mg lithium carbonate, 50-500 mg lithium carbonate, 50-495 mg lithium carbonate, 50-490 mg lithium carbonate, 50-485 mg lithium carbonate, 50-480 mg lithium carbonate, 50-475 mg lithium carbonate, 50-470 mg lithium carbonate, 50-465 mg lithium carbonate, 50-460 mg lithium carbonate, 50-455 mg lithium carbonate, 50-450 mg lithium carbonate, 50-445 mg lithium carbonate, 50-440 mg lithium carbonate, 50-435 mg lithium carbonate, 50-430 mg lithium carbonate, 50-425 mg lithium carbonate, 50-420 mg lithium carbonate, 50-415 mg lithium carbonate, 50-410 mg lithium carbonate, 50-405 mg lithium carbonate, 50-400 mg lithium carbonate, about 50-395 mg lithium carbonate, about 50-390 mg lithium carbonate, about 50-385 mg lithium carbonate, about 50-380 mg lithium carbonate, about 50-375 mg lithium carbonate, about 50-370 mg lithium carbonate, about 50-365 mg lithium carbonate, about 50-360 mg lithium carbonate, about 50-355 mg lithium carbonate, about 50-350 mg lithium carbonate, about 50-345 mg lithium carbonate, about 50-340 mg lithium carbonate, about 50-335 mg lithium carbonate, about 50-330 mg lithium carbonate, about 50-325 mg lithium carbonate, about 50-320 mg lithium carbonate, about 50-315 mg lithium carbonate, about 50-3500 mg lithium carbonate, about 50-305 mg lithium carbonate, about 50-300 mg lithium carbonate, about 50-300 mg lithium carbonate, about 50-295 mg lithium carbonate, about 50-290 mg lithium carbonate, about 50-285 mg lithium carbonate, about 50-280 mg lithium carbonate, about 50-275 mg lithium carbonate, about 50-270 mg lithium carbonate, about 50-265 mg lithium carbonate, about 50-260 mg lithium carbonate, about 50-255 mg lithium carbonate, about 50-250 mg lithium carbonate, about 50-245 mg lithium carbonate, about 50-240 mg lithium carbonate, about 50-235 mg lithium carbonate, about 50-230 mg lithium carbonate, about 50-225 mg lithium carbonate, about 50-220 mg lithium carbonate, about 50-215 mg lithium carbonate, about 50-210 mg lithium carbonate, about 50-205 mg lithium carbonate, about 50-200 mg lithium carbonate, about 50-195 mg lithium carbonate, about 50-190 mg lithium carbonate, about 50-185 mg lithium carbonate, about 50-180 mg lithium carbonate, about 50-175 mg lithium carbonate, about 50-170 mg lithium carbonate, about 50-165 mg lithium carbonate, about 50-160 mg lithium carbonate, about 50-155 mg lithium carbonate, about 50-150 mg lithium carbonate, about 50-145 mg lithium carbonate, about 50-140 mg lithium carbonate, about 50-135 mg lithium carbonate, about 50-130 mg lithium carbonate, about 50-125 mg lithium carbonate, about 50-120 mg lithium carbonate, about 50-115 mg lithium carbonate, about 50-110 mg lithium carbonate, about 50-105 mg lithium carbonate, about 50-100 mg lithium carbonate, about 50-95 mg lithium carbonate, about 50-90 mg lithium carbonate, about 50-85 mg lithium carbonate, about 50-80 mg lithium carbonate, about 50-75 mg lithium carbonate, about 50-70 mg lithium carbonate, about 50-65 mg lithium carbonate, about 50-60 mg lithium carbonate, or about 50-55 mg lithium carbonate.

Standard Doses of Lithium

In a specific embodiment, a "standard" dose of lithium is a daily dose of lithium that by itself, i.e. as a single dose, elicits brain c-fos signaling in an animal model, such as a mouse.

In certain embodiments, a "standard" dose of lithium is a daily dose of lithium that by itself, i.e. as lithium monotherapy, can treat depression, treatment resistant depression acute suicidality or bipolar disorder.

In certain embodiments, a "standard" dose of lithium in a human is a daily dose of more than about 10 mg/kg of lithium carbonate, which corresponds to a dose of more than about 600 mg lithium carbonate/day for an adult human.

In certain embodiments, a "standard" dose of lithium in mice is a daily dose in the range of about 120 mg/kg to about 480 mg/kg of lithium carbonate. The human equivalent dose corresponds to about 10 mg/kg and 40 mg/kg, respectively, which, for an adult 60 kg human, is a dose in the range of about 600 mg to about 2400 mg lithium carbonate/day.

In certain embodiments, a "standard" daily dose of lithium for an adult human patient refers to a daily dose in the range of about 600-2400 mg lithium carbonate, In certain embodiments, a "standard" daily dose of lithium for an adult human patient refers to a daily dose in the range of about 600-2400 mg lithium carbonate, In certain embodiments, a "standard" daily dose of lithium for an adult human patient refers to a daily dose in the range of about 600-2350 mg lithium carbonate, about 600-2300 mg lithium carbonate, about 600-2250 mg lithium carbonate, about 600-2200 mg lithium carbonate, about 600-2150 mg lithium carbonate, about 600-2100 mg lithium carbonate, about 600-2050 mg lithium carbonate, about 600-2000 mg lithium carbonate, about 600-1950 mg lithium carbonate, about 600-1900 mg lithium carbonate, about 600-1850 mg lithium carbonate, about 600-1800 mg lithium carbonate, about 600-1750 mg lithium carbonate, about 600-1700 mg lithium carbonate, about 600-1650 mg lithium carbonate, about 600-1600 mg lithium carbonate, about 600-1550 mg lithium carbonate, about 600-1500 mg lithium carbonate, about 600-1450 mg lithium carbonate, about 600-1400 mg lithium carbonate, about 600-1350 mg lithium carbonate, about 600-1300 mg lithium carbonate, about 600-1250 mg lithium carbonate, about 600-1200 mg lithium carbonate, about 600-1150 mg lithium carbonate, about 600-1100 mg lithium carbonate, about 600-1050 mg lithium carbonate, about 600-1000 mg lithium carbonate, about 600-950 mg lithium carbonate, about 600-900 mg lithium carbonate, about 600-850 mg lithium carbonate, about 600-800 mg lithium carbonate, about 600-750 mg lithium carbonate, about 600-700 mg lithium carbonate, or about 600-650 mg lithium carbonate.

In certain embodiments, a "standard" daily dose of lithium for an adult human patient refers to a daily dose in the range of about 600-2400 mg lithium carbonate, about 650-2400 mg lithium carbonate, about 700-2400 mg lithium carbonate, about 750-2400 mg lithium carbonate, about 800-2400 mg lithium carbonate, about 850-2400 mg lithium carbonate, about 900-2400 mg lithium carbonate, about 950-2400 mg lithium carbonate, about 1000-2400 mg lithium carbonate, about 1050-2400 mg lithium carbonate, about 1050-2400 mg lithium carbonate, about 1100-2400 mg lithium carbonate, about 1150-2400 mg lithium carbonate, about 1200-2400 mg lithium carbonate, about 1250-2400 mg lithium carbonate, about 1300-2400 mg lithium carbonate, about 1350-2400 mg lithium carbonate, about 1400-2400 mg lithium carbonate, about 1450-2400 mg lithium carbonate, about 1500-2400 mg lithium carbonate, about 1550-2400 mg lithium carbonate, about 1600-2400 mg lithium carbonate, about 1650-2400 mg lithium carbonate, about 1700-2400 mg lithium carbonate, about 1750-2400 mg lithium carbonate, about 1800-2400 mg lithium carbonate, about 1850-2400 mg lithium carbonate, about 1900-2400 mg lithium carbonate, about 1950-2400 mg lithium carbonate, about 2000-2400 mg lithium carbonate, about 2050-2400 mg lithium carbonate, about 2100-2400 mg lithium carbonate, about 2150-2400 mg lithium carbonate, about 2200-2400 mg lithium carbonate, about 2250-2400 mg lithium carbonate, about 2300-2400 mg lithium carbonate or about 2350-2400 mg.

Synergistic Combinations of Deuterated Gaboxadol and Lithium

The invention further discloses the discovery that deuterated gaboxadol and lithium act synergistically and thus are expected to provide enhanced therapeutic treatment of psychiatric disorders. An explanation of what is considered "synergy" follows below.

In specific embodiments, the effective amounts of lithium and deuterated gaboxadol are synergistic amounts. As used herein, "synergistic" is used in its art-accepted meaning. Thus, a synergistic combination of lithium and deuterated gaboxadol exhibits more than the additive effects of each (lithium and deuterated gaboxadol) alone.

In certain embodiments, the administration of a synergistic combination of lithium and deuterated gaboxadol to a subject in need thereof activates c-fos signaling in at least one region, at least two regions or at least three regions of the animal model's brain selected from the group consisting of: 1) a broad cortical activation comprising motor (MO), gustatory (GU), visceral (VISC), agranular insular (AI), somatosensory (SS), auditory, visual (VIS), auditory (AUD), prelimbic (PL) and infralimbic (ILA), retrosplenial (RSP), parietal (PTL), temporal associational (TEa), entorhinal (ECT), entorhinal (ENT), perirhinal (PERI), piriform (PIR), and anterior cingulate (ACA) cortex, claustrum (CLA), as well as 2) subcortical activation comprising hippocampal CA1 region, the bed nuclei stria terminalis (BST), central amygdala (CEA), cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), nucleus of reunions (RE), rhomboid nucleus (RH), and central medial nucleus (CM) of the thalamus, paraventricular hypothalamic nucleus (PVH), dorsomedial nucleus of the hypothalamus (DMH), tuberomammillary nucleus (TM), parasubthalamic nucleus (PSTN) and subthalamic nucleus (STN), parabrachial nucleus, locus coeruleus (LC), and nucleus of the solitary tract (NTS).

In certain embodiments, the administration of a synergistic combination of lithium and deuterated gaboxadol to a subject in need thereof activates c-fos signaling in at least one, two, three or more regions of the animal model's brain that are also activated by lithium monotherapy.

In certain embodiments, the administration of a synergistic combination of lithium and deuterated gaboxadol to a subject in need thereof activates c-fos signaling in at least one, two, three or more regions of the animal model's brain that are also activated by deuterated gaboxadol monotherapy.

In certain embodiments, a synergistic combination of lithium and deuterated gaboxadol comprises a sub-standard dose of lithium as described herein. In certain embodiments, the synergistic combination of lithium and deuterated gaboxadol comprises a standard dose of lithium as described herein.

In certain embodiments, a synergistic combination of lithium and deuterated gaboxadol comprises a dose of deuterated gaboxadol as described herein.

In certain embodiments, a sub-standard dose of lithium is administered with a dose of deuterated gaboxadol as exemplified in Example 19.

In certain embodiments, a synergistic combination of lithium and deuterated gaboxadol comprises a daily dose for an adult human patient in the range of about 50-600 mg lithium carbonate and in the range of about 1 to about 30 mg deuterated gaboxadol.

In certain embodiments, a synergistic combination of lithium and deuterated gaboxadol comprises a daily dose for an adult human patient in the range of about 50-600 mg lithium carbonate and in the range of about 5 to about 10 mg deuterated gaboxadol.

In certain embodiments, a synergistic combination of lithium and deuterated gaboxadol comprises a daily dose for an adult human patient in the range of about 600 mg to about 2400 mg lithium carbonate and in the range of about 1 to about 30 mg deuterated gaboxadol.

In certain embodiments, a synergistic combination of lithium and deuterated gaboxadol comprises a daily dose for an adult human patient in the range of about 600 mg to about 2400 mg lithium carbonate and in the range of about 5 to about 10 mg deuterated gaboxadol.

Several types of synergy are recognized by those skilled in the art. By way of example, some synergies may be recognized by the format 1+1=3, wherein the resulting effect of the combination is more than additive of the compounds administered individually. By way of another example, another synergy is of the type 0+0=1, wherein the resulting effect of the combination is more than additive of the compounds administered individually and wherein the two compounds which individually demonstrate no effect (at a given test dose) demonstrate full efficacy when administered together. The latter synergy is considered particularly remarkable when the test compounds are not known to act through similar or related pathways.

In certain embodiments, a synergistic combination of lithium and deuterated gaboxadol does not comprise lithium and deuterated gaboxadol at a molar ratio of 1:1.

In certain embodiments, synergy between lithium and deuterated gaboxadol results in an activation of an immediate early gene (e.g. c-fos, arc, egr-1, fosb and npas4) in the brain of an animal model that is at least about 5%, 10%, 20%, 30%, 40%, 50%, 100%, 200%, 400%, 500% or 1000% greater than the sum of the effects of lithium alone and deuterated gaboxadol alone on brain c-fos signaling.

In certain embodiments, synergy between lithium and deuterated gaboxadol results in an activation of c-fos gene expression in the brain of an animal model that is at least about 5%, 10%, 20%, 30%, 40%, 50%, 100%, 200%, 400%, 500% or 1000% greater than the sum of the effects of lithium alone and deuterated gaboxadol alone on brain c-fos signaling.

In certain embodiments, there is an additive effect between lithium and deuterated gaboxadol that results in an activation of an immediate early gene (e.g. c-fos, arc, egr-1, fosb and npas4) in the brain of an animal model that is equal to the sum of the effects of lithium alone and deuterated gaboxadol alone on brain c-fos signaling.

In certain embodiments, there is an additive effect between lithium and deuterated gaboxadol that results in an activation of the immediate early c-fos gene in the brain of an animal model that is equal to the sum of the effects of lithium alone and deuterated gaboxadol alone on brain c-fos signaling.

In certain embodiments, an "additive combination" of lithium and deuterated gaboxadol comprises a sub-standard dose of lithium as described herein.

In certain embodiments, an "additive combination" of lithium and deuterated gaboxadol comprises a standard dose of lithium as described herein.

In certain embodiments, an "additive combination" of lithium and deuterated gaboxadol comprises a low dose of deuterated gaboxadol as described herein.

In certain embodiments, an "additive combination" of lithium and deuterated gaboxadol comprises a standard dose of deuterated gaboxadol as described herein.

In certain embodiments, an "additive combination" of lithium and deuterated gaboxadol does not comprise lithium and deuterated gaboxadol at a molar ratio of 1:1.

In certain embodiments, lithium and deuterated gaboxadol can be administered as separate compositions for combination therapy (they are formulated separately) or together (they are formulated together). In certain embodiments, lithium and deuterated gaboxadol can be administered concurrently, simultaneously, sequentially, or contemporaneously as provided herein.

Treatment of Psychiatric Disorders with a Combination of Deuterated Gaboxadol and Lithium Based on the similarities of the pharmacomaps between the deuterated gaboxadol and lithium combination therapy and that seen with conventional lithium monotherapy (see Examples 15 and 19 herein), it is believed that ideuterated gaboxadol augments the established activity of lithium in the treatment of psychiatric disorders, such as but not limited to bipolar disorder, depression, treatment resistant depression and acute suicidality (see above).

Thus, in certain embodiments, a method of treating a psychiatric disorder is disclosed comprising administering a combination of deuterated gaboxadol and lithium, or a pharmaceutically acceptable salt of either or both compounds thereof, to a patient in need thereof.

In certain embodiments, the efficacy of the treatment can be monitored by a physician using a disease-specific psychiatric rating scale. A psychiatric rating scale refers to a psychological test that has been developed to provide a reliable and objective method of monitoring symptom severity of a particular mood disorder and measuring a response to treatment, see, e.g., Handbook of clinical rating scales and assessment in psychiatry and mental health by Baer, Lee and Blais, Mark A. New York; Humana Press, 2010; ISBN: 9781588299666, the content of which is incorporated by reference herein in its entirety. Exemplary psychiatric rating scales include, but are not limited to:

Beck Depression Inventory (BDI), Beck Hopelessness Scale, Centre for Epidemiological Studies-Depression Scale (CES-D), Center for Epidemiological Studies Depression Scale for Children (CES-DC), Edinburgh Postnatal Depression Scale (EPDS), Geriatric Depression Scale (GDS), Hamilton Rating Scale for Depression (HAM-D), Hospital Anxiety and Depression Scale, Kutcher Adolescent Depression Scale (KADS), Major Depression Inventory (MDI), Montgomery-Asberg Depression Rating Scale (MADRS), PHQ-9, Mood and Feelings Questionnaire (MFQ), Weinberg Screen Affective Scale (WSAS) and Zung Self-Rating Depression Scale for depression, Altman Self-Rating Mania Scale (ASRM), Bipolar Spectrum Diagnostic Scale, Child Mania Rating Scale, General Behavior Inventory, Hypomania Checklist, Mood Disorder Questionnaire (MDQ), Young Mania Rating Scale (YMRS) for mania and bipolar disorder and SAD PERSONS scale for suicide risk.

In certain therapies, the efficacy of the treatment can be monitored by a physician using an EEG recording during and in the period after the drug combination application, with drug-evoked biomarker changes in EEG based on drug-evoked biomarker changes established preclinically in animal models.

It is preferred that deuterated gaboxadol and lithium are administered to a patient at about the same time. Gaboxadol is cleared from the human body at a known rate. Administering lithium at a time after gaboxadol has been cleared from a patient's body is not expected to be as effective as administering both deuterated gaboxadol and lithium at about the same time. Most preferably, the deuterated gaboxadol and the lithium are administered simultaneously. In cases where lithium is administered to a patient more than once a day, it is preferred that deuterated gaboxadol is also administered on the same schedule of administration(s).

Formulations of Deuterated Gaboxadol and Lithium

The combination of deuterated gaboxadol and lithium may be administered in separate dosage forms, contemporaneously or separated in time, or they may be administered in a single combined fixed dosage form, by definition administered simultaneously. For independent administration, any of the previously described dosage forms may be employed. The following section elaborates on fixed-dose combinations of deuterated gaboxadol and lithium.

Methods of administration of the fixed dose combination of deuterated gaboxadol and lithium, or a pharmaceutically acceptable salt of either or both compounds thereof, include but are not limited to, oral, subcutaneous, intradermal, intramuscular (by way of non-limiting example, intramuscular depot, such as, for instance, as described in U.S. Pat. No. 6,569,449, the content of which are hereby incorporated by reference in its entirety), intraperitoneal, intravenous, intranasal, epidural, sublingual, intranasal, intracerebral, intravaginal, transdermal, rectally, by inhalation, or topically, particularly to the ears, nose, eyes, or skin. The mode of administration can be left to the discretion of the practitioner. In most instances, administration should result in the release of the compounds described herein or their pharmaceutically acceptable salts into the bloodstream.

In certain embodiments, the invention contemplates administration of the fixed dose combination of deuterated gaboxadol and lithium, or a pharmaceutically acceptable salt of either or both compounds thereof, designed for rapid onset of treatment effect. A wide variety of dose forms may be employed including those described previously in the literature. Preferred dose forms are suitable for oral or intranasal administration. A compositions for oral delivery can be in the form of a tablet, a lozenge, an aqueous or oily suspension, a solution, a granule, a capsule, a powder, a pill, a pellet, a capsule containing a liquid, an emulsion, a syrup, or an elixirs a suppository, a sustained-release formulation, or any other form suitable for use.

Orally administered fixed dose combination compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active compound of the invention are also suitable for oral administration. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can comprise standard excipients such as mannitol, lactose, starch, magnesium stearate, sodium saccharin, cellulose, and magnesium carbonate. In one embodiment, the excipients are of pharmaceutical grade.

The present fixed dose compositions can optionally comprise a suitable amount of a pharmaceutically acceptable excipient so as to provide the form for proper administration to the subject. Such pharmaceutical excipients can be liquids, such as water and oils, comprising those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the compounds of present invention or their pharmaceutically acceptable salts are administered intravenously. Saline solutions and aqueous dextrose and glycerol solutions can also be employed as liquid excipients, specifically for injectable solutions. Suitable pharmaceutical excipients also comprise starch, glucose, lactose, sucrose, gelatin, malt, rice, flour, chalk, silica gel, sodium stearate, glycerol monostearate, sodium chloride, dried skim milk, glycerol, propylene, glycol, water, ethanol and the like. The present compositions, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference in its entirety.

A particularly preferred form for rapid onset is an orally disintegrating dosage form (ODDF) which provides immediate release in the patient's buccal cavity enhancing buccal ab sorption of the drug. ODDFs and their use in the invention are described above in reference to the use of deuterated gaboxadol. ODDFs can also be used for fixed dose combinations of deuterated gaboxadol and lithium.

In specific embodiments, the fixed dose compositions described herein can be administered by controlled-release or sustained-release means or by other delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the synergistic combination of deuterated gaboxadol and lithium, or a pharmaceutically acceptable salt of either or both compounds thereof. In certain embodiments, the invention thus provides single unit dosage forms suitable for oral administration such as, but not limited to, tablets, capsules, gel caps, and caplets that are adapted for controlled- or sustained-release. In certain embodiments, the ingredients of a single unit dosage are supplied either separately or mixed together, for example, as a dry lyophilized-powder or water-free concentrate in a hermetically sealed container such as an ampule or sachet indicating the quantity of active agent. Where the compounds described herein or their pharmaceutically acceptable salts are to be administered by infusion, they can be dispensed, for example, with an infusion bottle containing sterile pharmaceutical grade water or saline. Where the compounds described herein or their pharmaceutically acceptable salts are administered by injection, an ampule of sterile water for injection or saline can be provided so that the ingredients can be mixed prior to administration.

Dose Regimen

The dosage regimen utilizing the combination of deuterated gaboxadol and lithium, or a pharmaceutically acceptable salt of either or both compounds thereof, can be selected in accordance with a variety of factors including type, species, age, weight, sex and medical condition of the subject; the severity of the condition to be treated; the route of administration; the renal or hepatic function of the subject; and the specific compound of the invention employed.

The combination of deuterated gaboxadol and lithium, or a pharmaceutically acceptable salt of either or both compounds thereof, can be administered in a single daily dose, or the total daily dosage can be administered in divided doses of two, three or four times daily.

In certain embodiments, combination of deuterated gaboxadol and lithium, or a pharmaceutically acceptable salt of either or both compounds thereof, can be administered in capsules having doses of, for example, 400 mg/10 mg, 400 mg/5 mg, 300 mg/10 mg, 300 mg/5 mg, 200 mg/5 mg or 100 mg/5 mg of lithium carbonate/deuterated gaboxadol.

In certain embodiments, the combination of deuterated gaboxadol and lithium is administered as a controlled release medicament. In a specific embodiment, the controlled release is release of substance (e.g., lithium and/or deuterated gaboxadol) at a selected or otherwise controllable rate, interval, and/or amount, which is not substantially influenced by the environment of use. "Controlled release" thus can be, but is not limited to, substantially continuous delivery or patterned delivery (e.g., intermittent delivery over a period of time that is interrupted by regular or irregular time intervals). In a specific embodiment, the drug delivery is "patterned" such that the delivery of drug is in a pattern, generally a substantially regular pattern, over a pre-selected period of time (e.g., other than a period associated with, for example a bolus injection). In a specific embodiment, the delivery is "patterned" such that the drug delivery is at an increasing, decreasing, substantially constant, or pulsatile, rate or range of rates (e.g., amount of drug per unit time, or volume of drug formulation for a unit time), and further can be delivery that is continuous or substantially continuous, or chronic.

In certain embodiments, an adult human diagnosed with bipolar disorder can be treated, for example, as follows. For acute treatment, for example in cases of mania or hypomania, a daily dose of lithium carbonate of about 50 to about 1800 mg, targeted to achieve a lithium serum level of about 0.4 to about 1.5 mmol/L, can be combined with about 1 to about 30 mg of a deuterated gaboxadol monohydrate. For chronic prophylactic treatment, for example in cases of mania or hypomania, a daily dose of lithium carbonate of about 50 to about 900 mg, targeted to achieve a lithium serum level of about 0.2 to about 1.2 mmol/L, can be combined with about 1 to about 30 mg of a deuterated gaboxadol monohydrate.

Kits

Kits for treating a psychiatric disorder comprise, optionally in one or more containers, one or a plurality of deuterated gaboxadol dosage forms with or without lithium, ketamine or other pharmaceutical dosage forms, and instructions for administering the dosage forms according to a predetermined dosage regimen. In a kit embodiment using a combination of deuterated gaboxadol with lithium (which serves as an example of other kit combinations of the invention), the predetermined dosing regimen may comprise administering doses of deuterated gaboxadol and lithium contemporaneously. The predetermined dosing regimen may provide that a dose of deuterated gaboxadol and lithium, or a pharmaceutically acceptable salt of either or both compounds thereof, be administered in the morning, e.g., at 6 am or between about 6 am and 9 am, and the lithium dose administered in the afternoon, e.g., at 12 pm (noon) or between about 12 pm and 3 pm, evening, e.g., at 6 pm or between about 6 pm and 9 pm, or late evening, e.g., at 12 am (midnight).

The kits may comprise a housing configured to organize the dosage forms according to the predetermined dosing regimen. For example, the housing may be configured to organize the plurality of dosage forms into morning dosage forms and evening dosage forms. In some variations, the housing may be configured to organize the plurality of deuterated gaboxadol and lithium dosage forms according to a rapidly or a gradually decreasing dosing regimen. In yet further variations, the housing may be configured to organize the deuterated gaboxadol and lithium dosage forms according to the day of the week to be taken.

The kits may comprise a housing configured to organize the dosage forms according to the predetermined dosing regimen. For example, the housing may be configured to organize the plurality of dosage forms into morning dosage forms and evening dosage forms. In some variations, the housing may be configured to organize the plurality of dosage forms according to a rapidly or a gradually decreasing dosing regimen. In yet further variations, the housing may be configured to organize the dosage forms according to the day of the week to be taken. The kits may also be tailored to treat particular bipolar conditions or subtypes. For example, the kits may be tailored to treat bipolar I disorder, bipolar II disorder, mixed bipolar disorders, rapidly-cycling bipolar disorder, acute mania, drug-induced mania, hypomania, cyclothymia, or combinations thereof.

Embodiments of the Invention

An aspect of the invention is a composition comprising ring carbon deuterated gaboxadol, said gaboxadol deuterated at ring carbon positions selected from the group consisting of 4,4; 5,5; 7,7; 4,4,5,5; 4,4,7,7; 5,5,7,7; and 4,4,5,5,7,7.

An aspect of the invention is a pharmaceutical composition comprising ring carbon deuterated gaboxadol, said gaboxadol deuterated at ring carbon positions selected from the group consisting of 4,4; 5,5; 7,7; 4,4,5,5; 4,4,7,7; 5,5,7,7; and 4,4,5,5,7,7 and a pharmaceutically acceptable carrier.

An aspect of the invention is a method for reducing a risk of suicide and/or achieving a rapid-acting relief of depressive symptoms comprising administering a first treatment of a pharmaceutical composition comprising ring carbon deuterated gaboxadol, to a patient in need thereof in an amount sufficient to reduce the risk of suicide and/or to rapidly alleviate depressive symptoms, and, optionally, administering a second treatment of a pharmaceutical composition comprising ring carbon deuterated gaboxadol, within less than 6 hours immediately following the administration of the first treatment, and if the patient experiences a recurrence of the risk of suicide and/or depressive symptoms, administering an additional treatment of a pharmaceutical composition comprising ring carbon deuterated gaboxadol, but not until at least 48 hours after the first treatment.

A preferred embodiment of this aspect is wherein the additional treatment of a pharmaceutical composition comprising ring carbon deuterated gaboxadol, is administered at least every 3, 4, 5, 6 or 7 days after the administration of the first treatment.

A preferred embodiment of this aspect is wherein the second treatment of a pharmaceutical composition comprising ring carbon deuterated gaboxadol, is administered if a neurological test of the patient demonstrates an insufficient response within 180 minutes immediately after administration of the first treatment.

A preferred embodiment of this aspect is wherein the insufficient response is an electroencephalogram (EEG) power density increase of less than 30% over baseline within 180 minutes after the first administration.

A preferred embodiment of this aspect is wherein the electroencephalogram (EEG) power density is calculated in a 0.25-8.0 Hz range.

A preferred embodiment of this aspect is wherein the electroencephalogram (EEG) power density is calculated in a 4.75-8.0 Hz range.

A preferred embodiment of this aspect is wherein the insufficient response is a whole head magnetoencephalography (MEG) planar gradiometer increase of less +3 in a combined delta, theta and alpha activity within 180 minutes after the administration of the first treatment.

A preferred embodiment of this aspect is wherein the method provides improvement in at least one symptom of risk of suicide selected from the group consisting of suicidal ideation, acute suicidality, recurrent thoughts of death, actions towards suicide and/or suicide attempts.

A preferred embodiment of this aspect is wherein the patient is further diagnosed with a condition selected from among suicidal ideation, acute suicidality, risk of self-harm and/or treatment-resistant depression.

A preferred embodiment of this aspect is wherein the patient has not been previously treated with, or is not currently being treated with, or is not responding to, an anti-depressive treatment.

A preferred embodiment of this aspect is wherein the administration of the first treatment comprises administering a pharmaceutical composition comprising about 1 mg to about 300 mg ring carbon deuterated gaboxadol.

A preferred embodiment of this aspect is wherein the administration of the first treatment comprises administering a pharmaceutical composition comprising about 1 mg to about 20 mg ring carbon deuterated gaboxadol.

A preferred embodiment of this aspect is wherein the administration of the first treatment comprises administering a pharmaceutical composition comprising about 5 mg to about 10 mg ring carbon deuterated gaboxadol.

A preferred embodiment of this aspect is wherein the first treatment is administered in an oral dosage form.

A preferred embodiment of this aspect is wherein the oral dosage form is an orally disintegrating form.

A preferred embodiment of this aspect is wherein the first treatment is administered intranasally.

A preferred embodiment of this aspect is further comprising administering a pharmaceutical composition comprising ring carbon deuterated gaboxadol to the patient, before, after or concurrently with the first treatment, any one of ketamine, SAGE-217, allopregnanolone, ganaxolone, alfadolone, alfaxolone, hydroxydione, minaxolone, pregnanolone, renanolone and other pregnane neurosteroids, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, gaboxadol, clozapine, [2-amino-4-(2,4,6-trimethylbenzylamino)-phenyl]-carbamic acid ethyl ester (AA29504) and pharmaceutically acceptable salts thereof.

A preferred embodiment of this aspect is wherein the first treatment comprises administering concurrently a synergistic dose of a pharmaceutical composition comprising ring carbon deuterated gaboxadol together with a synergistic dose of ketamine.

A preferred embodiment of this aspect is wherein the synergistic dose of ring carbon deuterated gaboxadol is about 10 mg or less.

A preferred embodiment of this aspect is wherein the synergistic dose of ketamine is about 10 mg or less.

An aspect of the invention is an improvement in a method for reducing a risk of suicide and/or achieving a rapid-acting relief of depressive symptoms comprising administering a first treatment of a pharmaceutical composition comprising gaboxadol to a patient in need thereof in an amount sufficient to reduce the risk of suicide and/or to rapidly alleviate depressive symptoms, and, optionally, administering a second treatment of a pharmaceutical composition comprising gaboxadol within less than 6 hours immediately following the administration of the first treatment, and, if the patient experiences a recurrence of the risk of suicide and/or depressive symptoms, administering an additional treatment of a pharmaceutical composition comprising gaboxadol but not until at least 48 hours after the first treatment, the improvement comprising administering a pharmaceutical composition comprising ring carbon deuterated gaboxadol at a dose of less than about two thirds of the effective amount of the dose of gaboxadol.

An aspect of this invention is a pharmaceutical composition comprising ring carbon deuterated gaboxadol and lithium, said gaboxadol deuterated at ring carbon positions selected from the group consisting of 4,4; 5,5; 7,7; 4,4,5,5; 4,4,7,7; 5,5,7,7; and 4,4,5,5,7,7 and a pharmaceutically acceptable carrier.

An aspect of this invention is a pharmaceutical composition comprising a combination of compounds, wherein the combination comprises of ring carbon deuterated gaboxadol, wherein the dose of ring carbon deuterated gaboxadol is about one third of the dose of non-deuterated gaboxadol required to achieve an equivalent synergistic effect and lithium, or a pharmaceutically acceptable salt of either or both compounds thereof.

A preferred embodiment of this aspect is a pharmaceutical composition wherein the lithium is a sub-standard daily dose of lithium.

A preferred embodiment of this aspect is a pharmaceutical composition wherein the sub-standard dose of lithium, when administered daily to a subject in need thereof, is below the medically recommended dose for treating psychiatric orders comprising bipolar disorder, depression, treatment-resistant depression, and suicidality A preferred embodiment of this aspect is a pharmaceutical composition wherein an animal equivalent of the sub-standard dose of lithium is ineffective at activating c-fos signaling in an animal model's brain as measured by Pharmacomapping.

A preferred embodiment of this aspect is a pharmaceutical composition wherein a human equivalent of the sub-standard dose of lithium is in a range from about 50 to about 600 mg lithium carbonate/day.

Preferred embodiments of aspects of this invention are pharmaceutical compositions wherein the gaboxadol has two ring carbon deuterium atoms.

Preferred embodiments of aspects of this invention are pharmaceutical compositions wherein the gaboxadol has four ring carbon deuterium atoms Preferred embodiments of aspects of this invention are pharmaceutical compositions wherein the gaboxadol has six ring carbon deuterium atoms Preferred embodiments of aspects of this invention are pharmaceutical compositions wherein the gaboxadol is a mixture of gaboxadols having two, four or six deuterium atoms Preferred embodiments of aspects of this invention are pharmaceutical compositions wherein the lithium is a standard dose of lithium.

Preferred embodiments of aspects of this invention are pharmaceutical compositions wherein the standard dose of lithium is in a range from about 600 to about 1800 mg, with a maximum daily dose of 2400 mg, of lithium carbonate/day.

Preferred embodiments of aspects of this invention are pharmaceutical compositions wherein the deuterated gaboxadol and the lithium are formulated in two separate compositions.

Preferred embodiments of aspects of this invention are pharmaceutical compositions wherein the combination consists of deuterated gaboxadol and lithium present as pharmaceutically acceptable salts thereof.

An aspect of this invention is a the pharmaceutical composition wherein the animal equivalent doses of lithium and ring carbon deuterated gaboxadol administered daily to an animal model in need thereof are synergistically effective at activating c-fos signaling in at least one region of an animal model's brain selected from the group consisting of 1) a broad cortical activation comprising motor (MO), gustatory (GU), visceral (VISC), agranular insular (AI), somatosensory (SS), auditory, visual (VIS), auditory (AUD), prelimbic (PL) and infralimbic (ILA), retrosplenial (RSP), parietal (PTL), temporal associational (TEa), ectorhinal (ECT), entorhinal (ENT), perirhinal (PERI), piriform (PIR), and anterior cingulate (ACA) cortex, claustrum (CLA), as well as 2) subcortical activation comprising hippocampal CA1 region, bed nuclei stria terminalis (BST), central amygdala (CEA), cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), nucleus of reunions (RE), rhomboid nucleus (RH), and central medial nucleus (CM) of a thalamus, paraventricular hypothalamic nucleus (PVH), dorsomedial nucleus of a hypothalamus (DMH), tuberomammillary nucleus (TM), parasubthalamic nucleus (PSTN) and subthalamic nucleus (STN), parabrachial nucleus, locus coeruleus (LC), and nucleus of a solitary tract (NTS).

An aspect of this invention is a pharmaceutical composition wherein the ring carbon deuterated gaboxadol and lithium, when administered daily to a subject in need thereof, act synergistically to treat the subject's psychiatric disorder selected from the group consisting of bipolar disorder, depression, treatment resistant depression, and acute suicidality and wherein the dose of ring carbon deuterated gaboxadol is about one third of amount of non-deuterated gaboxadol required to achieve an equivalent synergistic effect.

A preferred embodiment of this aspect is wherein the treatment of the subject's psychiatric disorder is effective at improving a score of at least one psychiatric rating scale specific for bipolar disorder, depression, treatment resistant depression, or suicidality.

Preferred embodiments of aspects of this invention are pharmaceutical compositions wherein the ring carbon deuterated gaboxadol and lithium, when administered to a subject diagnosed with bipolar depression, unipolar depression or treatment resistant depression are synergistically effective at increasing the subject's Montgomery-Asberg Depression Rating Scale (MADRS) score.

Preferred embodiments of aspects of this invention are pharmaceutical compositions wherein the ring carbon deuterated gaboxadol and lithium, when administered to a subject in need thereof, are synergistically effective at increasing a score of at least one psychiatric rating scale specific for bipolar disorder, depression, treatment resistant depression, or suicidality.

Preferred embodiments of aspects of this invention are pharmaceutical compositions wherein the lithium, when administered daily to a subject in need thereof, is in an amount sufficient to maintain the subject's serum level of lithium in a range of about 0.4 to about 1.2 mmol/L.

Preferred embodiments of aspects of this invention are pharmaceutical compositions wherein the lithium, when administered daily to a subject in need thereof, is in an amount sufficient to maintain the subject's serum level of lithium in a range of about 0.2 to about 0.8 mmol/L.

Preferred embodiments of aspects of this invention are pharmaceutical compositions wherein the pharmaceutical composition is in a form of a single tablet for oral consumption.

Preferred embodiments of aspects of this invention are pharmaceutical compositions wherein the pharmaceutical composition is in a form of a controlled release formulation.

Preferred embodiments of aspects of this invention are pharmaceutical compositions further comprising one or more inert pharmaceutically acceptable excipients.

Preferred embodiments of aspects of this invention are pharmaceutical compositions wherein the pharmaceutical composition is in a form of a single dosage unit having separate compartments for the lithium and ring carbon deuterated gaboxadol or a pharmaceutically acceptable salt of either or both compounds thereof.

An aspect of this invention is a kit comprising the pharmaceutical composition of aspects of this invention.

An aspect of this invention is a method for treating a subject in need thereof comprising administering the pharmaceutical composition of any aspect of this invention.

A preferred embodiment of this aspect is wherein the subject is diagnosed with a psychiatric disorder.

A preferred embodiment of this aspect is, wherein the psychiatric disorder is chosen from bipolar disorder, depression, treatment-resistant depression, or acute suicidality.

A preferred embodiment of this aspect is wherein the pharmaceutical composition reduces adverse side effects selected from the group consisting of nephrotoxicity, nephrogenic diabetes insipidus, chronic kidney disease, diarrhea, hand tremor, increased thirst, increased urination, vomiting, weight gain, impaired memory, poor concentration, drowsiness, muscle weakness, hair loss, acne and decreased thyroid function.

An aspect of this invention is a method for treating a human diagnosed with bipolar disorder, depression, or acute suicidality comprising administering carbon a synergistic combination of ring carbon deuterated gaboxadol at a dose ranging from about 5 to about 300 mg/day, contemporaneously with lithium a) at a dose from about 50 mg to about 1800 mg lithium carbonate; or b) from about 0.8 mg/kg to about 30 mg/kg lithium carbonate; or c) in an amount sufficient to achieve a lithium serum concentration of about 0.2 to 1.2 mmol/L; wherein the combination dose of ring carbon deuterated gaboxadol and lithium is administered at least once per day.

An aspect of this invention is a method for treating a human diagnosed with an acute form of bipolar disorder, depression, or suicidality comprising administering carbon a synergistic combination of ring carbon deuterated gaboxadol at a dose in a range of from about 5 mg to about 50 mg/day, contemporaneously with lithium a) at a dose of from about 50 mg to about 900 mg lithium carbonate/day; or b) in an amount sufficient to achieve a lithium serum concentration of 0.2 to 1.0 mmol/L;

wherein the combination dose of ring carbon deuterated gaboxadol and lithium is administered at least once per day.

An aspect of this invention is a method for treating a patient diagnosed with a chronic form of bipolar disorder, depression, or suicidality comprising administering carbon a synergistic combination of ring carbon deuterated gaboxadol at a dose in a range of from about 5 mg to about 30 mg/day, contemporaneously with lithium a) at a dose of from about 50 mg to about 600 mg lithium carbonate; or a) in an amount sufficient to achieve a lithium serum concentration of about 0.2 to 0.8 mmol/L;

wherein the combination dose of ring carbon deuterated gaboxadol and lithium is administered at least once per day.

An aspect of this invention is the use of a synergistic combination of ring carbon deuterated gaboxadol and lithium, or a pharmaceutically acceptable salt of either or both compounds thereof, for reducing one or symptoms of bipolar disorder, depression, or suicidality.

An aspect of this invention is the use of a synergistic combination of ring carbon deuterated gaboxadol and lithium, or a pharmaceutically acceptable salt of either or both compounds thereof, in the manufacture of a medicament for reducing one or symptoms of bipolar disorder, depression, or suicidality A first aspect is a ring carbon deuterated gaboxadol compound of Formula I

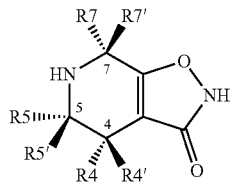

or a pharmaceutically acceptable salt thereof,
wherein R4, R4', R5, R5', R7 and R7' are independently H or D, and
wherein at least one of R4, R4', R5, R5', R7 and R7' is D.

A first preferred embodiment of the first aspect is a compound wherein the percentage incorporation of deuterium is at least 1%.

A second preferred embodiment of the first aspect is a compound wherein if none of R4, R4', R5, and R5' are H, then R7 and R7' are not both D.

A third preferred embodiment of the first aspect is a compound wherein if all of R4, R4', R5, and R5' are D, then at least one of R7 and R7' is D.

A fourth preferred embodiment of the first aspect is a compound wherein all of R4, R4', R5, R5', R7 and R7' are D.

A second aspect is a composition comprising one or more ring carbon deuterated gaboxadol compounds of Formula I

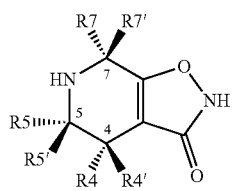

or a pharmaceutically acceptable salt thereof,
wherein R4, R4', R5, R5', R7 and R7' are independently H or D,
and wherein at least 1% of the compounds have D at one or more of R4, R4', R5, R5', R7 and R7', optionally wherein at least 1% of the compounds have D at all of R4, R4', R5, R5', R7 and R7'.

A first preferred embodiment of the second aspect is a composition wherein at least 10% of the compounds have D at one or more of R4, R4', R5, R5', R7 and R7'

A second preferred embodiment of the second aspect is a composition wherein at least 10% of the compounds have D at three or more of R4, R4', R5, R5', R7 and R7'.

A third preferred embodiment of the second aspect is a composition wherein at least 10% of the compounds have D at five or more of R4, R4', R5, R5', R7 and R7'.

A fourth preferred embodiment of the second aspect is a composition wherein in at least 70% of the compounds have D at five or more of R4, R4', R5, R5', R7 and R7'.

A fifth preferred embodiment of the second aspect is a composition wherein at least 90% of the compounds have D at five or more of R4, R4', R5, R5', R7 and R7'.

A sixth preferred embodiment of the second aspect is a composition wherein at least 75% of the compounds have D at all of R4, R4', R5, R5', R7 and R7'.

A seventh preferred embodiment of the second aspect is a composition comprising at least two different compounds of Formula I.

A third aspect is a pharmaceutical composition comprising the compound of any one of the aspects and embodiments above and a pharmaceutically acceptable carrier.

A first preferred embodiment of the third aspect is a pharmaceutical composition which is an oral dosage form.

A more preferred embodiment of the third aspect is a pharmaceutical composition of the first preferred embodiment of the third aspect which is a tablet.

A more preferred embodiment of the third aspect is a pharmaceutical composition of the first preferred embodiment of the third aspect wherein the oral dosage form is an orally disintegrating form.

A second preferred embodiment of the third aspect is a pharmaceutical composition comprising about 1 mg to about 300 mg of the compound.

A third preferred embodiment of the third aspect is a pharmaceutical composition comprising about 50 mg to about 100 mg of the compound.

A fourth preferred embodiment of the third aspect is a pharmaceutical composition comprising about 50 mg, about 75 mg, or about 100 mg of the compound.

A fifth preferred embodiment of the third aspect is a pharmaceutical composition comprising about 25 mg to about 50 mg of the compound.

A sixth preferred embodiment of the third aspect is a pharmaceutical composition comprising about 10 mg to about 30 mg of the compound.

A fourth aspect is a pharmaceutical composition comprising (a) the compound of any one of the first or second embodiments above; (b) at least one other compound selected from the group consisting of lithium, ketamine, AXS-05 (fixed combination of dextromethorphan and bupropion), SAGE-217, allopregnanolone, ganaxolone, alfadolone, alfaxolone, hydroxydione, minaxolone, pregnanolone, renanolone, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, clozapine, and [2-amino-4-(2,4,6-trimethylbenzylamino)-phenyl]-carbamic acid ethyl ester (AA29504); and (c) a pharmaceutically acceptable carrier.

A first preferred embodiment of the fourth aspect is a pharmaceutical composition of the fourth embodiment wherein the at least one other compound is lithium.

A fifth aspect is a pharmaceutical composition comprising one or more compounds of Formula I

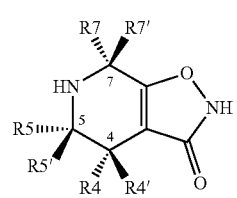

or a pharmaceutically acceptable salt thereof,
wherein R4, R4', R5, R5', R7 and R7' are independently H or D, and wherein all of R4, R4', R5, R5', R7 and R7' are D in at least 75% of the compounds.

A first preferred embodiment of the fifth aspect is a pharmaceutical composition wherein at least 95% of the total of all the positions R4, R4', R5, R5', R7 and R7' are D.

A second preferred embodiment of the fifth aspect is a pharmaceutical composition wherein not more than about 20% of the compounds are d5-gaboxadol.

A sixth aspect is a pharmaceutical composition comprising one or more compounds of Formula I

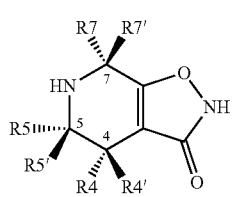

or a pharmaceutically acceptable salt thereof,
wherein R4, R4', R5, R5', R7 and R7' are independently H or D,
and wherein 3 or more of the positions R4, R4', R5, R5', R7 and R7' are D in no less than about 10% of the compounds.

A first preferred embodiment of the sixth aspect is a pharmaceutical composition wherein 3 or more of the positions R4, R4', R5, R5', R7 and R7' are D in no less than about 50% of the compounds.

A more preferred embodiment of the sixth aspect is a pharmaceutical composition of the first preferred embodiment wherein 3 or more of the positions R4, R4', R5, R5', R7 and R7' are D in no less than about 70% of the compounds.

A more preferred embodiment of the sixth aspect is a pharmaceutical composition of the first preferred embodiment wherein 3 or more of the positions R4, R4', R5, R5', R7 and R7' are D in no less than about 95% of the compounds.

A seventh aspect is a method of making d6-gaboxadol, said method comprising:
(a) treating 3-hydroxypyridine-4-carboxylic acid with deuterium oxide under catalytic hydrogenation conditions to provide 2,3,6-trideuterio-5-hydroxy-pyridine-4-carboxylic acid;
(b) treating 2,3,6-trideuterio-5-hydroxy-pyridine-4-carboxylic acid from step (a) above with a methylating agent, to provide methyl 2,3,6-trideuterio-5-hydroxy-pyridine-4-carboxylate;
(c) treating methyl 2,3,6-trideuterio-5-hydroxy-pyridine-4-carboxylate from step (b) above with hydroxylamine hydrochloride, to provide 2,3,6-trideuterio-5-hydroxy-pyridine-4-carbohydroxamic acid;
(d) treating 2,3,6-trideuterio-5-hydroxy-pyridine-4-carbohydroxamic acid from step (c) above with an activating agent, to provide 4,5,7-trideuterioisoxazolo[5,4-c]pyridin-3-one;
(e) treating 4,5,7-trideuterioisoxazolo[5,4-c]pyridin-3-one from step (d) above with a brominating agent to provide 6-benzyl-4,5,7-trideuterio-isoxazolo[5,4-c]pyridin-6-ium-3-ol bromide;
(f) treating 6-benzyl-4,5,7-trideuterio-isoxazolo[5,4-c]pyridin-6-ium-3-ol bromide from step (e) above with a reducing agent, to provide 6-benzyl-4,4,5,5,7,7-hexadeuterio-isoxazolo[5,4-c]pyridin-3-ol; and (g) deprotecting 6-benzyl-4,4,5,5,7,7-hexadeuterio-isoxazolo[5,4-c]pyridin-3-ol from step (f) above to remove the benzyl group to provide d6-gaboxadol.

A first preferred embodiment of the seventh aspect is a method comprising:
(a) treating 3-hydroxypyridine-4-carboxylic acid with deuterium oxide in the presence of Pt/C and/or Pd/C and hydrogen gas at a temperature greater than 100° C., to provide 2,3,6-trideuterio-5-hydroxy-pyridine-4-carboxylic acid;
(b) treating 2,3,6-trideuterio-5-hydroxy-pyridine-4-carboxylic acid from step (a) above with methanol and sulfuric acid at reflux temperature, to provide methyl 2,3,6-trideuterio-5-hydroxy-pyridine-4-carboxylate;
(c) treating methyl 2,3,6-trideuterio-5-hydroxy-pyridine-4-carboxylate from step (b) above with hydroxylamine chloride and aqueous sodium hydroxide solution, to provide 2,3,6-trideuterio-5-hydroxy-pyridine-4-carbohydroxamic acid;
(d) treating 2,3,6-trideuterio-5-hydroxy-pyridine-4-carbohydroxamic acid from step (c) above with thionyl chloride, to provide 4,5,7-trideuterioisoxazolo[5,4-c]pyridin-3-one;
(e) treating 4,5,7-trideuterioisoxazolo[5,4-c]pyridin-3-one from step (d) above with benzyl bromide, to provide 6-benzyl-4,5,7-trideuterio-isoxazolo[5,4-c]pyridin-6-ium-3-ol bromide;
(f) treating 6-benzyl-4,5,7-trideuterio-isoxazolo[5,4-c]pyridin-6-ium-3-ol bromide from step (e) above with deuterated sodiumborohydride (NaBD4) in a mixture of deuterated ethanol and/or deuterium oxide, to provide 6-benzyl-4,4,5,5,7,7-hexadeuterio-isoxazolo[5,4-c]pyridin-3-01; and
(g) treating 6-benzyl-4,4,5,5,7,7-hexadeuterio-isoxazolo[5,4-c]pyridin-3-ol from step (f) above with (i) methyl chloroformate in the presence of an inorganic base, followed by treatment with hydrobromic acid, or (ii) deuterated hydrobromic acid, to provide d6-gaboxadol.

A first preferred embodiment of the seventh aspect is a product of the methods of the seventh embodiment.

An eight aspect is a compound 4,5,7-trideuterioisoxazolo[5,4-c]pyridin-3-one.

A ninth aspect is a method of treating a psychiatric disorder comprising administering to a human patient in need thereof a therapeutically effective amount of a compound of the first aspect, a composition of the second aspect, or a pharmaceutical composition of the third aspect.

A first preferred embodiment of the ninth aspect is wherein the psychiatric disorder is depression, A second preferred embodiment of the ninth aspect is wherein the psychiatric is disorder major depression.

A third preferred embodiment of the ninth aspect is wherein the psychiatric disorder is suicidality, A fourth preferred embodiment of the ninth aspect is wherein the psychiatric disorder is treatment resistant depression.

A fifth preferred embodiment of the ninth aspect is wherein the psychiatric disorder bipolar disorder.

A sixth preferred embodiment of the ninth aspect is the method wherein the administering is once daily.

A seventh preferred embodiment of the ninth aspect is the method wherein the administering is of a daily dose of about 50-100 mg of the compound.

An eighth preferred embodiment of the ninth aspect is the method of the seventh preferred embodiment wherein the daily dose is 50, 75 or 100 mg of the compound.

A tenth preferred embodiment of the ninth aspect is the method wherein the psychiatric disorder is depression.

An eleventh preferred embodiment of the ninth aspect is the method which further comprises administering lithium to the patient to treat the psychiatric disorder.

A twelfth preferred embodiment of the ninth aspect is the method of the eleventh preferred embodiment wherein the compound and the lithium are in a single oral dosage form A thirteenth preferred embodiment of the ninth aspect is the method of the eleventh preferred embodiment wherein the compound and the lithium are in separate oral dosage forms.

A fourteenth preferred embodiment of the ninth aspect is the method wherein the administering is daily for a first time period, followed by a washout period of at least one day during which the compound is not administered, followed by daily administering for a second time period.

A fifteenth preferred embodiment of the ninth aspect is the method wherein the administering is two or three times per week.

A sixteenth preferred embodiment of the ninth aspect is a method of the fourteenth or fifteenth preferred embodiments wherein the daily administering is of a daily dose of about 50-100 mg of the compound.

A seventeenth preferred embodiment of the ninth aspect is a method of the twelfth preferred embodiment wherein the daily dose is 50, 75 or 100 mg of the compound.

An eighteenth preferred embodiment of the ninth aspect is a method of the fourteenth through seventeenth preferred embodiments wherein the compound is the sole active agent administered to treat said psychiatric disorder.

An eighteenth preferred embodiment of the ninth aspect is a method of the fourteenth through seventeenth preferred embodiments wherein the psychiatric disorder is bipolar mania.

A nineteenth preferred embodiment of the ninth aspect is a method of any of preferred embodiments wherein the compound is d6-gaboxadol.

A tenth aspect is the use of the pharmaceutical composition of the third aspect for treating a psychiatric disorder.

An eleventh aspect is the use of the compound of the first aspect in the manufacture of a medicament.

A twelfth aspect is the use of the compound of first aspect in the manufacture of a medicament for use in treating a psychiatric disorder.

A thirteenth aspect is a method for treating a subject diagnosed with a psychiatric disorder comprising administering to the subject an effective amount of ring carbon deuterated gaboxadol or a pharmaceutically acceptable salt thereof.

A first preferred embodiment of the thirteenth aspect is the method wherein the psychiatric disorder is bipolar disorder.

A second preferred embodiment of the thirteenth aspect is the method wherein the psychiatric disorder is depression.

A third preferred embodiment of the thirteenth aspect is the method wherein the psychiatric disorder is major depression.

A fourth preferred embodiment of the thirteenth aspect is the method wherein the psychiatric disorder is treatment-resistant depression and suicidality.

A fifteenth aspect is a method for treating a subject diagnosed with a psychiatric disorder comprising administering to the subject an effective amount of a ring carbon deuterated gaboxadol compound of Formula I

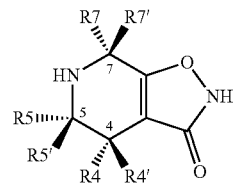

or a pharmaceutically acceptable salt thereof,
wherein R4, R4', R5, R5', R7 and R7' are independently H or D, and
wherein at least one of R4, R4', R5, R5', R7 and R7' is D.

A sixteenth aspect is a method for treating a subject diagnosed with a psychiatric disorder comprising administering to the subject an effective amount of a composition comprising one or more ring carbon deuterated gaboxadol compounds of Formula I

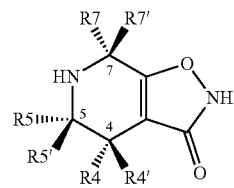

or a pharmaceutically acceptable salt thereof,
wherein R4, R4', R5, R5', R7 and R7' are independently H or D,
and wherein at least 1% of the compounds have D at one or more of R4, R4', R5, R5', R7 and R7'.

A first preferred embodiment of the sixteenth aspect is a method wherein at least 10% of the compounds have D at one or more of R4, R4', R5, R5', R7 and R7'

A second preferred embodiment of the sixteenth aspect is a method wherein at least 10% of the compounds have D at three or more of R4, R4', R5, R5', R7 and R7'.

A third preferred embodiment of the sixteenth aspect is a method wherein at least 10% of the compounds have D at five or more of R4, R4', R5, R5', R7 and R7'.

A fourth preferred embodiment of the sixteenth aspect is a method wherein in at least 70% of the compounds have D at five or more of R4, R4', R5, R5', R7 and R7'.

A fifth preferred embodiment of the sixteenth aspect is a method wherein at least 90% of the compounds have D at five or more of R4, R4', R5, R5', R7 and R7'.

A sixth preferred embodiment of the sixteenth aspect is a method wherein at least 75% of the compounds have D at all of R4, R4', R5, R5', R7 and R7'.

A seventh preferred embodiment of the sixteenth aspect is a method wherein the composition comprises at least two different compounds of Formula I.

An eight preferred embodiment of the sixteenth aspect is a method wherein the ring carbon deuterated gaboxadol is provided in a pharmaceutical composition comprising a pharmaceutically acceptable carrier.

A ninth preferred embodiment of the sixteenth aspect is a method of the eighth preferred embodiment wherein the psychiatric disorder is bipolar disorder.

A tenth preferred embodiment of the sixteenth aspect is a method of the eighth preferred embodiment wherein the psychiatric disorder is depression.

An eleventh preferred embodiment of the sixteenth aspect is a method of the eighth preferred embodiment wherein the psychiatric disorder is treatment-resistant depression.

A twelfth preferred embodiment of the sixteenth aspect is a method of the eighth preferred embodiment wherein the psychiatric disorder is suicidality A thirteenth preferred embodiment of the sixteenth aspect is a method of the ninth through twelfth preferred embodiments wherein the pharmaceutical composition is an oral dosage form.

A fourteenth preferred embodiment of the sixteenth aspect is a method of the twelfth preferred embodiment wherein the pharmaceutical composition comprises from about 1 mg to about 300 mg of a compound of Formula I.

A fifteenth preferred embodiment of the sixteenth aspect is a method of the twelfth preferred embodiment wherein the pharmaceutical composition comprises from about 50 mg to about 100 mg of a compound of Formula I.

A sixteenth preferred embodiment of the sixteenth aspect is a method of the twelfth preferred embodiment wherein the pharmaceutical composition comprises from about 25 mg to about 50 mg of a compound of Formula I.

A seventeenth preferred embodiment of the sixteenth aspect is a method of the twelfth preferred embodiment wherein the pharmaceutical composition comprises from about 10 mg to about 30 mg of a compound of Formula I.

An eighteenth preferred embodiment of the sixteenth aspect is a method of the ninth through twelfth preferred embodiments wherein the effective amount comprises an amount sufficient to rapidly alleviate risk of suicide, bipolar disorder and/or depressive symptoms.

A nineteenth preferred embodiment of the sixteenth aspect is a method of the eighteenth preferred embodiment further comprising administering a second pharmaceutical composition comprising ring carbon deuterated gaboxadol within less than 6 hours immediately following the prior administering step.

A twentieth preferred embodiment of the sixteenth aspect is a method of the nineteenth preferred embodiment wherein the second pharmaceutical composition comprising ring carbon deuterated gaboxadol is administered after a step of determining that a neurological test of the patient demonstrates an insufficient response within about 180 minutes immediately after the prior administering step A twenty first preferred embodiment of the sixteenth aspect is a method of the twentieth preferred embodiment wherein the insufficient response is an electroencephalogram (EEG) power density increase of less than 30% over baseline within about 180 minutes after the prior administering step.

A twenty second preferred embodiment of the sixteenth aspect is a method of the twenty first preferred embodiment wherein the electroencephalogram (EEG) power density is calculated in a 0.25-8.0 Hz range.

A twenty third preferred embodiment of the sixteenth aspect is a method of the twenty first preferred embodiment wherein the electroencephalogram (EEG) power density is calculated in a 4.75-8.0 Hz range.

A twenty fourth preferred embodiment of the sixteenth aspect is a method of the twentieth preferred embodiment wherein the insufficient response is a whole head magnetoencephalography (MEG) planar gradiometer increase of less +3 in a combined delta, theta and alpha activity within about 180 minutes after the prior administering step.

A twenty fifth preferred embodiment of the sixteenth aspect is a method wherein the effective amount is administered daily.

A twenty sixth preferred embodiment of the sixteenth aspect is a method wherein the effective amount is administered intermittently, separated by washout periods of at least one day during which no deuterated gaboxadol is administered.

A seventeenth aspect is a method for treating a subject diagnosed with a psychiatric disorder comprising administering to the subject a combination of a first pharmaceutical composition comprising an effective amount of ring carbon deuterated gaboxadol or a pharmaceutically acceptable salt thereof, and a second pharmaceutical composition comprising an agent selected from the group consisting of lithium, ketamine, SAGE-217, allopregnanolone ganaxolone, alfadolone, alfaxolone, hydroxydione, minaxolone, pregnanolone, renanolone and other pregnane neurosteroids, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, RO4995819), memantine, tiagabine, gaboxadol, clozapine, [2-amino-4-(2,4,6-trimethylbenzylamino)-phenyl]-carbamic acid ethyl ester (AA29504), AXS-05 (fixed combination of dextromethorphan and bupropion) and pharmaceutically acceptable salts thereof.

A first preferred embodiment of the seventeenth aspect is a method wherein the active agent in the second pharmaceutical composition is ketamine.

A second preferred embodiment of the seventeenth aspect is a method of the first preferred embodiment wherein the effective amount of ring carbon deuterated gaboxadol, or a pharmaceutically acceptable salt thereof, is about 20 mg or less.

A third preferred embodiment of the seventeenth aspect is a method of the first preferred embodiment wherein the effective amount of ketamine is about 10 mg or less.

An eighteenth aspect is a method for treating a subject diagnosed with a psychiatric disorder comprising administering at least once per day a combination of ring carbon deuterated gaboxadol and lithium, wherein the lithium is administered (a) in an amount of about 50 mg to about 1800 mg lithium carbonate; or (b) in an amount from about 0.8 mg/kg to about 30 mg/kg lithium carbonate; or (c) in an amount sufficient to achieve a lithium serum concentration of about 0.2 to 1.2 mmol/L.

A first preferred embodiment of the eighteenth aspect is a method wherein ring carbon deuterated gaboxadol is administered in an amount from about 10 mg to about 100 mg, and the lithium is administered (a) in an amount from about 50 mg to about 900 mg lithium carbonate, or (b) in an amount sufficient to achieve a lithium serum concentration of 0.2 to 1.0 mmol/L.

A second preferred embodiment of the eighteenth aspect is a method wherein ring carbon deuterated gaboxadol is administered in an amount from about 15 mg to about 50 mg, and the daily dose of lithium is administered (a) in an amount from about 50 mg to about 600 mg lithium carbonate, or (b) in an amount sufficient to achieve a lithium serum concentration of about 0.2 to 0.8 mmol/L.

A third preferred embodiment of the eighteenth aspect is a method wherein the psychiatric disorder is bipolar disorder.

A fourth preferred embodiment of the eighteenth aspect is a method wherein the psychiatric disorder is depression.

A fifth preferred embodiment of the eighteenth aspect is a method wherein the psychiatric disorder is treatment-resistant depression.

A sixth preferred embodiment of the eighteenth aspect is a method wherein the psychiatric disorder is suicidality.

A nineteenth aspect is the use of a combination of ring carbon deuterated gaboxadol and lithium, or a pharmaceutically acceptable salt of either or both compounds thereof, for treating a psychiatric disorder.

A twentieth aspect is the use of a combination of ring carbon deuterated gaboxadol and lithium, or a pharmaceutically acceptable salt of either or both compounds thereof, in the manufacture of a medicament for treating a psychiatric disorder.

A twenty first aspect is a pharmaceutical composition comprising a ring carbon deuterated gaboxadol of Formula I

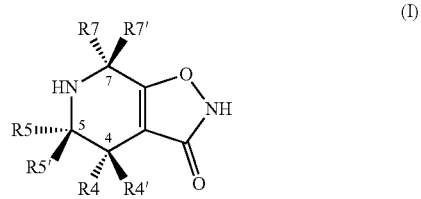

or a pharmaceutically acceptable salt thereof,
wherein R4, R4', R5, R5', R7 and R7' are independently H or D, and
wherein at least one of R4, R4', R5, R5', R7 and R7' is D;
and (b) lithium or a pharmaceutically acceptable salt of lithium.

A first preferred embodiment of the twentieth aspect is a pharmaceutical composition wherein ring carbon deuterated gaboxadol is present in the pharmaceutical composition in an amount that is about two-thirds or less of the dose of non-deuterated gaboxadol required to achieve an equivalent effect.

A second preferred embodiment of the twentieth aspect is a pharmaceutical composition wherein the lithium is present in the pharmaceutical composition an amount that is a sub-standard daily dose of lithium.

A third preferred embodiment of the twentieth aspect is a pharmaceutical composition of the second preferred embodiment wherein the sub-standard dose of lithium, when administered daily to a subject in need thereof, is below the medically recommended dose for treating psychiatric disorders comprising bipolar disorder, depression, treatment-resistant depression, suicidality.

A fourth preferred embodiment of the twentieth aspect is a pharmaceutical composition of the first preferred embodiment wherein the dose of ring carbon deuterated gaboxadol is about one third or less of the amount of non-deuterated gaboxadol required to achieve an equivalent effect.

A fifth preferred embodiment of the twentieth aspect is a pharmaceutical composition wherein the pharmaceutical composition is in a form of a single dosage unit having separate compartments for the lithium and ring carbon deuterated gaboxadol or a pharmaceutically acceptable salt of either or both compounds thereof.

A sixth preferred embodiment of the twentieth aspect is a pharmaceutical composition wherein the ring carbon deuterated gaboxadol is d6-gaboxadol.

A seventh preferred embodiment the twentieth aspect is a kit comprising the pharmaceutical composition of the twentieth aspect.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the methods of the invention may be made without departing from the spirit of the invention and the scope of the appended claims.

Although this invention has been described with a certain degree of particularity, it is to be understood that the present disclosure has been made only by way of illustration and that numerous changes in the details of construction and arrangement of parts may be resorted to without departing from the spirit and the scope of the invention.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict between the present explicit disclosure and a document incorporated by reference, the present explicit disclosure shall be the operative disclosure.

Examples 1 to 5: Synthesis of Ring Carbon Deuterated Gaboxadol

Ring carbon deuterated gaboxadol may be synthesized from deuterated precursors via synthetic pathways that result in the incorporation of deuterium at specific ring carbon locations. For the discussion of ring carbon deuterated gaboxadol, the numbering of the isoxazole and pyridine ring positions is shown in FIG. 2.

Example 1A: D2-Gaboxadol 7,7

One d2-gaboxadol, 4,5,6,7-tetrahydroisoxazolo[5,4-c]pyridin-3(2H)-one-7,7-$d_2$, was reportedly synthesized using a synthesis found in Journal of Labeled Compounds and Radiopharmaceuticals 19(5) 689-702 (1982), incorporated herein by reference. It is not known what percentage deuteration of compounds of Formula I in the composition was achieved by this method.

Example 1B: D2-Gaboxadol 7,7

Figure 3:
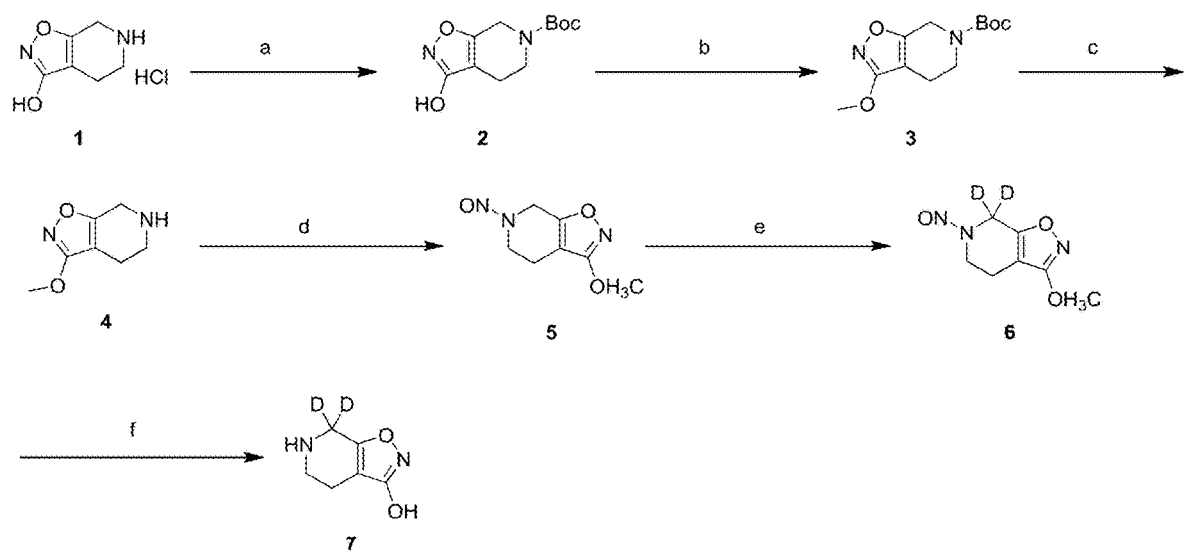
FIG. 3 shows a schema for the synthesis of 4,5,6,7-tetrahydroisoxazolo[5,4-c]pyridin-7,7-d2-3-ol (d2-gaboxadol 7,7).

Another synthesis for the compound, titled 4,5,6,7-tetrahydroisoxazolo[5,4-c]pyridin-3(2H)-one-7,7-$d_2$ (d2-gaboxadol 7,7) is shown below. This synthesis of d2-gaboxadol 7,7 is represented in the schema of FIG. 3.

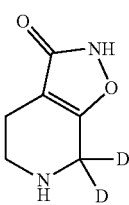 [SMILES: [2H]C1([2H])NCCc2c1o[nH]c2=O]

Reagents and conditions: (a) Boc$_2$O, TEA, THF, rt, 3 h; (b) CH$_2$N$_2$, Et$_2$O, 0° C., 4 h; (c) HCl, dioxane, 0° C. rt, 1 h; (d) acetate buffer (PH=4), NaNO$_2$, 0° C. rt, 2 h; (e) D$_2$O, TEA/dioxane, 65° C., 26 h; (f) HBr (33% wt. % in AcOH), 70° C., 1 h.

a. Synthesis of tert-butyl 3-hydroxy-4,7-dihydroisoxazolo[5,4-c]pyridine-6(5H)-carboxylate (2, FIG. 3)

To a mixture of 4,5,6,7-tetrahydroisoxazolo[5,4-c]pyridin-3-ol hydrochloride (8.2 g, 46.43 mmol) and Et$_3$N (4.93 g, 48.75 mmol) in THF (140 mL) was added Boc$_2$O (10.64 g, 48.75 mmol) at 0° C. The reaction mixture was stirred at room temperature for 3 h. The reaction was poured into water (150 mL) and extracted with EtOAc (100 mL×3). The combined organics were washed with brine (200 mL×1), dried over Na$_2$SO$_4$, concentrated and purified by silica gel chromatography (EA/PE=¼) to give the desired product as a white solid (9.2 g, 82% yield). LC/MS (ESI): m/z 241 [M+H]$^+$.

b. Synthesis of tert-butyl 3-methoxy-4,7-dihydroisoxazolo[5,4-c]pyridine-6(5H)-carboxylate (3, FIG. 3)

To a solution of tert-butyl 3-hydroxy-4,7-dihydroisoxazolo[5,4-c]pyridine-6(5H)-carboxylate (9.2 g, 38.29 mmol) in Et$_2$O (100 mL) was added dropwise the solution of CH$_2$N$_2$ (3.22 g, 76.58 mmol, prepared freshly) in Et$_2$O (130 mL) at 0° C. The reaction solution was stirred at 0° C. for 4 h. The reaction mixture was quenched with formic acid (3 mL), and pH of the solution was adjusted to ~10 by saturated aqueous NaHCO$_3$ (50 mL), extracted with EtOAc (100 mL×2). The combined organics were washed with brine (300 mL×1), dried over Na$_2$SO$_4$, concentrated and purified by silica gel chromatography (DCM) to give the desired product as a white solid (4.57 g, 47% yield). $^1$H NMR (400 MHz, CDCl$_3$): δ 4.46 (s, 2H), 3.99 (s, 3H), 3.61 (t, J=6.0 Hz, 2H), 2.41 (t, J=6.0 Hz, 2H), 1.48 (s, 9H). LC/MS (ESI): m/z 255 [M+H]$^+$.

Preparation of Diazomethane

To a solution of KOH aqueous (40%) (90 mL) in Et$_2$O (130 mL) was added 1-methyl-3-nitro-1-nitrosoguanidine (11.3 g, 76.58 mmol) in portions at 0° C. The mixture was stirred at 0° C. for 30 min. The Et$_2$O layer was used directly.

c. Synthesis of 3-methoxy-4,5,6,7-tetrahydroisoxazolo[5,4-c]pyridine (4, FIG. 3)

To a solution of tert-butyl 3-methoxy-4,7-dihydroisoxazolo[5,4-c]pyridine-6(5H)-carboxylate (4.57 g, 17.97 mmol) in dioxane (15 mL) was treated with HCl (60 mL, 4 N solution in 1,4-dioxane). The resulting mixture was stirred at room temperature for 1 h. The reaction mixture was concentrated and dried in vacuo to give the desired product of HCl salt as a white solid (3.4 g, 100% yield). LC/MS (ESI): m/z 155 [M+H]$^+$.

d. Synthesis of 3-methoxy-6-nitroso-4,5,6,7-tetrahydroisoxazolo[5,4-c]pyridine (5, FIG. 3)

To a solution of 3-methoxy-4,5,6,7-tetrahydroisoxazolo[5,4-c]pyridine hydrochloride (3.4 g, 17.94 mmol) in acetate buffer (180 mL, pH=4) was treated dropwise a solution of NaNO$_2$ (12.4 g, 179.7 mmol) in H$_2$O (60 mL) at 0° C. The resulting reaction was stirred at room temperature for 2 h. The reaction mixture was diluted in water (100 mL) and extracted with DCM (100 mL×2). The combined organics were washed with brine (200 mL×1), dried over Na$_2$SO$_4$, concentrated to offer the crude, which was triturated with PE/toluene (10/1) to give the desired product (3.0 g, 91%) as a yellow solid. LC/MS (ESI): m/z 184 [M+H]$^+$.

e. Synthesis of 3-methoxy-6-nitroso-4,5,6,7-tetrahydroisoxazolo[5,4-c]pyridine-7,7-d2 (6, FIG. 3)

A solution of 3-methoxy-6-nitroso-4,5,6,7-tetrahydroisoxazolo[5,4-c]pyridine (500 mg, 2.73 mmol) and D$_2$O (547 mg, 27.3 mmol) in Et$_3$N (5 mL) and 1,4-dioxane (5 mL) was stirred at 60° C. for 26 h. The reaction mixture was concentrated to give the crude, which was triturated with PE/toluene (10/1) to give the desired product as a yellow solid (400 mg, 79% yield). The $^1$H NMR data (CDCl$_3$) are consistent with 6 being a mixture (ca. ¼) of two rotamers. $^1$H NMR (400 MHz, CDCl$_3$): δ 4.54 (t, J=5.9 Hz, 1.6H), 4.05 (t, J=6.0 Hz, 0.4H), 4.03-3.93 (m, 3H), 2.73 (t, J=6.0 Hz, 1.6H), 2.43 (t, J=6.0 Hz, 0.4H). LC/MS (ESI): m/z 186 [M+H]$^+$.

f. Synthesis of 4,5,6,7-tetrahydroisoxazolo[5,4-c]pyridin-7,7-d2-3-ol (7, FIG. 3)

A mixture of 3-methoxy-6-nitroso-4,5,6,7-tetrahydroisoxazolo[5,4-c]pyridine (400 mg, 2.16 mmol) in HBr (8 mL, 33% wt. % in AcOH) was stirred at 70° C. for 1 h. The reaction mixture was concentrated and diluted in water (2 mL) and the pH was adjusted to 6.5 with Et$_3$N/EtOH (10%). The mixture was concentrated to give the crude, which was recrystallized in EtOH/H$_2$O (5/1, 5 mL) to give the desired product as a white solid (100 mg, 33% yield). $^1$H NMR (400 MHz, D$_2$O): δ 3.46 (t, J=6.0 Hz, 1H), 2.61 (t, J=5.9 Hz, 1H). LC/MS (ESI): m/z 143 [M+H]$^+$.

The yield % of the reaction (33% yield) is not directly relevant to the measure of deuterium incorporation.

TABLE V

Figure 4:
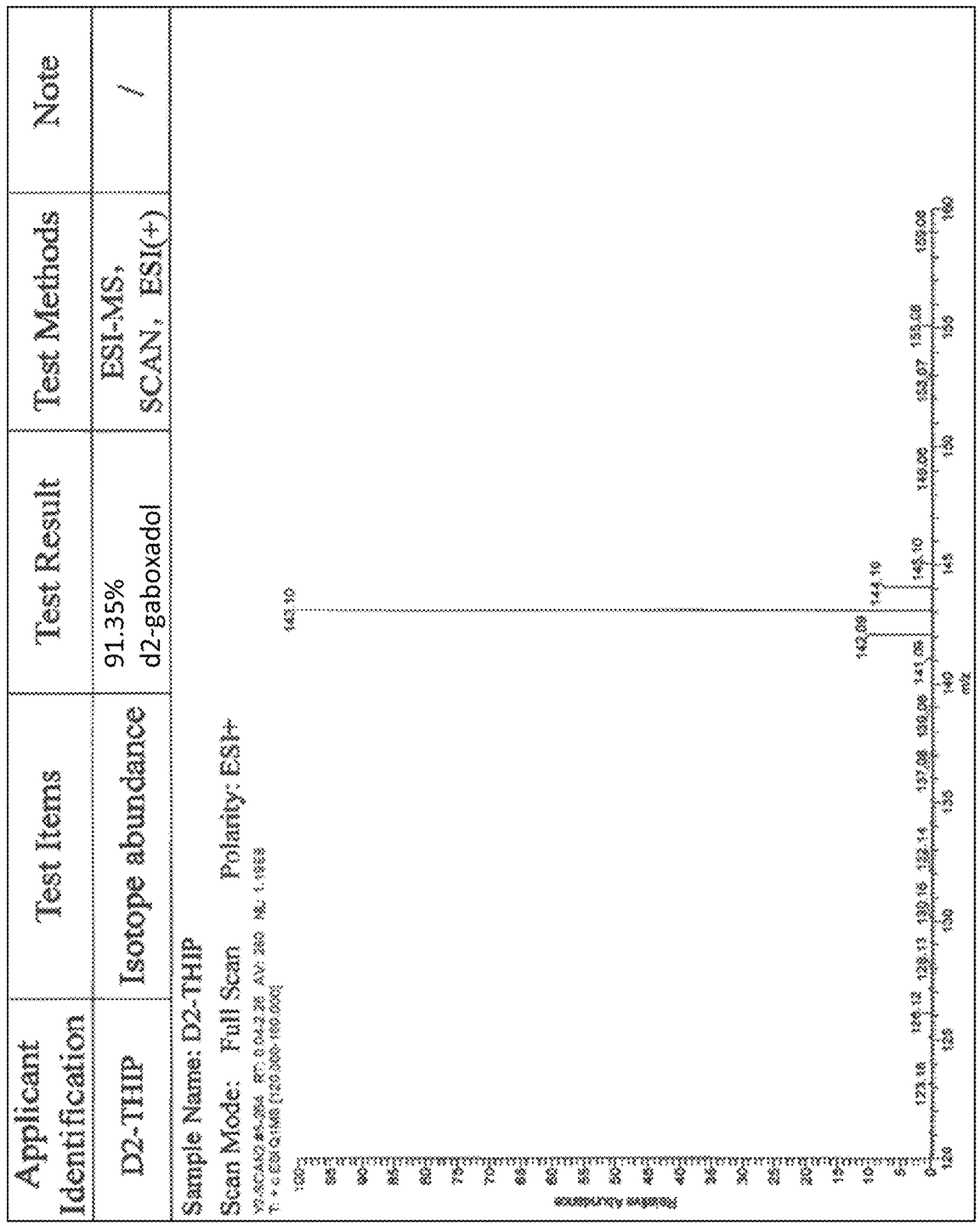
FIG. 4 shows the distribution of forms of deuterated gaboxadol in the composition of Example 1B. 91% of the deuterated gaboxadol in the composition was in the form of d2-gaboxadol-7,7 according to calculation from the raw data of peak intensity and abundance.

| Raw Data from FIG. 4 | | | | |
|---|---|---|---|---|
| Peak (m/z) | Compound represented | Intensity | Relative Abundance | Peak number |
| 141.09 | gaboxadol (non-deuterated) | 632533 | 0.53 | a |
| 142.09 | d1-gaboxadol | 11541101 | 9.73 | b |
| 143.10 | d2-gaboxadol | 118627522 | 100 | c |
| 144.10 | d2-gaboxadol ($^{13}$C isotope 1) | 8958123 | 7.55 | d |
| 145.10 | d2-gaboxadol ($^{13}$C isotope 2) | 966865 | 0.82 | e |

(The assessment of $^{13}$C isotope incorporation is based on ESI-MS analysis of a sample of a non-deuterated gaboxadol composition which demonstrated peaks at about 141, 142 and 143 in a ratio of 100:7.4:0.65 (data not shown).)

FIG. 4 shows a composition of 91.35% d2-gaboxadol as calculated from the raw data by peak size intensity and relative abundance using electrospray ionization mass spectrometry (FIG. 4). In this example the d2-gaboxadol peak at 143.10 is quantified (Intensity) and may be converted to relative abundance, set at 100 in this example. The intensity of other peaks are determined and relative abundance was set relative to the largest peak.

$$= (c + d + e)/(a + b + c + d + e) * 100\%$$
$$= (100 + 7.55 + 0.82)/(0.53 + 9.73 + 100 + 7.55 + 0.82))$$
$$= 91.35\%$$

The composition may also be described as 99.55% ring carbon deuterated gaboxadol (deuterated gaboxadol) when all species and forms of deuterated gaboxadol are combined and measured in relation to the amount of non-deuterated gaboxadol.

$$= (b + c + d + e)/(a + b + c + d + e) * 100\%$$
$$= (9.73 + 100 + 7.55 + 0.82)/(0.53 + 9.73 + 100 + 7.55 + 0.82))$$
$$= 99.55\%$$

Example 1C: D2-Gaboxadol 7,7

One can also synthesize 4,5,6,7-tetrahydroisoxazolo(5,4-c)pyridin-3(2H)-one-7,7-d2 by the scheme shown in FIG. 3 by adjusting the final two steps as follows:

e. Synthesis of 3-methoxy-6-nitroso-4,5,6,7-tetrahydroisoxazolo[5,4-c]pyridine-7,7-d2 (6, FIG. 3)

A flame dried 45 mL tube equipped with a magnetic stir bar was charged with 3-methoxy-6-nitroso-4,5,6,7-tetrahydroisoxazolo[5,4-c]pyridine (600 mg, 3.28 mmol) and $D_2O$ (1.31 g, 65.6 mmol) in $Et_3N$ (8 mL) and 1,4-dioxane (8 mL). The tube was sealed with aluminium cap quickly, and the resulting solution was stirred at 85° C. for 24 h. The reaction mixture was concentrated to give the crude, which was purified with Prep-TLC (eluent: 100% of DCM) to give the desired product as a white solid (500 mg, 82.4% yield). The $^1H$ NMR data ($CDCl_3$) was consistent with 6 being a mixture (ca. ¼) of two rotamers. $^1H$ NMR (400 MHz, $CDCl_3$): δ 4.54 (t, J=5.9 Hz, 1.6H), 4.05 (t, J=6.0 Hz, 0.4H), 4.03-3.93 (m, 3H), 2.73 (t, J=6.0 Hz, 1.6H), 2.43 (t, J=6.0 Hz, 0.4H). LC/MS (ESI): m/z 186 [M+H]$^+$.

f. Synthesis of 4,5,6,7-tetrahydroisoxazolo[5,4-c]pyridin-7,7-d2-3-ol (7, FIG. 3)

A mixture of 3-methoxy-6-nitroso-4,5,6,7-tetrahydroisoxazolo[5,4-c]pyridine (500 mg, 2.7 mmol) in HBr (10 mL, 33% wt. % in AcOH) was stirred at 70° C. for 1 h. The reaction mixture was concentrated and diluted in water (3 mL) and the pH was adjusted to 6.5 with $Et_3N$/EtOH (10%). The mixture was concentrated to give the crude, which was recrystallized in EtOH/$H_2O$ (5/1, 5 mL) to give the desired product as a white solid (250 mg, 64.7% yield). $^1H$ NMR (400 MHz, $D_2O$): δ 3.46 (t, J=6.0 Hz, 1H), 2.61 (t, J=5.9 Hz, 1H). LC/MS (ESI):
m/z 143 [M+H]$^+$.

Example 1D: D2-Gaboxadol 5,5

Another d2-gaboxadol deuterated with two deuterium atoms at position 5 of the tetrahydro-pyridine ring, named 4,5,6,7-tetrahydroisoxazolo[5,4-c]pyridin-3(2H)-one-5,5-d2 is shown below.

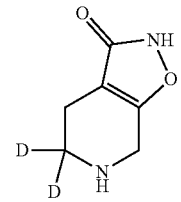

This compound may be prepared from methyl 4-aminobutanoate-4,4-d2 according to the procedures contained in DeFaveri et al WO 2016/150953. Ethylene glycol-$OD_2$ may be substituted for ethylene glycol in an intermediate step. Methyl 4-aminobutanoate-4,4-d2 may be prepared by reduction of succinimide with lithium aluminum tetradeuteride to provide pyrrolidin-2-one-5,5-$d_2$ according to similar procedure described in Wang et al. WO 2019/144885, followed by treatment with acidic methanol as described in DeFaveri et al WO 2016/150953.

Example 1E: D2-Gaboxadol 4,4

A third d2-gaboxadol, 4,5,6,7-tetrahydroisoxazolo[5,4-c]pyridin-3(2H)-one-4,4-d2 is shown below.

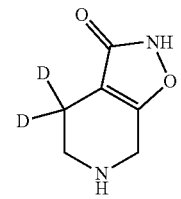

This compound may be prepared from known methyl 4-aminobutanoate-2,2,3,3-d4 (Wang et al. WO 2019/144885) according to the procedures contained in DeFaveri et al WO 2016/150953. Ethylene glycol-$OD_2$ may be substituted for ethylene glycol in an intermediate step.

Example 1F: D2-Gaboxadol 5,5

Alternatively, deuterated gaboxadol may be synthesized by the following procedures. For example, gaboxadol-D2, 4,5,6,7-tetrahydroisoxazolo[5,4-c]pyridin-3(2H)-one-5,5-d2

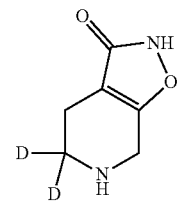

may be prepared from commercially available and known (Wheatly and Keay (2007) Journal of Organic Chemistry, 72(19), 7253-7259) dihydro-5d-2(3H)-furanone-5-d) (gamma-butyrolactone-5,5-d2) according to the procedure for 4,4,5,5-Gaboxadol-D4.

Example 1G: D2-Gaboxadol 4,4

Another d2 species, 4,5,6,7-tetrahydroisoxazolo[5,4-c]pyridin-3(2H)-one-4,4-d2

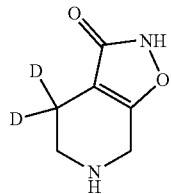

may be prepared from known dihydro-4d-2(3H)-furanone-4-d) (gamma-butyrolactone-4,4-$d_2$) (Wheatly and Keay (2007) Journal of Organic Chemistry, 72(19), 7253-7259) according to the procedure for 4,4,5,5-Gaboxadol-D4.

Example 1I1: D2-Gaboxadol

Figure 5:
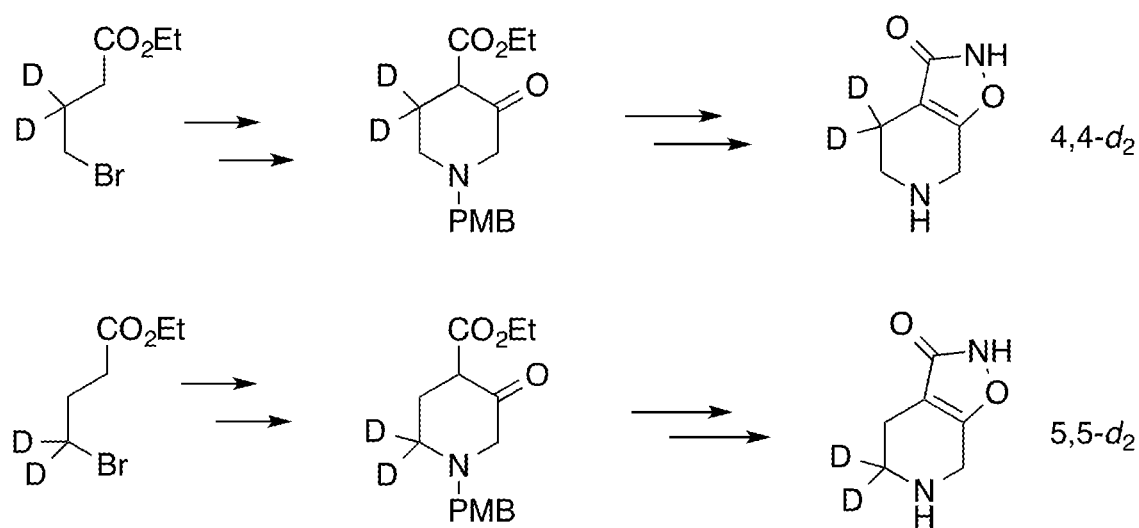
FIG. 5 shows exemplary synthetic pathways for deuterated d2-gaboxadol 4,4 and d2-gaboxadol 5,5.

FIG. 5 provides potential alternative synthetic routes for d2-gaboxadol, such as d2-gaboxadol 4,4 and d2-gaboxadol 5,5.

Example 2A: D4-Gaboxadol 4,4,5,5

Deuterated gaboxadol can be synthesized with 4 deuterium atoms located a ring carbon positions. One such d4-gaboxadol is 4,5,6,7-tetrahydroisoxazolo[5,4-c]pyridin-3(2H)-one-4,4,5,5-$d_4$ shown below.

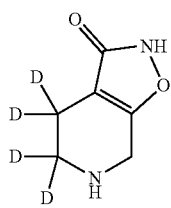

This compound may be prepared from known commercially available pyrrolidin-2-one-3,3,4,4,5,5-$d_6$ according to the procedures contained in DeFaveri et al WO 2016/150953. It may also be prepared according to Kall et al. (2007). It is not known what percentage deuteration of the composition is achieved with the method of Kall et. (2007)

Example 2B: D4-Gaboxadol 4,4,7,7

A second d4-gaboxadol is 4,5,6,7-tetrahydroisoxazolo[5,4-c]pyridin-3(2H)-one-4,4,7,7-$d_4$ shown below.

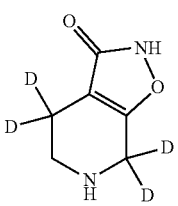 [SMILES: [2H]C1([2H])CNC([2H])([2H])c2o[nH]c(=O)c21]

This compound may be prepared from 4,5,6,7-tetrahydroisoxazolo[5,4-c]pyridin-3(2H)-one-4,4-$d_2$ according to procedure for 7,7-dideuterio incorporation contained in Krogsgaard-Larsen 1982 publication.

Example 2C: D4-Gaboxadol 5,5,7,7

Another d4-gaboxadol, 4,5,6,7-tetrahydroisoxazolo[5,4-c]pyridin-3(2H)-one-5,5,7,7-$d_4$ is shown below.

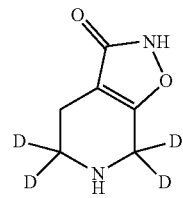 [SMILES: [2H]C1([2H])Cc2c(o[nH]c2=O)C([2H])([2H])N1]

This compound may be prepared from 4,5,6,7-tetrahydroisoxazolo[5,4-c]pyridin-3(2H)-one-5,5-d2 according to procedure for 7,7-dideuterium incorporation contained in Krogsgaard-Larsen 1982 publication.

Example 2D: D4-Gaboxadol 4,4,7,7

Alternatively, the title compound may be prepared from 4,5,6,7-tetrahydroisoxazolo[5,4-c]pyridin-3(2H)-one-4,4-d2 according to procedure contained herein for 4,5,6,7-tetrahydroisoxazolo[5,4-c]pyridin-3(2H)-one-4,4,5,5,7,7-d6.

Example 2E: D4-Gaboxadol 5,5,7,7

Another species of gaboxadol-D4,4,5,6,7-tetrahydroisoxazolo[5,4-c]pyridin-3(2H)-one-5,5,7,7-d4

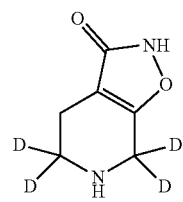 [SMILES: [2H]C1([2H])Cc2c(o[nH]c2=O)C([2H])([2H])N1]

may be prepared from 4,5,6,7-tetrahydroisoxazolo[5,4-c]pyridin-3(2H)-one-5,5-d2 according to procedure for 7,7-dideuterium incorporation contained in Krogsgaard-Larsen 1982 publication.

Example 2F: D4-Gaboxadol 5,5,7,7

Alternatively, the title compound may be prepared from 4,5,6,7-tetrahydroisoxazolo[5,4-c]pyridin-3(2H)-one-5,5-d2 according to procedure contained herein for 4,5,6,7-tetrahydroisoxazolo[5,4-c]pyridin-3(2H)-one-4,4,5,5,7,7-d6.

Example 2G: D4-Gaboxadol

Figure 6:
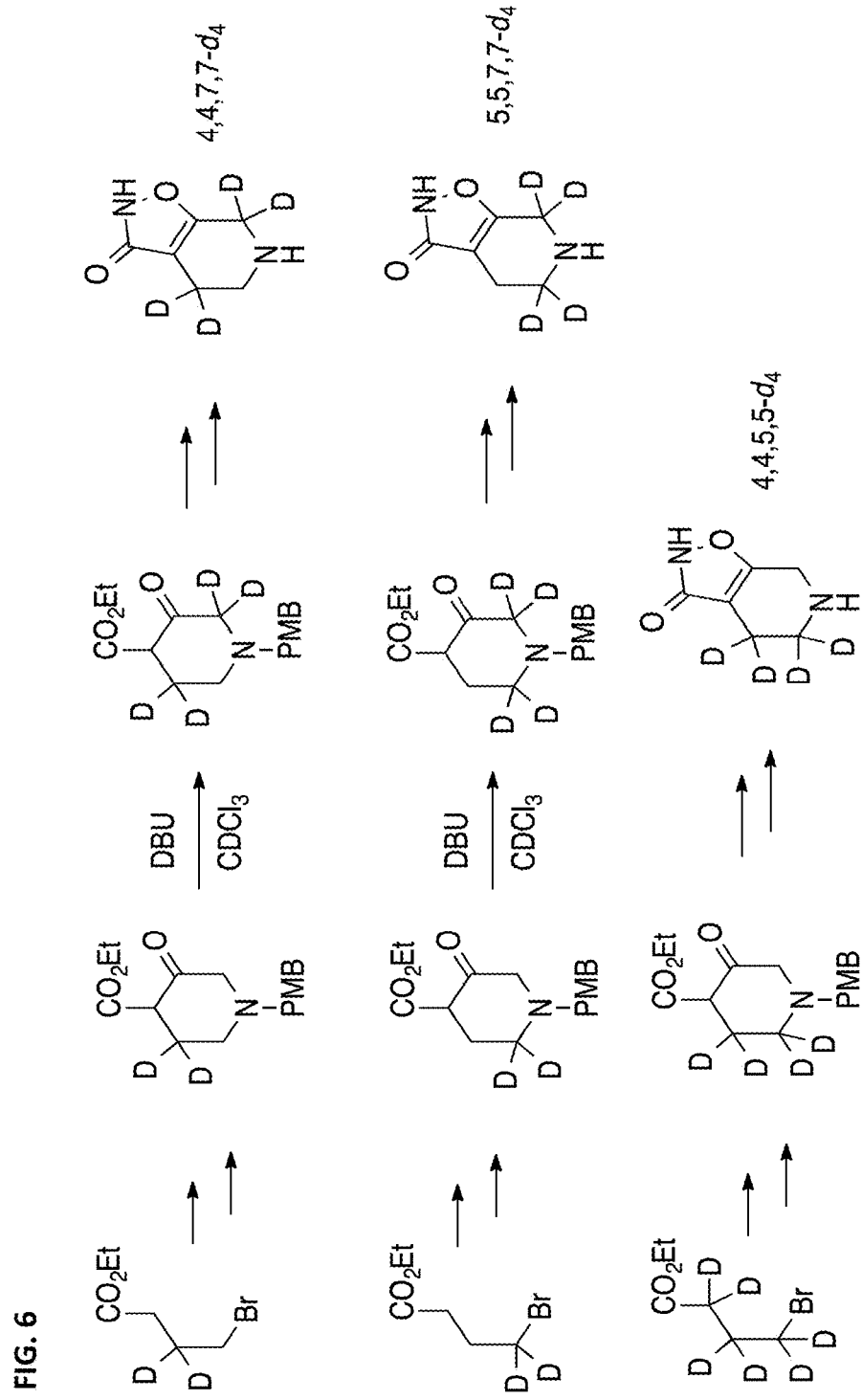
FIG. 6 shows exemplary synthetic pathways for deuterated d4-gaboxadol 4,4,7,7, d4-gaboxadol 5,5,7,7, and d4-gaboxadol 4,4,5,5.

FIG. 6 provides potential alternative synthetic routes for various species of d4-gaboxadol.

Example 3A: D6-Gaboxadol

The d6-gaboxadol 4,5,6,7-tetrahydroisoxazolo[5,4-c]pyridin-3(2H)-one-4,4,5,5,7,7-$d_6$ is shown below.

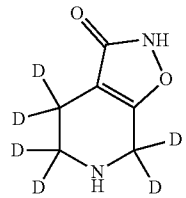

This compound may be prepared from 4,5,6,7-tetrahydroisoxazolo[5,4-c]pyridin-3(2H)-one-4,4,5,5-$d_4$ according to procedure for 7,7-dideuterium incorporation contained in Krogsgaard-Larsen 1982 publication.

Example 3B: D6-Gaboxadol

Figure 7:
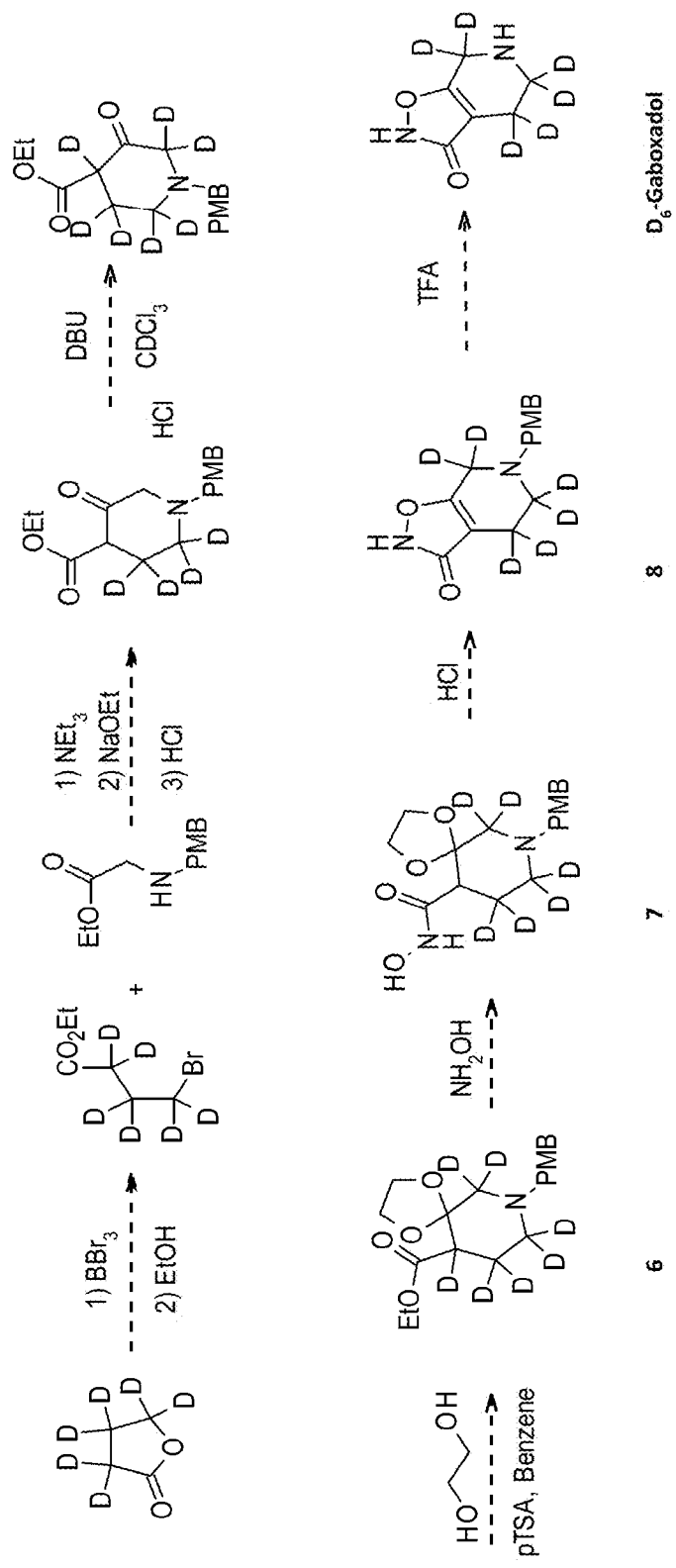
FIG. 7 shows exemplary synthetic pathways for deuterated d6-gaboxadol.

FIG. 7 provides potential alternative synthesis for d6-gaboxadol.

Example 4: Synthesis of Deuterated Gaboxadol

All temperatures are in degrees Celsius (° C.) and are uncorrected. Reagent grade chemicals and anhydrous solvent were purchased from commercial sources and unless otherwise mentioned, were used without further purification. The names of the products were determined using the naming software included in Biovia electronic lab notebook. Silica gel chromatography was performed on Teledyne Isco instruments using pre-packaged disposable $SiO_2$ stationary phase columns with eluent flow rate range of 15 to 200 mL/min, UV detection (254 and 280 nm). Reverse phase preparative HPLC was carried out using C18 columns, UV detection (214 and 254 nm) eluting with gradients of MeCN in $H_2O$ (0.03% $(NH4)_2CO_3$/0.375% $NH_4OH$, high pH) or MeCN in $H_2O$ (0.1% HCOOH, low pH). The analytical HPLC chromatograms were performed using an Agilent 1100 series instrument with DAD detector (190 nm to 300 nm). The mass spectra were recorded with a Waters Micromass ZQ detector at 130° C. The mass spectrometer was equipped with an electrospray ion source (ESI) operated in a positive or negative ion mode and was set to scan between m/z 150-750 or m/z 100-750 with a scan time of 0.3 s. Products and intermediates were analyzed by HPLC/MS on a Gemini-NX (5 μM, 2.0×30 mm) using a high pH buffer gradient of 5% to 100% of MeCN in $H_2O$ (0.03% $(NH4)_2CO_3$/0.375% $NH_4OH$) over 2.5 min at 1.8 mL/min for a 3.5 min run (B05) and EVO C18 (5 μM, 3.0×50 mm) using a low pH buffer gradient of 5% to 100% of MeCN in $H_2O$ (0.1% HCOOH) over 2.5 min at 2.2 mL/min for a 3.5 min run (A05). The $^1H$ NMR spectra were recorded on a Bruker UltraShield 500 MHz/54 mm instrument (BZH 43/500/70B, D221/54-3209). The chemical shifts are referenced to solvent peaks, which in $^1H$ NMR appear at 7.26 ppm for $CDCl_3$, 2.50 for DMSO-$d_6$, and 3.31 ppm for $CD_3OD$ and in $^{13}C$ NMR appear at 77.16 ppm for $CDCl_3$, 39.52 for DMSO-$d_6$, and 49.00 ppm for $CD_3OD$.

4.1. Gaboxadol D2 (d2-gaboxadol 7,7)

Figure 8:
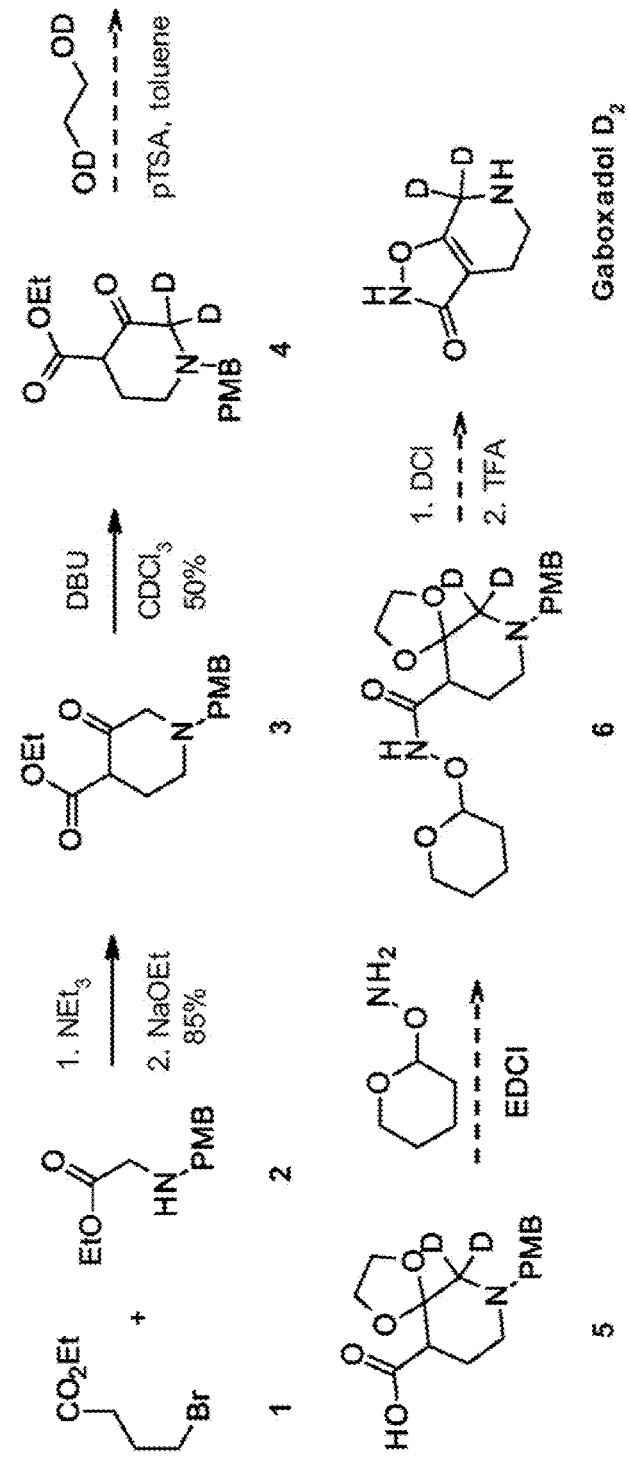
FIG. 8 shows an exemplary synthesis of d2-gaboxadol 7,7.

A general reaction scheme for Gaboxadol D2 (d2-gaboxadol 7,7) is provided in FIG. 8. Individual reaction steps are preferably achieved as follows.

Ethyl 1-[(4-methoxyphenyl)methyl]-3-oxo-piperidine-4-carboxylate; 3

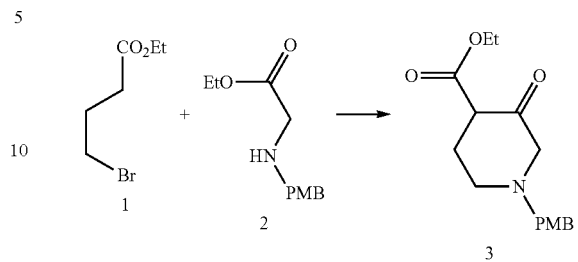

To a solution of Ethyl 2-[(4-methoxyphenyl)methyl-amino]acetate 2 (16.0 g, 71.7 mmol) and ethyl 4-bromobutyrate 1 (22.6 mL, 158 mmol) in dioxane (120 mL) was added triethylamine (30.2 mL, 214 mmol). The mixture was heated to reflux 18 h. The reaction mixture was cooled to room temperature and the solvent was removed under reduced pressure. The residue was diluted with water (200 mL) and the aqueous phase was extracted with EtOAc (3×50.0 mL). The combined organic layers were dried ($MgSO_4$), filtered and concentrated under reduced pressure. To the residue in toluene (150 mL) was added NaOEt (21% in EtOH, 58.1 mL, 156 mmol). The mixture was heated to reflux for 18 h. The mixture was cooled to room temperature, and the solvent was removed under reduced pressure. The residue was diluted with water (200 mL) and the aqueous phase was extracted with EtOAc (3×100 mL). The combined organic layers were dried ($Na_2SO_4$), filtered and concentrated under reduced pressure. The residue was purified by silica gel chromatography (80 g cartridge) using a gradient of 0-100% EtOAc in hexanes to afford title compound 3 (15.4 g) with 85% yield over 2 steps as an oil. $^1H$ NMR (400 MHz, $CDCl_3$) δ 11.92 (s, 1H), 7.38-7.11 (m, 2H), 6.85 (d, J=8.4 Hz, 2H), 4.21 (q, J=7.1 Hz, 2H), 3.80 (s, 3H), 3.54 (s, 2H), 3.07 (s, 2H), 2.56 (t, J=5.7 Hz, 2H), 2.32 (t, J=5.4 Hz, 2H), 1.28 (t, J=7.1 Hz, 3H).

4.1.2 Ethyl 2,2-dideuterio-1-[(4-methoxyphenyl)methyl]-3-oxo-piperidine-4-carboxylate; 4 (FIG. 8)

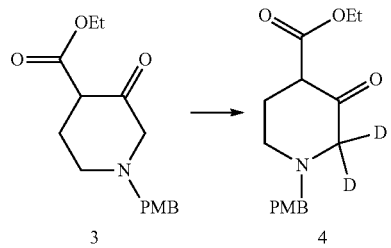

To a solution of ethyl 1-[(4-methoxyphenyl)methyl]-3-oxo-piperidine-4-carboxylate 3 (4.00 g, 13.7 mmol) in $CDCl_3$ (130 mL) was added DBU (8.86 mL, 68.6 mmol). The mixture was heated to reflux for 18 h. The mixture was cooled to room temperature, then concentrated under reduced pressure. The residue was purified by silica gel chromatography (80 g cartridge) using a gradient of 0-100% EtOAc in hexanes to afford title compound 4 (2.00 g) with 50% yield as an oil. $^1H$ NMR (400 MHz, $CDCl_3$) δ 11.91 (s, 1H), 7.25 (m, 2 Hz, 2H), 6.89-6.82 (m, 2H), 4.21 (q, J=7.1

Hz, 2H), 3.80 (s, 3H), 3.54 (s, 2H), 2.62-2.51 (m, 2H), 2.32 (t, J=5.8 Hz, 2H), 1.34-1.25 (m, 3H). 94% deuterium incorporation by NMR.

4.1.3 Reaction; 10,10-dideuterio-9-[(4-methoxyphenyl)methyl]-1,4-dioxa-9-azaspiro[4.5]decane-6-carboxylic Acid; 5 (FIG. 8)

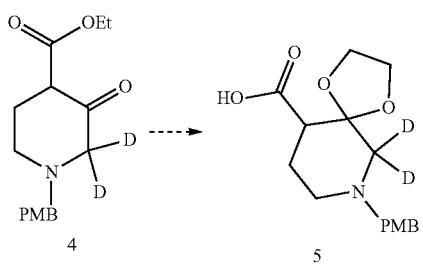

To a mixture of ethyl 2,2-dideuterio-1-[(4-methoxyphenyl)methyl]-3-oxo-piperidine-4-carboxylate 4 (900 mg, 3.07 mmol) and p-toluenesulfonic acid (26.4 mg, 0.153 mmol) in toluene (30.0 mL) is added 1,2-dideuteriooxyethane (10.7 mL, 184 mmol). The mixture is heated to reflux for 96 hours using a Dean-Stark apparatus. The mixture is cooled to room temperature, then diluted with an aqueous 1 M solution of $Na_2CO_3$ (20.0 mL). The aqueous phase is extracted with EtOAc (3×20.0 mL). The combined organic layers are dried ($Na_2SO_4$), filtered and concentrated under reduced pressure. The residue is purified by silica gel chromatography (40 g cartridge) using a gradient of 0-100% of EtOAc in hexanes to provide title compound 5.

4.1.4 Reaction; 10,10-dideuterio-9-[(4-methoxyphenyl)methyl]-N-tetrahydropyran-2-yloxy-1,4-dioxa-9-azaspiro[4.5]decane-6-carboxamide; 6 (FIG. 8)

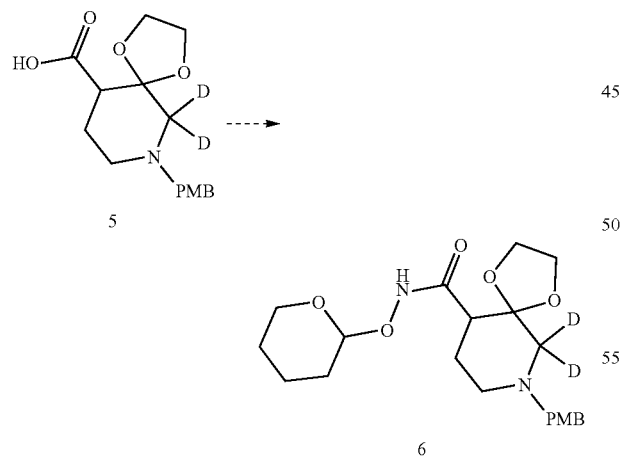

To a mixture of 10,10-dideuterio-9-[(4-methoxyphenyl)methyl]-1,4-dioxa-9-azaspiro[4.5]decane-6-carboxylic acid 5 (1.00 g, 3.23 mmol) and O-(Tetrahydro-2H-pyran-2-yl)hydroxylamine (416 mg, 3.55 mmol) in DMF (20.0 mL) at 0° C. is added EDCI* HCl (918 mg, 3.55 mmol) and DMAP (19.7 mg, 0.162 mmol). The mixture is stirred at room temperature for 18 h, then concentrated under reduced pressure. The residue is purified by silica gel chromatography (120 g cartridge) using a gradient of 0-100% EtOAc in hexanes to provide title compound 6.

4.1.5 Reaction; Ethyl 2,2-dideuterio-1-[(4-methoxyphenyl)methyl]-3-oxo-piperidine-4-carboxylate; Gaboxadol D2 (FIG. 8)

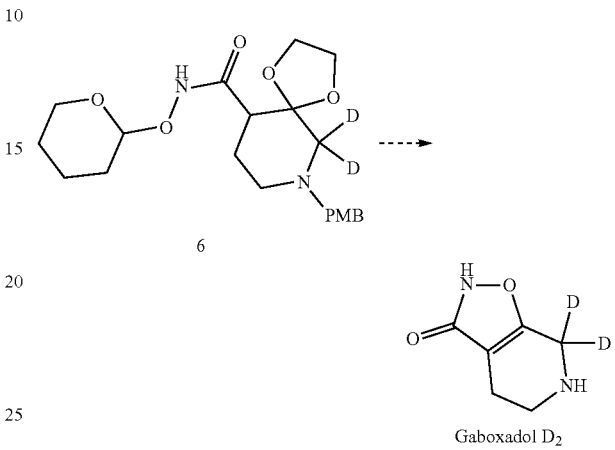

10,10-dideuterio-9-[(4-methoxyphenyl)methyl]-N-tetrahydropyran-2-yloxy-1,4-dioxa-9-azaspiro[4.5]decane-6-carboxamide 6 (1.00 g, 2.48 mmol) is added portion wise to 12N DCl at 0° C. The mixture was heated at 50° C. for 2 h, the cooled to room temperature. The pH was adjusted to 7 using an aqueous solution of 2N NaOH and EtOAc (100 mL) was added. The separated aqueous layer is extracted with EtOAc (3×50 mL). The combined organic layers are dried ($MgSO_4$), filtered and concentrated under reduced pressure. To the residue is added deuterated TFA (20 mL). The mixture is heated at 60° C. for 30 min, then cooled to room temperature. MeOH (50 mL) was added dropwise. The precipitate is filtered and rinsed with MeOH. The residue is purified by prep-HPLC using 10 mM AmBic pH 10 and MeCN to provide title compound Gaboxadol-D2,4,5,6,7-tetrahydroisoxazolo[5,4-c]pyridin-3(2H)-one-7,7-d2

4.2. Gaboxadol D4 (d4-gaboxadol 4,4,5,5)

Figure 9:
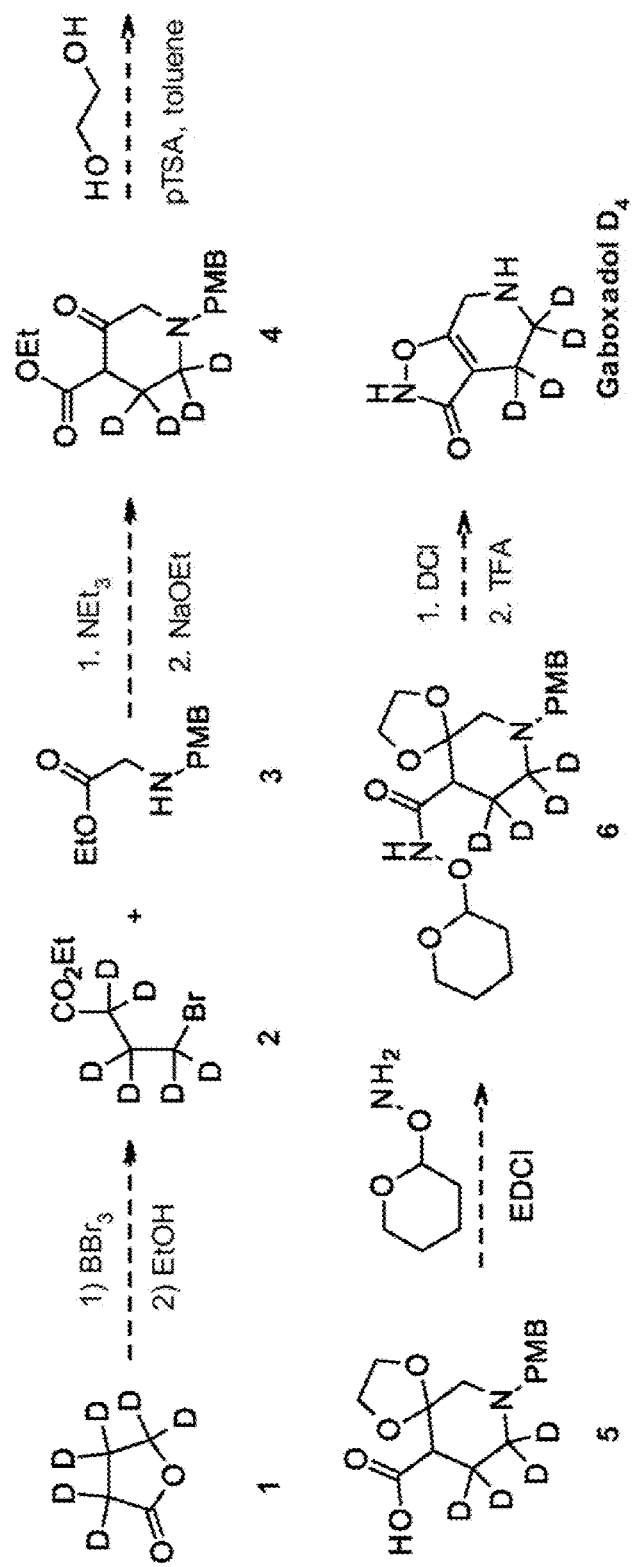
FIG. 9 shows an exemplary synthesis of d4-gaboxadol 4,4,5,5.

A general reaction scheme for Gaboxadol D4 (d4-gaboxadol 4,4,5,5) is provided in FIG. 9. Individual reaction steps are preferably achieved as follows.

4.2.1 Reaction; ethyl 4-bromo-2,2,3,3,4,4-hexadeuterio-butanoate; 2

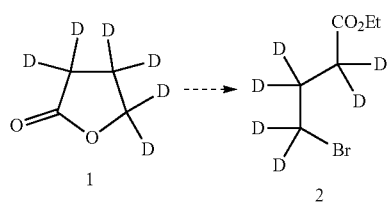 [SMILES: [2H]C1([2H])OC(=O)C([2H])([2H])C1([2H])[2H] ; [2H]C([2H])(Br)C([2H])([2H])C([2H])([2H])C(=O)OCC]

HBr (33% in AcOH, 20 mL) is added to EtOH (100 mL) at 0° C. 3,3,4,4,5,5-hexadeuteriotetrahydrofuran-2-one (5 g, 57.3 mmol). The mixture is heated to reflux for 5 h. The mixture is distillated under reduced pressure to provide title compound 2.

4.2.2 Reaction; ethyl 2,2,3,3-tetradeuterio-1-[(4-methoxyphenyl)methyl]-5-oxo-piperidine-4-carboxylate; 4

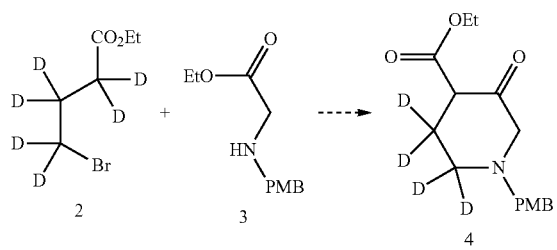

To a solution of Ethyl 2-[(4-methoxyphenyl)methyl-amino]acetate 3 (16.0 g, 71.7 mmol) and ethyl 4-bromo-2,2,3,3,4,4-hexadeuterio-butanoate 2 (15.9 g, 78.9 mmol) in dioxane (120 mL) is added triethylamine (30.2 mL, 214 mmol). The mixture is heated to reflux for 18 h. The reaction mixture is cooled to room temperature and the solvent is removed under reduced pressure. The residue is diluted with water (200 mL) and the aqueous phase is extracted with EtOAc (3×50.0 mL). The combined organic layers are dried (MgSO$_4$), filtered and concentrated under reduced pressure. To the residue in toluene (150 mL) is added NaOEt (21% in EtOH, 58.1 mL, 156 mmol). The mixture is heated to reflux for 18 h. The mixture is cooled to room temperature, and the solvent is removed under reduced pressure. The residue is diluted with water (200 mL) and the aqueous phase is extracted with EtOAc (3×100 mL). The combined organic layers are dried (Na$_2$SO$_4$), filtered and concentrated under reduced pressure. The residue is purified by silica gel chromatography (80 g cartridge) using a gradient of 0-100% EtOAc in hexanes to afford title compound 4.

4.2.3 Reaction; 7,7,8,8-tetradeuterio-9-[(4-methoxyphenyl)methyl]-1,4-dioxa-9-azaspiro[4.5]decane-6-carboxylic Acid; 5

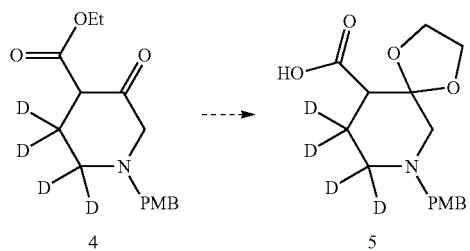

To a mixture of ethyl 2,2,3,3-tetradeuterio-1-[(4-methoxyphenyl)methyl]-5-oxo-piperidine-4-carboxylate 4 (900 mg, 3.05 mmol) and p-toluenesulfonic acid (26.1 mg, 0.153 mmol) in toluene (30.0 mL) is added ethylene glycol (11.4 g, 183 mmol). The mixture is heated to reflux for 96 hours using a Dean-Stark apparatus. The mixture is cooled to room temperature, then diluted with an aqueous 1 M solution of Na$_2$CO$_3$ (20.0 mL). The aqueous phase is extracted with EtOAc (3×20.0 mL). The combined organic layers are dried (Na$_2$SO$_4$), filtered and concentrated under reduced pressure. The residue is purified by silica gel chromatography (40 g cartridge) using a gradient of 0-100% of EtOAc in hexanes to provide title compound 5.

4.2.4 Reaction; 7,7,8,8-tetradeuterio-9-[(4-methoxyphenyl)methyl]-N-tetrahydropyran-2-yloxy-1,4-dioxa-9-azaspiro[4.5]decane-6-carboxamide; 6

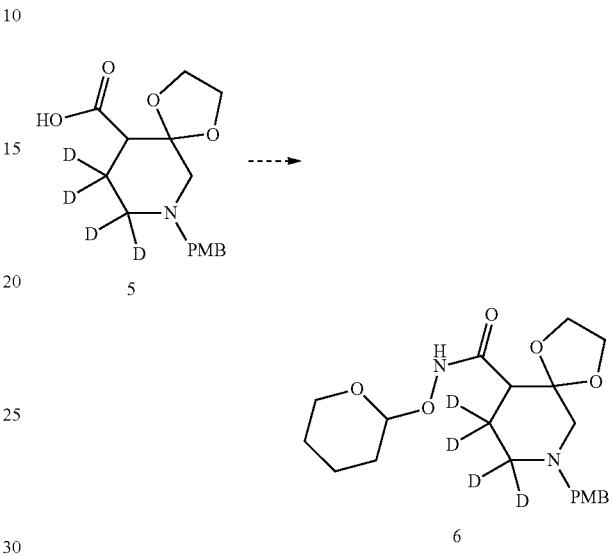

To a mixture of 7,7,8,8-tetradeuterio-9-[(4-methoxyphenyl)methyl]-1,4-dioxa-9-azaspiro[4.5] decane-6-carboxylic acid 5 (1.01 g, 3.23 mmol) and O-(Tetrahydro-2H-pyran-2-yl) hydroxylamine (416 mg, 3.55 mmol) in DMF (20.0 mL) at 0° C. is added EDCI* HCl (918 mg, 3.55 mmol) and DMAP (19.7 mg, 0.162 mmol). The mixture is stirred at rt for 18 h, then concentrated under reduced pressure. The residue is purified by silica gel chromatography (120 g cartridge) using a gradient of 0-100% EtOAc in hexanes to provide title compound 6.

4.2.5 Reaction; 4,4,5,5-tetradeuterio-6,7-dihydroisoxazolo[5,4-c]pyridin-3-one; Gaboxadol D4

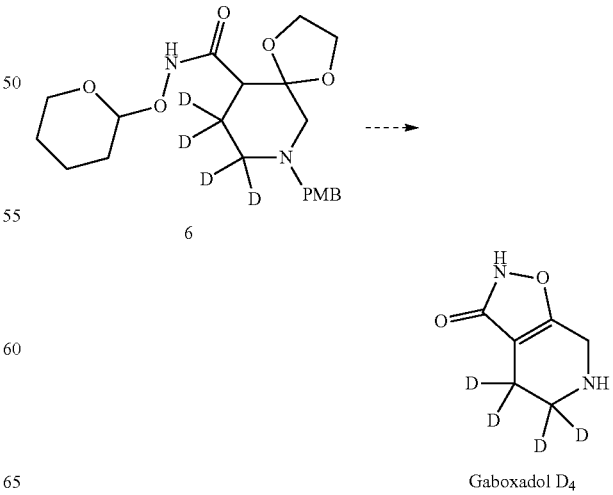

Gaboxadol D$_4$ 7,7,8,8-tetradeuterio-9-[(4-methoxyphenyl)methyl]-N-tetrahydropyran-2-yloxy-1,4-dioxa-9-azaspiro[4.5]decane-6-carboxamide 6 (1.01 g, 2.48 mmol) is added portion wise to 12N DCl at 0° C. The mixture is heated at 50° C. for 2 h, the cooled to room temperature. The pH is adjusted to 7 using an aqueous solution of 2N NaOH and EtOAc (100 mL). The separated aqueous layer is extracted with EtOAc (3×50 mL). The combined organic layers are dried (MgSO$_4$), filtered and concentrated under reduced pressure. To the residue is added deuterated TFA (20 mL). The mixture was heated at 60° C. for 30 min, then cooled to room temperature. MeOH (50 mL) is added dropwise. The precipitate is filtered and rinsed with MeOH. The residue is purified by prep-HPLC using 10 mM AmBic pH 10 and MeCN to provide title compound Gaboxadol-d4.

The title compound 4,5,6,7-tetrahydroisoxazolo[5,4-c]pyridin-3(2H)-one-4,4,5,5-d$_4$ may also be synthesized according to Kall et al. (2007).

4.3. Gaboxadol D6

Figure 10:
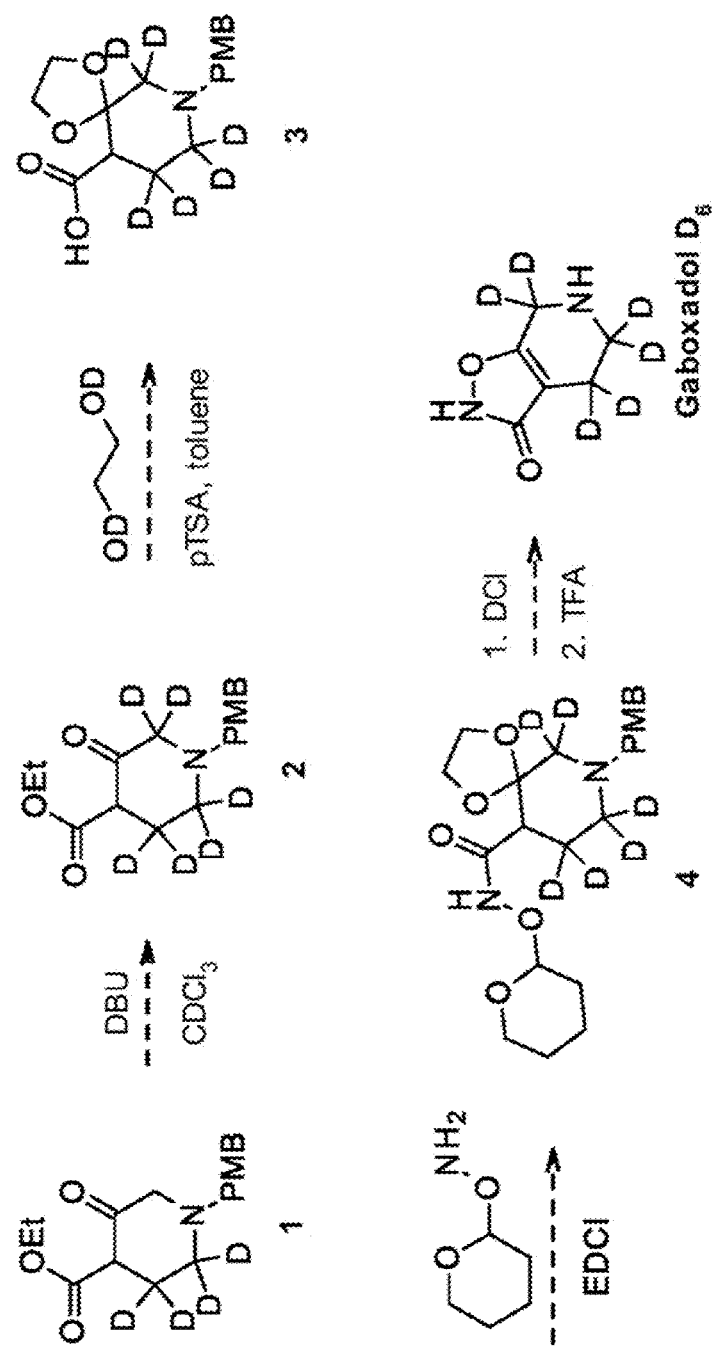
FIG. 10 shows an exemplary synthesis of d6-gaboxadol.

A general reaction scheme for Gaboxadol D6 is provided in FIG. 10. Individual reaction steps are preferably achieved as follows.

4.3.1 Reaction; ethyl 2,2,3,3,6,6-hexadeuterio-1-[(4-methoxyphenyl)methyl]-5-oxo-piperidine-4-carboxylate; 2

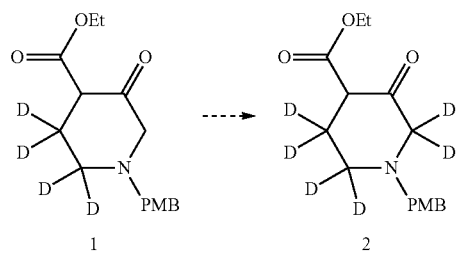

To a solution of e ethyl 2,2,3,3-tetradeuterio-1-[(4-methoxyphenyl)methyl]-5-oxo-piperidine-4-carboxylate 1 (4.05 g, 13.7 mmol) in CDCl$_3$ (130 mL) was added DBU (8.86 mL, 68.6 mmol). The mixture was heated to reflux for 18 h. The mixture was cooled to room temperature, then concentrated under reduced pressure. The residue was purified by silica gel chromatography (80 g cartridge) using a gradient of 0-100% EtOAc in hexanes to afford title compound 2 (2.00 g).

4.3.2 Reaction; 7,7,8,8,10,10-hexadeuterio-9-[(4-methoxyphenyl)methyl]-1,4-dioxa-9-azaspiro[4.5]decane-6-carboxylic Acid; 3

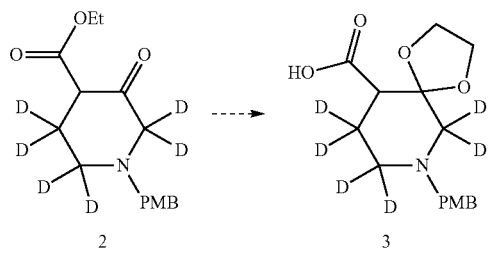

To a mixture of ethyl 2,2,3,3,6,6-hexadeuterio-1-[(4-methoxyphenyl)methyl]-5-oxo-piperidine-4-carboxylate 2 (913 mg, 3.07 mmol) and p-toluenesulfonic acid (26.4 mg, 0.153 mmol) in toluene (30.0 mL) is added 1,2-dideuterioooxyethane (10.7 mL, 184 mmol). The mixture is heated to reflux for 96 hours using a Dean-Stark apparatus. The mixture is cooled to room temperature, then diluted with an aqueous 1 M solution of Na$_2$CO$_3$ (20.0 mL). The aqueous phase is extracted with EtOAc (3×20.0 mL). The combined organic layers are dried (Na$_2$SO$_4$), filtered and concentrated under reduced pressure. The residue is purified by silica gel chromatography (40 g cartridge) using a gradient of 0-100% of EtOAc in hexanes to provide title compound 3.

4.3.3 Reaction; 7,7,8,8,10,10-hexadeuterio-9-[(4-methoxyphenyl)methyl]-N-tetrahydropyran-2-yloxy-1,4-dioxa-9-azaspiro[4.5]decane-6-carboxamide; 4

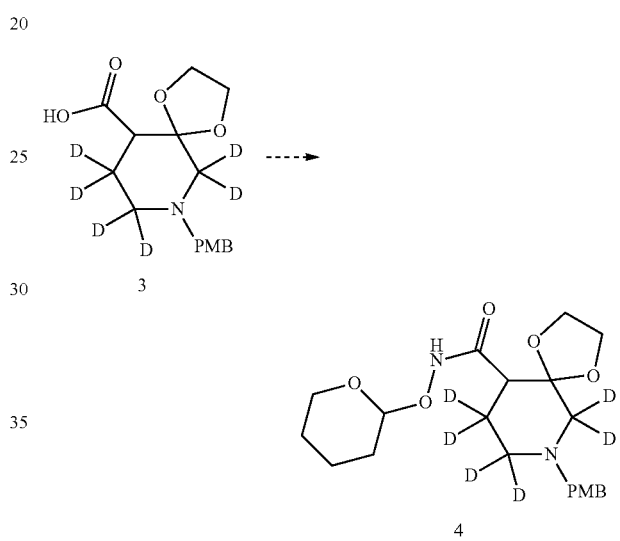

To a mixture of 7,7,8,8,10,10-hexadeuterio-9-[(4-methoxyphenyl)methyl]-1,4-dioxa-9-azaspiro[4.5]decane-6-carboxylic acid 3 (1.01 g, 3.23 mmol) and O-(Tetrahydro-2H-pyran-2-yl) hydroxylamine (416 mg, 3.55 mmol) in DMF (20.0 mL) at 0° C. is added EDCI* HCl (918 mg, 3.55 mmol) and DMAP (19.7 mg, 0.162 mmol). The mixture is stirred at room temperature for 18 h, then concentrated under reduced pressure. The residue is purified by silica gel chromatography (120 g cartridge) using a gradient of 0-100% EtOAc in hexanes to provide title compound 4.

4.3.4 Reaction; 4,4,5,5,7,7-hexadeuterio-6H-isoxazolo[5,4-c]pyridin-3-one; Gaboxadol D$_6$

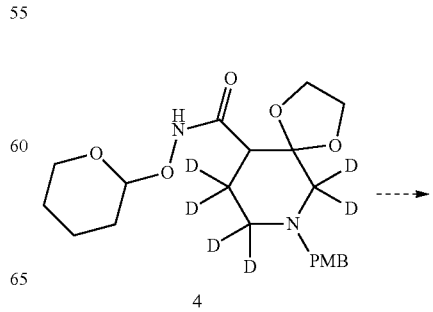

-continued

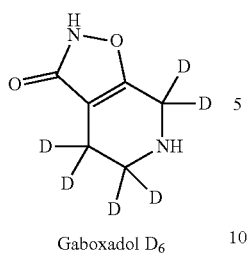

Gaboxadol D6

7,7,8,8,10,10-hexadeuterio-9-[(4-methoxyphenyl)methyl]-N-tetrahydropyran-2-yloxy-1,4-dioxa-9-azaspiro[4.5]decane-6-carboxamide 4 (1.02 g, 2.48 mmol) is added portion wise to 12N DCl at 0° C. The mixture is heated at 50° C. for 2 h, the cooled to room temperature. The pH is adjusted to 7 using an aqueous solution of 2N NaOH and EtOAc (100 mL) is added. The separated aqueous layer is extracted with EtOAc (3×50 mL). The combined organic layers are dried (MgSO$_4$), filtered and concentrated under reduced pressure. To the residue is added deuterated TFA (20 mL). The mixture is heated at 60° C. for 30 min, then cooled to room temperature. MeOH (50 mL) is added dropwise. The precipitate is filtered and rinsed with MeOH. The residue is purified by prep-HPLC using 10 mM AmBic pH 10 and MeCN to provide title compound Gaboxadol-D$_6$, 4,5,6,7-tetrahydroisoxazolo[5,4-c]pyridin-3(2H)-one-4,4,5,5,7,7-d6.

Example 5: Synthesis of Deuterated Gaboxadol D6 (i.e., D6-Gaboxadol)

All temperatures are in degrees Celsius (° C.) and are uncorrected. Reagent grade chemicals and anhydrous solvent were purchased from commercial sources and unless otherwise mentioned, were used without further purification. The names of the products were determined using the naming software included in Biovia electronic lab notebook. Silica gel chromatography was performed on Teledyne Isco instruments using pre-packaged disposable SiO$_2$ stationary phase columns with eluent flow rate range of 15 to 200 mL/min, UV detection (254 and 280 nm). Reverse phase preparative HPLC was carried out using C18 columns, UV detection (214 and 254 nm) eluting with gradients of MeCN in H$_2$O (0.03% (NH4)$_2$CO$_3$/0.375% NH$_4$OH, high pH) or MeCN in H$_2$O (0.1% HCOOH, low pH). The analytical HPLC chromatograms were performed using an Agilent 1100 series instrument with DAD detector (190 nm to 300 nm). The mass spectra were recorded with a Waters Micromass ZQ detector at 130° C. The mass spectrometer was equipped with an electrospray ion source (ESI) operated in a positive or negative ion mode and was set to scan between m/z 150-750 or m/z 100-750 with a scan time of 0.3 s. Products and intermediates were analyzed by HPLC/MS on a Gemini-NX (5 µM, 2.0×30 mm) using a high pH buffer gradient of 5% to 100% of MeCN in H$_2$O (0.03% (NH$_4$)$_2$CO$_3$/0.375% NH$_4$OH) over 2.5 min at 1.8 mL/min for a 3.5 min run (B05) and EVO C18 (5 µM, 3.0×50 mm) using a low pH buffer gradient of 5% to 100% of MeCN in H$_2$O (0.1% HCOOH) over 2.5 min at 2.2 mL/min for a 3.5 min run (A05). The $^1$H NMR spectra were recorded on a Bruker UltraShield 500 MHz/54 mm instrument (BZH 43/500/70B, D221/54-3209). The chemical shifts were referenced to solvent peaks, which in $^1$H NMR appear at 7.26 ppm for CDCl$_3$, 2.50 for DMSO-d$_6$, and 3.31 ppm for CD$_3$OD and in $^{13}$C NMR appear at 77.16 ppm for CDCl$_3$, 39.52 for DMSO-d$_6$, and 49.00 ppm for CD$_3$OD.

A Synthetic Scheme for d6-Gaboxadol

Figure 11:
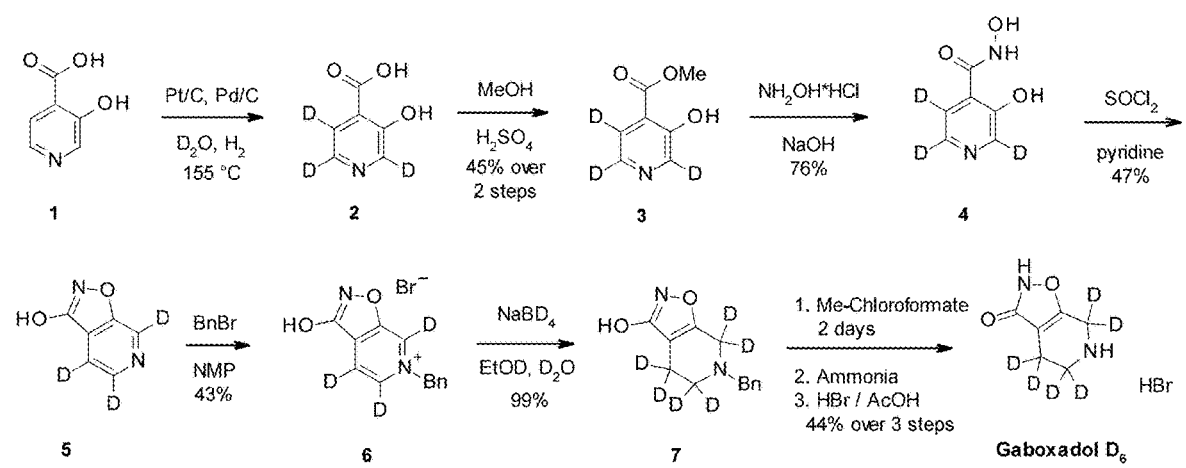
FIG. 11 shows an exemplary synthesis of d6-gaboxadol.

The scheme for this synthesis is seen in FIG. 11.

5.1.1
2,3,6-Trideuterio-5-hydroxy-pyridine-4-carboxylic Acid; 2 (FIG. 11)

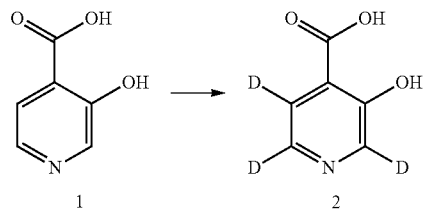 [SMILES: O=C(O)c1ccncc1O ; [2H]c1nc([2H])c(O)c(C(=O)O)c1[2H]]

A high-pressure stainless-steel vessel was charged with 3-hydroxypyridine-4-carboxylic acid 1 (5.0 g, 35.9 mmol), 10% wt. Pt/C (6.31 g, 3.23 mmol) and 10% wt. Pd/C (1.15 g, 1.08 mmol), followed with deuterium oxide (175 mL, 9.70 mol). The reaction mixture was bubbled with H$_2$ for 5 min, then the apparatus was sealed, and the reaction was stirred at 155° C. for 16 h. The mixture was cooled to room temperature, then degassed with N$_2$ for 5 min. An aqueous solution of 1N HCl (250 mL) was added, and the mixture was stirred for 1 h. The mixture was filtered on Celite and washed with 1M HCl in MeOH (3×100 mL). The filtrate was concentrated under reduced pressure to provide title compound 2 (6 g) as a solid, which was used in the next step without further purification.

5.1.2 Methyl 2,3,6-trideuterio-5-hydroxy-pyridine-4-carboxylate; 3 (FIG. 11)

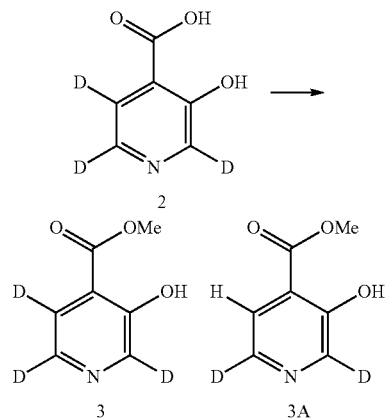

To a solution of 2,3,6-trideuterio-5-hydroxy-pyridine-4-carboxylic acid 2 (5.11 g, 36.0 mmol) in MeOH (100 mL) was added concentrated H$_2$SO$_4$ (9.63 mL, 0.18 mol), and the mixture was heated to reflux for 16 h. The mixture was cooled to rt, then poured into ice-water (500 mL). Solid NaHCO$_3$ was added portionwise to reach pH 7. The aqueous layer was extracted with DCM (3×100 mL). The combined organic layers were dried (Na₂SO₄), filtered and concentrated under reduced pressure to provide title compound 3 (2.5 g, 45% yield over 2 steps) as a solid. Compound 3 was confirmed by ¹H NMR (500 MHz, DMSO-d₆) δ 3.87 (s, 3H). The pyridine ring was 96% deuterated and contained 3% of impurity 3A.

5.1.3 2,3,6-Trideuterio-5-hydroxy-pyridine-4-carbohydroxamic Acid; 4 (FIG. 11)

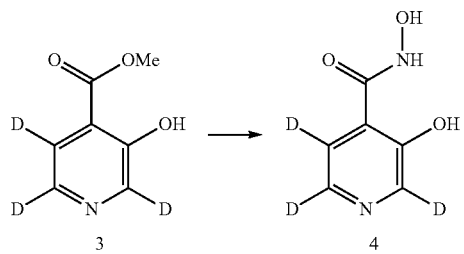 [SMILES: [2H]c1nc([2H])c(O)c(C(=O)OC)c1[2H] ; [2H]c1nc([2H])c(O)c(C(=O)NO)c1[2H]]

To a suspension of methyl 2,3,6-trideuterio-5-hydroxypyridine-4-carboxylate 3 (2.5 g, 16 mmol) in ice-water (15 mL), was added hydroxylamine hydrochloride (1.67 g, 24 mmol), followed by the addition dropwise of a 28% w/v aqueous NaOH solution (4 mL). The reaction mixture was stirred at rt for 3 h, then heated at 60° C. At this temperature, concentrated HCl was added dropwise to reach pH 5.4. The reaction mixture was then cooled to 0° C., and the pH was adjusted to 4 with concentrated HCl, followed by stirring at 0° C. for 90 min. The suspension was filtered and the solid was washed with water (3×10 mL) and dried under reduced pressure to afford title compound 4 (1.90 g, 76% yield) as a solid, which was used in the next step without further purification. Compound 4 was confirmed by ¹H NMR (500 MHz, DMSO-d6) δ 11.65 (br s, 1H), 11.38 (br s, 1H), 9.48 (s, 1H). MS (ESI) [M−H]⁻ 156.0.

5.1.4 4,5,7-Trideuterioisoxazolo[5,4-c]pyridin-3-one; 5 (FIG. 11)

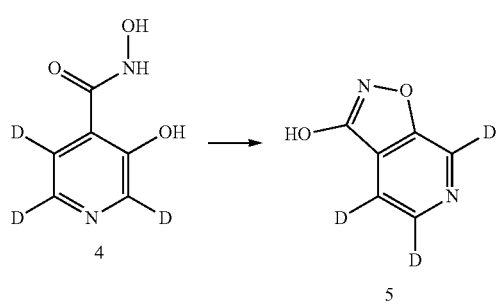 [SMILES: [2H]c1nc([2H])c(O)c(C(=O)NO)c1[2H] ; [2H]c1nc([2H])c2onc(O)c2c1[2H]]

A suspension of 2,3,6-trideuterio-5-hydroxy-pyridine-4-carbohydroxamic acid 4 (1.65 g, 10.5 mmol) in pyridine (13 mL) was stirred for 15 min, then cooled to 0° C. Thionyl chloride (1.42 mL, 19.4 mmol) was added dropwise while maintaining the temperature below 10° C., followed by warming to rt once addition is complete. The reaction mixture was poured on ice-water (100 mL) with vigorous stirring, then concentrated HCl was added until pH 3. The resulting suspension was stirred for 2 h at 0° C. and the suspension was filtered. The solid was washed with water (10 mL), EtOH (10 mL) and Et₂O (10 mL), then dried under reduced pressure to provide title compound 5 (680 mg, 47% yield) as a solid, which was used in the next step without further purification. Compound 5 was confirmed by ¹H NMR (500 MHz, DMSO-d₆) δ 12.91 (br s, 1H).

The inventors note that this compound was newly created specifically for performing this synthesis.

5.1.5 6-Benzyl-4,5,7-trideuterio-isoxazolo[5,4-c]pyridin-6-ium-3-ol Bromide; 6 (FIG. 11)

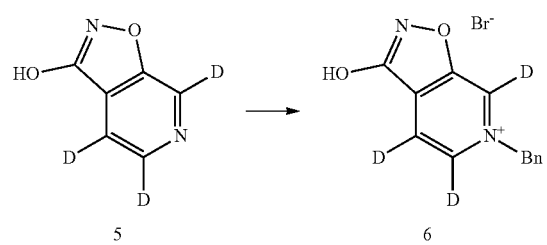 [SMILES: [Br-] ; [2H]c1nc([2H])c2onc(O)c2c1[2H] ; [2H]c1c([2H])[n+](Cc2ccccc2)c([2H])c2onc(O)c12]

To a solution of 4,5,7-trideuterioisoxazolo[5,4-c]pyridin-3-one 5 (680 mg, 4.89 mmol) in N-methylpyrrolidone (NMP) (2 ml) was added benzyl bromide (697 μL, 5.87 mmol), and the reaction mixture was stirred at rt for 16 h. Acetone (5.00 mL) was added, and the resulting solid was filtered, washed with acetone (2 mL), Et₂O (5 mL) and dried under pressure to provide title compound 6 (650 mg, 43% yield) as a solid, which was used in the next step without further purification. Compound 6 was confirmed by ¹H NMR (400 MHz, DMSO-d₆) δ 7.58 (d, J=5.5 Hz, 2H), 7.45 (d, J=5.6 Hz, 3H), 6.00 (s, 2H). MS (ESI) [M+H]⁺ 230.1.

5.1.6 6-Benzyl-4,4,5,5,7,7-hexadeuterio-isoxazolo[5,4-c]pyridin-3-ol; 7 (FIG. 11)

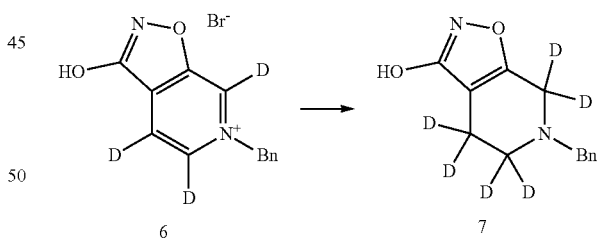

To a stirred solution of 6-benzyl-4,5,7-trideuterio-isoxazolo[5,4-c]pyridin-6-ium-3-ol bromide 6 (770 mg, 2.48 mmol) in Ethanol-OD (8 mL) and D2O (8 mL) was added NaBD4 (208 mg, 4.97 mmol). Note: reaction mixture foamed upon NaBD4 addition. The mixture was stirred at rt for 2 h. Acetone (1 mL) was added, and volatiles were removed under reduced pressure. The residue was purified by preparative HPLC (BEH column, C18, 30×150 mm) using a gradient of 10-40% MeCN and 10 mM ammonium formate (pH 3.8) in water to afford title compound 7 (490 mg, 99% yield) as a solid. Compound 7 was confirmed by ¹H NMR (500 MHz, DMSO-d₆) δ 7.35-7.31 (m, 4H), 7.30-7.24 (m, 1H), 3.67 (s, 2H). MS (ESI) [M+H]⁺ 237.1.

5.1.7 Gaboxadol D6

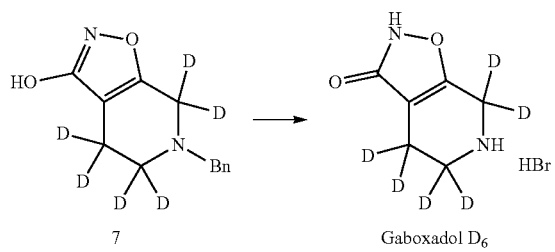 [SMILES: [2H]C1([2H])c2onc(O)c2C([2H])([2H])C([2H])([2H])N1Cc1ccccc1 ; [2H]C1([2H])NC([2H])([2H])C([2H])([2H])c2c1o[nH]c2=O ; Br]

7 → Gaboxadol D$_6$

To a solution of 6-benzyl-4,4,5,5,7,7-hexadeuterio-isoxazolo[5,4-c]pyridin-3-ol 7 (67 mg, 0.28 mmol) in EtOAc (5 mL) at rt was added DIEA (100 μL, 0.57 mmol) and methyl chloroformate (130 μL, 1.7 mmol), and the mixture was stirred for 48 h at rt. The mixture was cooled to 0° C., and a 25% w/v solution of aqueous ammonia (1 mL) was added. After 15 min, the aqueous phase was separated, and the pH was adjusted to 1 using concentrated HCl. The aqueous phase was extracted with EtOAc (2×5 mL). The combined organic fractions were dried (MgSO$_4$), filtered and concentrated under reduced pressure. The residue was purified by prep-HPLC (BEH column, C18, 30×150 mm) using MeCN and 10 mM ammonium formate (pH 3.8) in water. The fractions were combined and lyophilized. The residue was diluted in 33% HBr in AcOH (2 mL) and the mixture was stirred at 40° C. for 6 h. The reaction mixture was cooled to rt and lyophilized directly. The solid was triturated in MeCN (5 mL), and the suspension was filtered; the mother liquor was discarded. The solid was lyophilized to provide title compound Gaboxadol d6 (20 mg, 44% yield over 3 steps) as a solid. MS (ESI) [M+H]$^+$ 147.1.

Analysis of the final product of the synthesis is shown below in Table IV.

TABLE IV

| Number of Deuterium Atoms per Molecule | m/z [M + H]* | Intensity | Corrected Intensity | Relative % of Molecules in the Sample |
| --- | --- | --- | --- | --- |
| 3 | 144.0900 | 4 | 4 | 0.1 |
| 4 | 145.0903 | 55 | 54 | 1.7 |
| 5 | 146.0977 | 633 | 629 | 19.8 |
| 6 | 147.1037 | 2542 | 2495 | 78.4 |

*Assuming same sensitivity of the MS for each compound.

The measured mass of compound C$_6$H$_2$D$_6$N$_2$O$_2$ differed by −0.0008 Dalton from the calculated value.

Analysis of the product of this particular synthesis indicated that it was 78.4% d6 gaboxadol by HRMS. The presence of gaboxadol, gaboxadol d1 and gaboxadol d2 were not observed; but trace amounts of gaboxadol d3 (0.1%) and gaboxadol d4 (1.7%) were detected by HRMS. The presence of gaboxadol d5 (19.8%) might be due to incomplete deuteration at the first step and/or isotope erosion at last step via the following scheme:

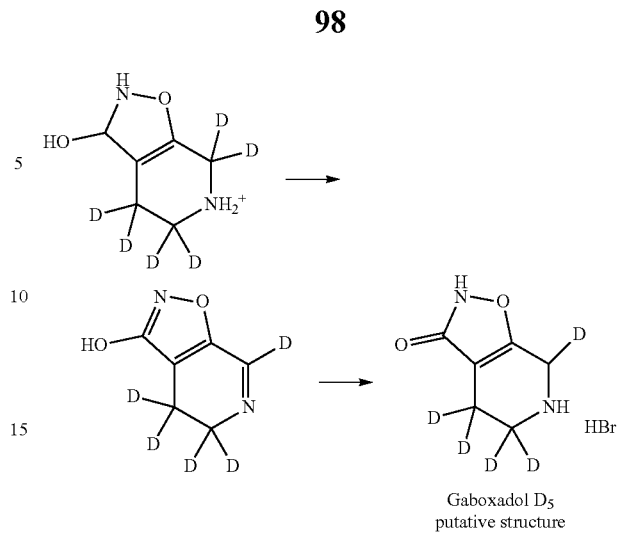

Gaboxadol D$_5$
putative structure

The potential isotope erosion can be improved by performing the benzyl deprotection using DBr in AcOD. The exact position of the H in d5 gaboxadol is not presently known.

Since non-deuterated gaboxadol was not detected, the final composition obtained by the above method can be described as having at least 98% deuterated gaboxadol, at least 99% deuterated gaboxadol, or possibly 100% deuterated gaboxadol. Further the final composition obtained by the above method can be described as 78.4% d6-gaboxadol to indicate the amount of d6-gaboxadol specifically.

Example 6: Whole-Brain Drug Screening Platform

Many preclinical assays are currently used to try to elucidate or predict the clinical effects of new drugs on the brain. These include in vitro high-content screening (HCS) assays that measure a drug's pharmacokinetics for specific molecular target(s) and its effect(s) in simple cellular assays, in vivo assays that measure global responses at relatively low resolution (PET/CT, PET/MRI, fMRI) or local responses at high, cellular resolution (electrophysiology or two-photon imaging), and behavioral assays that measure animal's performance in various tasks (Jain and Heutink, 2010; Judenhofer et al., 2008; Markou et al., 2009).

To assess neuronal activity in regions less accessible to live imaging, Immediate Early Genes (IEGs) such as c-fos, whose expression levels reflect recent changes in neuronal activity, have been used as proxies. The first in vivo example of induced c-fos expression in neurons was reported in the dorsal horn of the spinal cord following a nociceptive stimulus (Hunt et al., 1987). Since then, the up-regulation of expression of IEGs like c-fos, arc, egr-1, fosb and npas4 have been used as a surrogates for neuronal activity in most neuronal systems and in most regions of the brain.

The pharmacomapping approach to preclinical testing of psychiatric drugs is based on the proposition that a direct readout of drug-evoked brain activation or inhibition in an animal is the most relevant preclinical assay, because psychiatric drugs exert their effects via activation or inhibition of specific neural circuits and cell types in the brain.

Importantly, in contrast to the limitations of other methods to measure brain activation, such as PET/CT, PET/MRI and phMRI that suffer from low spatial resolution, or electrophysiology or two-photon imaging that suffer from a limited spatial scope, the disclosed "pharmacomapping" approach enables the direct visualization and measurement of drug-evoked brain activation or inhibition across the entire mouse brain at an unprecedented single cell resolution.

This method called "pharmacomapping" (implemented by CRO Certerra, Inc. Farmingdale, N.Y.) is based on a largely automated drug-screening platform (Renier, et al., (2016); Azevedo, et. al 2020a; Azevedo, et al., 2020b) that comprises whole-brain detection of drug-evoked neuronal activation represented by drug-evoked expression of the immediate early gene (IEG) c-fos (Herrera and Robertson 1996). Until pharmacomapping, the detection of c-fos as a marker of brain activation required time-consuming, laborious methods such as in situ hybridization or immunohistochemistry in brain tissue sections, followed by mounting the sections on microscopic slides, manual imaging, and largely visual quantification. Nevertheless, over the last two decades a number of studies used these methods to test drug-evoked activity in the mouse or rat brain for various psychoactive medications, including antipsychotics, antidepressants, stimulants and anxiolytics (Engber et al., 1998; Kiss, 2018; Salminen et al., 1996; Semba et al., 1996; Slattery et al., 2005; Sumner et al., 2004). These studies, even though typically examining only a few brain regions at a time, represent a validation for the concept of using c-fos expression in the rodent brain in psychoactive drug screening (Sumner, et al., 2004).

Figure 12:
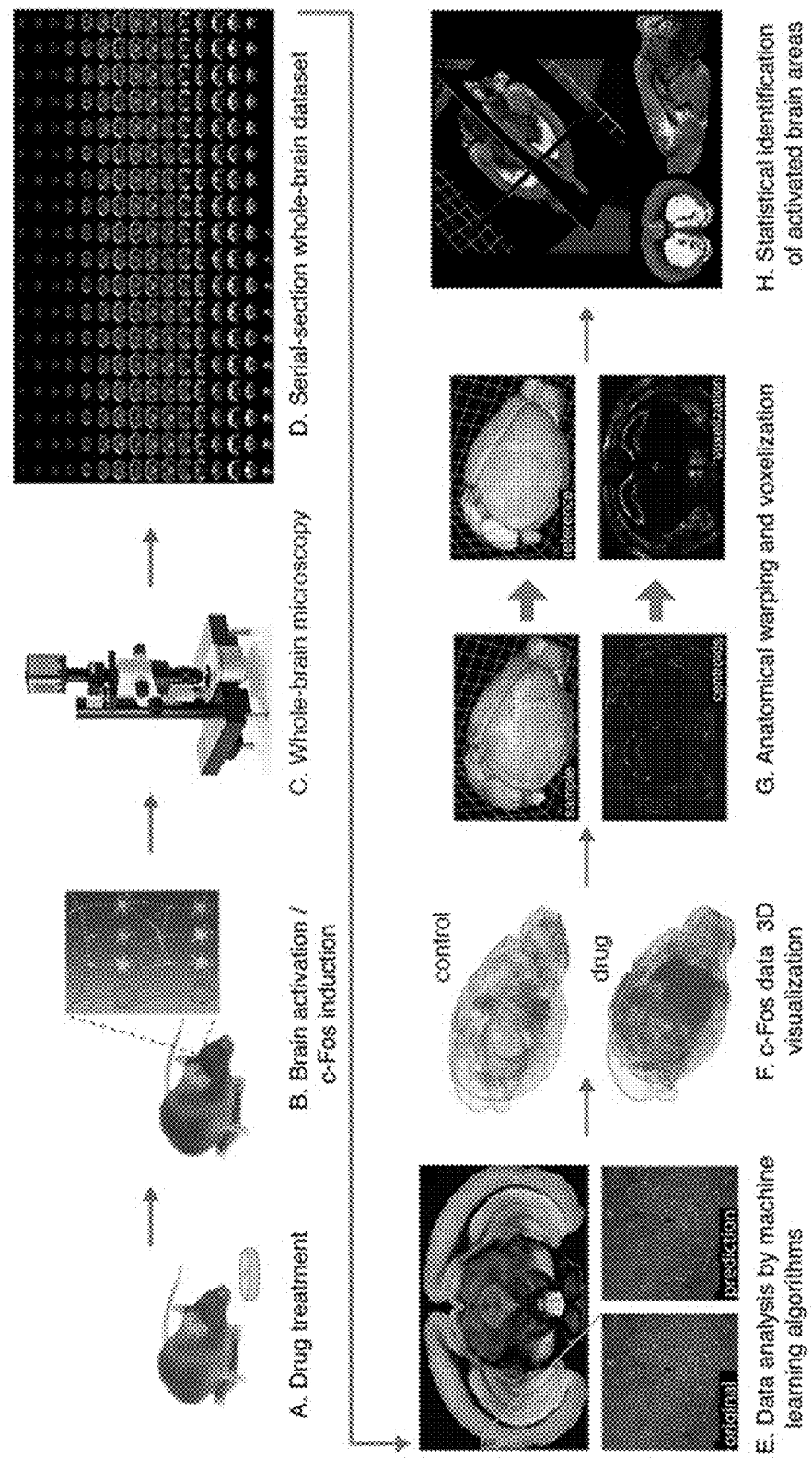
FIG. 12 shows exemplary whole-brain Pharmacomaps representing drug-evoked brain activation in the mouse. (A) Mice are treated with a drug or vehicle solution for the control group using either intraperitoneal (i.p.), per oral (p.o.). subcutaneous (s.c.), intramuscular (i.m.) or intravenous (i.v.) delivery. (B) This leads to the induction of the immediate early gene c-fos in activated neurons that peaks typically within 1.5 to 3 hrs depending on the drug's pharmacokinetics. (C) After that period the mice are killed, the c-fos induction is visualized using whole-brain immunostaining, the brains are chemically cleared and finally imaged by light-sheet fluorescent microscopy (LSFM). (D) The whole-brain scans are represented as serial section datasets typically with XYZ resolution of 4×4×5 microns. (E) The c-fos+ cells are detected in these datasets using custom trained machine learning algorithms. (F) The whole-brain distribution of the detected c-fos+ cells is represented in 3D as a spatial map of centroid points in the 3D space of the mouse brain. (G) This 3D map distribution is registered to a reference mouse brain and spatially voxelized using overlapping 150-micron sphere voxels. (H) Finally, the drug-evoked Pharmacomap is generated by a statistical comparison of the c-fos+ cell distributions of the drug-treated and control vehicle-treated mice, typically using 6 animals per group.

In contrast to the older methods, the pharmacomapping method uses largely automated and standardized whole-brain immunostaining and brain clearing together with advanced microscopy (light-sheet fluorescence microscopy, LSFM), computational (e.g. machine learning) and statistical methods (FIG. 12; see, for example, the published U.S. Patent Application No. 2014/0297199, the content of which is incorporated by reference herein in its entirety). The first generation of this platform used serial two-photon tomography (STPT) as a method for imaging and c-fos-GFP mice expressing green fluorescent protein (GFP) under the control of the c-fos promoter (see, e.g., published U.S. Patent Application No. 2014/0297199, the content of which is incorporated by reference herein in its entirety).

The second generation of the pharmacomapping platform currently employed by Certerra uses whole-brain immunostaining and clearing procedure named iDISCO+ and whole-brain imaging by light-sheet fluorescence microscopy to detect c-fos-positive neurons in wild type mice (Renier et al., 2016). The pharmacomapping platform thus uses the well-established concept of c-fos expression as a cellular marker of neuronal activation and applies it as a standardized and highly quantitative whole-brain assay capable of generating detailed and reproducible drug-evoked whole-brain activation patterns, called PHARMACOMAPS®.

Example 7: Mapping the Effect of Deuterated Gaboxadol in Evoking Brain Activation(s) Related to Achieving Rapid Relief of Depression Symptoms The use of Pharmacomapping was described above with reference to FIG. 12. To test the activity of the deuterated d2-gaboxadol, 4,5,6,7-tetrahydroisoxazolo[5,4-c]pyridin-3 (2H)-one-7,7-d2 (d2-gaboxadol 7,7), in a whole-brain Pharmacomapping assay, d2-gaboxadol 7,7 was first tested at 6 mg per kg concentration, the lower range of the expected clinical efficacy of a human equivalent dose (HED) of 30 mg dose.

The formulation of d2-gaboxadol 7,7 (or vehicle as a control) prepared as per Example 1B above was formulated in a pharmaceutically acceptable carrier and administered to 6 mice by intraperitoneal (i.p.) injection at the indicated doses (see FIGS. 13-19). At 2.5 hour post administration, the mice were euthanized and brains were immediately preserved by 4% paraformaldehyde (PFA).

Figure 13:
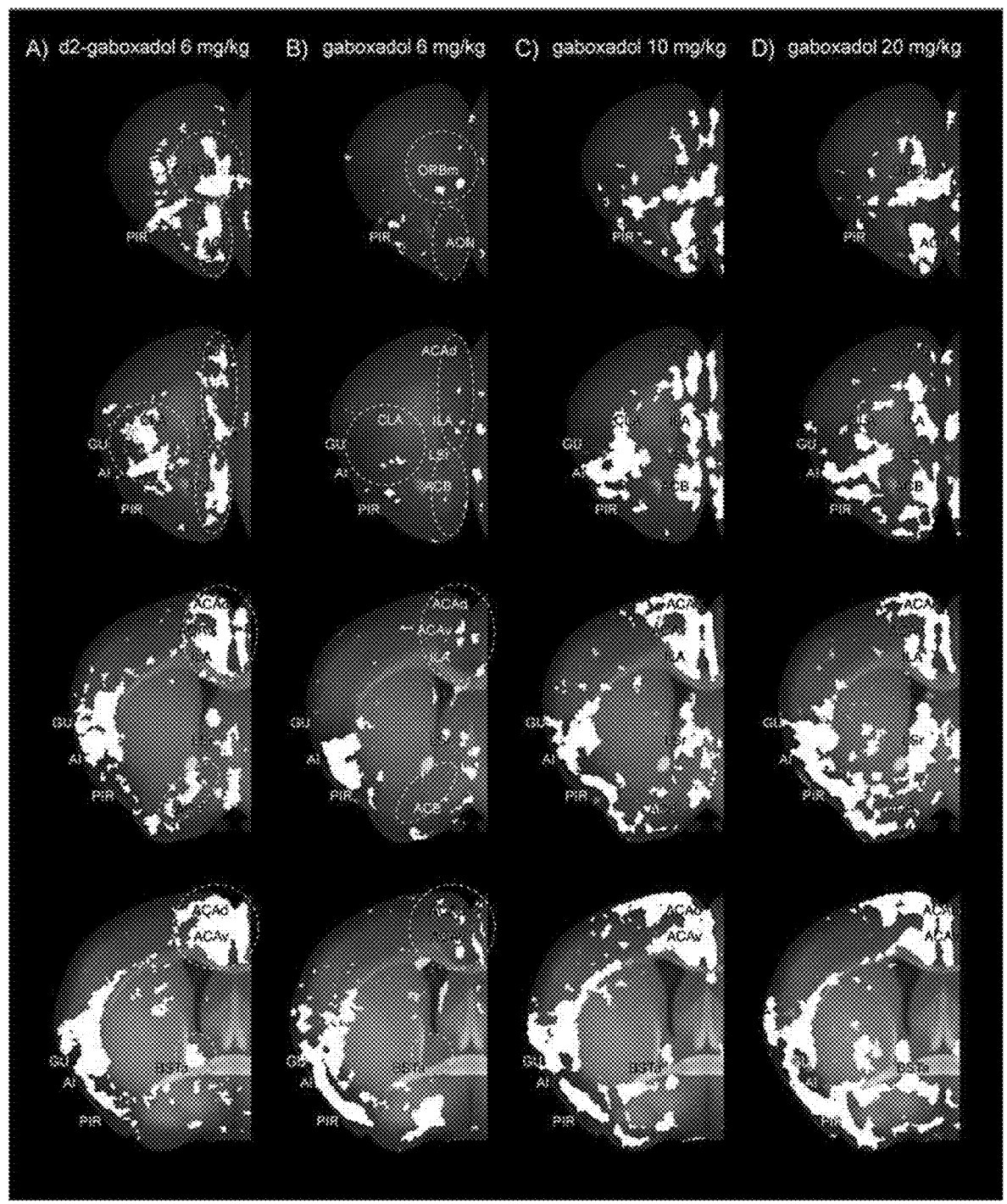
FIG. 13 shows a Pharmacomap-based comparison of d2-gaboxadol 7,7 at 6 mg/kg and gaboxadol at 6, 10 and 20 mg/kg. White color indicates the spatial areas of significant drug-evoked activation for A) d2-gaboxadol at 6 mg/kg, B) gaboxadol at 6 mg/kg, C) gaboxadol at 10 mg/kg, and D) gaboxadol at 20 mg/kg. The areas with significant brain activation considerably stronger in the d2-gaboxadol 6 mg/kg compared to gaboxadol 6 mg/kg pharmacomap are highlighted by white dashes lines and include: the medial orbital cortex (ORBm), infralimbic cortex (ILA), dorsal and ventral anterior cingulate cortex (ACAd and ACAv), associational cortical areas such as agranular insular cortex (AI), gustatory cortex (GU), visceral cortex (VISC), accessory olfactory nucleus (AON) and claustrum (CLA), the rostral part of the lateral septum and the anterior portion of the bed nuclei stria terminalis (BSTa), and subregions of the nucleus accumbens (ACB). In these areas the magnitude of d2-gaboxadol-evoked brain activation was in fact comparable to non-deuterated gaboxadol at higher doses of 10 or even 20 mg/kg (panels C and D). This comparison is further quantified in FIG. 15.
Figure 14:
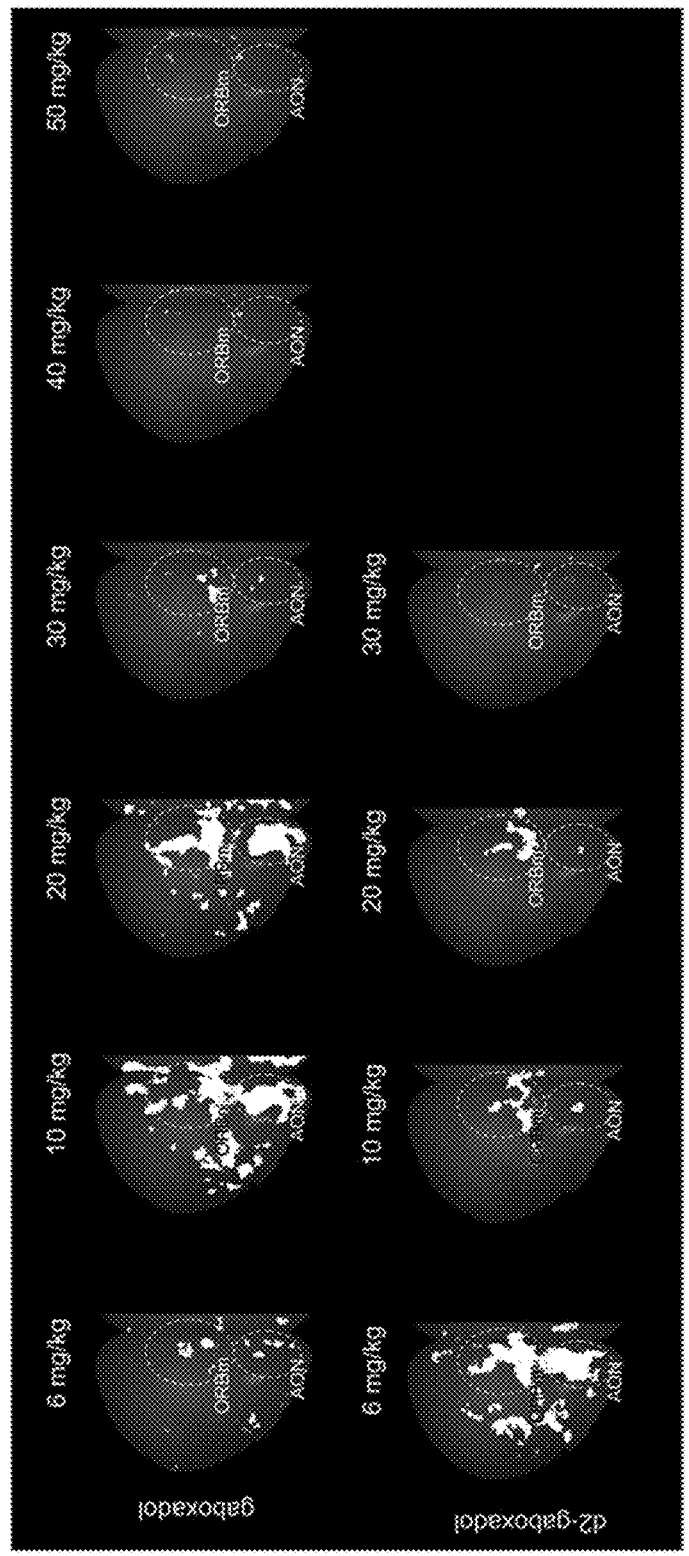
FIG. 14 shows a Pharmacomap-based comparison of d2-gaboxadol 7,7 at 6 to 30 mg/kg and gaboxadol at 6 to 50 mg/kg. White color indicates the spatial areas of significant drug-evoked activation: in top row: gaboxadol at 6, 10, 20, 30, 40 and 50 mg/kg; bottom row: d2-gaboxadol at 6, 10, 20 and 30 mg/kg. Strong activation of the medial orbital cortex (ORBm) and accessory olfactory nucleus (AON) is seen with gaboxadol at 10 and 20 mg/kg as well as d2-gaboxadol at 6 mg/kg, but this response is strongly diminished with gaboxadol at 30 mg/kg and higher doses as well as with d2-gaboxadol at 10 mg/kg and higher doses. This comparison is further quantified in FIG. 19.
Figure 15:
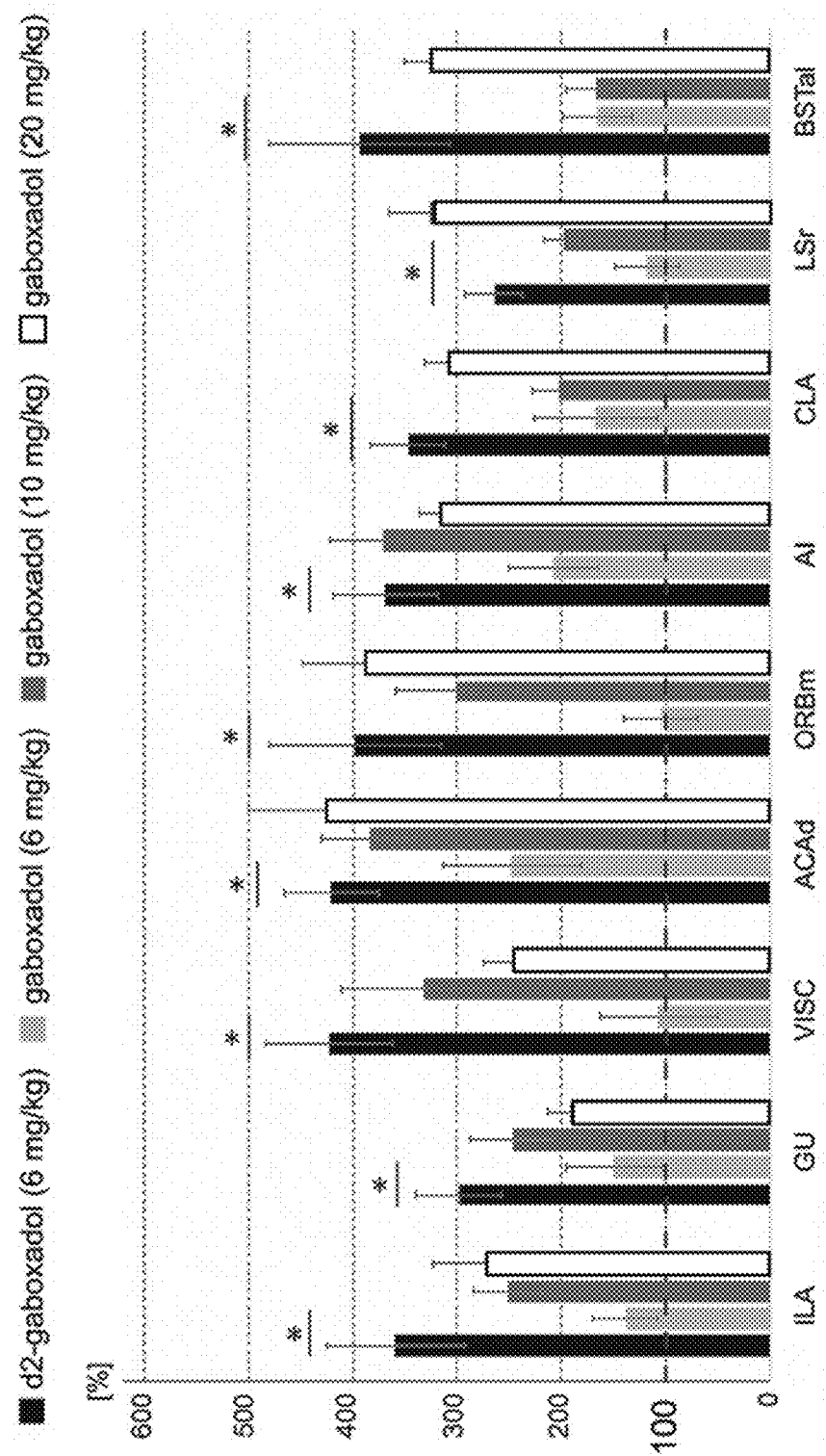
FIG. 15 shows a quantification of the Pharmacomap-based comparison of d2-gaboxadol 7,7 at 6 mg/kg and gaboxadol at 6 to 20 mg/kg in selected brain areas shown in FIG. 13. The increase in c-fos+ cell counts in drug treated mice is expressed in percent from control saline-treated mice for each group: d2-gaboxadol at 6 mg/kg, gaboxadol at 6 mg/kg, gaboxadol at 10 mg/kg and gaboxadol at 20 mg/kg. The statistical difference between d2-gaboxadol at 6 mg/and gaboxadol at 6 mg/kg or 10 mg/kg is marked by asterisks above the corresponding bar graphs. The name abbreviations of the brain areas analyzed are listed above (see FIG. 13 legend).

As shown in FIGS. 13 and 14, d2-gaboxadol 7,7 at 6 mg/kg surprisingly evoked considerably higher brain activation than non-deuterated gaboxadol in several brain areas implicated in cognitive processing and antidepressant drug activity. These areas included frontal cortical areas such as the medial orbital cortex (ORBm), infralimbic cortex (ILA), dorsal anterior cingulate cortex (ACAd), associational cortical areas such as agranular insular cortex (AI), gustatory cortex (GU), visceral cortex (VISC), and claustrum (CLA), the rostral part of the lateral septum (LSr) and the anterior portion of the bed nuclei stria terminalis (BSTa). In these areas the magnitude of d2-gaboxadol-evoked brain activation was more comparable to non-deuterated gaboxadol at higher doses of 10 or 20 mg/kg (FIGS. 13-15). These data show a left shift of dose response for the d2-gaboxadol form, with a lower dose of d2-gaboxadol needed to evoke comparable brain activation as non-deuterated gaboxadol. Note that the drug dose-response relationship describes the magnitude of the drug-evoked response as a function of increasing doses, which can be described by dose-response curves. Measuring dose response, dose response curve and developing dose-response models are central to determining safe dosages for drugs. A left-shift in the dose-response relationship or curve can mean, for example, that a drug exhibiting the left-shift evokes a comparable desired biological response at lower doses, which can translate to a safer drug profile.

Another way to view the data is to observe that increasing doses of both deuterated gaboxadol and non-deuterated gaboxadol evoke a certain maximum level of brain activation in many particular areas, which is followed by a decrease in evoked activation at higher drug doses. The physiological basis for the decrease in drug-evoked brain activation at higher doses in particular areas is not fully understood but it is presumed to be significant for therapeutic consequences of treatment. For deuterated gaboxadol, the maximum brain area activation is achieved at a significantly lower dose than non-deuterated gaboxadol. This also demonstrates a leftward shift of dose response.

Gaboxadol at higher doses than 20 mg/kg shows more complex brain activation patterns, with some brain areas activated less at higher doses, such as the frontal areas of the ORBm, ILA and ACAd cortex, and other brain areas activated only at the higher than 20 mg/kg doses, such as the dorsal striatum, also known as caudoputamen (CP).

Figure 16:
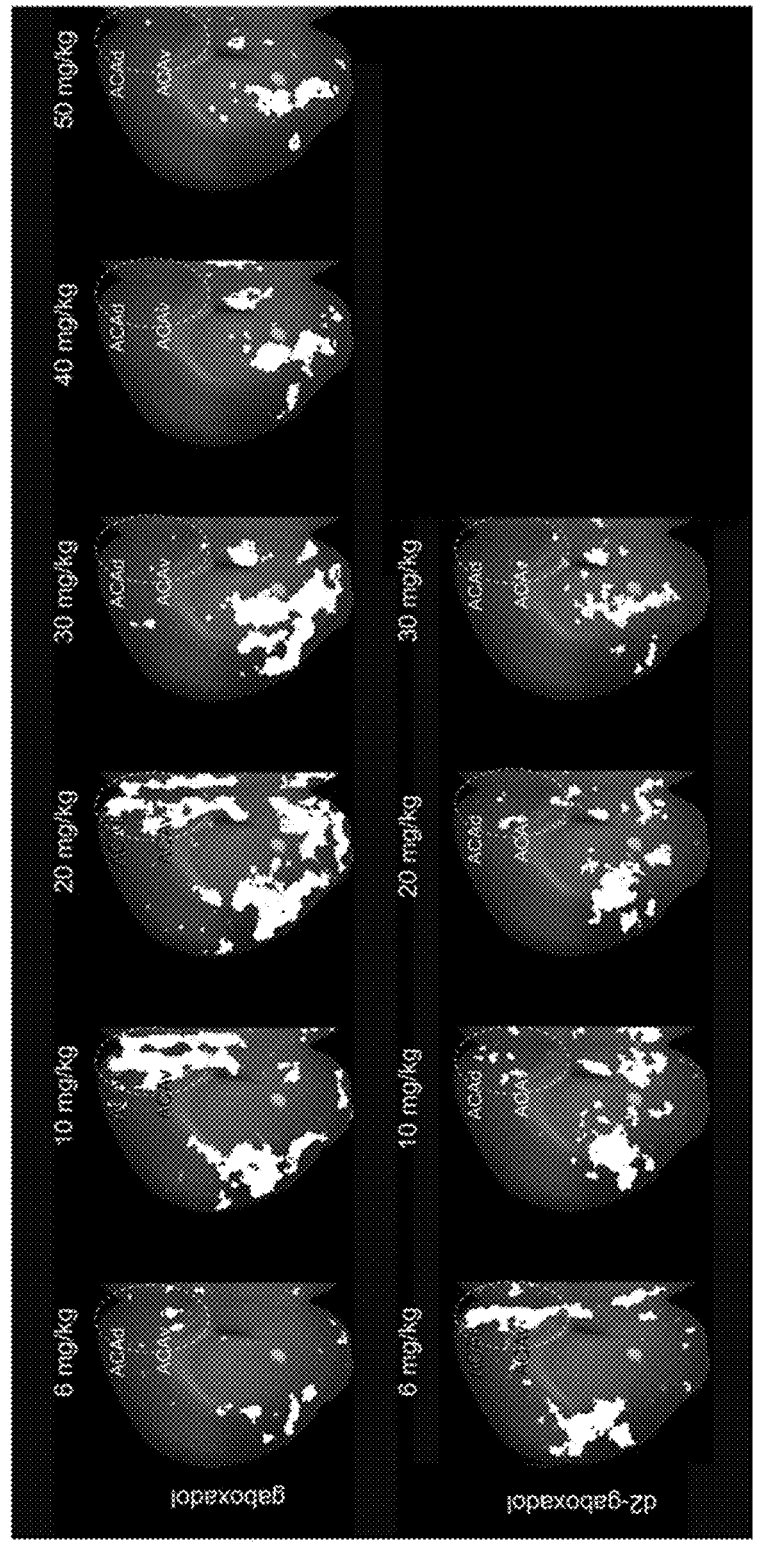
FIG. 16 shows a Pharmacomap-based comparison of d2-gaboxadol 7,7 at 6 to 30 mg/kg and gaboxadol at 6 to 50 mg/kg. White color indicates the spatial areas of significant drug-evoked activation for—in top row—gaboxadol at 6, 10, 20, 30, 40 and 50 mg/kg and—in bottom row—d2-gaboxadol at 6, 10, 20 and 30 mg/kg. As described in the text, strong activation of the dorsal and ventral anterior cingulate cortex (ACAd and ACAv) is seen with gaboxadol at 10 and 20 mg/kg as well as d2-gaboxadol at 6 mg/kg, but this response is strongly diminished with gaboxadol at 30 mg/kg and higher doses as well as d2-gaboxadol at 10 mg/kg and higher doses. This comparison is further quantified in FIGS. 18 and 19.
Figure 17:
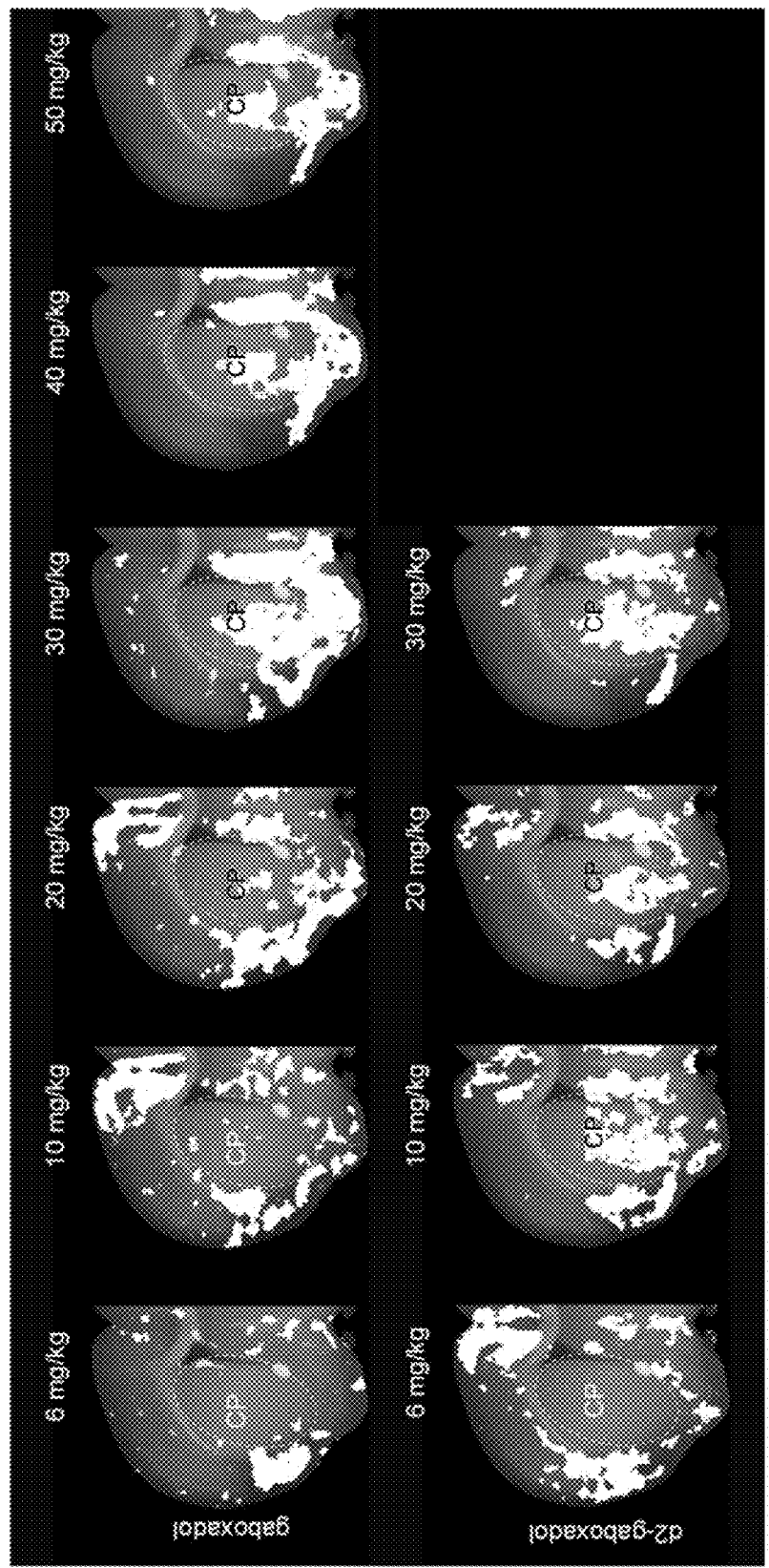
FIG. 17 shows Pharmacomap-based comparison of d2-gaboxadol 7,7 at 6 to 30 mg/kg and gaboxadol at 6 to 50 mg/kg. White color indicates the spatial areas of significant drug-evoked activation for—in top row—gaboxadol at 6, 10, 20, 30, 40 and 50 mg/kg and—in bottom row—d2-gaboxadol at 6, 10, 20 and 30 mg/kg. As described in the text, strong activation of the caudoputamen (CP) is seen with gaboxadol only at higher doses of 30, 40 and 50 mg/kg but with d2-gaboxadol already at 10 mg/kg as well as at 20 and 30 mg/kg. This comparison is further quantified in FIG. 19.
Figure 18:
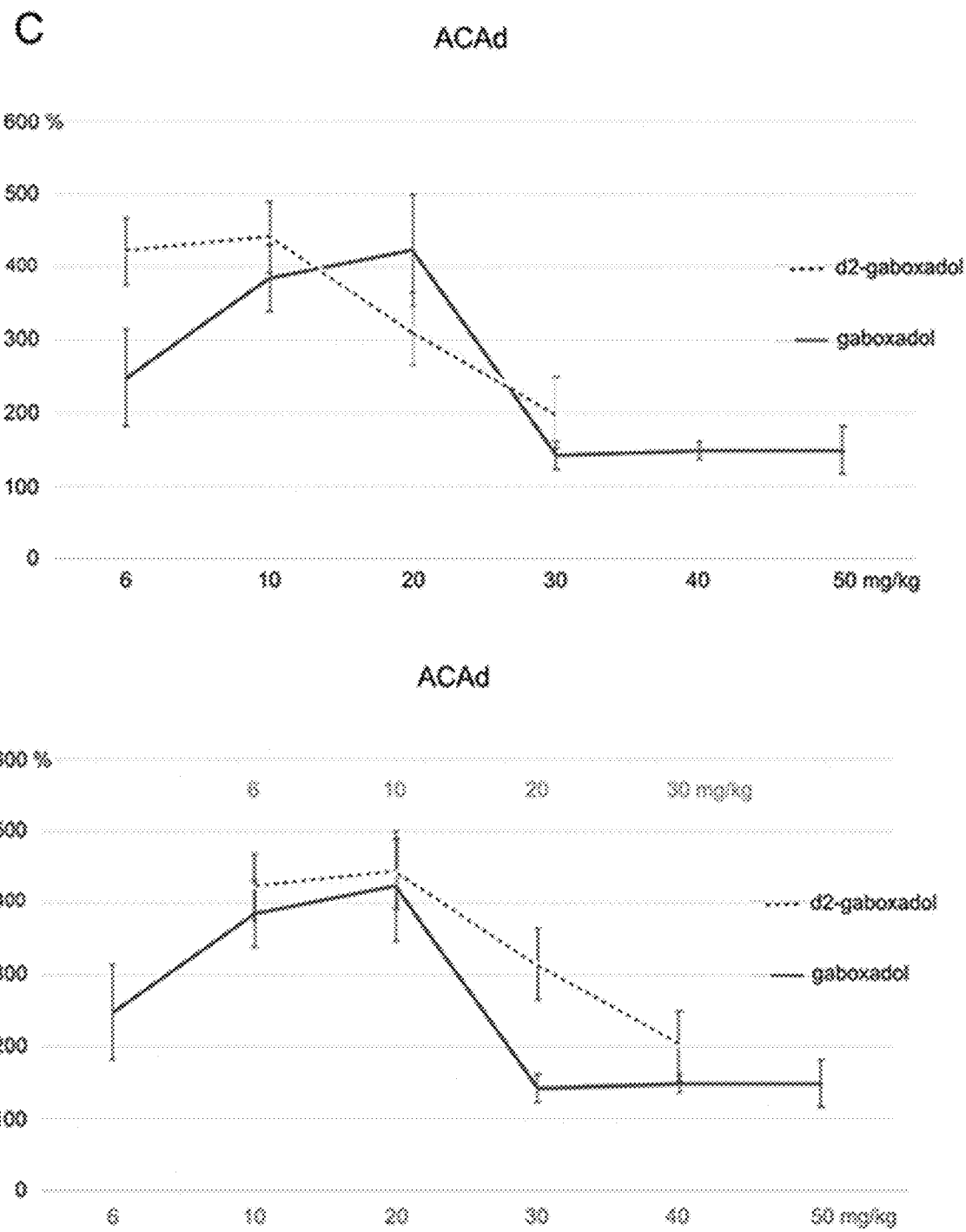
FIG. 18 shows quantification of the Pharmacomap-based comparison of d2-gaboxadol 7,7 at 6 to 30 mg/kg and gaboxadol at 6 to 50 mg/kg in selected brain areas shown in FIGS. 16 to_17. The increase in c-fos+cell counts in drug treated mice is expressed in percent from control saline-treated mice for the selected brain regions: A) infralimbic (ILA), B) orbital medial (ORBm), C) dorsal part of the anterior cingulate (ACAv). In the top panels the concentration of the d2-gaboxadol is given below the graph and is aligned for d2-gaboxadol and gaboxadol. In the bottom panels, the concentration of the d2-gaboxadol is given above each graph and the concentration of the gaboxadol is given below each graph and the dose curves are shifted to approximately match the responses, with d2-gaboxadol 6 mg/kg aligning to gaboxadol 10 mg/kg, d2-gaboxadol 10 mg/kg aligning to gaboxadol 20 mg/kg, d2-gaboxadol 20 mg/kg aligning to gaboxadol 30 mg/kg, and finally d2-gaboxadol 30 mg/kg aligning to gaboxadol 40 mg/kg.

To test whether the left shift in dose response seen for d2-gaboxadol persists at higher doses we next determined brain activation evoked by d2-gaboxadol at 6, 10 and 20, 30 mg/kg. As shown in FIGS. 16 and 17, d2-gaboxadol at 6, 10 and in some cases 20 mg/kg doses indeed evoked a level of brain activation in certain brain areas (e.g, the ILA and CP) that was higher than the level of activation obtained by the same doses of non-deuterated gaboxadol, confirming the dose shift response seen above for d2-gaboxadol at 6 mg/kg. This is further quantified in FIGS. 18 and 19.

Figure 19:
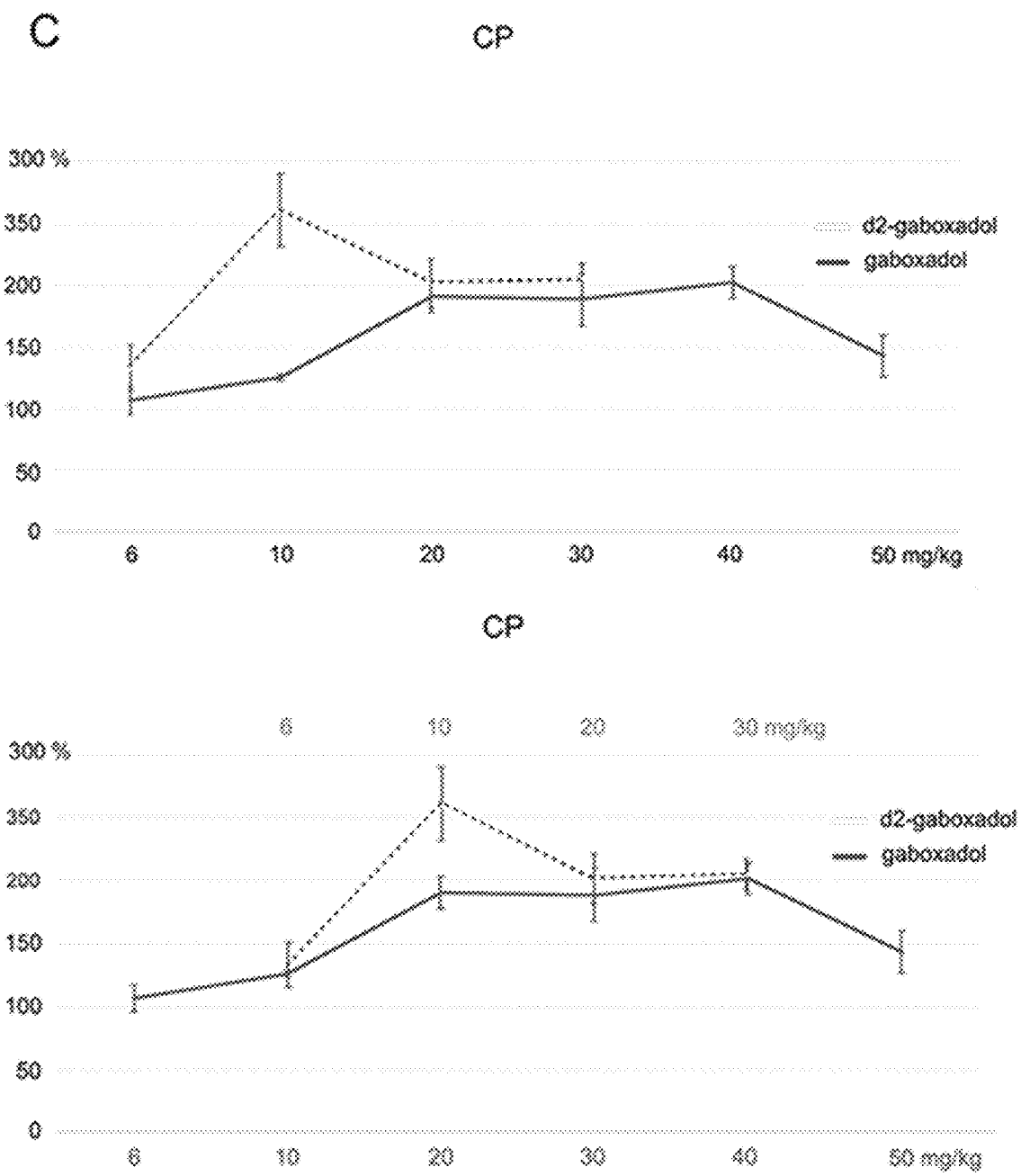
FIG. 19 shows quantification of the Pharmacomap-based comparison of d2-gaboxadol 7,7 at 6 to 30 mg/kg and gaboxadol at 6 to 50 mg/kg in selected brain areas shown in FIGS. 16 to 17. The increase in c-fos+cell counts in drug treated mice is expressed in percent from control saline-treated mice for the selected brain regions: A) ventral part of the anterior cingulate (ACAv), B) claustrum (CLA), and C) caudoputamen (CP). In the top panels the concentration of the d2-gaboxadol is given below the graph and is aligned for d2-gaboxadol and gaboxadol. In the bottom panels, the concentration of the d2-gaboxadol is given above each graph and the concentration of the gaboxadol is given below each graph and the dose curves are shifted to approximately match the responses, with d2-gaboxadol 6 mg/kg aligning to gaboxadol 10 mg/kg, d2-gaboxadol 10 mg/kg aligning to gaboxadol 20 mg/kg, d2-gaboxadol 20 mg/kg aligning to gaboxadol 30 mg/kg, and finally d2-gaboxadol 30 mg/kg aligning to gaboxadol 40 mg/kg.

FIG. 19 presents the increase in c-fos+cell counts in drug treated mice expressed in percent from control saline-treated mice for the selected brain regions: A) ventral part of the anterior cingulate (ACAv), B) claustrum (CLA), and C) caudoputamen (CP). In the left top panels the concentration of the d2-gaboxadol is given below the graph and is aligned for d2-gaboxadol and gaboxadol. In the right panel bottom panels, the concentration of the d2-gaboxadol is given above each graph and the concentration of the gaboxadol is given below each graph and the dose curves are aligned to approximately match the responses, with d2-gaboxadol 6 mg/kg aligning to gaboxadol 10 mg/kg, d2-gaboxadol 10 mg/kg aligning to gaboxadol 20 mg/kg, d2-gaboxadol 20 mg/kg aligning to gaboxadol 30 mg/kg, and finally d2-gaboxadol 30 mg/kg aligning to gaboxadol 40 mg/kg.

Example 8: Mapping the Effect of D6-Gaboxadol in Evoking Brain Activation(s) Related to Reducing the Risk of Suicide and/or Achieving Rapid Relief of Depression Symptoms To test the activity of the d6-gaboxadol in the whole-brain Pharmacomapping assay, d6-gaboxadol was tested in comparison to non-deuterated gaboxadol at 6, 10 and 20 mg per kg concentration. As shown in FIGS. 20 to 24, d6-gaboxadol evoked considerably higher brain activation than non-deuterated gaboxadol at the same dose across a number of brain areas implicated in cognitive processing as well as antidepressant drug activity.

A formulation of d6-gaboxadol (or vehicle as a control) was prepared as per Example 5 above and was formulated in a pharmaceutically acceptable carrier (0.9% saline) and administered to 6 mice by intraperitoneal (i.p.) injection at the indicated doses. At 2.5 hour post administration, the mice were euthanized and brains were immediately preserved by 4% paraformaldehyde (PFA).

Figure 20:
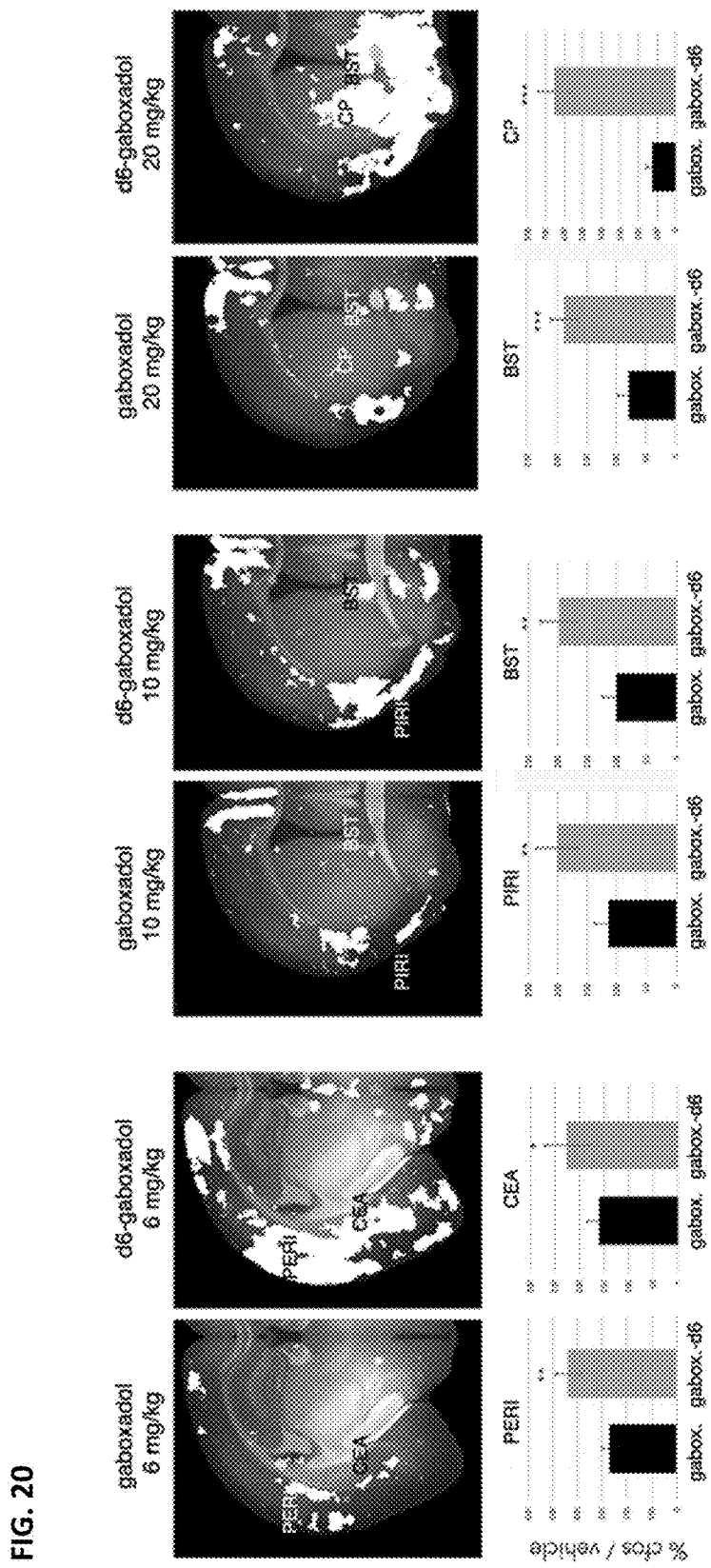
FIG. 20 shows a Pharmacomap-based comparison of d6-gaboxadol at 6, 10 and 20 mg/kg and gaboxadol at 6, 10 and 20 mg/kg. Top: White color indicates the spatial areas of significant drug-evoked activation. Left two panels: The shown areas with significant brain activation considerably stronger in the d6-gaboxadol 6 mg/kg compared to gaboxadol 6 mg/kg pharmacomap include the perirhinal cortex (PERI) and central amygdala (CEA). Middle two panels: The shown areas with significant brain activation considerably stronger in the d6-gaboxadol 10 mg/kg compared to gaboxadol 10 mg/kg pharmacomap include piriform cortex (PIRI) and bed nuclei stria terminalis (BST). Right two panels: The shown areas with significant brain activation considerably stronger in the d6-gaboxadol 20 mg/kg compared to gaboxadol 20 mg/kg pharmacomap include BST and caudoputamen (CP). Bottom: A quantification of the Pharmacomap-based comparison of d6-gaboxadol and gaboxadol at 6 mg/kg (left two bar graphs), 10 mg/kg (middle two bar graphs) and 20 mg/kg (right two bar graphs). The increase in c-fos+ cell counts in drug treated mice is expressed in percent from control saline-treated mice for each group: d6-gaboxadol data are shown in black bars and gaboxadol data are shown in light gray bars. The statistical difference between d2-gaboxadol at 6 mg/ and gaboxadol at 6 mg/kg or 10 mg/kg is marked by asterisks above the corresponding bar graphs, with FDR-corrected q values of <0.05, <0.01 and <0.001 marked by *,  and *, respectively.
Figure 21:
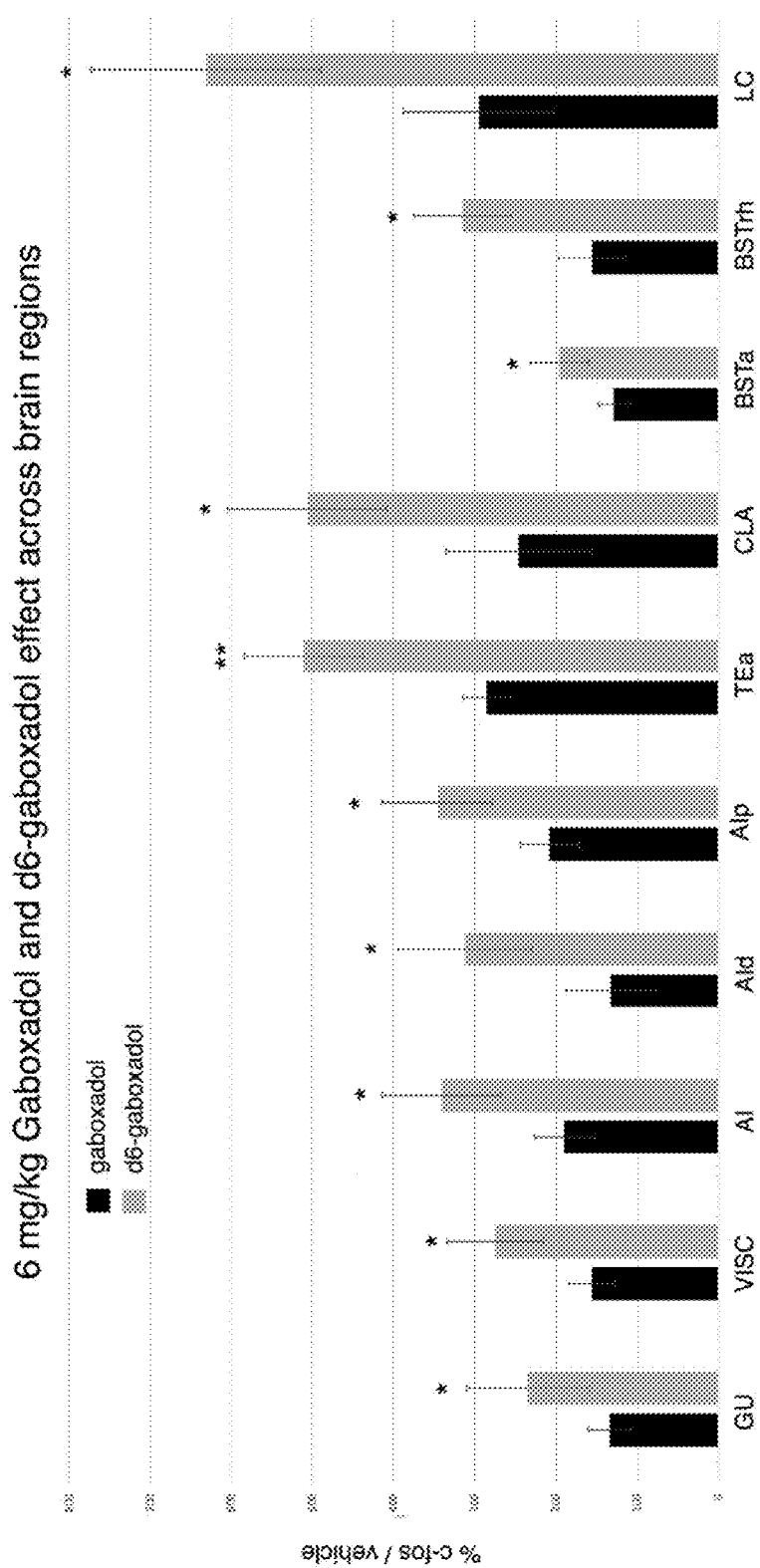
FIG. 21 shows additional quantification of the Pharmacomap-based comparison of d6-gaboxadol and gaboxadol at 6 mg/kg across brain regions with largest differences at this drug doses: associational cortex including the gustatory (GU), visceral (VISC), agranular insular (AI) both dorsal (AId) and a posterior (AIp), temporal associational (TEa) area and claustrum (CLA), in addition to the anterior part of the bed nucleus stria terminalis (BSTa), including the BST rhomboid nucleus (BSTrh), and locus coeruleus (LC). The increase in c-fos+ cell counts in drug treated mice is expressed in percent from control saline-treated mice with gaboxadol data shown in black bars and d6-gaboxadol data shown in light gray bars. The statistical difference between d2-gaboxadol at 6 mg/ and gaboxadol at 6 mg/kg or 10 mg/kg is marked by asterisks above the corresponding bar graphs, with ANOVA and FDR-corrected q values of <0.05 and <0.01 marked by * and ** respectively.
Figure 22:
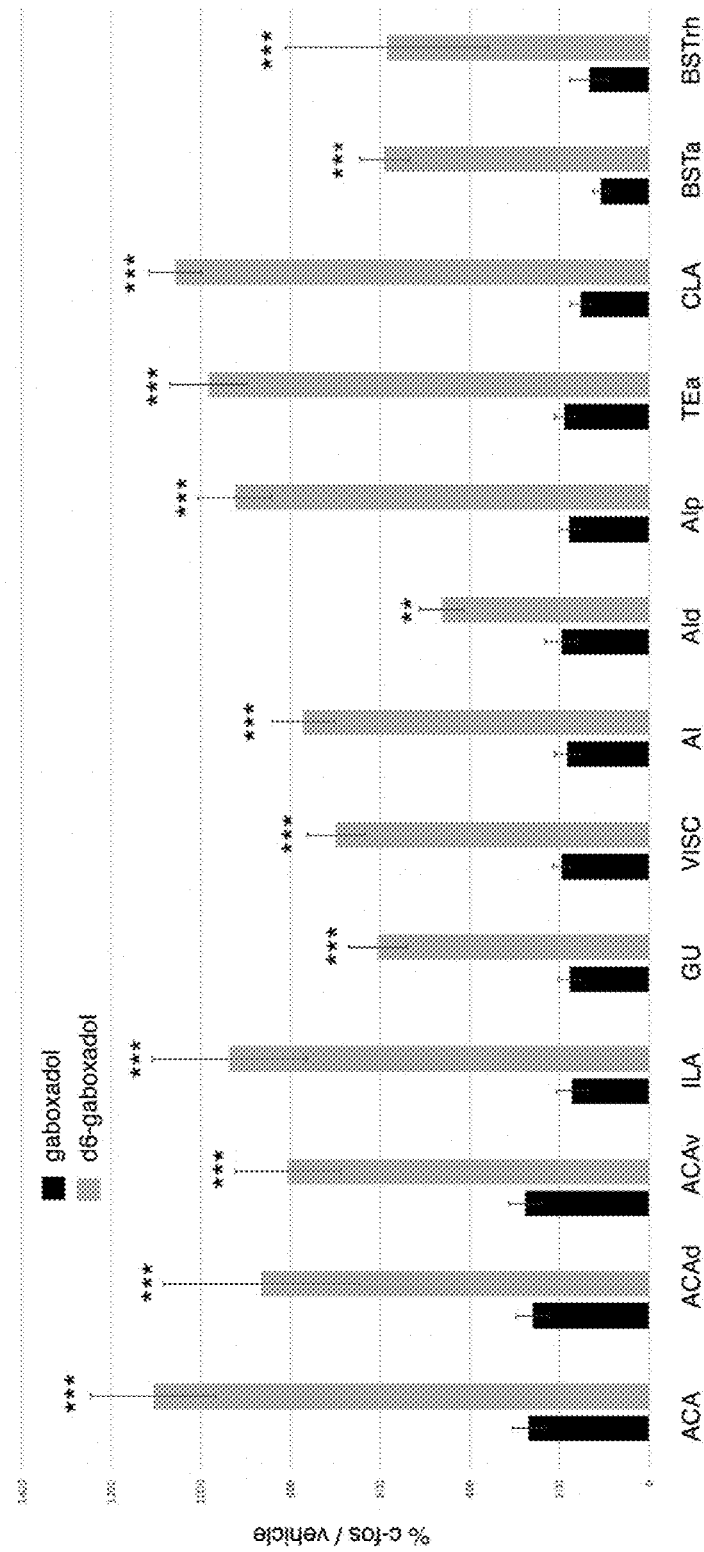
FIG. 22 shows additional quantification of the Pharmacomap-based comparison of d6-gaboxadol and gaboxadol at 10 mg/kg across brain regions with largest differences at this drug doses: anterior cingulate cortex (ACA), including the dorsal (ACAd) and ventral (ACAv) part, infralimbic cortex (ILA), the associational cortical areas including the gustatory (GU), visceral (VISC), agranular insular (AI) both dorsal (AId) and a posterior (AIp), temporal associational (TEa) area and the claustrum (CLA), in addition to the anterior part of the bed nucleus stria terminalis (BSTa), including the BST rhomboid nucleus (BSTrh). The increase in c-fos+ cell counts in drug treated mice is expressed in percent from control saline-treated mice with gaboxadol data shown in black bars and d6-gaboxadol data shown in light gray bars. The statistical difference between d2-gaboxadol 7,7 at 6 mg/ and gaboxadol at 6 mg/kg or 10 mg/kg is marked by asterisks above the corresponding bar graphs, with ANOVA and FDR-corrected q values of <0.01 and <0.001 marked by  and *, respectively.
Figure 23:
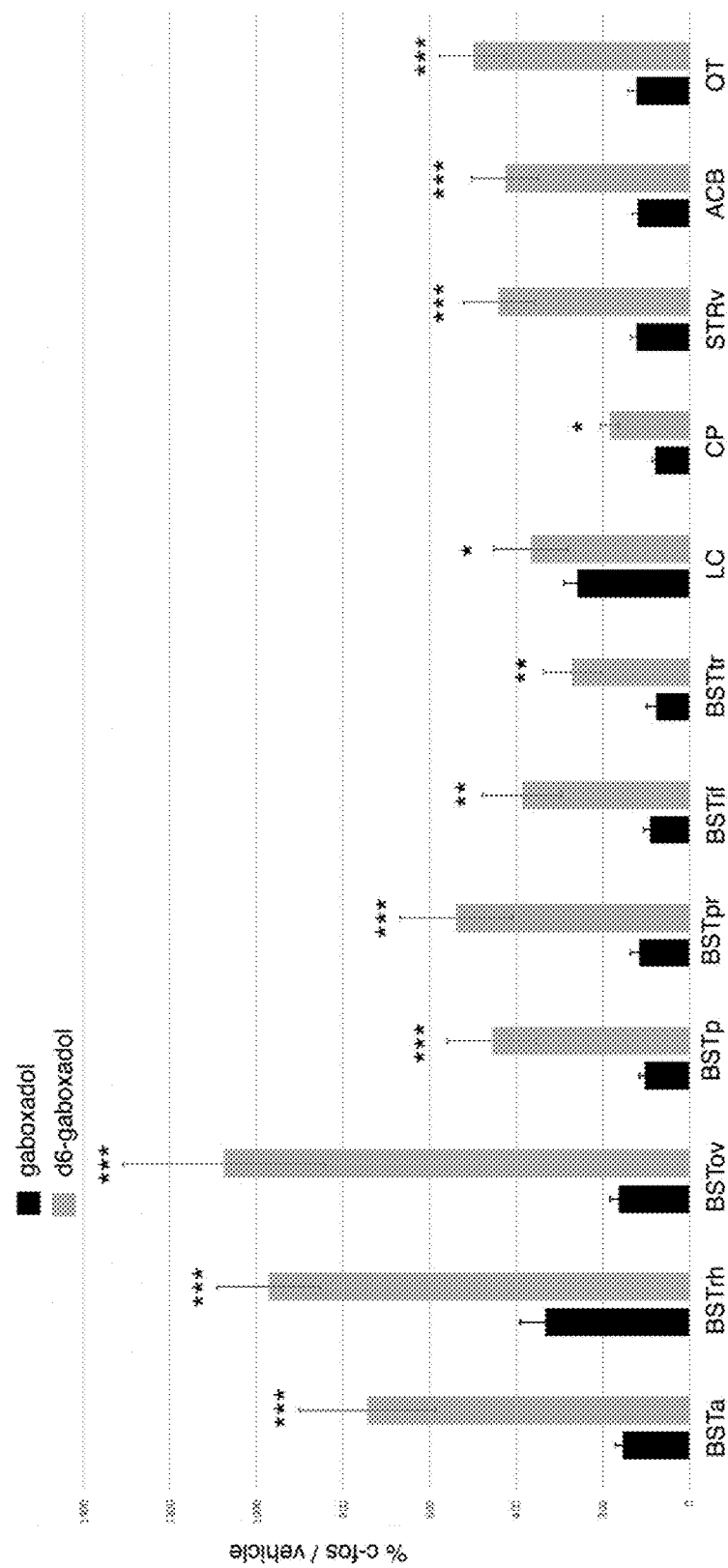
FIG. 23 shows additional quantification of the Pharmacomap-based comparison of d6-gaboxadol and gaboxadol at 20 mg/kg across brain regions with largest differences at this drug doses: the anterior part of the bed nucleus stria terminalis (BSTa), including the BST rhomboid nucleus (BSTrh), BST oval nucleus (BSTov), the posterior part of the bed nucleus stria terminalis (BSTp), including BST principal nucleus (BSTpr), BST interfascicular nucleus (BSTif) and BST transverse nucleus (BSTtr), locus coeruleus (LC), caudoputamen (CP) and ventral striatum (STRv) including nucleus accumbens (ACB) and olfactory tubercle (OT). The increase in c-fos+ cell counts in drug treated mice is expressed in percent from control saline-treated mice with gaboxadol data shown in black bars and d6-gaboxadol data shown in light gray bars. The statistical difference between d2-gaboxadol 7,7 at 6 mg/ and gaboxadol at 6 mg/kg or 10 mg/kg is marked by asterisks above the corresponding bar graphs, with ANOVA and FDR-corrected q values of <0.05, <0.01 and <0.001 marked by *,  and *, respectively.

Starting in FIG. 20, side by side images in top panels show parts of Pharmacomap patterns evoked by d6-gaboxadol and gaboxadol at 6 mg per kg (left two panels), 10 mg per kg (mid two panels) and 20 mg/kg right two panels, with corresponding bar graph quantifications below each panel. Together these experiments revealed that d6-gaboxadol evoked consistently higher brain activation than gaboxadol, including in the perirhinal cortex (PERI) and central amygdala (CEA) at 6 mg per kg, piriform cortex (PIRI) and bed nuclei stria terminalis (BST) at 10 mg per kg and BST and caudoputamen (CP) at 20 mg per kg. The comparison for each drug dose between the d6-gaboxadol and gaboxadol is further quantified in FIGS. 21-23. Specifically, d6-gaboxadol evoked higher brain activation than gaboxadol at 6 mg per kg in the associational cortex including the gustatory (GU), visceral (VISC), agranular insular (AI) both dorsal (AId) and a posterior (AIp), temporal associational (TEa) area and claustrum (CLA), in addition to the anterior part of the bed nucleus stria terminalis (BSTa), including the BST rhomboid nucleus (BSTrh), and locus coeruleus (LC) (FIG. 21), while at 10 mg per kg d6-gaboxadol was more efficacious in evoking brain activation than gaboxadol in the anterior cingulate cortex (ACA), including the dorsal (ACAd) and ventral (ACAv) part, infralimbic cortex (ILA), the associational cortical areas including the gustatory (GU), visceral (VISC), agranular insular (AI) both dorsal (AId) and a posterior (AIp), temporal associational (TEa) area and the claustrum (CLA), in addition to the anterior part of the bed nucleus stria terminalis (BSTa), including the BST rhomboid nucleus (BSTrh) (FIG. 22), and finally, at 20 mg per kg d6-gaboxadol evoked higher brain activation than gaboxadol in the anterior part of the bed nucleus stria terminalis (BSTa), including the BST rhomboid nucleus (BSTrh), BST oval nucleus (BSTov), the posterior part of the bed nucleus stria terminalis (BSTp), including BST principal nucleus (BSTpr), BST interfascicular nucleus (BSTif) and BST transverse nucleus (BSTtr), locus coeruleus (LC), caudoputamen (CP) and ventral striatum (STRv) including nucleus accumbens (ACB) and olfactory tubercle (OT) (FIG. 23). Taken together these data show that d6-gaboxadol has a higher efficacy in evoking brain activation than gaboxadol across the three tested doses in many cortical brain regions linked to cognitive processing that may be affected in depression and subcortical brain regions linked to emotional and motivational processing also likely affected in depression.

Figure 24:
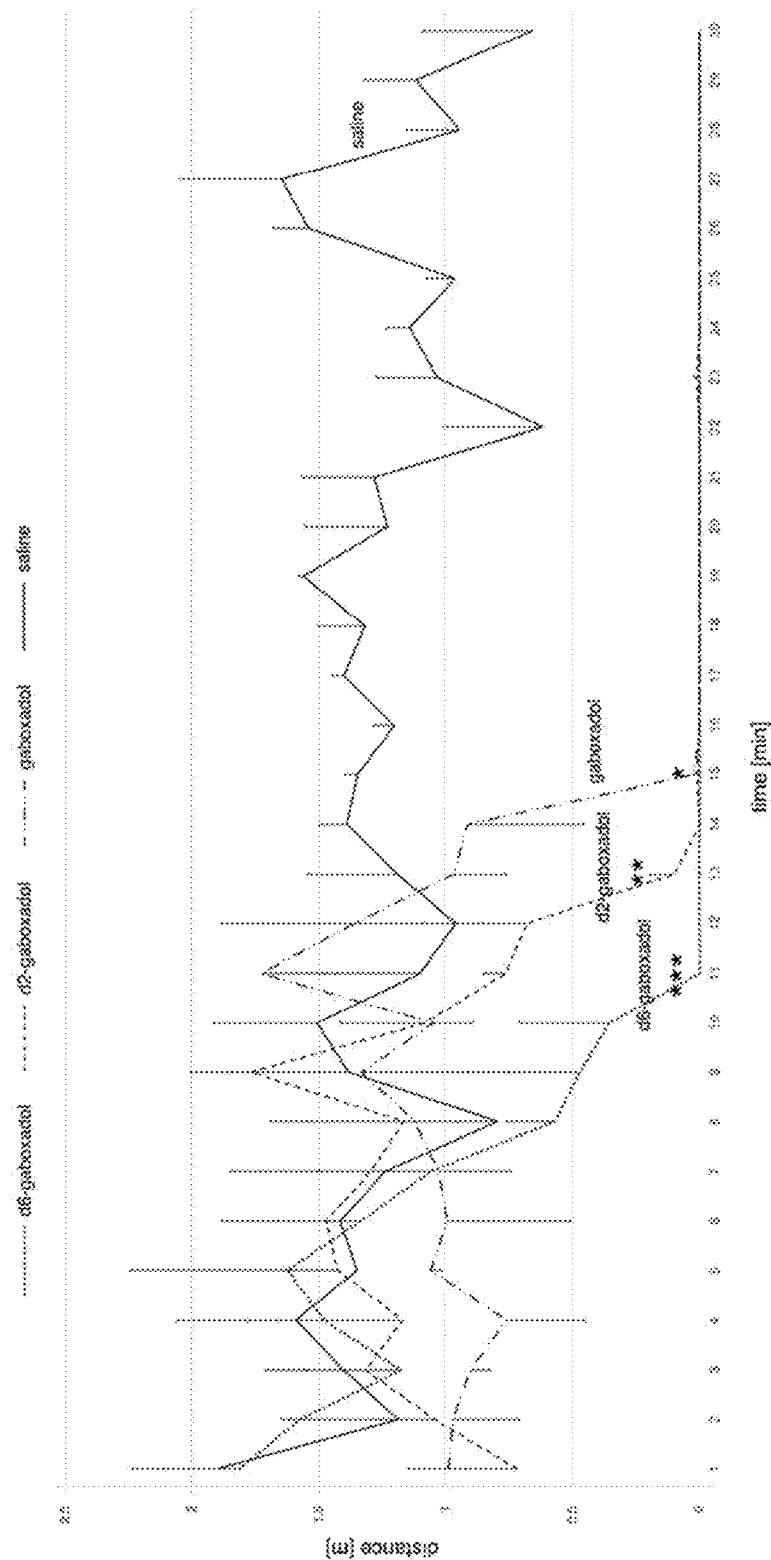
FIG. 24 shows a time course of the onset of sedation in mice induced by d6-gaboxadol (short-dash line), d2-gaboxadol 7,7 (long-dash line) and gaboxadol (short-long-dash line) in comparison to control mice treated with only saline (vehicle) injection (full line). The movement of mice (in meters per minute) is quantified on they axis, while time (in minutes) is shown on the x axis. The data show that d6-gaboxadol-induced onset of sedation at 11 min (reflected by a start of immobility) was faster than that of d2-gaboxadol at 13 to 14 min, while both d6-gaboxadol- and d2-gaboxadol-induced onset of sedation was faster than that of gaboxadol at 15 min. The statistical significance is marked by asterisks, with ANOVA p values of <0.05, <0.01 and <0.001 marked by *,  and *, respectively.

In a further set of experiments, the onset of sedation in mice was compared among d6-gaboxadol, d2-gaboxadol 7,7 and non-deuterated gaboxadol, with the aim to use the sedation—represented as the animal becoming immobile while being video-recorded in the open field test (OFT)—as a proxy of the time point when the different forms of gaboxadol reach the brain of the animal and cause this behavioral effect. As shown in FIG. 24, d6-gaboxadol-induced onset of sedation at 11 min (reflected by a start of immobility) was faster than that of d2-gaboxadol 7,7 at 13 min, while both d6-gaboxadol- and d2-gaboxadol 7,7-induced onset of sedation was faster than that of gaboxadol at 15 min. These data revealed that the deuterated forms of gaboxadol have faster onset of their effect in the brain, in addition to higher efficacy of evoked brain activation shown in the Pharmacomapping experiments, with the d6-gaboxadol-induced effect having even faster onset than that of d2-gaboxadol 7,7.

Example 9: Mapping the Brain Activation Underlying the Action of Ketamine as a Fast-Acting Antidepressant Traditional antidepressants, when applied acutely as a single dose chosen to match human equivalent doses used in clinical treatments of depression, evoke a discreet brain activation pattern comprising frontal cortex, the bed nuclei of the stria terminalis (BST), central amygdala (CEA), paraventricular hypothalamus (PVH), paraventricular thalamic nucleus (PVT), and locus coeruleus (LC) (Slattery et al., 2005; Sumner et al., 2004). Intravenous ketamine used acutely at subanesthetic doses was shown to act as a very rapid and robust antidepressant, with a positive therapeutic effect within a few hours instead of the typical two to three weeks that are needed for a therapeutic effect of traditional antidepressants (Artigas, 2015; Greden, 2002). While this clinical efficacy of ketamine has been reproduced in a number of clinical studies, the mechanism by which ketamine achieves this effect remains largely speculative.

Using the Pharmacomapping platform, the whole-brain effect of acute single dose ketamine was screened at three doses: 1) 5 mg/kg (human equivalent dose, HED 25 mg) which is below the subanesthetic dose shown to act as a rapid antidepressant; 2) 10 mg/kg (HED 50 mg) which is comparable to the clinical rapid antidepressant dose, 3) 100 mg/kg which is an anesthetic dose not known to have any antidepressant properties (Galvez et al., 2018; Lapidus et al., 2014; Lowe et al., 2020). This experiment revealed a striking bell shaped dose-response curve that comprised a modest activation at 5 and 100 mg/kg but a very robust and broad activation comprising many cortical areas and midline thalamic nuclei as well as several other brain structures only at the 10 mg/kg dose (FIG. 25). This pattern is not only very robust, but it is believed that it does not match any other patterns from the FDA-approved drugs screened by Pharmacomapping to date.

Starting from the rostral part of the brain at bregma 1.5 mm, ketamine at 10 mg/kg (but not at 5 or 100 mg/kg) evoked a prominent activation of the anterior cingulate (ACA), prelimbic (PL) and infralimbic (ILA) cortex, as well as piriform cortex (PIR) and the nucleus accumbens of the ventral striatum (ACB) (FIG. 25). Moving caudally, ACA and PIR continue to show a prominent activation by ketamine at 10 mg/kg, and similar activation is seen for the associational visceral (VISC), gustatory (GU), agranular insular (AIp) cortical areas. The lateral septum (LS) and the anterior part of the bed nuclei of the stria terminalis (BSTa) are also activated. At bregma level—1.8 mm, cortical areas continue to show a very broad pattern of activation selectively at 10 mg/kg, including retrosplenial (RSP), motor (MO), somatosensory (SS), auditory (AUD), temporal associational (TEa), perirhinal (PERI) and entorhinal cortex. In addition, midline thalamic nuclei, including the paraventricular nucleus (PVT), intermediodorsal nucleus (IMB), central medial nucleus (CM), and rhomboid nucleus (RH), as well as cortical amygdala and central amygdala (CEA) were also activated. The very broad cortical activation continues further caudally and includes the visual (VIS), ectorhinal (ECT) TEa, AUD, PERI and ENT cortical areas, as well as medial geniculate complex (MG) and the periaqueductal gray (PAG) and the noradrenergic locus coeruleus (LC) (FIG. 25).

Example 10: Discovery of Gaboxadol's Unexpected Potential as a Rapid Antidepressant and Anti-Suicidal Effect The ketamine dose of 10 mg/kg, which evoked broad activation in the Pharmacomapping assay, was also shown by others to have acute positive effect in a number of mouse behavioral studies used to model depression, such as forced swim, tail suspension and learned helplessness (Autry et al., 2011; Browne and Lucki, 2013). Importantly, the corresponding HED of 50 mg ketamine per 60 kg man, is within the human dose range of 0.5 to 1 mg/kg used to achieve rapid antidepressant effect even in treatment-resistant patients and alleviate suicidal ideation in clinically depressed patients (Domany et al., 2020; McIntyre et al., 2021; Marcantoni et al., 2020; Zhou et al., 2020; Lowe et al., 2020). Therefore, based on the Pharmacomapping results, it is predicted that the above described 10 mg/kg ketamine-induced activation pattern represents a neuronal circuit-based mechanism of action for ketamine's rapid and dramatic therapeutic effect in depression and suicidal ideation seen in the clinics. Based on this assumption we would also predict that other compounds that evoke a comparable Pharmacomap in our assay should also act as rapid antidepressants in the clinics.

This discovery demonstrated that non-deuterated gaboxadol at the dose of 10 mg/kg evokes a very similar brain activation as ketamine, providing the first evidence that gaboxadol may in fact act as a rapid antidepressant and anti-suicidal agent. As shown in FIG. 26, the wide cortical activation and to a lesser degree the midline thalamic activation and the activation of midbrain PAG and brainstem LC are very similar between gaboxadol and ketamine, suggesting that gaboxadol at HED 50 mg (60 kg man) may have the same therapeutic efficacy as ketamine in treating depression and suicidal ideation.

What further is striking and worth noting about this discovery is that gaboxadol and ketamine are structurally unrelated molecules and act via two entirely different molecular targets: ketamine is an antagonist at the NMDA type glutamatergic receptors that are an important part of excitatory synaptic transmission in the brain, whereas gaboxadol is an agonist at the δ subunit containing GABAergic receptors that are an important part of inhibitory synaptic transmission in the brain. Thus, the discovery that gaboxadol evokes brain-wide activation matching the pattern of ketamine is entirely unexpected and could not have been predicted based on previous scientific literature or knowledge. The unexpected nature of that discovery is also clear from the fact that gaboxadol was most tested by Lundbeck as a sleep medication with the expectation that it would act via the target inhibitory GABA receptors to suppress brain excitation, though it failed for this indication in clinical trials. Similarly, gaboxadol was tested for its ability to suppress abnormally increased brain excitation in two developmental disorders, the Angelman syndrome and Fragile X syndrome (ClinicalTrials.gov Identifier: NCT03697161 and NCT04106557). Thus, the believed inhibitory action of gaboxadol is the exact opposite of the present discovery of gaboxadol-evoked broad brain excitation.

Example 11: Synergistic Effect of Gaboxadol and Ketamine

Based on this hypothesis of shared downstream circuits, the data show that non-deuterated gaboxadol at 10 mg/kg and ketamine at 10 mg/kg evoked comparable brain activation patterns. As mentioned above, gaboxadol and ketamine act via very different molecular targets, $GABA_A$ receptors and NMDA receptors, respectively, and thus may be expected to initially involve different signaling events. At the same time, the similarity of the evoked activation patterns suggests that the initial compound-specific signaling events lead to a common downstream brain circuit activation.

It was next tested whether non-deuterated gaboxadol and ketamine may in fact synergize in their brain activation effects. As shown in FIG. 27A, neither gaboxadol at 3 mg/kg nor ketamine at 6 mg/kg alone evoked any brain activation detectable using the assay. However, the combination of gaboxadol at 3 mg/kg plus ketamine at 6 mg/kg elicited a clear activation of a number of cortical areas; these areas were also activated by each drug individually when administered at a full dose of 10 mg/kg as described above. A synergistic effect also was observed with the combination of non-deuterated gaboxadol at 5 mg/kg plus ketamine at 5 mg/kg as shown in FIG. 27B. These data show that non-deuterated gaboxadol and ketamine can synergize in their brain activation action, suggesting that a combination therapy at a sub-threshold dose of each (a synergistic dose) is an effective strategy to achieve the desired rapid onset therapeutic effect while avoiding possible side-effects specific for each drug.

Example 12: Gaboxadol and Ketamine Effect in Forced Swim Task

The forced swim test is a frequently used behavioral protocol with a well-established therapeutic predictability for a broad range of antidepressants including ketamine (Porsolt et al. 1977; Cryan and Mombereau 2004; Cryan et al. 2005; Lucki et al. 2001). In this test the mouse is put in a beaker filled with water and the time spent struggling, swimming and floating is measured, with the time spent floating—when the mouse stops struggling to swim—being used as a behavioral correlate of depression.

To test whether non-deuterated gaboxadol shows the same behavioral effect as ketamine, the effect of single dose of ketamine (10 mg/kg) or non-deuterated gaboxadol (10 mg/kg) on forced swim behavior 1 hour and 24 hours after the drug delivery was compared. As shown in FIG. 28, previous results from other groups showing that ketamine at this dose significantly decreases the time the drug treated mice spent floating both at the 1 hour and 24-hour time point compared to a vehicle treated control group was reproduced (Autry et al., 2011; Browne and Lucki, 2013). Remarkably, the group of mice treated with gaboxadol exhibited a nearly identical behavioral effect as the ketamine group (FIG. 28). This supports the conclusion from the Pharmacomap brain activation data shown in FIG. 26 that gaboxadol (10 mg/kg) acts in a comparable way to ketamine (10 mg/kg) and is likely to show similar efficacy for treatment-resistant depression and suicidal ideation. The data in FIGS. 13-19, as well as 20-24 further support that deuterated gaboxadol demonstrates higher efficacy at lower doses than non-deuterated gaboxadol.

In summary, the data demonstrated that 1) ketamine (10 mg/kg) acts via an entirely novel way as an antidepressant, evoking a very broad cortical and midline thalamus activation in contrast to traditional antidepressants that evoked a much more restricted brain activation; 2) gaboxadol (10 mg/kg), despite having no structural similarity and acting via different molecular targets evokes a very similar pattern of activation as ketamine; 3) gaboxadol and ketamine synergize in their brain activation effect, 4) in agreement with the brain activation data gaboxadol also shows a nearly identical effect in a forced swim test. Thus, based on this data, gaboxadol may have comparable efficacy in treating psychiatric disorders such as depression and suicidal ideation as ketamine. Further, in certain instances, deuterated gaboxadol demonstrates a higher level of brain activation in certain brain areas than the level of brain activation afforded by lower doses of non-deuterated gaboxadol.

Other rodent behavior models are commonly used to test neuropsychiatric modulators and may be used to demonstrate the effect of compounds on animals. Standard tests as described in Wang et al (2017) Progress in Neuro-Psychopharmacology and Biological Psychiatry Volume 77, 3 Jul. 2017, Pages 99-109 https://doi.org/10.1016/j.pnpbp.2017.04.008; and by Krishnan and Nestler "Animal Models of Depression: Molecular Perspectives" (in J. J. Hagan (ed.), Molecular and Functional Models in Neuropsychiatry, Current Topics in Behavioral Neurosciences 7, DOI 10.1007/7854_2010_108 ©Springer-Verlag Berlin Heidelberg 2011, published online 12 Jan. 2011) are incorporated herein by reference in their entireties.

Example 13: Deuterated Gaboxadol Orally Disintegrating Film

A hydrophilic film-forming agent is made from a graft copolymer having a film-forming block of polyvinyl alcohol (PVA) Kollicoat IR® (marketed by BASF), molecular weight about 45,000 Da, and a polyethylene glycol (PEG) plasticizer. The gelling agent is Gelcarin 379. (commercially available from FMC Biopolymer), a compound of the carrageenan family. Kollicoat IR® is introduced into 70% of the amount of purified water under stirring. Agitation is maintained until dissolution of Kollicoat IR®. Since gas bubbles are generated, the solution may be dissolved under a vacuum or the solution can stand (its viscosity is very low) until the gas is dispersed. Tween 80 is incorporated to the stirred solution and flavorings (condensed licorice extract and essential oil of peppermint) and sweetener (acesulfame potassium) are added. Stirring is continued until complete dissolution of all powder. Deuterated gaboxadol is introduced with stirring until it is dispersed in the mixture, then the remaining water (30%) is added. Gelcarin 379® is incorporated into suspension under agitation to prevent the formation of aggregates. The final mixture consists of deuterated gaboxadol 6% w/w, Kollicoat IR® 15% w/w, Gelcarin 379® 5% w/w, Tween 80 0.2% w/w, acesulfame potassium 0.05% w/w, flavorings 1.5% w/w, purified water qs. Mixing aliquots are then coated on a polyester backing and dried in a type Lab Dryer Coater (Mathis equipment). The coated surfaces are cut using a manual press in 6 cm² units, and then manually packaged in sealed bags.

Example 14: Prospective Assessment of the Efficacy of Deuterated Gaboxadol in Patients at Risk of Suicide This study is designed to determine whether deuterated gaboxadol will lead to an improvement in one or more symptoms of risk of suicide such as suicidal ideation. A randomized clinical trial of oral deuterated gaboxadol compared with intranasal ketamine hydrochloride is conducted in patients with major depressive disorder who have clinically significant suicidal ideation, as assessed by score on the Scale for Suicidal Ideation (SSI) (Beck A T, Kovacs M, Weissman A: Assessment of suicidal intention: the Scale for Suicide Ideation. J Consult Clin Psychol 1979; 47:343-352). The primary outcome measure is SSI score 24 hours after administration. Other outcome measures comprise global depression ratings, clinical ratings during 6-week open follow-up treatment, and safety measures. The study will test whether deuterated gaboxadol can produce an equal or greater reduction in suicidal ideation at 24 hours compared with ketamine yet without the dissociative effects of ketamine. The trial is adapted from Murrough et al. (2015) and Grunebaum et al (2017), (Grunebaum et al., 2018).

Methods a) Participants

Eligible patients are 18-65 years old and have a DSM-IV diagnosis of major depressive disorder, a score >16 on the 17-item Hamilton Depression Rating Scale (HAM-D) (Hamilton, 1960), and a score >4 on the SSI, which is considered a clinically significant cutoff for suicidal ideation (Brown et al., 2000; Holi et al., 2005; Price et al., 2014) A prospective study of 6,891 psychiatric outpatients (Brown et al., 2000) found that a baseline SSI score >2 predicted suicide during up to 20 years of follow-up, adjusting for other risk factors. Eligible patients have a voluntary admission to an inpatient research unit, and patients are discharged when assessed as stable and not an imminent safety risk. Exclusion criteria includes unstable medical or neurological illness, significant electrocardiographic abnormality, pregnancy or lactation, current psychosis, history of gaboxadol or ketamine abuse or dependence, other drug or alcohol dependence within the past 6 months, suicidal ideation due to binge substance use or withdrawal, prior ineffective trial of or adverse reaction to gaboxadol or ketamine, daily opioid use greater than 20 mg of oxycodone or equivalent during the 3 days before infusion, a score <25 on the Mini-Mental State Examination for persons <60 years old, lack of capacity to consent, and inadequate understanding of English. There is no exclusion for body mass index or weight. Participants are allowed to continue on stable dosages of current psychiatric medications, except that benzodiazepines are not taken within 24 hours before the infusion. Recruitment is conducted via Internet and local media advertisements and clinician referral. The protocol is approved by the Institutional Review Board, and written informed consent is obtained from all participants.

Intervention

Participants are randomly assigned to receive daily deuterated gaboxadol hydrochloride in, a dose ranging study, at, for example, 5 mg, 10 mg, 15 mg, 20 mg, 25 mg, 50 mg, 75 mg, or 100 mg per day as an oral capsule, or ketamine at 0.5 mg/kg in 100 mL normal saline infused over 40 minutes. Blood pressure, heart rate, and respiratory rate are monitored every 5 minutes. A psychiatrist or psychiatric nurse certified in advanced cardiac life support administers the treatment and an anesthesiologist is available for consultation by telephone.

A baseline EEG or MEG may be established in the 30 minutes preceding treatment of the patient. EEG or MEG may continue throughout the treatment, or it may be re-assessed at specific time points, such as 30, 45, 60, 90, 120, 150 or 160 minutes after administration.

If patient examination reveals an insufficient response to deuterated gaboxadol treatment observed during the first 160 minutes after administration, by any measure, the treating physician may optionally administer a second administration of deuterated gaboxadol. Insufficient response may be defined as an EEG power density increase of less than 30% at the time point 160 minutes after the first administration. Preferably the EEG power density is calculated in the 4.75-8.0 Hz range.

Alternatively, insufficient response is a whole head MEG planar gradiometer increase of less +3 in the combined delta, theta and alpha activity at the time point 160 minutes after the first administration. The second administration of deuterated gaboxadol is given within about 12 hours of the first administration. Insufficient response may also comprise observable clinical symptoms demonstrating lack of response.

After assessments at 24 hours, participants receive optimized standard clinical pharmacological treatment for 6 months, with weekly research ratings for the first 6 weeks in an uncontrolled follow-up observation.

b) Outcome and Measures

Raters are doctoral- or master's-level psychologists. Diagnoses, including substance abuse or dependence, are made using the Structured Clinical Interviews for DSM-IV axis I and II disorders (SCID I and II) (First et al., 1995a, b) in a weekly consensus conference of research psychologists and psychiatrists. Suicidal ideation due to binge substance abuse is assessed by clinical history, and past antidepressant trials and current medications are inventoried with our baseline clinical-demographic form, which surveys a range of variables not captured by other instruments. Videotaped assessments are used for weekly reliability monitoring. Intraclass correlation coefficients for key clinical ratings were 0.94 for the SCID I, 0.96 for the HAM-D, and 0.98 for the SSI. The clinician-rated SSI assessed current severity of suicidal ideation with 19 items scaled from 0 (least severe) to 2 (most severe) (Beck et al., 1979). Items probe wish to die, passive and active suicide attempt thoughts, duration and frequency of ideation, sense of control, deterrents, and preparatory behavior for an attempt (Brown et al., 2000). The SSI has moderately high internal consistency and good concurrent and discriminant validity. It is administered at screening, at baseline within 24 hours before infusion, at 230 minutes after infusion, at 24 hours after infusion, and at weeks 1-6 of follow-up. For brevity we use "day 1" to refer to the 24-hour treatment assessment. Depressive symptoms are assessed with the 17- and 24-item HAM-D (Hamilton, 1960), the Beck Depression Inventory (BDI) (Beck et al, 1961), and the Profile of Mood States (POMS) (McNair et al., 1992). Anxiety is measured with a 5-point Likert scale asking patients to self-rate from 0 (not at all) to 4 (extremely anxious). Adverse effects are measured with the Systematic Assessment for Treatment Emergent Events—General Inquiry (Levine and Schooler, 1986), the Clinician-Administered Dissociative States Scale (CADS S; score range, 0-92) (Bremner et al., 1998), and the positive symptom subscale of the Brief Psychiatric Rating Scale (BPRS), which includes conceptual disorganization, grandiosity, hallucination, and delusions (sub scale score range, 0-24) (Overall and Gorham, 1962). Efficacy ratings and the CADSS and BPRS positive symptom subscale (at baseline, at 230 minutes, and at day 1) are collected by psychologist raters who are not present during the treatment. Administration of the immediate post-treatment CADSS and BPRS positive symptom subscale and all adverse effect ratings are done by the physician who supervises the infusion. Participants are asked at 3 and 6 months about post-study deuterated gaboxadol use.

d) Randomization and Blinding

A permuted, blocked design is used, with 1:1 assignment between treatments and block size randomized between 4 and 6 with equal probability. Randomization is stratified on two baseline factors: whether the patient is taking psychiatric medication (yes/no), and whether the patient's baseline SSI score is <8 or >8. The latter stratification factor, based on median baseline SSI score in a previous clinical trial in suicidal depressed patients (Grunebaum et al., 2012), is to increase the likelihood that the treatment groups are similar in baseline SSI severity. Patients and study personnel are blind to treatment. To assess the adequacy of the blind, patients and raters are asked in the day 1 ratings whether they thought the infusion is ketamine or deuterated gaboxadol or if they have "no idea."

Treatment response is defined as a day 1 SSI score >50% below baseline. We define remission more stringently as a day 1 SSI score >50% below baseline and less than the eligibility threshold of 4. A remission level of improvement is defined to ensure that the ketamine group has every opportunity to receive deuterated gaboxadol. Non-remitters are unblinded, and those who have received ketamine are offered an open deuterated gaboxadol infusion, usually the following day. Preexisting medications are held constant from pre-infusion baseline until completion of day 1 ratings after the final infusion. Remitters remain blind and receive a letter from the pharmacy after completing follow-up treatment informing them of their randomized drug.

e) Statistical Analysis

The study is powered assuming a two-sided test of the group effect at an alpha level of 0.05. Effect size estimates, standard deviations, and correlations are based on previous reports (Grunebaum et al., 2012) (Price et al., 2009). A planned sample size of 70, assigned 1:1 to each treatment, provides >80% power to detect a 25% reduction in SSI score over 24 hours in the deuterated gaboxadol group and none in the ketamine group. The actual sample size is about 80. Histograms and residual plots of outcomes are inspected for normality. Group comparisons on baseline characteristics are made using the chi-square test or Fisher's exact test as appropriate for categorical variables and the two-sample t test for continuous variables. The modified intent-to-treat analysis includes all randomized participants who are assessed for the primary outcome measure, SSI score at day 1 (N=80). The primary hypothesis is tested using an analysis of covariance (ANCOVA) model of the change in SSI score from baseline to day 1, with treatment group and baseline SSI score as the predictors. Randomization stratum (taking or not taking psychiatric medication), by definition not associated with treatment group, is not associated with the primary outcome measure (p=0.84) and so is not included in the model.

Effect size calculations used Cohen's d and number needed to treat. Cohen's d is calculated as the difference in mean group change divided by the standard deviation of baseline values for the whole sample. Secondary analyses use ANCOVA models to test for differential change between groups in SSI score and depressive symptom ratings (the 17- and 24-item HAM-D, the BDI, and the POMS) from baseline to 230 minutes and in depressive symptom ratings from baseline to day 1.

Response is compared by drug using logistic regression. Linear regression is used in an exploratory analysis of treatment effects on the suicidal desire/ideation and planning subscales of the SSI (Witte et al., 2006). Mediation analyses are performed using a structural equation modeling framework in Mplus, version 7 (Muthén and Muthén, 1998). Paired t tests are used to determine whether the participants assigned to ketamine who received an open deuterated gaboxadol treatment after day 1 (N=35) experience significant subsequent change in SSI or HAM-D scores. For the longitudinal data analysis, mixed-effects linear regression of SSI and 17-item HAM-D scores over the 6-week follow-up period are used to test for significant change from baseline across the entire sample, regardless of treatment group, since 35 of 40 patients in the ketamine group are non-remitters and receive a subsequent open deuterated gaboxadol infusion. Safety analyses include univariate tests comparing infusion-related cardiorespiratory effects, adverse events, and postinfusion severity of positive, dissociative, and anxiety symptom ratings between groups. SAS, version 9.4 (SAS Institute, Cary, N.C.), and SPSS, version 23 (IBM, Armonk, N.Y.), are used for the analyses.

f) Results

Primary Outcome Measure: Day 1 Suicidal Ideation The average SSI score at day 1 in the deuterated gaboxadol group is compared with the ketamine group. Cohen's d for the difference in mean group change is calculated to determine whether it demonstrates a greater than medium effect size. Baseline borderline personality disorder diagnosis is included as a covariate to determine whether this has little effect on the results.

g) Secondary Outcome Measures

Suicidal ideation. It is determined whether the proportion of responders on the SSI at day 1 is significantly higher in the deuterated gaboxadol group than the ketamine group. It is determined whether the decrease in suicidal ideation at 230 minutes after the infusion is greater in the deuterated gaboxadol group compared with the ketamine group.

Depressive symptoms. It is determined whether the day 1 POMS total mood disturbance score and/or scores on the depression subscale show greater improvement in the deuterated gaboxadol group compared with the ketamine group.

Example 15: Mapping the Brain Activation Underlying the Therapeutical Action of Lithium in Psychiatry To understand the mechanism of action of lithium across the entire brain, the aforementioned pharmacomapping technique was used to map lithium evoked brain activation in response to the following doses in the mouse (mg/kg): 120, 150, 200, and 300 which corresponds approximately to human equivalent doses (mg): 600, 750, 1000, and 1500. These experiments revealed a dose-dependent increase in the pattern of brain activation that comprised a modest to moderate activation of a few brain areas at 120 and 150 mg/kg and a considerably broader activation at 200 and 300 mg/kg (FIG. 29). The activation patterns observed with a lithium dose of 120 and 150 mg/kg included the anterior portion of the bed nuclei stria terminalis (BSTa), central amygdala (CEA), and locus coeruleus (LC) (FIG. 29, top two rows). The same areas were also prominently activated by lithium at 200 and 300 mg/kg, in addition to an activation of the prelimbic (PL) and infralimbic (ILA) cortex, piriform cortex (PIR) and nucleus accumbens (ACB) at bregma 1.5 mm, the gustatory (GU), agranular insular (AIp) cortical areas, motor (MO), somatosensory (SS), auditory (AUD), temporal associational (TEa), perirhinal (PERI) and entorhinal cortex, as well as midline thalamic nuclei, including the paraventricular nucleus (PVT), intermediodorsal nucleus (IMB), central medial nucleus (CM), and rhomboid nucleus (RH) at bregma 0.15 to −1.8 mm, and the visual (VIS), ectorhinal (ECT) TEa, AUD, PERI and ENT cortical areas, as well as medial geniculate complex (MG) cortical amygdala at bregma 2.7 mm (FIG. 29, bottom two rows).

Figure 30:
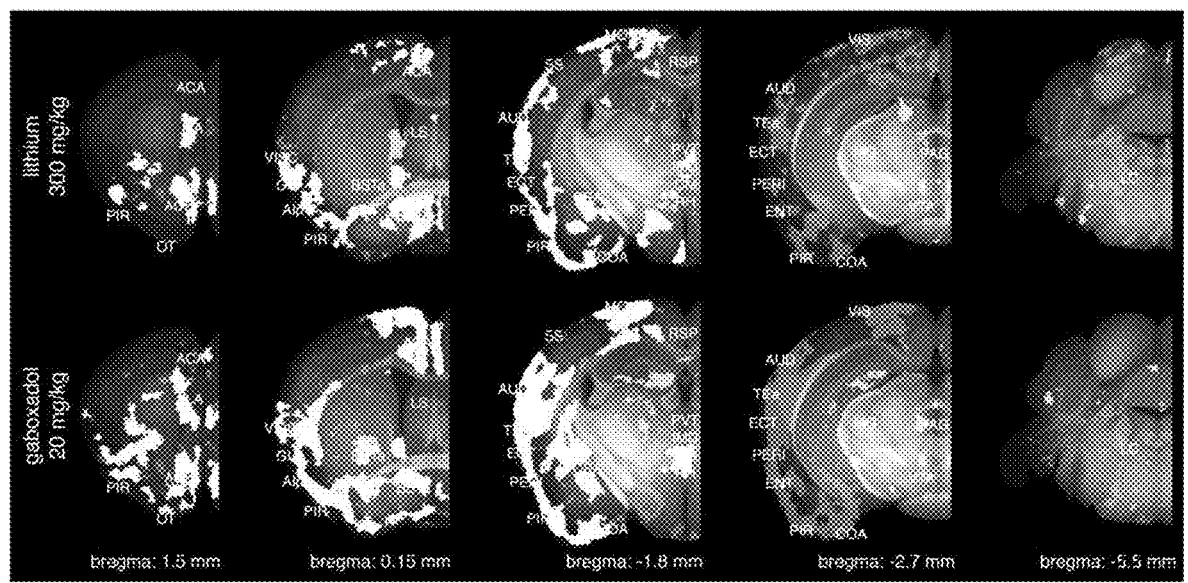
FIG. 30 shows exemplary lithium induced brain activation is similar to that of gaboxadol. White color indicates the spatial areas of significant lithium-evoked induction of c-fos activity in a mouse brain. The broad activation pattern evoked by lithium at a dose of 300 mg/kg (top row; human equivalent dose about 1500 mg) appears similar to the effect of gaboxadol at 20 mg/kg (bottom row; human equivalent dose about 100 mg), including the following anatomical structures: Cortex: infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (Tea), perirhinal (PERI) and entorhinal (ENT), and ectorhinal (ECT) cortex; Basal ganglia: the nucleus accumbens (ACB), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG); Brainstem: locus coeruleus (LC).

Example 16: the Pattern of Lithium-Induced c-Fos Activation Closely Matches that of the GABA$_A$ Agonist, Gaboxadol Mapping the effect of lithium across the mouse brain using the aforementioned pharmacomapping platform permits a direct comparison of the lithium-evoked brain activation pattern with that of other test compounds. Strikingly, the pharmacomap pattern evoked by a dose of 300 mg/kg lithium closely matched that of gaboxadol at 20 mg/kg, comprising c-fos activation of 1) a broad cortical activation comprising motor (MO), gustatory (GU), visceral (VISC), agranular insular (AI), somatosensory (SS), auditory, visual (VIS), auditory (AUD), prelimbic (PL) and infralimbic (ILA), retrosplenial (RSP), parietal (PTL), temporal associational (TEa), ectorhinal (ECT), entorhinal (ENT), perirhinal (PERI), piriform (PIR), and anterior cingulate (ACA) cortex, claustrum (CLA), as well as 2) subcortical activation comprising hippocampal CA1 region, the bed nuclei stria terminalis (BST), central amygdala (CEA), cortical amygdala (COA), basolateral and basomedial amygdala (BLA and BMA), medial amygdala (MEA), thalamic ventral posteromedial nucleus (VPM), subparafascicular nucleus (SPF), medial geniculate complex (MG), suprageniculate nucleus (SGN), nucleus of reunions (RE), rhomboid nucleus (RH), and central medial nucleus (CM) of the thalamus, paraventricular hypothalamic nucleus (PVH), dorsomedial nucleus of the hypothalamus (DMH), tuberomammillary nucleus (TM), parasubthalamic nucleus (PSTN) and subthalamic nucleus (STN), parabrachial nucleus, locus coeruleus (LC), and nucleus of the solitary tract (NTS) (FIG. 30).

This discovery is all the more surprising because gaboxadol and lithium are structurally unrelated molecules with different mechanisms of action: gaboxadol is an agonist at the delta-subunit containing GABAergic receptors that are believed to constitute an extra-synaptic population of inhibitory GABA$_A$ receptors in the brain, while the mechanism of action for lithium in the brain remains not well established, though several studies have suggested involvement in signaling cascades downstream of inhibition of glycogen synthase kinase 3-beta, leading to neurotrophic effects and enhanced neuroplasticity and cellular resilience (Won and Kim, 2017). Thus, the discovery that lithium evokes brain-wide activation that matches the pattern seen with gaboxadol is entirely unexpected and could not have been predicted based on reports in the scientific literature.

Figure 31:
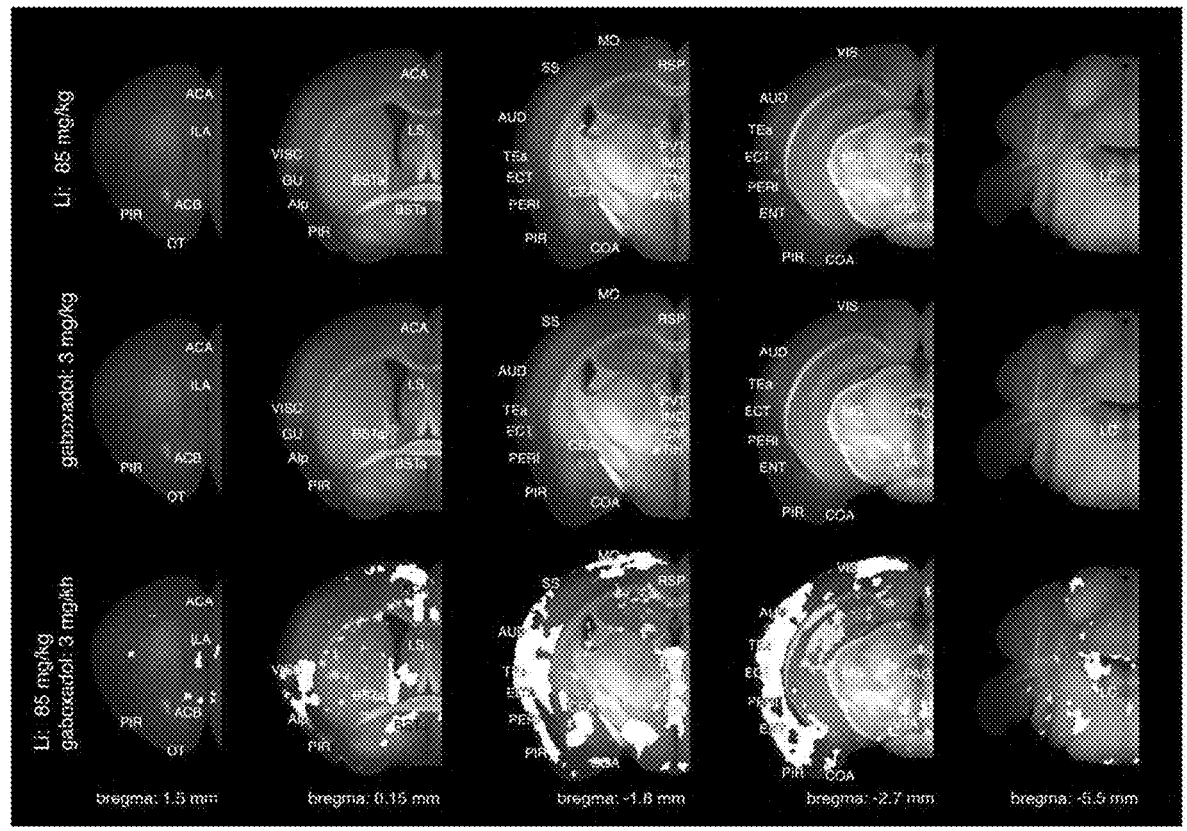
FIG. 31 shows an exemplary synergistic effect from the co-administration of gaboxadol and sub-standard dose of lithium White color indicates the spatial areas of significant lithium-evoked induction of c-fos activity in a mouse brain. While neither lithium at 85 mg/kg (top row; human equivalent dose about 425 mg), nor gaboxadol at 3 mg/kg (middle row; human equivalent dose about 15 mg) induced any brain activation on their own, the combination of these doses induced a prominent and broad activation (bottom row) indicating a synergy between the two compounds within multiple anatomical brain structures, including: Cortex: infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (Tea), perirhinal (PERI) and entorhinal (ENT), and ectorhinal (ECT) cortex; Basal ganglia: the nucleus accumbens (ACB), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG); Brainstem: locus coeruleus (LC). The weak pattern of inhibition (green color) seen across the caudoputamen (CP) and hippocampus (HIPP) suggest a modest sedation induced by the two compounds.

Example 17: Synergy Between Lithium and Gaboxadol in a Pharmacomapping Assay The similarity of the lithium and non-deuterated gaboxadol pharmacomaps suggested that the initial compound-specific signaling events lead to a common downstream brain circuit activation. This Example tested whether non-deuterated gaboxadol and lithium are able to act in synergy with one another, two doses of each compound were combined under conditions where the dose of each compound on their own did not evoke any acute brain activation. As shown in FIG. 31, neither gaboxadol at 3 mg/kg nor lithium at 85 mg/kg alone evoked any brain activation in mice detectable using the pharmacomapping assay (FIG. 31, top two rows). However, the combination of gaboxadol at 3 mg/kg plus lithium at 85 mg/kg elicited a strong activation of a number of mouse brain areas (FIG. 31, bottom row), showing a synergistic effect; these areas were activated by each drug individually when administered at the higher doses of 20 mg/kg (gaboxadol) and 300 mg/kg (lithium), as described above in Example 16.

Figure 32A:
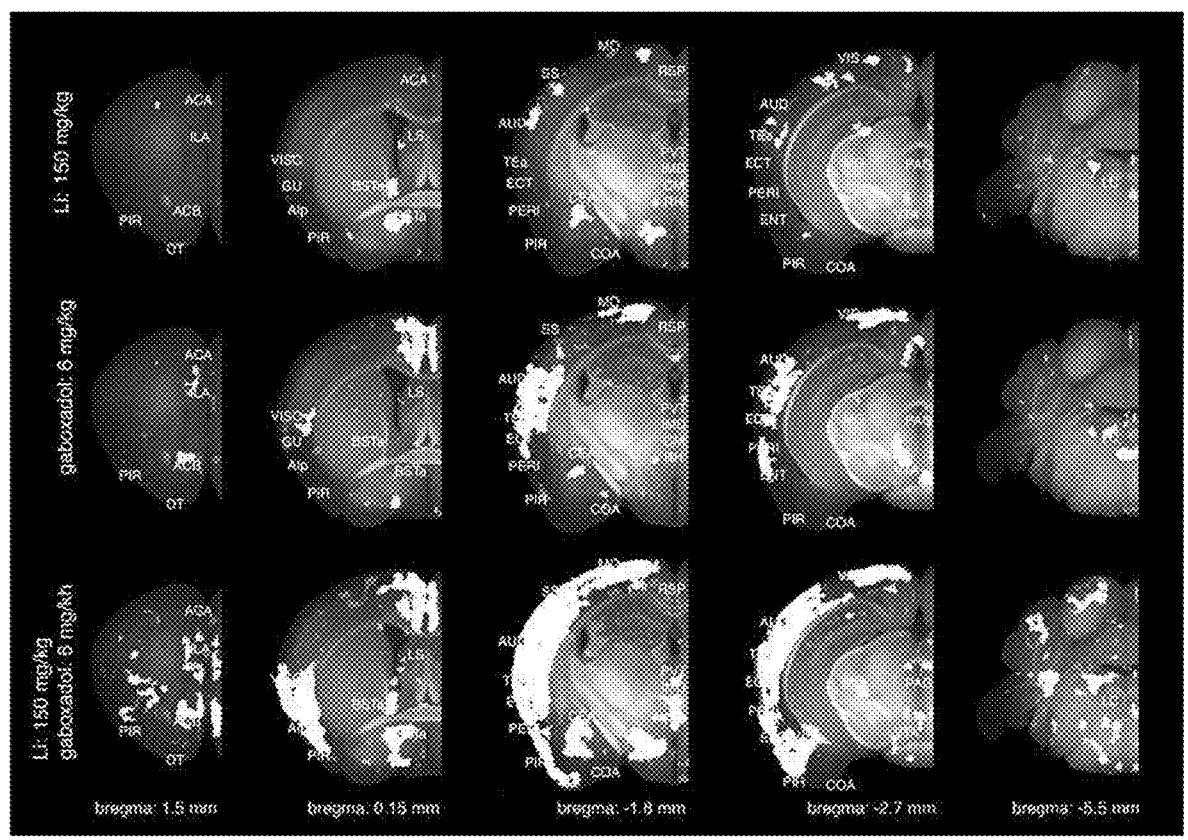
FIG. 32A shows an exemplary synergistic and additive brain activation effect of co-administration of gaboxadol and standard dose of lithium. White color indicates the spatial areas of significant lithium-evoked induction of c-fos activity in a mouse brain. While lithium at 150 mg/kg (top row; human equivalent dose about 750 mg) and gaboxadol at 6 mg/kg (middle row; human equivalent dose about 30 mg) evoked moderate brain activation on their own, including infralimbic (ILA) cortex, the anterior part of the bed nuclei of the stria terminalis (BSTa), locus coerules (LC) and some additional cortical areas, the combination of these two doses evoked a considerably more prominent activation (bottom row) further demonstrating a synergy and additive action between the two compounds, including the following anatomical structures: Cortex: infralimbic (ILA) cortex, piriform cortex (PIR), associational visceral (VISC), gustatory (GU), agranular insular (AIp) cortical areas, retrosplenial (RSP), motor (MO), somatosensory (SS), auditory (AUD), visual (VIS), temporal associational (Tea), perirhinal (PERI) and entorhinal (ENT), and ectorhinal (ECT) cortex; Basal ganglia: the nucleus accumbens (ACB), the anterior part of the bed nuclei of the stria terminalis (BSTa), cortical amygdala and central amygdala (CEA); Midline thalamus: paraventricular nucleus (PVT), intermediodorsal nucleus (IMB), central medial nucleus (CM), and rhomboid nucleus (RH); Midbrain: geniculate complex (MG); Brainstem: locus coeruleus (LC). The weak pattern of inhibition (green color) seen across the caudoputamen (CP) and hippocampus (HIPP) suggest a modest sedation induced by the two compounds.
Figure 32B:
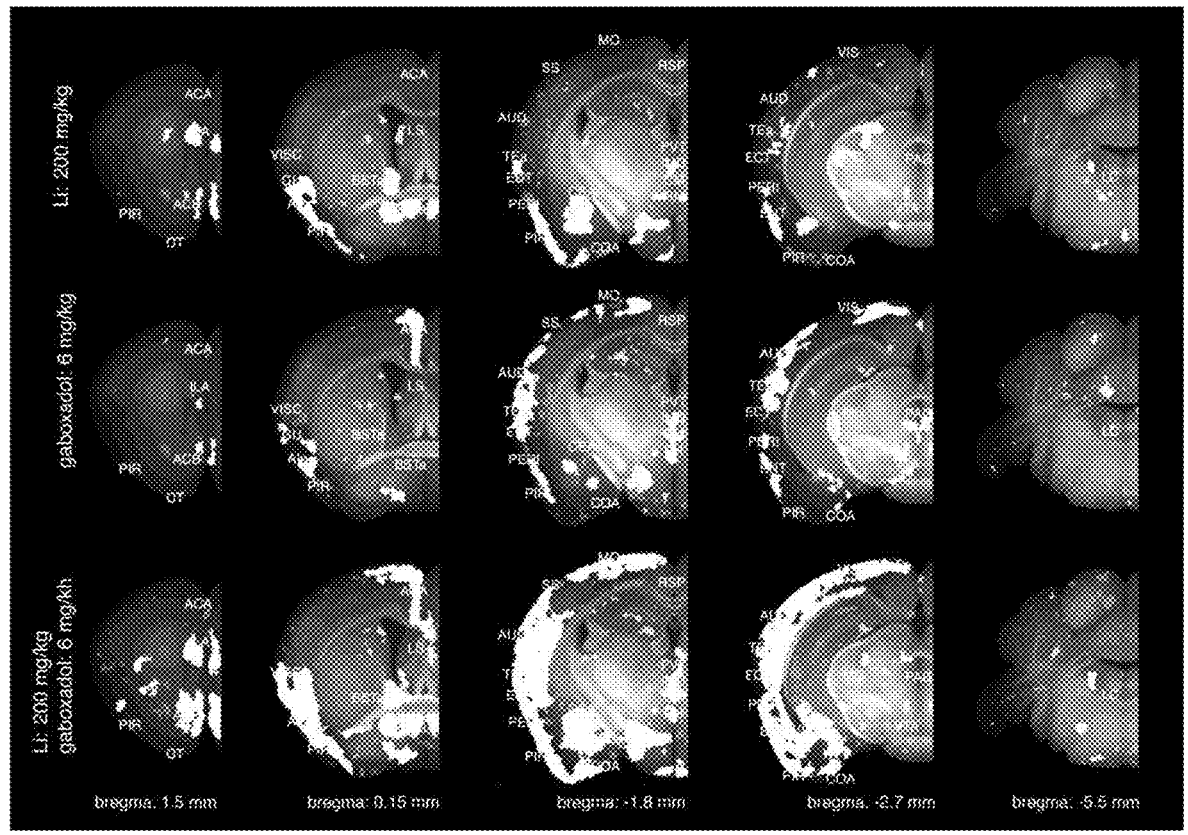
FIG. 32B shows an exemplary synergistic and additive brain activation effect of co-administration of gaboxadol and standard dose of lithium. White color indicates the spatial areas of significant lithium-evoked activation in a mouse brain. While lithium at 200 mg/kg (top row; human equivalent dose about 1000 mg) and gaboxadol at 6 mg/kg (middle row; human equivalent dose about 30 mg) evoked moderate brain activation on their own, including infralimbic (ILA) cortex, the anterior part of the Vnitial 20 min, the treatment with d-amphetamine induced a sharp increase in locomotion in the vehicle treated animals (top dark blue line), that was not moderated by lithium at 14.1 mg/kg alone (second from top orange line) and only modestly (Anova p value=0.007, Fisher's PLSD test p=0.6) by gaboxadol at 3 mg/kg alone (second from bottom yellow line), whereas a combination of lithium at 14.1 mg/kg and gaboxadol at 3 mg/kg (bottom light blue line) showed a pronounced moderation in locomotion (Anova p value=0.007, Fisher's PLSD test p=<0.01), demonstrating synergy between the two molecules.

Furthermore, this synergy is not limited to the lowest dosages of lithium (<100 mg/kg) and gaboxadol (<5 mg/kg), but is also seen in combinations of the two compounds at higher doses, such as gaboxadol at 6 mg/kg and lithium at 150 mg/kg (FIG. 32A) or gaboxadol at 6 mg/kg and lithium at 200 mg/kg (FIG. 32B). At the higher drug combinations, in addition to synergy, additive effects between gaboxadol and lithium are also observed. Taken together, these data clearly demonstrate that lithium and gaboxadol can synergize in their brain activation action, indicating that a combination therapy is an effective strategy to achieve lithium efficacy while lowering lithium induced side effects. It is also important to note that gaboxadol has been tested in clinical trials and found to have no significant adverse side-effects at human doses equivalent to the mouse 6 mg/kg dose used in the current study. For example, in the early 1980s gaboxadol was the subject of a series of pilot studies that tested its efficacy as an analgesic and anxiolytic, as well as a treatment for tardive dyskinesia, Huntington's disease, Alzheimer's disease, and spasticity (Foster et al., 1983; Hoehn-Saric, 1983; Kasper et al., 2012; Kjaer and Nielsen, 1983; Korsgaard et al., 1982; Mohr et al., 1986; Mondrup and Pedersen, 1983). In the 1990s gaboxadol moved into late stage development for the treatment of insomnia, but the development was discontinued after the compound failed to show significant effects in sleep onset and sleep maintenance in a three-month efficacy study (ClinicalTrials.gov Identifier: NCT00209963).

Example 18: Lithium and Gaboxadol Synergize in an Amphetamine Induced Rodent Model of Mania The stimulant d-amphetamine-induced hyperactivity has been used as a therapeutically predictive rodent test of mania, as pretreatment with lithium was shown to suppress the amphetamine-induced hyperlocomotion (Berggren et al., 1978; Cappeliez and Moore, 1990; Kato et al., 2007). The brain activation synergy action between lithium and gaboxadol seen in the pharmacomapping experiments described above suggests that the two molecules should also synergize in the d-amphetamine test, leading to an enhanced suppression of hyperlocomotion than seen with either molecule alone.

Figure 33:
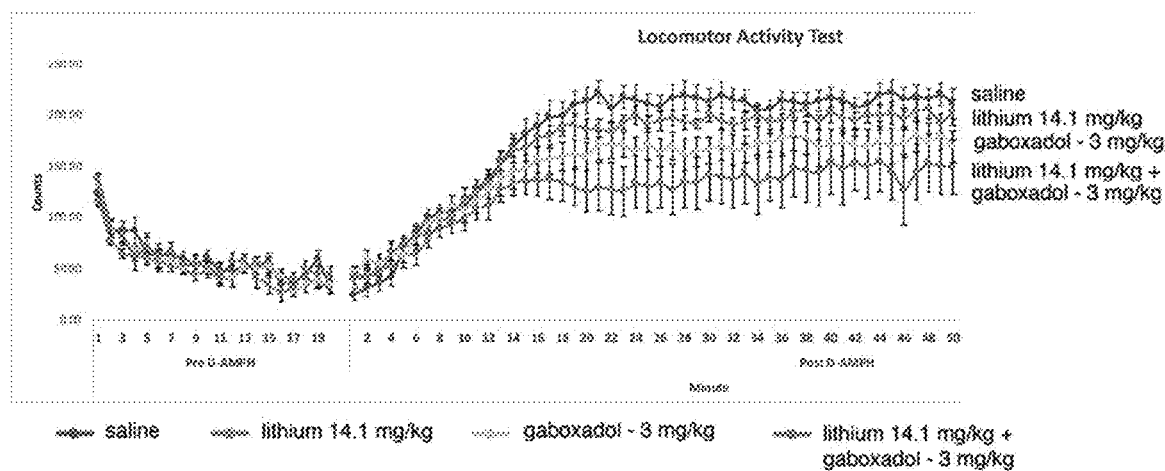
FIG. 33 shows the results of an experiment on the effect of lithium, gaboxadol, and a combination thereof on amphetamine-induced hyperlocomotion.

As shown in FIG. 33, while pretreatment with a sub-standard dose (14.1 mg/kg) of lithium had no behavioral effect, pretreatment with the 14.1 mg/kg sub-effective dose of lithium in combination with a dose of 3 mg/kg gaboxadol had an effect in suppressing amphetamine-induced hyperlocomotion that was greater than either lithium or gaboxadol alone.

Example 19: Mapping the Synergy Between D2-Gaboxadol and Lithium in Evoking Brain Activation Results presented in this example demonstrate that the combination of d2-gaboxadol 7,7 and lithium evokes a synergistic brain activation compared to each compound acting alone. Pharmacomapping was performed on six mice per experiment. The images presented represent the average of the six mice.

Figure 37:
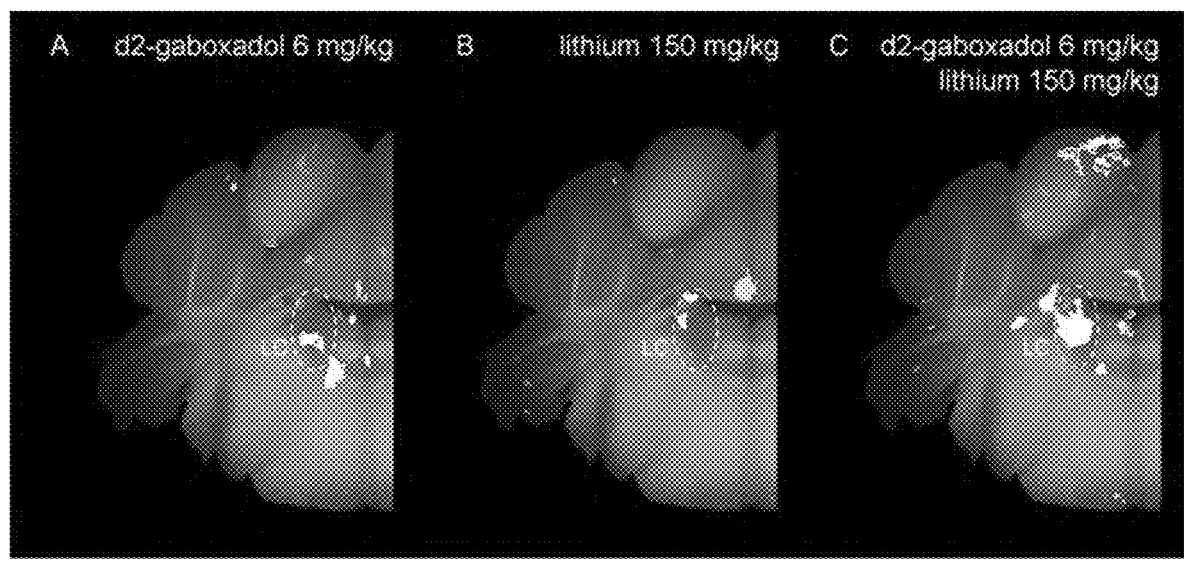
FIG. 37 shows a Pharmacomap-based comparison of d2-gaboxadol 7,7 at 6 mg/kg, lithium at 150 mg/kg and the combination of d2-gaboxadol 7,7 at 6 mg/kg and lithium at 150 mg/kg and at the locus coeruleus (LC).
Figure 38:
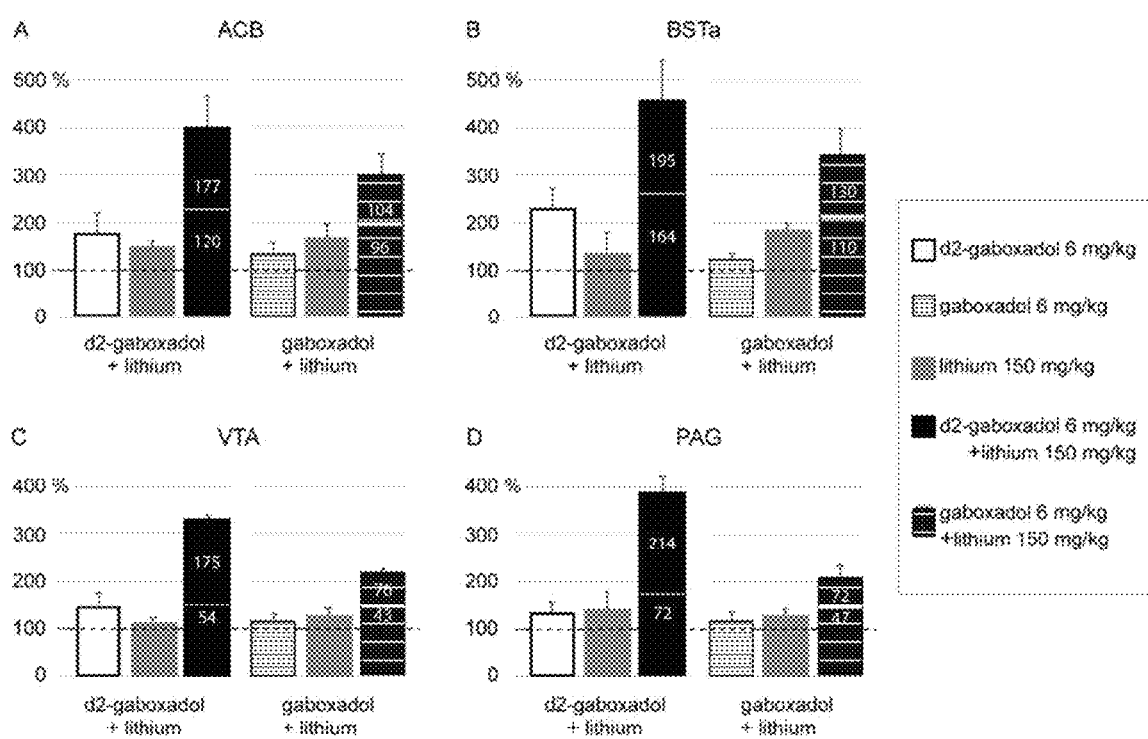
FIG. 38 shows a quantification of the Pharmacomap-based comparison of d2-gaboxadol 7,7 and gaboxadol at 6 mg/kg, lithium at 150 mg/kg and the combination of d2-gaboxadol 7,7, gaboxadol and lithium at the identified brain areas: nucleus accumbens (ACB), the anterior portion of the bed nuclei stria terminalis (BSTa), the ventral tegmental area (VTA) and the locus coeruleus (LC).

To test whether the ring carbon deuterated gaboxadol combines synergistically with lithium we compared brain activation evoked by d2-gaboxadol 7,7 at 6 mg/kg, lithium at 150 mg/kg and the combination of d2-gaboxadol 7,7 at 6 mg/kg and lithium at 150 mg/kg. As shown in FIGS. 34 to 38, these experiments indeed revealed a synergistic activation between the two compounds across a number of brain areas, including the nucleus accumbens (ACB) (FIG. 34), the anterior portion of the bed nuclei stria terminalis (BSTa) (FIG. 35), ventral tegmental area (VTA) (FIG. 36) and the locus coeruleus (LC) (FIG. 37). In these areas the brain activation by the combination of d2-gaboxadol 7,7 and lithium was considerably higher than the summation of the brain activation effect evoked by each compound alone, demonstrating a synergy between d2-gaboxadol 7,7 and lithium (FIG. 38).

Figure 34:
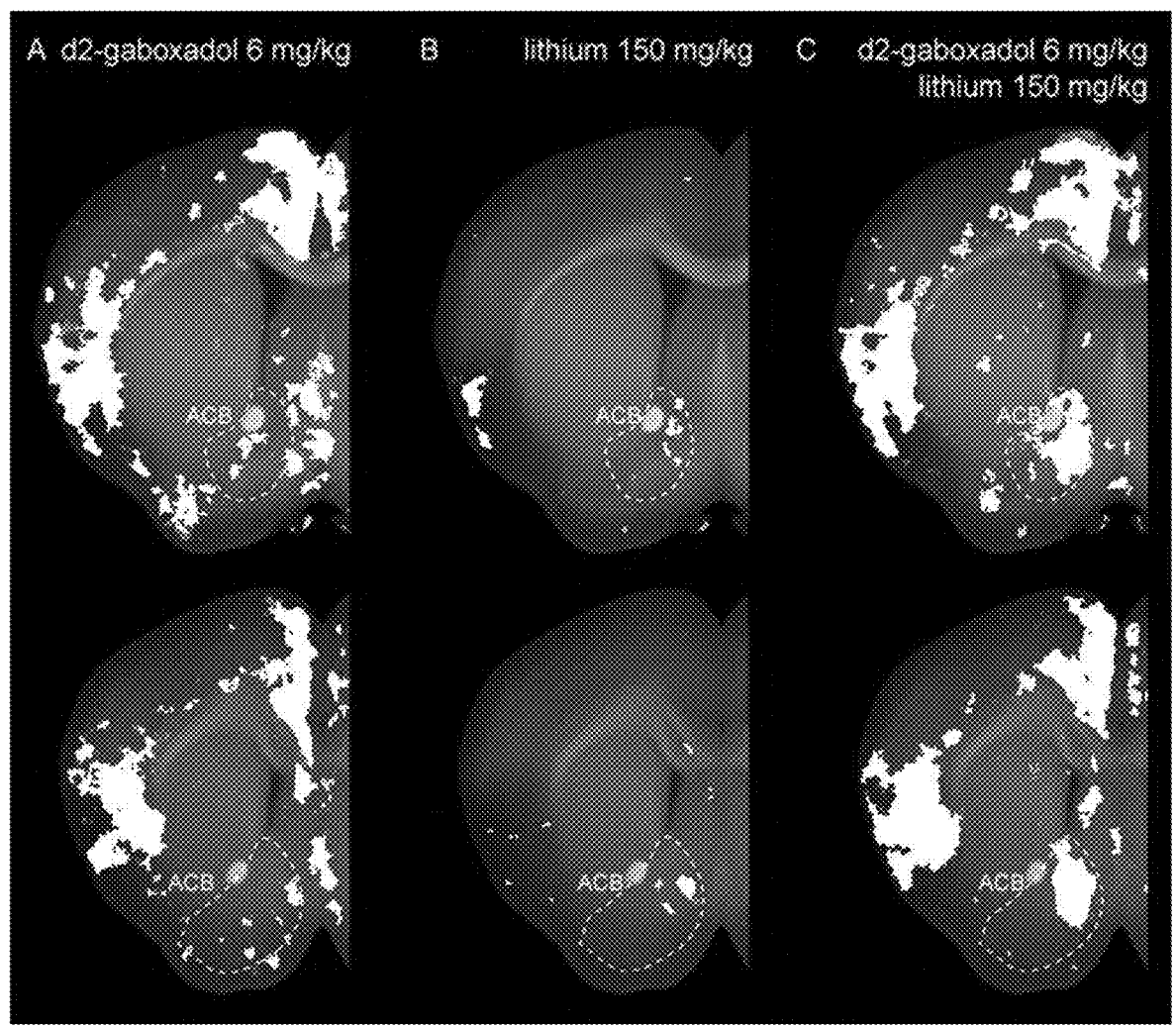
FIG. 34 shows a Pharmacomap-based comparison of d2-gaboxadol 7,7 at 6 mg/kg, lithium at 150 mg/kg and the combination of d2-gaboxadol 7,7 at 6 mg/kg and lithium at 150 mg/kg at the nucleus accumbens (ACB).

Referring to FIG. 34, the white color indicates the spatial areas of significant drug-evoked activation for A) d2-gaboxadol 7,7 at 6 mg/kg, B) lithium at 150 mg/kg and C) combination of d2-gaboxadol 7,7 at 6 mg/kg and lithium at 150 mg/kg. The area of nucleus accumbens (ACB) is highlighted by dashed lines. The combination of d2-gaboxadol 7,7 at 6 mg/kg and lithium at 150 mg/kg appears to have evoked synergistic activation of ACB compared to each compound alone.

Figure 35:
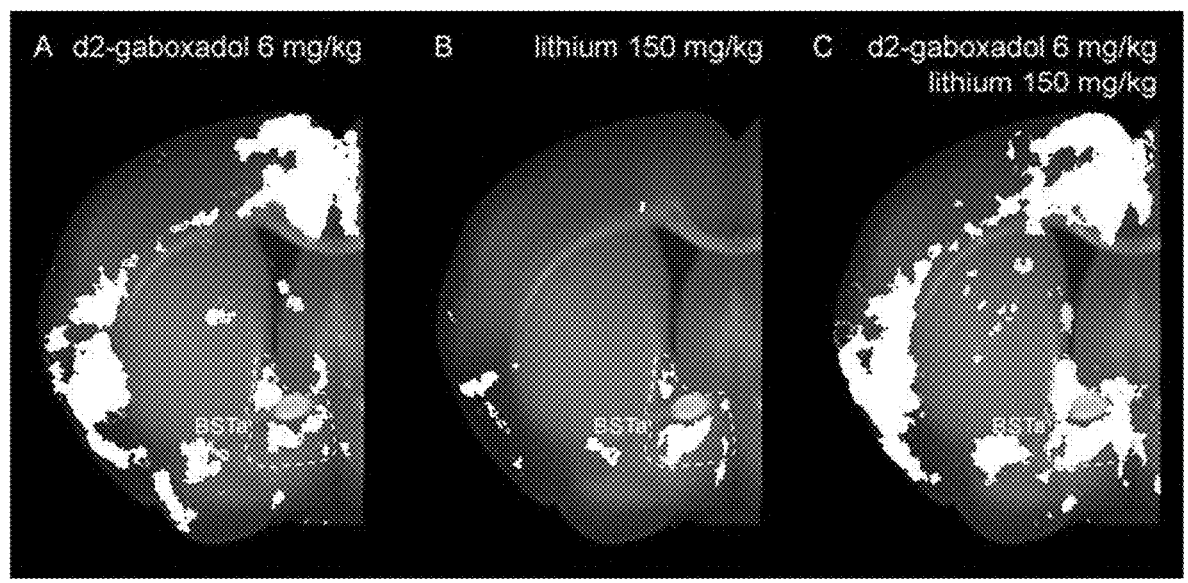
FIG. 35 shows Pharmacomap-based comparison of d2-gaboxadol 7,7 at 6 mg/kg, lithium at 150 mg/kg and the combination of d2-gaboxadol 7,7 at 6 mg/kg and lithium at 150 mg/kg at the anterior portion of the bed nuclei stria terminalis (BSTa).

In FIG. 35 the white color indicates the spatial areas of significant drug-evoked activation for A) d2-gaboxadol 7,7 at 6 mg/kg, B) lithium at 150 mg/kg and C) combination of d2-gaboxadol 7,7 at 6 mg/kg and lithium at 150 mg/kg. The area of the anterior part of the bed nuclei terminalis (BSTa) is highlighted by dashed lines. The combination of d2-gaboxadol 7,7 at 6 mg/kg and lithium at 150 mg/kg appears to have evoked synergistic activation of BSTa compared to each compound alone.

Figure 36:
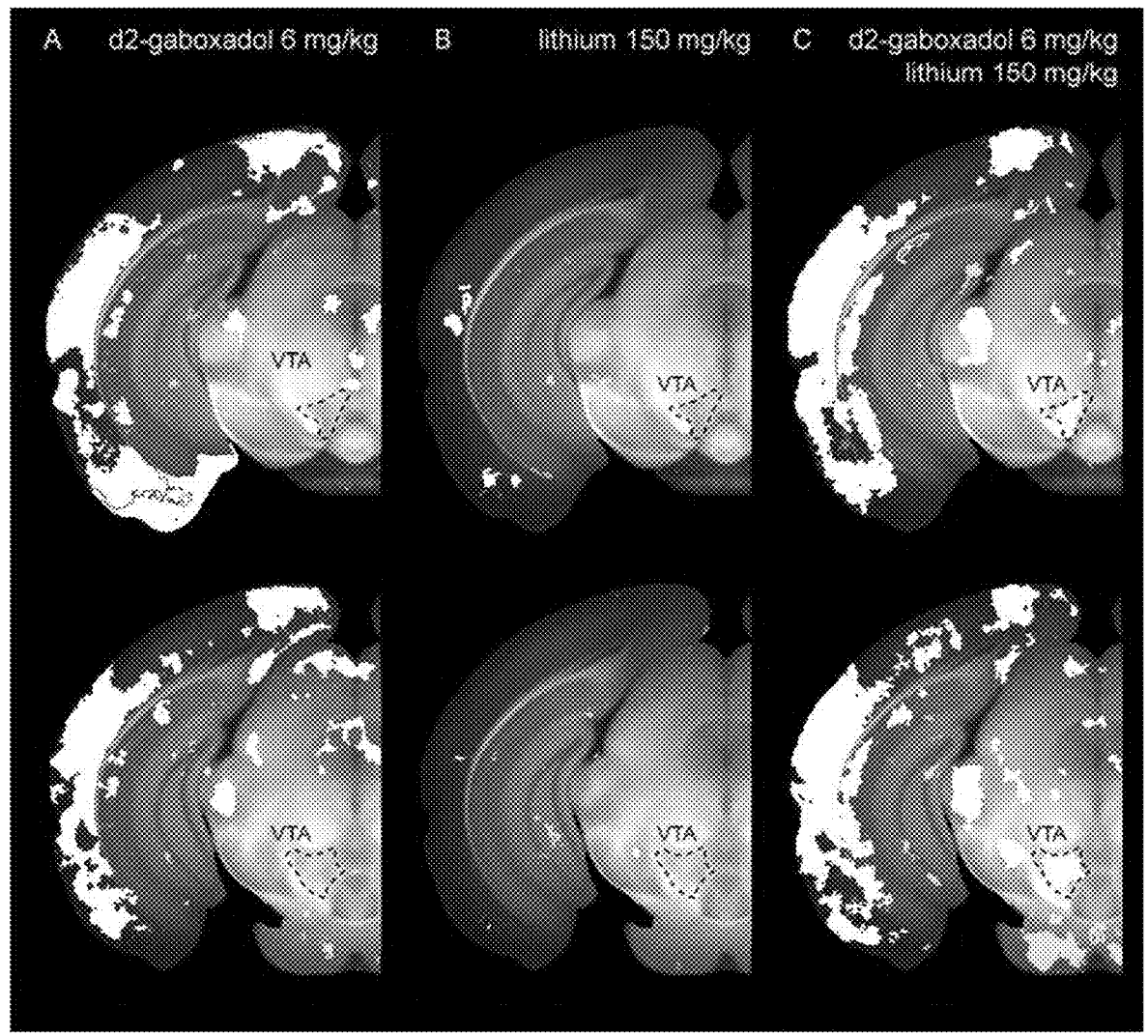
FIG. 36 shows a Pharmacomap-based comparison of d2-gaboxadol 7,7 at 6 mg/kg, lithium at 150 mg/kg and the combination of d2-gaboxadol 7,7 at 6 mg/kg and lithium at 150 mg/kg at the ventral tegmental area (VTA).

In FIG. 36 the white color indicates the spatial areas of significant drug-evoked activation for A) d2-gaboxadol 7,7 at 6 mg/kg, B) lithium at 150 mg/kg and C) combination of d2-gaboxadol 7,7 at 6 mg/kg and lithium at 150 mg/kg. The area of ventral tegmental area (VTA) is highlighted by dashed lines. The combination of d2-gaboxadol 7,7 at 6 mg/kg and lithium at 150 mg/kg appears to have evoked synergistic activation of ACB compared to each compound alone.

In FIG. 37 the white color indicates the spatial areas of significant drug-evoked activation for A) d2-gaboxadol 7,7 at 6 mg/kg, B) lithium at 150 mg/kg and C) combination of d2-gaboxadol 7,7 at 6 mg/kg and lithium at 150 mg/kg. The area of locus coeruleus (LC) is highlighted by dashed lines. The combination of d2-gaboxadol 7,7 at 6 mg/kg and lithium at 150 mg/kg appears to have evoked synergistic activation of ACB compared to each compound alone.

FIG. 38 quantifies the comparisons illustrated in FIGS. 34-37. The increase in c-fos+ cell counts in drug treated mice is expressed in percent from control saline-treated mice for each group: d2-gaboxadol 7,7 at 6 mg/kg, lithium at 150 mg, d2-gaboxadol 7,7 at 6 mg/kg and lithium at 150 mg, gaboxadol at 6 mg/kg, and gaboxadol at 6 mg/kg and lithium at 150 mg/kg for (A) nucleus accumbens (ACB), (B) anterior part of the bed nuclei terminalis (BSTa), (C) ventral tegmental area VTA) and (D) periaqueductal gray (PAG). The dashes line highlights 100% control baseline. Each d2-gaboxadol 7,7+lithium and gaboxadol+lithium combination column includes the calculated additive summation effect (above dashed line) and the measured additional synergistic effect (above full line) in percent of control.

Thus, d2-gaboxadol 7,7 provides significantly stronger enhancement of synergies with lithium than is found with non-deuterated gaboxadol. The greater effect of deuterated gaboxadol relative to nondeuterated is also shown in Examples herein above. The inventors contemplate that significantly lower doses of deuterated gaboxadol may be used as effectively as higher doses of non-deuterated gaboxadol and the synergies with lithium may be higher as well as seen in FIG. 38.

Various references such as patents, patent applications, patent publications, journals, scientific articles, books, papers, web contents, and other publications have been made in this disclosure. All such documents are hereby incorporated herein by reference in their entireties for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Those skilled in the art will recognize or be able to ascertain using no more than routine experimentation, many equivalents to the specific embodiments described herein. Such equivalents are intended to be encompassed by the claims.

Although this invention has been described with a certain degree of particularity, it is to be understood that the present disclosure has been made only by way of illustration and that numerous changes in the details of construction and arrangement of parts may be resorted to without departing from the spirit and the scope of the invention.

CITED REFERENCES

Abou-Saleh, M. T., Müller-Oerlinghausen, B., and Coppen, A. J. (2017). Lithium in the episode and suicide prophylaxis and in augmenting strategies in patients with unipolar depression. International journal of bipolar disorders 5, 11.

Ando, S., Koike, S., Shimodera, S., Fujito, R., Sawada, K., Terao, T., Furukawa, T. A., Sasaki, T., Inoue, S., and Asukai, N. (2017). Lithium Levels in Tap Water and the Mental Health Problems of Adolescents: An Individual-Level Cross-Sectional Survey. The Journal of clinical psychiatry 78, e252-e256.

Andrade Nunes, M., Araujo Viel, T., and Sousa Buck, H. (2013). Microdose lithium treatment stabilized cognitive impairment in patients with Alzheimer's disease. Current Alzheimer Research 10, 104-107.

Artigas, F. (2015). Developments in the field of antidepressants, where do we go now? European Neuropsychopharmacology 25, 657-670.

Association, A. P. (2002). Practice guideline for the treatment of patients with bipolar disorder (revision) (American Psychiatric Pub).

Autry, A. E., Adachi, M., Nosyreva, E., Na, E. S., Los, M. F., Cheng, P.-f., Kavalali, E. T., and Monteggia, L. M. (2011). NMDA receptor blockade at rest triggers rapid behavioural antidepressant responses. Nature 475, 91-95.

Azevedo, H., Ferreira, M., Mascarello, A., Osten, P., and Guimarães, C. R. W. (2020a). Brain-wide mapping of c-fos expression in the single prolonged stress model and the effects of pretreatment with ACH-000029 or prazosin. Neurobiology of Stress, 100226.

Azevedo, H., Ferreira, M., Mascarello, A., Osten, P., and Werneck Guimaraes, C. R. (2020b). The serotonergic and alpha-1 adrenergic receptor modulator ACH-000029 ameliorates anxiety-like behavior in a post-traumatic stress disorder model. Neuropharmacology 164, 107912.

Baldessarini, R. J., Tondo, L., Davis, P., Pompili, M., Goodwin, F. K., and Hennen, J. (2006). Decreased risk of suicides and attempts during long-term lithium treatment: a meta-analytic review. Bipolar disorders 8, 625-639.

Baldessarini, R. J., Tondo, L., and Hennen, J. (2003). Lithium treatment and suicide risk in major affective disorders: update and new findings. Journal of clinical psychiatry 64, 44-52.

Beck A T, Kovacs M, Weissman A: Assessment of suicidal intention: the Scale for Suicide Ideation. J Consult Clin Psychol (1979); 47:343-352.

Beck, A., Ward, C., Mendelsohn, M., Mock, J., and Erbaugh, J. (1961). An inventory for measuring depression Arch Gen Psychiatry 4: 561-571.

Berggren, U., Tallstedt, L., Ahlenius, S., and Engel, J. (1978). The effect of lithium on amphetamine-induced locomotor stimulation. Psychopharmacology 59, 41-45.

Bersani, G., Quartini, A., Zullo, D., and Iannitelli, A. (2016). Potential neuroprotective effect of lithium in bipolar patients evaluated by neuropsychological assessment: preliminary results. Human Psychopharmacology: Clinical and Experimental 31, 19-28.

Boateng et al., Int J Pharm. 2010 Apr. 15; 389 (1-2):24-31.

Bremner, J. D., Krystal, J. H., Putnam, F. W., Southwick, S. M., Marmar, C., Charney, D. S., and Mazure, C. M. (1998). Measurement of dissociative states with the clinician-administered dissociative states scale (CADSS). Journal of Traumatic Stress: Official Publication of The International Society for Traumatic Stress Studies 11, 125-136.

Brown, G. K., Beck, A. T., Steer, R. A., and Grisham, J. R. (2000). Risk factors for suicide in psychiatric outpatients: a 20-year prospective study. Journal of consulting and clinical psychology 68, 371.

Browne, C. A., and Lucki, I. (2013). Antidepressant effects of ketamine: mechanisms underlying fast-acting novel antidepressants. Frontiers in pharmacology 4, 161.

Cade J F Med J Aust. 1949; 2(10):349-52

Cappeliez, P., and Moore, E. (1990). Effects of lithium on an amphetamine animal model of bipolar disorder. Progress in Neuro-Psychopharmacology and Biological Psychiatry 14, 347-358. Carter, L., Zolezzi, M., and Lewczyk, A. (2013). An updated review of the optimal lithium dosage regimen for renal protection. The Canadian Journal of Psychiatry 58, 595-600.

Ciper and Bodmeier, Int J Pharm. 2005 Oct. 13; 303 (1-2):62-71.

Cipriani, A., Hawton, K., Stockton, S., and Geddes, J. R. (2013). Lithium in the prevention of suicide in mood disorders: updated systematic review and meta-analysis. Bmj 346, f3646.

Cipriani, A., Pretty, H., Hawton, K., and Geddes, J. R. (2005). Lithium in the prevention of suicidal behavior and all-cause mortality in patients with mood disorders: a systematic review of randomized trials. American Journal of Psychiatry 162, 1805-1819.

Chaturvedi et al., Curr Drug Deliv. 2011 July; 8 (4):373-80.

Cogram, Deacon et al. (2019) Front Behav Neurosci. 2019; 13: 141.

Cryan and Mombereau (2004) Mol Psychiatry April; 9(4): 326-57.

Cryan J F, Valentino R J, Lucki I. (2005) Neurosci Biobehav Rev.; 29(4-5):547-69.

Davis, J., Desmond, M., and Berk, M. (2018a). Lithium and nephrotoxicity: a literature review of approaches to clinical management and risk stratification. BMC nephrology 19, 305.

Davis, J., Desmond, M., and Berk, M. (2018b). Lithium and nephrotoxicity: Unravelling the complex pathophysiological threads of the lightest metal. Nephrology 23, 897-903.

Deligiannidis, K. M., Byatt, N., and Freeman, M. P. (2014). Pharmacotherapy for mood disorders in pregnancy: a review of pharmacokinetic changes and clinical recommendations for therapeutic drug monitoring. Journal of clinical psychopharmacology 34, 244.

Dijk et al. (2010) J. Psychopharmacology. 24(11) 1613-1618.

Engber, T. M., Koury, E. J., Dennis, S. A., Miller, M. S., Contreras, P. C., and Bhat, R. V. (1998). Differential patterns of regional c-Fos induction in the rat brain by amphetamine and the novel wakefulness-promoting agent modafinil. Neuroscience letters 241, 95-98.

Domany, Y., Shelton, R. C., and McCullumsmith, C. B. (2020). Ketamine for acute suicidal ideation. An emergency department intervention: A randomized, double-blind, placebo-controlled, proof-of-concept trial. Depression and anxiety 37, 224-233.

First, M. B., Spitzer, R. L., Gibbon, M., and Williams, J. B. (1995a). The structured clinical interview for DSM-III-R personality disorders (SCID-II). Part I: Description. Journal of Personality disorders 9, 83-91.

First, M. B., Spitzer, R. L., Gibbon, M., and Williams, J. B. (1995b). Structured clinical interview for DSM-IV axis I disorders-patient edition (SCID-I/P, Version 2.0). New York: Biometrics Research Department, New York State Psychiatric Institute 722.

Foster, N. L., Chase, T. N., Denaro, A., Hare, T. A., and Tamminga, C. A. (1983). THIP treatment of Huntington's disease. Neurology 33, 637-637.

Galvez, V., Li, A., Huggins, C., Glue, P., Martin, D., Somogyi, A. A., Alonzo, A., Rodgers, A., Mitchell, P. B., and Loo, C. K. (2018). Repeated intranasal ketamine for treatment-resistant depression—the way to go? Results from a pilot randomised controlled trial. Journal of Psychopharmacology 32, 397-407.

Gelenberg, A. J., Kane, J. M., Keller, M. B., Lavori, P., Rosenbaum, J. F., Cole, K., and Lavelle, J. (1989). Comparison of standard and low serum levels of lithium for maintenance treatment of bipolar disorder. New England Journal of Medicine 321, 1489-1493.

Grandjean, E. M., and Aubry, J.-M. (2009). Lithium: updated human knowledge using an evidence-based approach. CNS drugs 23, 397-418.

Greden, J. F. (2002). Unmet need: what justifies the search for a new antidepressant? Journal of Clinical Psychiatry 63, 3-7.

Grunebaum, M. F., Ellis, S. P., Keilp, J. G., Moitra, V. K., Cooper, T. B., Marver, J. E., Burke, A. K., Milak, M. S., Sublette, M. E., and Oquendo, M. A. (2017). Ketamine versus midazolam in bipolar depression with suicidal thoughts: A pilot midazolam-controlled randomized clinical trial. Bipolar disorders 19, 176-183.

Grunebaum, M. F., Ellis, S. P., Duan, N., Burke, A. K., Oquendo, M. A., and Mann, J. J. (2012). Pilot randomized clinical trial of an SSRI vs bupropion: effects on suicidal behavior, ideation, and mood in major depression. Neuropsychopharmacology 37, 697-706.

Grunebaum, M. F., Galfalvy, H. C., Choo, T.-H., Keilp, J. G., Moitra, V. K., Parris, M. S., Marver, J. E., Burke, A. K., Milak, M. S., and Sublette, M. E. (2018). Ketamine for rapid reduction of suicidal thoughts in major depression: a midazolam-controlled randomized clinical trial. American Journal of Psychiatry 175, 327-335.

Hamilton, M. (1960). A rating scale for depression. Journal of neurology, neurosurgery, and psychiatry 23, 56.

Herrera, D. G., and Robertson, H. A. (1996). Activation of c-fos in the brain. Prog Neurobiol 50, 83-107.

Hoehn-Saric, R. (1983). Effects of THIP on chronic anxiety. Psychopharmacology 80, 338-341.

Holi, M. M., Pelkonen, M., Karlsson, L., Kiviruusu, O., Ruuttu, T., Heilä, H., Tuisku, V., and Marttunen, M. (2005). Psychometric properties and clinical utility of the Scale for Suicidal Ideation (SSI) in adolescents. BMC psychiatry 5, 1-8.

Horton, S., Tuerk, A., Cook, D., Cook, J., and Dhurjati, P. (2012). Maximum recommended dosage of lithium for pregnant women based on a PBPK model for lithium absorption. Advances in bioinformatics 2012.

Hunt S P, Pini A and Evan G (1987) Induction of c-fos-like protein in spinal cord neurons following sensory stimulation. Nature 13-19; 328(6131):632-4.

Ivkovic, A., and Stern, T. A. (2014). Lithium-induced neurotoxicity: clinical presentations, pathophysiology, and treatment. Psychosomatics 55, 296.

Jain, S., and Heutink, P. (2010). From single genes to gene networks: high-throughput-high-content screening for neurological disease. Neuron 68, 207-217.

Judenhofer, M. S., Wehrl, H. F., Newport, D. F., Catana, C., Siegel, S. B., Becker, M., Thielscher, A., Kneilling, M., Lichy, M. P., and Eichner, M. (2008). Simultaneous PET-MRI: a new approach for functional and morphological imaging. Nature medicine 14, 459-465.

Kall et al (2007) Journal of Chromatography B, 858 (2007) 168-176.

Kasper, S., Ebert, B., Larsen, K., and Tonnoir, B. (2012). Combining escitalopram with gaboxadol provides no additional benefit in the treatment of patients with severe major depressive disorder. International Journal of Neuropsychopharmacology 15, 715-725.

Kato, T., Kubota, M., and Kasahara, T. (2007). Animal models of bipolar disorder. Neuroscience & Biobehavioral Reviews 31, 832-842.

Kessing, L. V., Bauer, M., Nolen, W. A., Severus, E., Goodwin, G. M., and Geddes, J. (2018). Effectiveness of maintenance therapy of lithium vs other mood stabilizers in monotherapy and in combinations: a systematic review of evidence from observational studies. Bipolar disorders 20, 419-431.

Kiss, A. (2018). c-Fos expression in the hypothalamic paraventricular nucleus after a single treatment with a typical haloperidol and nine atypical antipsychotics: a pilot study. Endocrine regulations 52, 93-100.

Kjaer, M., and Nielsen, H. (1983). The analgesic effect of the GABA-agonist THIP in patients with chronic pain of malignant origin. A phase-1-2 study. British journal of clinical pharmacology 16, 477-485.

Korsgaard, S., Casey, D. E., Gerlach, J., Hetmar, O., Kaldan, B., and Mikkelsen, L. B. (1982). The Effect of Tetrahydroisoxazolopyridinol (THIP) in Tardive Dyskinesia: A New β-Aminobutyric Acid Agonist. Archives of general psychiatry 39, 1017-1021.

Krogsgaard-Larsen (1982) Journal of Labeled Compounds and Radiopharmaceuticals 19(5) 689-702.

Lamey and Lewis (1990) "Buccal and Sublingual Delivery of Drugs" Ch 2 in "Routes of Drug Administration" Ed. Florence and Salole (Butterworth-Heinemann).

Lapidus, K. A., Levitch, C. F., Perez, A. M., Brallier, J. W., Parides, M. K., Soleimani, L., Feder, A., Iosifescu, D. V., Charney, D. S., and Murrough, J. W. (2014). A randomized controlled trial of intranasal ketamine in major depressive disorder. Biological psychiatry 76, 970-976.

Larsen et al. (2010) Eur J Pharm Sci. January 31; 39(1-3): 68-75.

Levine and Schooler (1986) SAFTEE: a technique for the systematic assessment of side effects in clinical trials. Psychopharmacology bulletin 22, 343-381.

Ljubicic, D., Letica-Crepulja, M., Vitezic, D., Bistrovic, I. L., and Ljubicic, R. (2008). Lithium treatments: single and multiple daily dosing. The Canadian Journal of Psychiatry 53, 323-331.

Lowe, D. J., Müller, D. J., and George, T. P. (2020). Ketamine treatment in depression: a systematic review of clinical characteristics predicting symptom improvement. Current topics in medicinal chemistry 20, 1398-1414.

Lucki I, Dalvi A, Mayorga A J. (2001) Psychopharmacology (Berl). 2001 May; 155(3):315-22.

Lundahl et al. (2011) J Psychopharmacol 26: 1081

Madhusudhan, B. (2014). Nonconvulsive status epilepticus and Creutzfeldt-Jakob-like EEG changes in a case of lithium toxicity. Epilepsy & behavior case reports 2, 203-205.

Marcantoni, W. S., Akoumba, B. S., Wassef, M., Mayrand, J., Lai, H., Richard-Devantoy, S., and Beauchamp, S. (2020). A systematic review and meta-analysis of the efficacy of intravenous ketamine infusion for treatment resistant depression: January 2009-January 2019. Journal of Affective Disorders.

Markou, A., Chiamulera, C., Geyer, M. A., Tricklebank, M., and Steckler, T. (2009). Removing obstacles in neuroscience drug discovery: the future path for animal models. Neuropsychopharmacology 34, 74-89.

McIntyre, R. S., Rosenblat, J. D., Nemeroff, C. B., Sanacora, G., Murrough, J. W., Berk, M., Brietzke, E., Dodd, S., Gorwood, P., and Ho, R. (2021). Synthesizing the evidence for ketamine and esketamine in treatment-resistant depression: an international expert opinion on the available evidence and implementation. American Journal of Psychiatry, appi. ajp. 2020.20081251.

McNair, D. M., Lorr, M., and Droppleman, L. F. (1992). EdITS Manual for the Profile of Mood States (POMS) (Educational and industrial testing service).

Megarbane, B., Hanak, A.-S., and Chevillard, L. (2014). Lithium-related neurotoxicity despite serum concentrations in the therapeutic range: risk factors and diagnosis. Shanghai archives of psychiatry 26, 243.

Mohr, E., Bruno, G., Foster, N., Gillespie, M., Cox, C., Hare, T. A., Tamminga, C., Fedio, P., and Chase, T. N. (1986). GABA-agonist therapy for Alzheimer's disease. Clinical neuropharmacology 9, 257-263.

Mondrup, K., and Pedersen, E. (1983). The acute effect of the GABA-agonist, THIP, on proprioceptive and flexor reflexes in spastic patients. Acta Neurologica Scandinavica 67, 48-54.

Murrough, J. W., Soleimani, L., DeWilde, K., Collins, K., Lapidus, K., Iacoviello, B., Lener, M., Kautz, M., Kim, J., and Stern, J. (2015). Ketamine for rapid reduction of suicidal ideation: a randomized controlled trial. Psychol Med 45, 3571-3580.

Ohlund, L., Ott, M., Oja, S., Bergqvist, M., Lundqvist, R., Sandlund, M., Renberg, E. S., and Werneke, U. (2018). Reasons for lithium discontinuation in men and women with bipolar disorder: a retrospective cohort study. BMC psychiatry 18, 37.

Mohr, Bruno et al. Clin Neuropharmacol. 1986; 9(3):257-63

Muthén, L. K., and Muthén, B. O. (1998). Mplus user's guide (Version 7). Los Angeles, C A: Author.

Muthukumaraswamy S D. The use of magnetoencephalography in the study of psychopharmacology (pharmaco-MEG). J Psychopharmacol. 2014 September; 28(9):815-29.

Muthukumaraswamy, S. (2015). Differences between magnetoencephalographic (MEG) spectral profiles of drugs acting on GABA at synaptic and extrasynaptic sites: a study in healthy volunteers. Neuropharmacology 88, 155-163.

Nagar et al., Journal of Applied Pharmaceutical Science, 2011; 01 (04):35-45

Nutt, D., Wilson, S., Lingford-Hughes, A., Myers, J Papadopoulos, A., and

Overall, J. E., and Gorham, D. R. (1962). The brief psychiatric rating scale. Psychological reports 10, 799-812.

Porsolt, R., Le Pinchon, M. & Jalfre, M. Depression: a new animal model sensitive to antidepressant treatments. Nature 266, 730-732 (1977). Price, R. B., Nock, M. K., Charney, D. S., and Mathew, S. J. (2009). Effects of intravenous ketamine on explicit and implicit measures of suicidality in treatment-resistant depression. Biological psychiatry 66, 522-526.

Price, R. B., Iosifescu, D. V., Murrough, J. W., Chang, L. C., Al Jurdi, R. K., Iqbal, S. Z., Soleimani, L., Charney, D. S., Foulkes, A. L., and Mathew, S. J. (2014). Effects of ketamine on explicit and implicit suicidal cognition: A randomized controlled trial in treatment-resistant depression. Depression and anxiety 31, 335-343.

Quartini, A., Iannitelli, A., and Bersani, G. (2016). Lithium: from mood stabilizer to putative cognitive enhancer. Neural regeneration research 11, 1234.

Rej, S., Beaulieu, S., Segal, M., Low, N. C., Mucsi, I., Holcroft, C., Shulman, K., and Looper, K. J. (2014). Lithium dosing and serum concentrations across the age spectrum: from early adulthood to the tenth decade of life. Drugs & aging 31, 911-916.

Renier, N., Adams, E. L., Kirst, C., Wu, Z., Azevedo, R., Kohl, J., Autry, A. E., Kadiri, L., Umadevi Venkataraju, K., Zhou, Y., et al. (2016). Mapping of Brain Activity by Automated Volume Analysis of Immediate Early Genes. Cell 165, 1789-1802.

Roberts, E., Cipriani, A., Geddes, J. R., Nierenberg, A. A., and Young, A. H. (2017). The evidence for lithium in suicide prevention. The British Journal of Psychiatry 211, 396-396.

Rybakowski, J. K., and Suwalska, A. (2010). Excellent lithium responders have normal cognitive functions and plasma BDNF levels. International Journal of Neuropsychopharmacology 13, 617-622.

Salminen, O., Lahtinen, S., and Ahtee, L. (1996). Expression of Fos protein in various rat brain areas following acute nicotine and diazepam. Pharmacology Biochemistry and Behavior 54, 241-248.

Sani, G., Perugi, G., and Tondo, L. (2017). Treatment of bipolar disorder in a lifetime perspective: is lithium still the best choice? Clinical drug investigation 37, 713-727.

Schou, M., Amdisen, A., and Trap-Jensen, J. (1968). Lithium poisoning. American Journal of Psychiatry 125, 520-527.

Scott, J., Geoffroy, P. A., Sportiche, S., Brichant-Petit-Jean, C., Gard, S., Kahn, J.-P., Azorin, J.-M., Henry, C., Etain, B., and Bellivier, F. (2017). Cross-validation of clinical characteristics and treatment patterns associated with phenotypes for lithium response defined by the Alda scale. Journal of affective disorders 208, 62-67.

Semba, J. I., Sakai, M., Miyoshi, R., Mataga, N., Fukamauchi, F., and Kito, S. (1996). Differential expression of c-fos mRNA in rat prefrontal cortex, striatum, N. accumbens and lateral septum after typical and atypical antipsychotics: an in situ hybridization study. Neurochem Int 29, 435-442.

Sechzer, J. A., Lieberman, K. W., Alexander, G. J., Weidman, D., and Stokes, P. E. (1986). Aberrant parenting and delayed offspring development in rats exposed to lithium. Biological psychiatry 21, 1258-1266

Severus, E., Taylor, M. J., Sauer, C., Pfennig, A., Ritter, P., Bauer, M., and Geddes, J. R. (2014). Lithium for prevention of mood episodes in bipolar disorders: systematic review and meta-analysis. International journal of bipolar disorders 2, 15.

Shepard et al., Suicide Life Threat Behav. (2016) 46(3):352-62.).

Singh, L. K., Nizamie, S. H., Akhtar, S., and Praharaj, S. K. (2011). Improving tolerability of lithium with a once-daily dosing schedule. American journal of therapeutics 18, 288-291.

Slattery, D. A., Morrow, J. A., Hudson, A. L., Hill, D. R., Nutt, D. J., and Henry, B. (2005). Comparison of alterations in c-fos and Egr-1 (zif268) expression throughout the rat brain following acute administration of different classes of antidepressant compounds. Neuropsychopharmacology 30, 1278.

Sumner, B. E., Cruise, L. A., Slattery, D. A., Hill, D. R., Shahid, M., and Henry, B. (2004). Testing the validity of c-fos expression profiling to aid the therapeutic classification of psychoactive drugs. Psychopharmacology (Berl) 171, 306-321.

Tiihonen, J., Lahteenvuo, M., Hoti, F., Vattulainen, P., Taipale, H., and Tanskanen, A. (2016). Real-World Effectiveness of Pharmacological Treatments in Severe Unipolar Depression in a Nationwide Cohort of 123,712 Patients. American College of Neuropsychopharmacology: Hollywood, Fla.

Toffol, E., Hatonen, T., Tanskanen, A., Lönnqvist, J., Wahlbeck, K., Joffe, G., Tiihonen, J., Haukka, J., and Partonen, T. (2015). Lithium is associated with decrease in all-cause and suicide mortality in high-risk bipolar patients: a nationwide registry-based prospective cohort study. Journal of affective disorders 183, 159-165.

Vita, A., De Peri, L., and Sacchetti, E. (2015). Lithium in drinking water and suicide prevention: a review of the evidence. International clinical psychopharmacology 30, 1-5.

Wang et al (2017) Progress in Neuro-Psychopharmacology and Biological Psychiatry Volume 77, 3 Jul. 2017, Pages 99-109 https://doi.org/10.1016/j.pnpbp.2017.04.008; and by Krishnan and Nestler "Animal Models of Depression: Molecular Perspectives" (in J. J. Hagan (ed.), Molecular and Functional Models in Neuropsychiatry, Current Topics in Behavioral Neurosciences 7, DOI 10.1007/7854_2010_108 ©Springer-Verlag Berlin Heidelberg 2011, published online 12 Jan. 2011)

Wesseloo, R., Wierdsma, A. I., van Kamp, I. L., Munk-Olsen, T., Hoogendijk, W. J., Kushner, S. A., and Bergink, V. (2017). Lithium dosing strategies during pregnancy and the postpartum period. The British Journal of Psychiatry 211, 31-36.

Wheatly and Keay (2007) Journal of Organic Chemistry, 72(19), 7253-7259.

Witte, T. K., Joiner Jr, T. E., Brown, G. K., Beck, A. T., Beckman, A., Duberstein, P., and Conwell, Y. (2006). Factors of suicide ideation and their relation to clinical and other indicators in older adults. Journal of affective disorders 94, 165-172.

Won, E., and Kim, Y.-K. (2017). An oldie but goodie: lithium in the treatment of bipolar disorder through neuroprotective and neurotrophic mechanisms. International journal of molecular sciences 18, 2679.

Zhou, Y., Liu, W., Zheng, W., Wang, C., Zhan, Y., Lan, X., Zhang, B., Zhang, C., and Ning, Y. (2020). Predictors of response to repeated ketamine infusions in depression with suicidal ideation: an ROC curve analysis. Journal of affective disorders 264, 263-27.

What is claimed is:

1. A ring carbon deuterated gaboxadol compound of Formula I

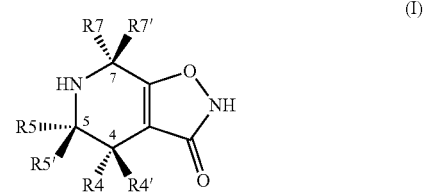

or a pharmaceutically acceptable salt thereof,
wherein all of R4, R4', R5, R5', R7 and R7' are D, and
wherein the percentage of incorporation of deuterium is at least 1%.

2. A pharmaceutical composition comprising the compound or salt of claim 1 and a pharmaceutically acceptable carrier.

3. The pharmaceutical composition of claim 2, which is an oral dosage form.

4. The pharmaceutical composition of claim 3, wherein the oral dosage form is a tablet.

5. The pharmaceutical composition of claim 3, wherein the oral dosage form is an orally disintegrating form.

6. The pharmaceutical composition of claim 2 comprising about 1 mg to about 300 mg of the compound or salt.

7. The pharmaceutical composition of claim 2 comprising about 50 mg to about 100 mg of the compound or salt.

8. The pharmaceutical composition of claim 2 comprising about 50 mg, about 75 mg, or about 100 mg of the compound or salt.

9. The pharmaceutical composition of claim 2 comprising about 25 mg to about 50 mg of the compound or salt.

10. The pharmaceutical composition of claim 2 comprising about 10 mg to about 30 mg of the compound or salt.

11. The pharmaceutical composition of claim 2, further comprising at least one other compound selected from the group consisting of lithium, ketamine, AXS-05 (fixed combination of dextromethorphan and bupropion), SAGE-217, allopregnanolone, ganaxolone, alfadolone, alfaxolone, hydroxydione, minaxolone, pregnanolone, renanolone, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, R04995819), memantine, tiagabine, clozapine, and [2-amino-4-(2,4,6-trimethylbenzylamino)-phenyl]-carbamic acid ethyl ester (AA29504).

12. The pharmaceutical composition of claim 11, wherein the at least one other compound is lithium.

13. A method of making d6-gaboxadol, said method comprising:
   (a) treating 3-hydroxypyridine-4-carboxylic acid with deuterium oxide under catalytic hydrogenation conditions to provide 2,3,6-trideuterio-5-hydroxy-pyridine-4-carboxylic acid;
   (b) treating 2,3,6-trideuterio-5-hydroxy-pyridine-4-carboxylic acid from step (a) above with a methylating agent, to provide methyl 2,3,6-trideuterio-5-hydroxy-pyridine-4-carboxylate;
   (c) treating methyl 2,3,6-trideuterio-5-hydroxy-pyridine-4-carboxylate from step (b) above with hydroxylamine hydrochloride, to provide 2,3,6-trideuterio-5-hydroxy-pyridine-4-carbohydroxamic acid;
   (d) treating 2,3,6-trideuterio-5-hydroxy-pyridine-4-carbohydroxamic acid from step (c) above with an activating agent, to provide 4,5,7-trideuterioisoxazolo[5,4-c]pyridin-3-one;
   (e) treating 4,5,7-trideuterioisoxazolo[5,4-c]pyridin-3-one from step (d) above with a brominating agent to provide 6-benzyl-4,5,7-trideuterio-isoxazolo[5,4-c]pyridin-6-ium-3-ol bromide;
   (f) treating 6-benzyl-4,5,7-trideuterio-isoxazolo[5,4-c]pyridin-6-ium-3-ol bromide from step (e) above with a reducing agent, to provide 6-benzyl-4,4,5,5,7,7-hexadeuterio-isoxazolo[5,4-c]pyridin-3-ol; and
   (g) deprotecting 6-benzyl-4,4,5,5,7,7-hexadeuterio-isoxazolo[5,4-c]pyridin-3-ol from step (f) above to remove the benzyl group to provide d6-gaboxadol.

14. A method of treating a psychiatric disorder comprising administering to a human patient in need thereof a therapeutically effective amount of the compound or salt of claim 1, wherein the psychiatric disorder is bipolar disorder, depression, treatment-resistant depression, major depressive disorder, postpartum depression, or suicidality.

15. The method of claim 14, wherein the psychiatric disorder is depression.

16. A method of treating major depressive disorder comprising administering to a human patient in need thereof a therapeutically effective amount of the compound or salt of claim 1.

17. The method of claim 14, wherein the administering is once daily.

18. The method of claim 14, wherein the administering is of a daily dose of about 50-100 mg of the compound or salt.

19. The method of claim 18, wherein the daily dose is 50, 75 or 100 mg of the compound or salt.

20. The method of claim 14, which further comprises administering lithium to the patient to treat the psychiatric disorder.

21. The method of claim 20, wherein the compound and the lithium are in a single oral dosage form.

22. The method of claim 14, wherein the administering is daily for a first time period, followed by a washout period of at least one day during which the compound or salt is not administered, followed by daily administering of the compound or salt for a second time period.

23. The method of claim 14, wherein the administering is two or three times per week.

24. The method of claim 20, wherein the psychiatric disorder is bipolar mania.

25. A method for treating a psychiatric disorder comprising administering to a human patient in need thereof a therapeutically effective amount of ring carbon deuterated gaboxadol or a pharmaceutically acceptable salt thereof, wherein the psychiatric disorder is bipolar disorder, depression, treatment-resistant depression, major depressive disorder, postpartum depression, or suicidality.

26. The method of claim 25, wherein the psychiatric disorder is depression.

27. A method for treating major depressive disorder comprising administering to a human patient in need thereof a therapeutically effective amount of ring carbon deuterated gaboxadol or a pharmaceutically acceptable salt thereof.

28. The method of claim 14, further comprising administering to the patient a second pharmaceutical composition comprising ring carbon deuterated gaboxadol within less than 6 hours immediately following the prior administering step.

29. The method of claim 28, wherein the second pharmaceutical composition is administered after a step of determining that a neurological test of the patient demonstrates an insufficient response within about 180 minutes immediately after the prior administering step.

30. The method of claim 14, wherein the therapeutically effective amount is administered intermittently, separated by washout periods of at least one day during which no deuterated gaboxadol is administered.

31. A method for treating a psychiatric disorder comprising administering to a human patient in need thereof a combination of a first pharmaceutical composition comprising an effective amount of the compound or salt of claim 1, and a second pharmaceutical composition comprising an agent selected from the group consisting of lithium, ketamine, SAGE-217, allopregnanolone ganaxolone, alfadolone, alfaxolone, hydroxydione, minaxolone, pregnanolone, renanolone and other pregnane neurosteroids, AV-101 (L-4-Chlorokynurenine), rapastinel (GLYX-13), MGS0039, LY-341,495, MK-801 (dizocilpine), Ro 25-6981, rislenemdaz (CERC-301, MK-0657), apimostinel (NRX-1074), lanicemine (AZD6765), traxoprodil (CP-101606), (2R,6R)-hydroxynorketamine, decoglurant (INN) (RG1578, R04995819), memantine, tiagabine, gaboxadol, clozapine, [2-amino-4-(2,4,6-trimethylbenzylamino)-phenyq-carbamic acid ethyl ester (AA29504), AXS-05 (fixed combination of dextromethorphan and bupropion) and pharmaceutically acceptable salts thereof; wherein the psychiatric disorder is bipolar disorder, depression, treatment-resistant depression, major depressive disorder, postpartum depression, or suicidality.

32. The method of claim 31, wherein the agent in the second pharmaceutical composition is ketamine.

33. The pharmaceutical composition of claim 12, wherein the lithium is present in the pharmaceutical composition in an amount that is a sub-standard daily dose of lithium.

34. The pharmaceutical composition of claim 12, wherein the pharmaceutical composition is in a form of a single dosage unit having separate compartments for the lithium and ring carbon deuterated gaboxadol or a pharmaceutically acceptable salt of either or both compounds thereof.

35. A kit comprising the pharmaceutical composition of claim 12.

36. The method of claim 14, wherein the psychiatric disorder is bipolar disorder.

37. The method of claim 14, wherein the psychiatric disorder is treatment-resistant depression.

38. The method of claim 14, wherein the psychiatric disorder is suicidality.

39. The method of claim 14, wherein the psychiatric disorder is postpartum depression.

40. The method of claim 36, wherein the administering is once daily.

41. The method of claim 36, wherein the administering is of a daily dose of about 50-100 mg of the compound or salt.

42. The method of claim 36, wherein the daily dose is 50, 75 or 100 mg of the compound or salt.

43. The method of claim 36, which further comprises administering lithium to the patient to treat the psychiatric disorder.

44. The method of claim 43, wherein the compound and the lithium are in a single oral dosage form.

45. The method of claim 16, 37, 38 or 39, wherein the administering is of a daily dose of about 50-100 mg of the compound or salt.

46. The method of claim 16, 37, 38 or 39, wherein the administering is daily for a first time period, followed by a washout period of at least one day during which the compound or salt is not administered, followed by daily administering of the compound or salt for a second time period.

47. The method of claim 16, 37, 38 or 39, wherein the administering is two or three times per week.

48. A method of treating a psychiatric disorder comprising administering to a human patient in need thereof a pharmaceutical composition; said pharmaceutical composition comprising a therapeutically effective amount of the compound or salt of claim 1 and a pharmaceutically acceptable carrier, wherein the psychiatric disorder is bipolar disorder, depression, treatment-resistant depression, major depressive disorder, postpartum depression, or suicidality.

49. The method of claim 48, wherein the psychiatric disorder is bipolar disorder.

50. The method of claim 48, wherein the psychiatric disorder is depression.

51. The method of claim 48, wherein the psychiatric disorder is treatment-resistant depression.

52. The method of claim 48, wherein the psychiatric disorder is major depressive disorder.

53. The method of claim 48, wherein the psychiatric disorder is postpartum depression.

54. The method of claim 48, wherein the psychiatric disorder is suicidality.

* * * * *